(12) United States Patent
De La Huerga

(10) Patent No.: US 7,978,564 B2
(45) Date of Patent: Jul. 12, 2011

(54) INTERACTIVE MEDICATION CONTAINER

(76) Inventor: Carlos De La Huerga, Milwaukee, WI (US)

(*) Notice: Subject to any disclaimer, the term of this patent is extended or adjusted under 35 U.S.C. 154(b) by 746 days.

(21) Appl. No.: 09/832,770

(22) Filed: Apr. 11, 2001

(65) Prior Publication Data

US 2001/0028308 A1   Oct. 11, 2001

Related U.S. Application Data

(63) Continuation-in-part of application No. 09/185,137, filed on Nov. 3, 1998, now Pat. No. 6,259,654, which is a continuation-in-part of application No. 09/168,783, filed on Oct. 8, 1998, now Pat. No. 6,611,733, which is a continuation-in-part of application No. 08/832,613, filed on Mar. 28, 1997, now Pat. No. 5,852,590.

(51) Int. Cl.
*G04B 47/00* (2006.01)
*B65B 59/00* (2006.01)
*G08B 13/14* (2006.01)
*G06F 17/00* (2006.01)

(52) U.S. Cl. ......... 368/10; 221/15; 235/375; 340/572.1; 700/242

(58) Field of Classification Search .............. 368/88, 368/276, 281, 286, 287, 291–300, 309, 10, 368/11, 107–109; 221/2, 3, 15; 340/571, 340/572.1, 572.8, 309.16; 235/375; 700/236, 700/242, 244; 705/2, 3, 5
See application file for complete search history.

(56) References Cited

U.S. PATENT DOCUMENTS

| 3,227,127 A | 1/1966 | Gayle |
| 3,762,601 A | 10/1973 | McLaughlin |
| 4,094,561 A | 6/1978 | Wolff et al. |
| 4,207,992 A | 6/1980 | Brown |

(Continued)

FOREIGN PATENT DOCUMENTS

GB        2154344        9/1985

(Continued)

OTHER PUBLICATIONS

Paul Lavin, "Small but perfectly informed Will a Java Ring become the next must-have fashion accessory?" The Independent, London, Apr. 7, 1998.

(Continued)

*Primary Examiner* — Vit W Miska
(74) *Attorney, Agent, or Firm* — Quarles & Brady

(57) ABSTRACT

This invention relates to an interactive medication container or console that hold or otherwise organizes one or more medication vials or containers. Each vial has a memory strip containing medication and prescription information. Each vial can also include a reminder unit that is attached to and portable with the individual vials. The console or reminder unit reads the information strip of the vial and communicates this information to or interacts with a patient to remind them to take the medication. The medication container or reminder unit also gathers or tracks information such as consumption time, quantity remaining, patient feedback, and contraindication information. The medication container or reminder unit interacts with the patient by displaying questions or receiving and recording input from the patient before, during or after a dose of medication is taken. The patient input can be used to modify the dosing regimen for future doses of medication. The medication container reorders medication when the quantity remaining reaches a threshold level. Contraindication information in the memory strip is downloaded to a personal home computer or a hospital or nursing home computer.

51 Claims, 41 Drawing Sheets

U.S. PATENT DOCUMENTS

| | | | |
|---|---|---|---|
| 4,220,330 A * | 9/1980 | Montgomery | 273/452 |
| 4,360,125 A | 11/1982 | Martindale et al. | |
| 4,368,988 A | 1/1983 | Tahara et al. | |
| 4,384,288 A | 5/1983 | Walton | |
| 4,437,579 A | 3/1984 | Obland | |
| 4,476,381 A | 10/1984 | Rubin | |
| 4,483,626 A | 11/1984 | Noble | |
| 4,504,153 A | 3/1985 | Schollmeyer et al. | |
| 4,526,474 A | 7/1985 | Simon | |
| 4,546,901 A | 10/1985 | Buttarazzi | |
| 4,573,606 A | 3/1986 | Lewis et al. | |
| 4,575,621 A | 3/1986 | Dreifus | |
| 4,598,275 A | 7/1986 | Ross et al. | |
| 4,616,316 A | 10/1986 | Hanpeter et al. | |
| 4,617,557 A | 10/1986 | Gordon | |
| 4,626,105 A | 12/1986 | Miller | |
| 4,664,289 A | 5/1987 | Shimizu et al. | |
| 4,674,651 A | 6/1987 | Scidmore et al. | |
| 4,674,652 A | 6/1987 | Aten et al. | |
| 4,682,299 A * | 7/1987 | McIntosh et al. | 702/177 |
| 4,694,284 A | 9/1987 | Leveille et al. | |
| 4,695,954 A | 9/1987 | Rose et al. | |
| 4,717,261 A | 1/1988 | Kita et al. | |
| 4,725,997 A | 2/1988 | Urquhart et al. | |
| 4,730,849 A | 3/1988 | Siegel | |
| 4,732,411 A | 3/1988 | Siegel | |
| 4,733,362 A | 3/1988 | Haraguchi | |
| 4,733,797 A | 3/1988 | Haber | |
| 4,785,969 A | 11/1988 | McLaughlin | |
| 4,811,764 A | 3/1989 | McLaughlin | |
| 4,817,050 A | 3/1989 | Komatsu et al. | |
| 4,823,982 A | 4/1989 | Aten et al. | |
| 4,835,372 A | 5/1989 | Gombrich et al. | |
| 4,839,806 A | 6/1989 | Goldfischer et al. | |
| 4,847,764 A | 7/1989 | Halvorson | |
| 4,850,009 A | 7/1989 | Zook et al. | |
| 4,857,713 A | 8/1989 | Brown | |
| 4,857,716 A | 8/1989 | Gombrich et al. | |
| 4,885,571 A | 12/1989 | Pauley et al. | |
| 4,898,578 A | 2/1990 | Rubalcaba, Jr. | |
| 4,911,327 A | 3/1990 | Shepherd et al. | |
| 4,916,441 A | 4/1990 | Gombrich | |
| 4,939,705 A | 7/1990 | Hamilton et al. | |
| 4,952,928 A | 8/1990 | Carroll et al. | |
| 4,953,745 A | 9/1990 | Rowlett, Jr. | |
| 4,967,928 A | 11/1990 | Carter | |
| 4,971,221 A | 11/1990 | Urquhart et al. | |
| 4,973,944 A | 11/1990 | Maletta | |
| 4,978,335 A | 12/1990 | Arthur, III | |
| 4,980,671 A | 12/1990 | McCurdy | |
| 4,984,709 A | 1/1991 | Weinstein | |
| 5,012,229 A | 4/1991 | Lennon et al. | |
| 5,014,875 A | 5/1991 | McLaughlin et al. | |
| 5,032,823 A | 7/1991 | Bower et al. | |
| 5,047,948 A | 9/1991 | Turner | |
| 5,048,870 A | 9/1991 | Mangini et al. | |
| 5,071,168 A | 12/1991 | Shamos | |
| 5,075,670 A | 12/1991 | Bower et al. | |
| 5,078,683 A | 1/1992 | Sancoff et al. | |
| 5,088,056 A | 2/1992 | McIntosh et al. | |
| 5,099,463 A | 3/1992 | Lloyd et al. | |
| 5,104,374 A | 4/1992 | Bishko et al. | |
| 5,115,223 A | 5/1992 | Moody | |
| 5,161,199 A | 11/1992 | David | |
| 5,166,498 A | 11/1992 | Neeley | |
| 5,176,285 A | 1/1993 | Shaw | |
| 5,181,189 A | 1/1993 | Hafner | |
| 5,193,855 A | 3/1993 | Shamos | |
| 5,202,929 A | 4/1993 | Lemelson | |
| 5,204,670 A | 4/1993 | Stinton | |
| 5,208,762 A | 5/1993 | Charhut et al. | |
| 5,213,232 A | 5/1993 | Kraft et al. | |
| 5,233,571 A | 8/1993 | Wirtschafter | |
| 5,239,491 A * | 8/1993 | Mucciacciaro | 702/177 |
| 5,256,157 A | 10/1993 | Samiotes et al. | |
| 5,267,174 A * | 11/1993 | Kaufman et al. | 700/242 |
| 5,272,318 A | 12/1993 | Gorman | |
| 5,273,318 A | 12/1993 | Nakayama et al. | |
| 5,289,157 A | 2/1994 | Rudick et al. | |
| 5,313,439 A | 5/1994 | Albeck | |
| 5,317,506 A | 5/1994 | Coutre et al. | |
| 5,319,363 A | 6/1994 | Welch et al. | |
| 5,319,711 A | 6/1994 | Servi | |
| 5,337,919 A | 8/1994 | Spaulding et al. | |
| 5,347,453 A | 9/1994 | Maestre | |
| 5,348,061 A | 9/1994 | Riley et al. | |
| 5,381,487 A | 1/1995 | Shamos | |
| 5,392,952 A | 2/1995 | Bowden | |
| 5,398,220 A | 3/1995 | Barker | |
| 5,401,059 A | 3/1995 | Ferrario | |
| 5,405,048 A | 4/1995 | Rogers et al. | |
| 5,408,443 A | 4/1995 | Weinberger | |
| 5,408,655 A | 4/1995 | Oren et al. | |
| 5,412,372 A | 5/1995 | Parkhurst et al. | |
| 5,431,299 A | 7/1995 | Brewer et al. | |
| 5,445,621 A | 8/1995 | Poli et al. | |
| 5,455,851 A | 10/1995 | Chaco et al. | |
| 5,460,294 A | 10/1995 | Williams | |
| 5,472,113 A | 12/1995 | Shaw | |
| 5,477,511 A | 12/1995 | Englehardt | |
| 5,480,062 A | 1/1996 | Rogers et al. | |
| 5,491,482 A | 2/1996 | Dingwall et al. | |
| 5,491,774 A | 2/1996 | Norris et al. | |
| 5,493,805 A | 2/1996 | Penuela et al. | |
| 5,499,626 A | 3/1996 | Willham et al. | |
| 5,502,445 A | 3/1996 | Dingwall et al. | |
| 5,502,944 A | 4/1996 | Kraft et al. | |
| 5,504,474 A | 4/1996 | Libman et al. | |
| 5,508,499 A | 4/1996 | Ferrario | |
| 5,511,000 A | 4/1996 | Kaloi et al. | |
| 5,512,879 A | 4/1996 | Stokes | |
| 5,512,880 A | 4/1996 | Abrams et al. | |
| 5,519,808 A | 5/1996 | Benton, Jr. et al. | |
| 5,522,525 A * | 6/1996 | McLaughlin et al. | 221/4 |
| 5,525,969 A | 6/1996 | LaDue | |
| 5,527,289 A | 6/1996 | Foster et al. | |
| 5,532,705 A | 7/1996 | Hama | |
| 5,541,580 A | 7/1996 | Gerston et al. | |
| 5,541,583 A | 7/1996 | Mandelbaum | |
| 5,548,566 A | 8/1996 | Barker | |
| 5,548,660 A | 8/1996 | Lemelson | |
| 5,564,005 A | 10/1996 | Weber et al. | |
| 5,583,831 A * | 12/1996 | Churchill et al. | 368/10 |
| 5,593,267 A | 1/1997 | McDonald et al. | |
| 5,594,786 A | 1/1997 | Chaco et al. | |
| 5,602,963 A | 2/1997 | Bissonnette et al. | |
| 5,609,268 A | 3/1997 | Shaw | |
| 5,609,716 A | 3/1997 | Mosher et al. | |
| 5,612,675 A | 3/1997 | Jennings et al. | |
| 5,621,384 A | 4/1997 | Crimmins et al. | |
| 5,623,242 A | 4/1997 | Dawson, Jr. et al. | |
| 5,627,520 A | 5/1997 | Grubbs et al. | |
| 5,629,981 A | 5/1997 | Nerlikar | |
| 5,642,906 A | 7/1997 | Foote et al. | |
| 5,643,212 A | 7/1997 | Coutre et al. | |
| 5,646,912 A | 7/1997 | Cousin | |
| 5,650,766 A | 7/1997 | Burgmann | |
| 5,659,741 A | 8/1997 | Eberhardt | |
| 5,660,176 A | 8/1997 | Lliff | |
| 5,678,925 A | 10/1997 | Garmaise et al. | |
| 5,681,285 A | 10/1997 | Ford et al. | |
| 5,689,567 A | 11/1997 | Miyauchi | |
| 5,713,856 A | 2/1998 | Eggers et al. | |
| RE35,743 E | 3/1998 | Pearson | |
| 5,732,401 A | 3/1998 | Conway | |
| 5,742,233 A | 4/1998 | Hoffman et al. | |
| 5,745,366 A | 4/1998 | Higham et al. | |
| 5,768,813 A | 6/1998 | Reboul et al. | |
| 5,771,001 A | 6/1998 | Cobb | |
| 5,772,635 A | 6/1998 | Dastur et al. | |
| 5,774,865 A * | 6/1998 | Glynn | 705/2 |
| 5,781,442 A | 7/1998 | Engleson et al. | |
| 5,782,805 A | 7/1998 | Meinzer et al. | |
| 5,793,290 A | 8/1998 | Eagleson et al. | |
| 5,812,064 A * | 9/1998 | Barbour | 340/5.91 |
| 5,826,217 A | 10/1998 | Lerner | |
| 5,827,180 A * | 10/1998 | Goodman | 600/300 |

| | | | |
|---|---|---|---|
| 5,833,599 A | 11/1998 | Schrier et al. | |
| 5,839,836 A | 11/1998 | Yuyama et al. | |
| 5,851,186 A | 12/1998 | Wood et al. | |
| 5,852,590 A | 12/1998 | de la Huerga | |
| 5,852,911 A | 12/1998 | Yuyama et al. | |
| 5,855,395 A | 1/1999 | Foote et al. | |
| 5,868,669 A | 2/1999 | Lliff | |
| 5,877,675 A | 3/1999 | Rebstock et al. | |
| 5,877,742 A | 3/1999 | Klink | |
| 5,882,338 A | 3/1999 | Gray | |
| 5,883,370 A | 3/1999 | Walker et al. | |
| 5,883,576 A | 3/1999 | de la Huerga | |
| 5,924,074 A | 7/1999 | Evans | |
| 5,936,529 A | 8/1999 | Reisman et al. | |
| 5,945,651 A | 8/1999 | Chorosinski et al. | |
| 5,954,700 A | 9/1999 | Kovelman | |
| 5,960,085 A | 9/1999 | de la Huerga | |
| 5,963,136 A * | 10/1999 | O'Brien | 340/573.1 |
| 5,970,388 A | 10/1999 | Will | |
| 5,979,757 A | 11/1999 | Tracy et al. | |
| 5,980,501 A | 11/1999 | Gray | |
| 5,997,476 A | 12/1999 | Brown | |
| 6,019,745 A | 2/2000 | Gray | |
| 6,032,085 A * | 2/2000 | Laurent et al. | 700/242 |
| 6,032,155 A * | 2/2000 | de la Huerga | 707/104.1 |
| 6,036,231 A | 3/2000 | Foote et al. | |
| 6,070,148 A | 5/2000 | Mori et al. | |
| 6,070,761 A | 6/2000 | Bloom et al. | |
| 6,104,295 A | 8/2000 | Gaisser et al. | |
| 6,108,588 A * | 8/2000 | McGrady | 700/231 |
| 6,110,152 A | 8/2000 | Kovelman | |
| 6,140,936 A | 10/2000 | Armstrong | |
| 6,144,303 A | 11/2000 | Federman | |
| 6,150,942 A * | 11/2000 | O'Brien | 340/573.1 |
| 6,169,707 B1 | 1/2001 | Newland | |
| 6,198,383 B1 * | 3/2001 | Sekura et al. | 340/309.4 |
| 6,219,587 B1 | 4/2001 | Ahlin et al. | |
| 6,255,951 B1 | 7/2001 | de la Huerga | |
| 6,259,654 B1 | 7/2001 | de la Huerga | |
| 6,263,330 B1 | 7/2001 | Bessette | |
| 6,283,761 B1 | 9/2001 | Joao | |
| 6,294,999 B1 | 9/2001 | Yarin et al. | |
| 6,317,390 B1 | 11/2001 | Cardoza | |
| 6,324,123 B1 | 11/2001 | Durso | |
| 6,335,907 B1 * | 1/2002 | Momich et al. | 368/10 |
| 6,346,886 B1 | 2/2002 | de la Huerga | |
| 6,421,650 B1 * | 7/2002 | Goetz et al. | 705/3 |
| 6,539,281 B2 * | 3/2003 | Wan et al. | 700/236 |
| 6,636,780 B1 * | 10/2003 | Haitin et al. | 700/236 |
| 2004/0036623 A1 | 2/2004 | Chung | |

FOREIGN PATENT DOCUMENTS

WO     WO 02/31629 A3     4/2002

OTHER PUBLICATIONS

"Medical alerty systems," The University of California Berkley Wellness Letter, vol. 7, No. 1, p. 1, Oct. 1990.

"Surgical patients carry records on wristband", USA Today, vol. 126, No. 2631, p. 7, Dec. 1997.

Magic Medicine Cabinet: A Situated Portal for Consumer Healthcare, HUC '99, Dadong Wan, Center for Strategic Technology Research Accenture, Northbrook IL (4 pages).

Magic Medicine Cabinet: A Situated Portal for Consumer Healthcare, HUC '99, Dadong Wan, Center for Strategic Technology Research Accenture, Northbrook IL (4 pages), 1999.

* cited by examiner

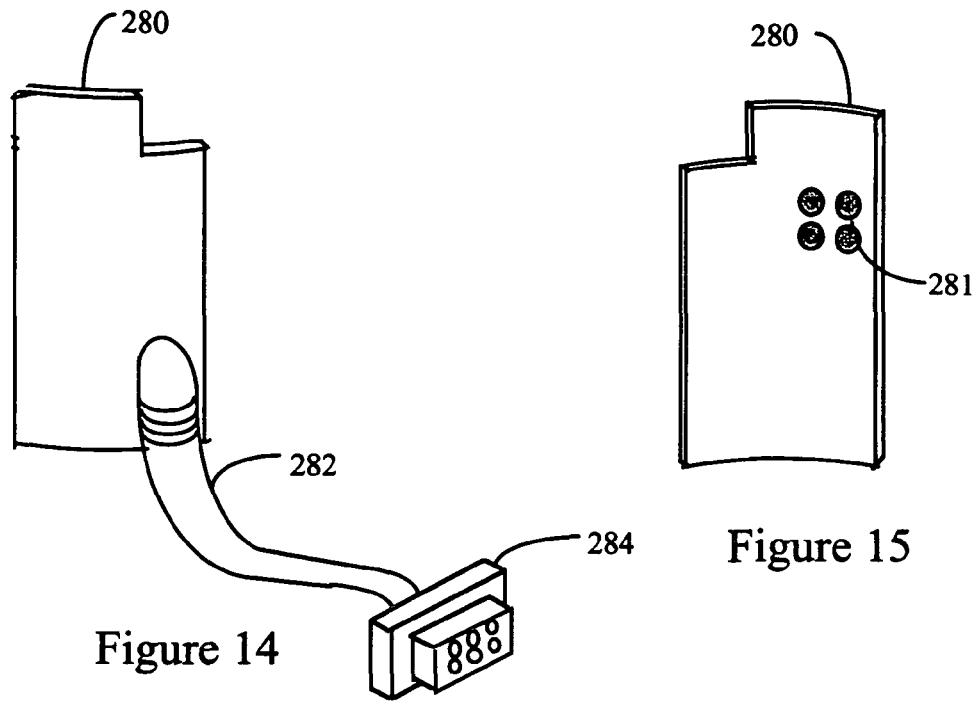
Figure 14
Figure 15
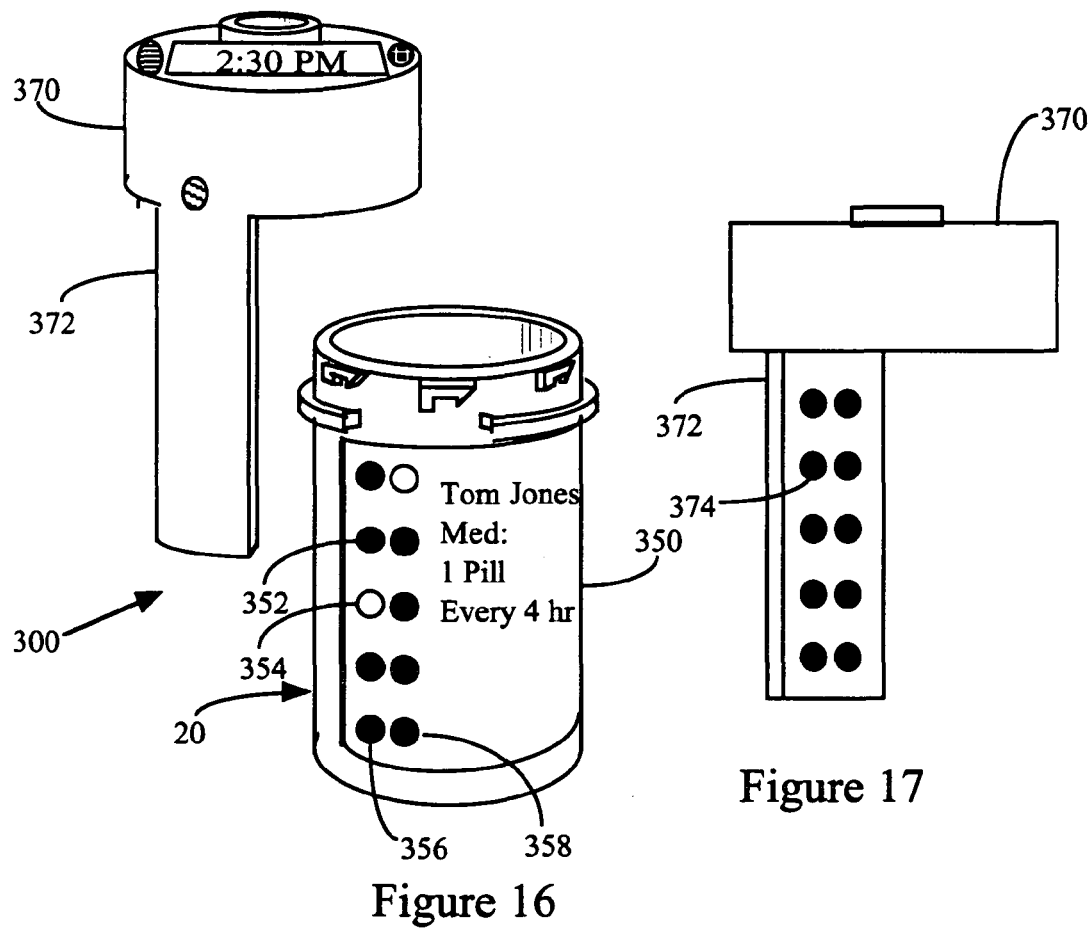
Figure 16
Figure 17

| Medication Consumption Table | | | |
|---|---|---|---|
| Medication 1<br>Monday 7:15 am<br>Monday 1:00 pm<br>Monday 6:30 pm<br>Tuesday 7:45 am<br>Tuesday 1:20<br>○<br>○<br>○ | Medication 2<br>Monday 7:16 am<br><br>Monday 6:30 pm<br>Tuesday 7:24 am<br><br>○<br>○<br>○ | Medication 3<br>Monday 7:16 am<br><br><br>Tuesday 7:25 am<br><br>○<br>○<br>○ | ○ ○ ○ |

INTERACTIVE MEDICATION CONTAINER

CROSS-REFERENCE TO RELATED APPLICATIONS

This is a continuation in part of U.S. patent application Ser. No. 09/185,137 which was filed on Nov. 3, 1998 and is entitled "Multi-vial Medication Organizer and Dispenser" now U.S. Pat. No. 6,259,654 which is a continuation-in-part of U.S. application Ser. No. 09/168,783 filed Oct. 8, 1998 now U.S. Pat. No. 6,611,733 titled "Medication Dispensing Machine Cassette With Interactive Information Strip" and which was a continuation in part of Ser. No. 08/832,613, filed Mar. 28, 1997, now U.S. Pat. No. 5,852,590 entitled "Interactive Label for Medication Containers and Dispensers" which issued on Dec. 22, 1998. Each of the above references are incorporated herein by reference.

STATEMENT REGARDING FEDERALLY SPONSORED RESEARCH OR DEVELOPMENT

Not applicable.

BACKGROUND OF THE INVENTION

This invention relates to an interactive medication container that includes one or more containers, each having an information strip containing medication and prescription information, and a reminder unit or console that reads the information strip or strips and communicates information to and interacts with a patient to remind them to take the medication or to track or gather information such as consumption time, quantity, and patient feedback information.

Medication containers that remind a patient to take their medication or keep track of the number of doses of medication in the container are well known. Examples of such automated containers are disclosed in U.S. Pat. No. 3,227,127 (Gayle); U.S. Pat. No. 4,207,992 (Brown); U.S. Pat. No. 4,360,125 (Martindale); U.S. Pat. No. 4,483,626 (Noble); U.S. Pat. No. 4,504,153 (Schollmeyer); U.S. Pat. No. 4,526,474 (Simon); U.S. Pat. No. 4,573,606 (Lewis); U.S. Pat. No. 4,695,954 (Rose); U.S. Pat. No. 4,725,997 (Urguhart); U.S. Pat. No. 4,939,705 (Hamilton); U.S. Pat. No. 4,984,709 (Weinstein); U.S. Pat. No. 5,099,463 (Lloyd); U.S. Pat. No. 5,181,189 (Hafner); U.S. Pat. No. 5,213,332 (Kraft); U.S. Pat. No. 5,313,439 (Albeck); U.S. Pat. No. 5,392,952 (Bowden); U.S. Pat. No. 5,472,113 (Shaw) and U.S. Pat. No. 522,525 (McLaughlin), the disclosures of which are incorporated by reference.

The general purpose of an automated container is to improve patient compliance in taking the appropriate medication on schedule. While taking a particular medication on a regular schedule may seem a simple process, it is often difficult to accomplish, especially when the patient has been prescribed to take several medications. Dosing regimens that require the patient to take different doses of different medications at different times can be particularly confusing. For example, a prescription that requires a patient to take two doses of medication A and one dose of medication B can be confusing. A patient can inadvertently take one dose of medication A and two doses of medication B. In addition, some medications are taken in a paired dosing regimen, with medication A being taken on Monday, medication B being taken on Tuesday, medication A on Wednesday, etc. Other medications are not intended to be taken together at all because they either neutralize each other or cause adverse side effects that can result in illness or even death. This situation is particularly problematic when more than one physician is prescribing medication to the patient. Conventional medication containers designed for a patient's personal use on an out-patient basis do not assist the patient in taking the correct medication at the correct time, particularly when several medications have been prescribed.

The ability to comply with prescribed medication dosing requirements is complicated in situations where dosing amounts change over time. For example, prescribed dosing amounts are frequently a function of ongoing laboratory tests that determine the patient's medication needs. In these situations, physicians need to be able to easily communicate changes in dosing amounts to their patients as quickly as possible. Medication compliance is particularly important when powerful medications are prescribed, and over-medicating or under-medicating a patient can lead to serious side effects, illness and even death. Yet, keeping patients in hospitals for a prolonged period of time to ensure that dosing regimens are changed when necessary is not considered a practical solution.

The process of taking several medications at the appropriate time is further complicated if the medication or an illness causes the person to think less clearly or to be forgetful. There is the anxiety of being uncertain if you took the medication earlier in the day. Then, there is the problem of patients completely forgetting to take their medication. The first condition is alleviated by simply indicating when the medication is to be taken next. If the container indicates a future time or day to take the next medication, the patient knows that they have taken the current dosage. If the container indicates a present or past time, the patient knows that they should take the medication now. To solve the problem of completely forgetting to take a dosage of medication, a container will typically contain an alarm to remind the patient to take the medication. Unfortunately, the presently available products and the above patents suffer from one or more problems or limitations.

One problem in reminding patients to take their medication on time is that many automated medication systems are not transportable and not intended for use on an outpatient basis. This is especially true of systems that handle complicated dosing regimes, handle a variety of medications, or provide fairly detailed information about the medications being consumed. Yet, many patients are not home bound. In fact, the purpose of many medications is to enable people that would otherwise be incapacitated to live normal, ambulatory lives. To be effective, medication alerting methods must be easily transportable, not just an in-home alarming system.

An additional problem is childproofing the automated medication container. Childproofing is frequently necessary to prevent an infant, child, or mentally handicapped or medicated person from gaining unsupervised access to the medication. The childproofing features must cooperate with the automated features of the container.

A further problem is that some automated dispensers dispense a variety of different pills at the same time. Some dispensers empty a preloaded number of pills from the container as it passes over an open dispensing chute. If the patient does not take all the medication, there is no place to put the excess. The medication either remains in the dispensing area, possibly resulting in an accidental overdose at a later time or consumption by a child, or the medication is thrown out. If an attempt is made to reload the medication into the dispenser, the dispensing patterns can be inadvertently altered. This is particularly problematic if the dispenser is handling medications that are similar in appearance.

A still further problem is that errors can occur when a caregiver removes a variety of medications from the pharmacist supplied containers and inserts the medications into a different medication container or machine. An example being a container with separate compartments marked "breakfast, lunch and dinner", or "Monday, Tuesday, Wednesday, etc." In fact, there is some question regarding the legality of a care giver removing medications from pharmacist supplied containers and placing them into other containers. There is good reason for caution regarding the shuffling of medication from one container to another. Given the strength of many medications in use today, any confusion about the medications put in the secondary container or any confusion regarding the prescription regimens could have a significant adverse affect on the patient.

A still further problem is that the patient must program a timing or alarming mechanism in an automated dispenser by manual entry of additional coded data. A magnetic strip or smart card can also be used to enter the data. Unfortunately, the cards are easily misplaced and errors can result if the wrong data is entered into the dispensing machine manually or via an incorrect card. In addition, such dispensing machines have to be returned to the pharmacist frequently for reprogramming when a new medication is prescribed.

A still further problem is that many medication containers do not provide a means for counting the number of pills remaining in the container or the number of pills taken to date. The patient or caregiver must manually enter the amount of medication dispensed or account for the quantity of medication remaining after each dose is consumed. In situations where the unused portion of a prescribed medication is returned to the pharmacy, such as in a hospital setting, the pharmacist must manually count the number of pills left in the container.

A still further problem with conventional automated medication containers is that they do not record the actual dosing regimen taken by the patient. A patient could take the medication too early, too late or completely miss taking the medication at various times. This results in a sporadic actual consumption or dosing regimen for the medication. The containers in use today do not provide an easy method of communicating the sporadic extent of the actual consumption regimen to the patient, or his or her pharmacist or physician.

A still further problem in designing an automated medication container is that the container should be compatible with conventional, non-automated medication containers used by the pharmaceutical industry today. (See FIG. 1). A dramatic deviation from the conventional design would inhibit the adoption of the automated container design. A compatible design would enable the pharmacist to continue using conventional, non-automated containers in situations where such a container is appropriate, but would enable the pharmacist to provide an automated container in situations where this type of container is appropriate.

A still further problem with designing an automated medication container is that the more expensive automated components should be reusable. The increased cost of providing a microprocessor, memory displays, alarms and circuitry in a container would likely be prohibitive if the entire container disposed of after a single prescription is consumed. As many components as possible must be designed to be reused.

The present invention overcomes these and other limitations in existing medication dispensing products.

SUMMARY OF THE INVENTION

This invention relates to an interactive medication container or console that hold or otherwise organizes one or more medication vials or containers. Each vial has a memory strip containing medication and prescription information. Each vial can also include a reminder unit that is attached to and portable with the individual vials. The console or reminder unit reads the information strip of the vial and communicates this information to or interacts with a patient to remind them to take the medication. The medication container or reminder unit also gathers or tracks information such as consumption time, quantity remaining, patient feedback, and contraindication information. The medication container or reminder unit interacts with the patient by displaying questions or receiving and recording input from the patient before, during or after a dose of medication is taken. The patient input can be used to modify the dosing regimen for future doses of medication. The medication container reorders medication when the quantity remaining reaches a threshold level. Contraindication information in the memory strip is downloaded to a personal home computer or a hospital or nursing home computer.

One embodiment of the interactive medication container invention relates to a multi-piece, medication container having a first piece with an interactive label that includes a machine readable memory strip. The memory strip contains prescription information, medication information and program codes that are downloaded to a second piece having a computer processor. The interactive label is affixed to a vial of a standard or slightly modified childproof container sealed by a cap. An automated reminder unit is attached to the vial and positioned so that memory sensors in the reminder are able to read the prescription information, medication information and codes on the memory strip. This can be ensured by using an alignment device such as a plate or the interactive memory strip can be arranged uniformly around the perimeter of the vial, so as to be read simply by inserting the vial into a hole or socket. The automated reminder includes its own memory for storing the information and codes. The automated reminder also includes a display for visually or audibly indicating desired information to the patient, such as alerts when to take the next dose of medication.

The reminder unit can be designed to mate with a wide variety of medication containers. For example, when the interactive label is part of an alignment plate, the plate can be attached or adhered to vials, bottles, boxes, blister packs, inhalation cartridges and other types of containers. Now the reminder is part of a universal system helping patients to properly consume virtually all forms of medication.

When a consumption alert is presented, indicating medication is to be consumed, the alert can be canceled by pressing a button on the reminder. Pressing the button indicates to the reminder that the dose of medication has been consumed. The reminder then writes actual medication consumption information to the memory of the reminder. When the container or vial includes a readable and writable memory strip, the consumption information can be written to the memory strip. Recording this consumption information enables the reminder to track the actual dosing regimen for the actual time medication was consumed. The consumption information can also be used to determine inventory or remaining quantity information regarding the number of medication doses remaining in the container or the time the medication was consumed. The reminder unit includes a computer controlled locking assembly that prevents the removal of the cap before the prescribed time for taking the next dose of medication.

The actual medication consumption information is downloaded into the memory strip. The patient returns the vial and memory strip to the pharmacist or physician for analyzing the patient's input in response to questions asked during use to determine the effectiveness of the medication. The pharmacist or physician reads the information on the memory strip via a separate sensing element kept in their office. The patient retains the reminder for further use.

One advantage of the present invention is that the interactive label contains a wide variety of information that is not practical to print out in textual form on a relatively small label. The memory or memory strip contains information regarding the number of pills or capsules to be taken per dosage and the dosing regimen, e.g. daily, four times a day, before a meal, etc. The memory strip also contains information regarding the medication, such as the medication name, expiration date, quantity in container, patient name, pharmacy name, address and telephone number, pharmacy prescription number, prescribing doctor name and telephone number.

Another advantage of the present invention is that the memory strip contains special prescription requirements and instructions that are expressed in the form of a series of processor instructions such as those written in the Java or other computer language, as opposed to a simple four times per day dosing regime. The prescription requirements can, for example, indicate frequent dosages of a medication when starting a medication, then indicate a gradual reduction of medication, and finally indicate a sustained steady dose after several days.

A further advantage of the present invention is that the memory strip can contain prescription requirements that include instructions for alternating between differing medications in a controlled sequence. For example, some advances in Acquired Immune Deficiency Syndrome (AIDS) medication protocols require the patient to consume two or more medications, but on alternating or sequential days. Although each medication is held in a separate and distinct medication container, the memory strip on each medication container could provide instructions on taking both medications.

The patient can elect to consume medication earlier than normal. The patient indicates his or her desire to consume a dose of medication by triggering an access warning indicator such as by pressing one or more buttons, attempting to open the container or vial holding the medication, or by other means of indicating that access to the medication is desired. The reminder then uses the prescription information, medication information or codes previously stored in the memory of the reminder to determine if the medication can be safely consumed at this time. For example, the reminder will determine if a medication that is normally taken once a day at a certain time can be consumed 2 hours early. If the medication can be safely consumed at this early time, the reminder indicates this to the patient and then writes the actual medication consumption information to the memory or memory strip as noted above. The reminder will then skip over the next scheduled predetermined time to take a dose of medication and skip or forego presenting an alert to the patient to consume medication at that time so the patient is not confused and directed to consume another dose of medication. If the medication cannot be safely consumed at a particular time, the reminder will present an access alert to the patient to not consume the medication.

The medication information can include questionnaires to be presented to the patient related to the consumption of medication. A questionnaire can ask the patient how they feel or to instruct him or her to record their blood pressure. The questionnaire is typically presented to the patient either before or after consuming the medication, but can be presented as the medication is consumed. The response to the questionnaire can be entered using one or more buttons, or the information requested can be transferred from a separate medical device (e.g. glucometer, blood pressure device, or heart rate monitor) to the reminder unit and stored in the memory of the interactive label of the vial or the memory of the reminder unit or transferred to a remote care giver computer system.

The patient can indicate to the reminder that he or she wants to withdraw the next dose of medication even if the time is presently too early to safely consume a dose of medication. This allows the patient to leave his or her home or a nursing home or care giver setting for a day without taking the interactive medication container with him or her. By pressing one or more buttons, the reminder indicates to the patient when the next dose is to be consumed and how many pills are to be consumed. The patient then removes the dose or doses of medication from the vial and places them in his or her purse, pocket, or an accessory portable medication container. When the patient removes the medication for later consumption, the reminder records the consumption information as though the medication were consumed at the next normal dosing time. The reminder will not present a consumption alert to consume medication at that next normal dosing time.

The accessory portable container can include an electronic reminder unit of its own. When the patient removes the medication from the vial and places it in the accessory portable container, the reminder unit mated to the vial communicates (e.g. via infrared, radio frequency, or by direct electrical contact) to the reminder of the accessory portable container the prescription information and medication information used to alert the patient to consume the medication at the next dosing time. The patient indicates to the portable container when he or she is consuming the medication. This time is recorded as consumption information in the memory of the portable reminder. Alternately, the portable container can have sensors that indicate to its reminder when medication is being removed from the portable container. When this occurs, consumption information is recorded to the memory of the portable reminder unit. In either, case when the portable container is brought back to the medication vial reminder unit, the consumption information can be transferred from the memory of the portable reminder unit to the reminder mated to the vial and recorded in memory of the interactive label or the memory of reminder unit.

At the next dosing time, the patient is alerted to consume the medication in the container. As noted above for the interactive medication container, the patient indicates his or her desire to consume a dose of medication by triggering an access indicator such as by pressing one or more buttons on the portable container, attempting to open the portable container, or by other means, when they are consuming the medication. This cancels the consumption alert and the current time is recorded as consumption information in the memory of the portable reminder. If the patient wants to consume the medication early they indicate this by pressing an override button. The current time is recorded as the consumption information and the scheduled consumption alert at the normal dosing time is canceled. Alternately, the portable container can have sensors that indicate to its reminder when medication is being removed from the portable container. When the sensors detect the removal of medication, such as by the removal of a cap, consumption information is recorded to the memory of the portable reminder unit and the alert for the next normally scheduled consumption or dose time is canceled. In either case, when the portable container is brought back to the interactive medication container, the consumption information is transferred from the memory of the portable container and recorded to the memory of the interactive medication container or the memory strip of the interactive label of the vial.

In another embodiment of the interactive medication container, the reminder has medication removal sensors for obtaining actual medication consumption information based on when medication is removed from its associate vial or container. The removal sensor can be in the form of a cap sensor (e.g. a micro switch). The reminder unit is mated or otherwise attached to its associated vial or container so that the memory sensors (e.g. electrical contacts) are aligned or otherwise positioned to read the information from the memory strip of the interactive label. The memory sensors can also take the form of a medication removal sensor (e.g. a micro switch) located in a discharge opening of the vial or container. The memory sensor is positioned to monitor the removal or an attempt to remove medication from the vial or container (e.g. removing a cap that breaks the electrical contacts or the passage of a dose of medication by the micro switch trips the micro switch). Once disrupted, tripped or otherwise activated or deactivated, the reminder writes the actual consumption information to the memory of the reminder or the memory strip of the interactive label of the vial.

A still further advantage of the present invention is that the memory strip of the interactive label provides sufficient information to enable a single vial or container to hold a variety of medications. Although the medications would have to be sufficiently different looking in appearance to avoid confusion, the memory strip provides enough detailed information so that the interactive medication container can provide the patient with instructions for taking all the types of medication in the vial or container. The interactive medication container alleviates the need for the patient to carry around several containers at once.

A still further advantage of the present interactive medication container invention is that the microprocessor, memory sensors, display and alarms are located in the reminder unit. The memory strip is affixed to the vial or container. This enables a patient to reuse the automated reminder for different prescriptions. The vial and its memory strip, which contains information specific to the prescription for the medication in the container is discarded or returned to the pharmacist or physician. The more expensive automated reminder is reused for subsequent prescriptions, thereby reducing the long-term cost of the automated container.

A still further advantage of the present invention is that the information in the interactive label and the microprocessor memory are used to alert the patient when it is time to take a dose of medication and how many pills or capsules to consume. The interactive label and microprocessor are also used to warn the patient to defer taking medication at the present time, or indicate at what time the next dose of medication is to be taken. These alarms and indicators should increase patient compliance in taking medication according to the prescribed regimen.

A still further advantage of the present invention is that the automated medication container can convey information to a separate device such as a patient's home computer to aid in alerting the patient to take the medication in a timely manner. For example, the interactive medication container can take the form of a multi-container medication dispenser or medication system and used with remote communication devices described below.

A still further advantage of the present invention is that the interactive label and automated reminder are compatible with a conventional medication container having a cylindrical vial and childproof cap as shown in FIG. 1. The pharmacist can dispense medication in a standard or slightly modified childproof container affixed with the interactive label. The patient is then free to attach or mate the vial to the automated reminder.

Conventional medication containers are easily modified to facilitate use with the interactive label. A plate with the interactive label can be adhered to virtually any container. The container and plate are then received by or mated to the automated reminder. When the reminder has a medication removal indicator or sensor (e.g., a micro switch), the plate is adhered to the container so that the removal sensor is properly positioned to detect medication being removed from the container (e.g., passing through a discharge opening).

A still further advantage of the invention is that the automated reminder includes a battery or photocell, a microprocessor with a timing circuit, and a LCD display. The timing circuit enables the reminder to provide the time of day, day of the week or date to the patient.

An additional advantage of the present invention is that it can record actual medication consumption information. The timing circuit enables the automated reminder to obtain actual consumption information by recording when the cap is removed from or a dose of medication passes through a discharge opening of the vial or container. Removal of the cap disrupts the communication of the cap sensor with the processor. This disruption in communication, which may also take the form of returning the cap to seal the vial and the corresponding reengagement of communication, establishes the time and date the user consumed the medication. The prescription timing regimen is used to compute the next time the patient should take the medication. When the cap is replaced, the microprocessor determines that the user just removed the cap, consumed a dose of medication, and replaced the cap. A similar scenario occurs when a medication removal indicator or sensor (e.g., a micro switch) is used.

A still further advantage of the present invention is that the reminder computes the next time the patient is to take the medication and displays this information to the patient. The time and or date or day is displayed via a display such as a LCD device in the reminder. By reading the display, the user can easily and reliably determine the next time to take the medication. The LCD display includes the number of pills or capsules to be consumed. Given enough display area, specific instructions for taking the medication will be presented, e.g., "consume 2 hours before eating."

A still further advantage of the present invention is that the reminder can alert the patient to take the medication by sounding an audible alarm, illuminating an indicator such as an LCD, or rotating an eccentrically positioned weight to cause a vibration alert. These alarms are intended to improve patient compliance.

A still further advantage of the present invention is that prescription information on the memory strip of the vial or container is conveyed to the patient's personal home computer, or a hospital or nursing home computer. The information on the memory strip controls additional alerting means, such as additional light sources, audible alarms, via telecommunication to call the patient at home or office depending on the time of day to remind the patient to take the medication. The patient responds by using a telephone keypad to indicate whether a dose was taken. In this way, patient compliance with the physician prescription is tracked. Alternately, the personal home computer can page the patient to indicate which medication is to be taken. The memory strip information is copied to the home or business personal computer via a separate sensing element capable of communicating with the personal or business computer. The automated reminder can also be equipped with an infrared transmitter, radio frequency, telephone modem, or Ethernet adapter to send the memory strip information to the personal computer or remote medication system.

A still further advantage of the present invention is that the childproof container helps prevent the patient from taking medication too soon or too frequently. The reminder is equipped with a locking mechanism that interacts with the childproof locking features. When the cap is in place, a solenoid activated armature in the reminder prevents any attempt to open the cap until the appropriate time for taking the medication. When it is time to consume the medication, the solenoid releases the armature. The locking mechanism can also limit the number of times a day the patient can gain access to medication that is consumed on an as needed basis (e.g., for use with medication to control pain). This helps prevent the patient from taking the medication too many times in any given day or from repeating dosages of the medication within too short a time period. This feature helps inhibit or avoid addictions to the medication.

In a further embodiment of the invention, the interactive medication container organizes several vials or containers of different types of medication. These vials or containers can take on different sizes and shapes. Each vial or container is mated or otherwise secured to a console or unitary dispenser. A machine readable memory strip is affixed to each vial. A separate memory strip is affixed or otherwise joined to each vial or container. Each memory strip contains prescription information and medication information pertaining to the medication in its vial. The console or unitary dispenser is equipped with one or more sensors that read each memory strip and transmit their information to the computer processor and its associated memory device. The processor determines when each medication is to be taken and signals or otherwise communicates with the patient to take the appropriate medication from the appropriate vial at the appropriate time. Indicator lights and a display are preferably provided for this purpose. The vials are standard or slightly modified childproof pill containers, but can take the form of other containers such as bottles, inhalers, boxes, and blister packs or dispensers. The console or dispenser is provided with one or more access control mechanisms that allow the removal of medication from the vials or containers, and obtains actual medication consumption information based on when and from what vial or container the medication was removed. When a dosing time occurs, a consumption alert is sounded or otherwise communicated to the patient. This alert or communication indicates the vial or container containing the intended medication for this dosing time. The patient then removes the indicated vial or container from the console. The removal of the vial or container is conveyed to the processor in the console by a disruption of the sensed contact or connection with the interactive memory strip, or via a micro switch. The processor detects this disruption in communication and notes this event as access information, removal information or actual consumption information. This information is used to keep inventory information regarding the number of doses of each type of medication remaining in each vial or container. The memory strips can be machine readable and writable so that they can be altered to include actual consumption information, inventory information, or other information such as patient responses to questionnaires.

The console or dispenser can be adapted to releasably mate with a vial or container equipped with its own individual reminder unit. The console or dispenser receives prescription and medication information from the reminder and uses this information to alert the patient when he or she is to consume medication. Although the console is preferably adapted to receive the reminder unit with the vial or container riding on the reminder, the console could easily be adapted so that the reverse is possible. The individual reminder unit no longer presents alerts to the patient when it or the vial it is attached to the console. When the vial and its individual reminder unit are removed from the console, the console will discontinue its alerts to the patient. As noted above, the reminder unit mated to the vial now presents dosing alerts. The reminder unit records consumption information to the memory strip of the interactive label or to the memory of the reminder unit. When the vial and its individual reminder unit are again mated to the console, the recorded consumption information is transferred to the memory of the console.

The console or dispenser is further able to determine if a patient is attempting to consume a medication too early and present an appropriate access alert warning the patient not to consume the medication. The dispenser can use an access control device (e.g. a solenoid and plunger) to prevent the premature removal of a vial. If the medication can be consumed early based on prescription and medication information, the patient can remove the vial or container from the dispenser and consume the medication. The dispenser then cancels the next medication dosing alert, so the patient is not guided to take a dose at the normal dosing time.

The console or dispenser can also be used with an accessory portable container with its own electronic reminder unit. The patient indicates to the reminder that he or she wants to withdraw the next dose of medication, even if the interactive medication container determines that the present time is too early to safely consume that medication. This feature is valuable when the patient is going to be gone for the day and he or she does not want to take the console with him or her. By pressing one or more override buttons, the console indicates to the patient which types of medication are to be removed for independent consumption, when the next dose of each removed medication is to be consumed and how many pills of that type of medication are to be consumed at that time. The patient then removes the medications from the appropriate vials and places them in his or her purse, pocket, or an accessory portable medication container. When the patient removes medication for later consumption, the reminder records the consumption information for each removed medication as though they medication were consumed at their next normal dosing time. The reminder will not present an alert to consume medication at these times.

The accessory portable container can include an electronic reminder unit of its own. When the patient removes the medication from one of the vials and places it in the portable container and the console communicates the prescription information and medication information to the reminder of the portable container (e.g. via infrared, radio frequency, or by direct electrical contact) to alert the patient to take the medication at the next dosing time for that medication. At the next dosing time, the patient is alerted to consume the medication in the portable container. The patient presses a consumption indicator or button to indicate to the portable container that they are consuming the medication. This cancels the next scheduled dosing alert, and the current time is recorded as consumption information in the memory of the portable reminder. The patient can indicate if they want to consume the medication early by pressing another override button. The current time is recorded as consumption information and the scheduled alert at the normal dosing time is canceled. Alternately, the portable container can have an access or removal indicator or sensor that indicates to its reminder when medication is being removed from the portable container. When the sensor is disrupted, tripped or otherwise activated or deactivated, consumption information is recorded to the memory of the portable reminder unit and the next scheduled alert for that type of medication is canceled. In either case, when the portable container is brought back to the medication console, the consumption information is transferred from the memory of the portable container and recorded to the memory of the console, the memory of a reminder unit mated to a vial of the consumed medication, or the memory of the memory strip of the interactive label of the vial for the consumed medication.

The console or dispenser communicates questionnaires recorded in the interactive label or the memory of the console, or transferred via RF communications or a communications network from a remote medication system to the patient. The questionnaires are presented to the patient in relationship to the consumption of one or more of the medications in the multiple vials mated to the dispenser. The questionnaire responses are recorded in the memory of the interactive label, the memory of the console, or transferred for storage in the memory of a remote medication system.

One advantage of the present interactive medication container invention is to improve patient compliance in selecting the appropriate medication from several vials of different medications, and taking that appropriate medication on schedule. The invention is of particular use when the patient has been prescribed to take several medications with dosing regimens that require the patient to take different amounts or doses of different medications at different times. The automated console or dispenser can easily instruct the patient to take two doses of medication A by lighting an indicator light by the appropriate vial and displaying a message to take two pills. Once medication A has been dispensed or removed, the console or dispenser can instruct the patient to take one dose of medication B in a similar manner. This prevents a patient from inadvertently taking one dose of medication A and two doses of medication B. The automated dispenser is also helpful when medications are taken in a paired dosing regimen, with medication A being taken on Monday, medication B being taken on Tuesday, medication A on Wednesday, etc. The dispenser indicates when each medication is to be taken so that the patient does not have to rely on his or her memory. The container is even programmed to display a message stating when the last dose of medication A or B was dispensed or when the next dose of medication A or B is due.

Another advantage of the present invention is the systems ability to handle contraindication information. Contraindication information is stored in each information strip and transmitted to the automated console or dispenser. Contraindication information is also stored in the memory of the dispenser or transferred from a medication system via a communication network to the dispenser. In the later case, only the contraindications for the medications in vials that have been mated to the dispenser need to be transferred. The automated dispenser will sound or otherwise indicate a warning when vials of two different medications are secured to the dispenser that are not intended to be taken together. This is particularly advantageous in the relatively common situation where several physicians are prescribing different medication to the same patient, and the patient is being handled on an outpatient basis.

A further advantage of the present invention is that the console or dispenser can quickly receive updated prescription and medication information for a specific medication on an outpatient basis via a portable paging device or communication network. The dispenser then records the information to the memory of the dispenser, the memory of a reminder unit or the interactive label for the specific medication. The patient does not need to go to the physician to obtain a new written prescription or to a pharmacy to obtain a new vial with new dosing instructions. This is desirable when prescribed medication dosing requirements change over time, such as in situations where ongoing laboratory tests are used to determine the patient's medication needs. The quickness of this system of sending updated medication dosing information to a patient is particularly important when powerful medications are prescribed, and over-medicating or under-medicating a patient can lead to serious side effects, illness and even death. The quickness of the system enables a patient to live a more normal life while receiving treatment on an outpatient basis, avoids a prolonged hospital stay and helps to reduce the cost of treating the individual.

A still further embodiment of the invention relates to an medication system used in conjunction with the reminder unit and the multi-container console or dispenser. The medication system is intended for operation by a pharmacy or healthcare giver (e.g. a physician or home health monitoring agency). The medication system communicates with dispensers or reminder units via a RF paging network or other communications network (e.g. the Internet) to send information to or to receive information from the dispenser related to consumption of medication. The medication system includes a memory or database that stores medication contraindication information, special instructions for consuming individual medication, questionnaires related to the consumption of medication, and can store individual patient consumption information and questionnaire responses.

The console or dispenser uses an Internet address, stored in the interactive memory strip, to connect with the medication system. Alternately the medication system can connect with the dispenser using address information stored in the system memory. In either case information that is normally stored in the interactive memory strip or in the memory of the dispenser is stored in the memory of the medication system. For example the consumption information can be transferred to the system. The system uses this information to determine if a patient is not consuming medication on time or at all. The medication system uses this information with program codes to send a warning message to a care giver for the patient indicating this potentially serious situation. The medication system can also receive the medication information for each medication mated to the dispenser and determine if any of the medications are mutually contraindicated and then send a contraindication alert to the dispenser or to the care giver.

The console or medication system uses medication information in conjunction with the amount of medication remaining in each vial to determine if a reorder of the medication should be made to ensure the patient a continuous supply of the medication. Medication information stored in the interactive strip or the medication system is used to indicate which medication can be reordered, which can be reordered only with the approval of the physician, and those that cannot be reordered. When the quantity of medication in a vial reaches a reorder level the patient is queried to determine if he or she wants to reorder the medication. If the patient indicates by pressing a reorder button that the medication is to be reordered, a message is sent to the medication system to reorder the medication for the patient. The medication system then sends a reorder request to the pharmacist. The reorder level is determined to ensure there is sufficient amount of time to allow the pharmacy to refill the medication. Additional time can be added in the cases where the reorder quantity will be met during a weekend or holiday and the reorder might not be processed quickly enough. A differing and typically larger reorder quantity is used if the approval of a physician is required, reflecting the greater time required to request and receive such approvals.

The invention contemplates that the pharmacy address for reordering a medication is obtained from either the interactive memory strip of a vial or from the memory of the dispenser. The former ensures that all future reorder requests go to the pharmacy that originally filled the prescription for a specific vial or container. The later ensures that all future reorder requests go to a single pharmacy, independent of where the prescription for a specific vial or container was originally filled.

The automated console or dispenser contains a receiver for obtaining updated medication dosing information based on current laboratory tests or physical observations of the physician regarding the patient. For example, in response to a questionnaire communicated by the console to the patient, the patient may measure his or her blood clotting time and enter or transfer this information to the console. The console then transfers this measurement to the medication system. The medication system then presents the measurement to a healthcare giver. By using codes or algorithms, the medication system can compute a recommended dosing regimen change for the patient that is presented to the healthcare giver. Whether presented with a recommended change or not, the healthcare giver can use the medication system to enter a changed dosing regimen of a medication affecting blood clotting times for the patient. The new dosing regimen is then sent from the medication system to the console. The dosing regimen is then recorded in the memory of the console or in the memory of the interactive memory strip of the vial that hold the medication being changed. The medication system can use codes or algorithms to compute a new dosing regimen for the patient, and transmit the new regimen to the console, without requiring the approval of the healthcare giver.

The invention also includes a medication system for performing at least one health safety function, the system comprising at least one container for holding doses of medication, the container having an RF memory device containing specifying information useable to determine a prescribed dosing regimen for the medication an RF sensor defining a sensing area, the sensor for receiving the specifying information when the RF memory device is within the sensing area and a processor wherein the processor receives and uses the specifying information to identify prescribed dosing regimen information and the processor performs at least one health safety function as a function of the prescribed dosing regimen information.

In several embodiments the system further includes a communication device and a timing device, the processor linked to the timing device and linkable to the communication device and, wherein, the processor further uses the specifying information to determine a predetermined time to take the medication, uses the timing device to identify the predetermined time and causes the communication device to indicate when the predetermined time occurs.

The sensor may define a sensor surface adjacent the antenna and the sensing area may be adjacent the sensor surface. The sensor surface may be horizontal and the container may be supportable on the sensor surface such that the RF device is within the sensing area. When the container is supported on the sensing surface the container may include at least one essentially downward facing container surface and the RF device may be attached to the downward facing container surface. The sensor may be embedded in the container surface.

In some embodiments the sensor surface includes a sensing section and a non-sensing section, the sensing area is only adjacent the sensing section and the sensor includes an aligner distinguishing the sensing section from the non-sensing section. The aligner may include indicia on the sensing surface. The downward facing surface may have a first shape and the indicia may have a second shape and the first and second shapes may be essentially identical. Here the container may be a vial including a bottom surface and the downward facing surface may be the bottom surface.

In several embodiments the communication device and the sensor are integral. In some embodiments the timing device, processor, communication device and sensor form a portable device. Here, the portable device may include a strap such that the device is wrist mountable. In other embodiments the timing device, processor, communication device and sensor form a console for stationary use.

In many embodiments the at least one container includes several containers, each container includes an RF memory device, the sensing area can receive more than one RF memory device at a time and, wherein, when more than one RF memory device is within the sensing area, the sensor retrieves the specifying information from each of the RF memory devices.

The system may further include a separate communication device for each of the several containers, the communication devices attached to the containers.

The health safety function may include indicating when a medication is being consumed at a non-optimal time, the system further including a consumption indicator, the consumption indicator activatable to indicate when a dose of medication is to be consumed, wherein the processor receives and uses the specifying information to identify a predetermined prescribed time to take the medication, the processor monitors the consumption indicator to determine when a medication is to be consumed and, when a medication is to be consumed, the processor uses the timing device to determine if the time to consume is consistent with the predetermined time to consume. Here, the system may further include a communication devices linkable to the processor and wherein, when the time to consume is inconsistent with the predetermined time to consume, the processor indicates that the medication should not be consumed at the time indicated by the consumption indicator.

The indicator and the sensor may be integral so that one of placing the specifying device on and removing the specifying device from the sensor area indicates the consumption time.

The system further includes a medication system for performing at least one health safety function, the system comprising at least one container for holding doses of medication, the container having a specifying device containing specifying information useable to determine a prescribed dosing regimen for the medication, a sensor defining a sensing area, the sensing area capable of receiving at least two specifying devices at the same time, the sensor for receiving the specifying information from each of the specifying devices within the sensing area, and a processor, wherein the processor receives and uses the specifying information to identify prescribed dosing regimen information and the processor performs at least one health safety function as a function of the prescribed dosing regimen information.

Here the system may further include a communication device linkable to the processor the communication device capable of indicating any of the containers. This system may also include a timing device linked to the processor wherein, when more than one specifying device is within the sensing area, the processor receives and uses the specifying information for each specifying device in the sensing area to identify prescribed dosing regimen information and a predetermined time to take each of the medications, the processor uses the timing device to determine when the predetermined time occurs for each of the medications and the processor causes the communication device to indicate the medications to be consumed at the predetermined times.

The sensing area may include at least first and second separate sensing areas for receiving specifying information from separate specifying devices. The communication device may include a separate visual warning indicator adjacent each of the sensing areas and, wherein, the communication device indicates which medication to consume by activating the visual warning indicator adjacent medication to be consumed.

The sensor may define a horizontal sensor surface, when containers are supported on the sensing surface the containers each include at least one essentially downward facing surface, the specifying devices are attached to the downward facing surfaces, the sensor surface includes a sensing section and a non-sensing section for each of the sensing areas, the sensing areas only adjacent the sensing sections and the sensor includes a separate aligner for each of the sensing sections distinguishing the sensing sections from the non-sensing section. The aligners may include indicia on the sensing surface. The downward facing surfaces may each have a first shape and the indicia each have a second shape and the first and second shapes are essentially identical.

In many embodiments the communication device includes at least one communication device for each container and a separate communication device is attached to each container.

The processor may periodically cause the sensor to scan the sensing area to identify specifying devices in the sensing area. Each container may include a separate communication device and the processor may be linkable to the communication devices to control each communication device. This linkage may be via wireless communication.

The system may also be for use in recording medication consumption times, the system further including a readable and writable memory device and a consumption indicator that are linkable to the processor, the consumption indicator operable to obtain consumption time information which the processor records in the memory device. The sensor and consumption indicator may also be integral such that one of placing and removing a specifying device in the sensing area comprises operation of the consumption indicator. The memory device and the specifying device may further be integral.

The invention further includes a medication system for performing at least one health safety function, the system comprising at least one container for holding doses of medication, the container having a specifying device containing specifying information useable to determine a prescribed dosing regimen for the medication, the specifying information including a serial number, a sensor defining a sensing area, the sensor for receiving the specifying information when the specifying device is within the sensing area and a processor linkable to a memory device that correlates serial numbers with prescribed dosing regimens, wherein the processor receives the specifying information, correlates the serial number and the regimen to determine the prescribed regimen for a medication and then performs at least one health safety function as a function of the prescribed dosing regimen information.

Another embodiment of the invention includes a medication system for recording medication consumption times, the system comprising at least one container for holding doses of medication, the container having a specifying device containing specifying information useable to determine the type of medication in the container, a readable and writable memory device, an indication device, a sensor defining a sensing area, the sensor for receiving the specifying information when the specifying device is within the sensing area and a processor in communication with a timing device and also linkable to the consumption indicator, the memory device and the sensor, wherein the processor receives and uses the specifying information to identify the medication type, when the consumption indicator is operated the timing device determines consumption time and the processor stores the consumption time and medication type in the memory device.

Here, the specifying device may be an Rf memory device, the sensor may include an Rf identification antenna for sensing information in the specifying device and the sensing area may be adjacent the antenna. In one aspect the sensor may define a sensor surface adjacent the antenna and the sensing area may be adjacent the sensor surface. In another aspect the sensor surface may be horizontal and the container may be supportable on the sensor surface such that the RF device is within the sensing area. In yet another aspect, when the container is supported on the sensing surface the container may include at least one essentially downward facing container surface and the RF device may be attached to the downward facing container surface. The Rf device may be embedded in the container surface.

In some embodiments the sensor surface includes a sensing section and a non-sensing section, the sensing area is only adjacent the sensing section and the sensor includes an aligner distinguishing the sensing section from the non-sensing section. The aligner may include indicia on the sensing surface. In some embodiments the downward facing surface has a first shape and the indicia has a second shape and the first and second shapes are essentially identical.

In some embodiments the sensor and consumption indicator are integral such that one of placing and removing a specifying device in the sensing area comprises operation of the consumption indicator. Also, in some embodiments the processor and the timing device are integral with the communication device and the sensor.

In several embodiments the timing device, processor, consumption indicator and sensor form a console for stationary use. In other embodiments the timing device, processor, consumption indicator and sensor form a portable device. Where the device is portable the device may include a strap such that the device is wrist mountable.

In several embodiments the sensor defines a sensor surface adjacent the antenna and the sensing area is adjacent the sensor surface. In some of these embodiments the sensor surface is horizontal and the containers are supportable on the sensor surface such that the RF devices are within the sensing area.

Other embodiments of the invention include a system for indicating times when medication should be consumed. In some of these embodiments the system includes at least one container for holding doses of medication, the container having a specifying device containing specifying information useable to determine a prescribed dosing regimen for the medication, a communication device, a sensor defining a sensing area, the sensor for receiving the specifying information when the specifying device is within the sensing area and a processor in communication with a timing device and also linkable to the communication device and the sensor, wherein the processor receives and uses the specifying information to identify prescribed dosing regimen information and a predetermined time to take the medication, the timing device determines when the predetermined time occurs and the processor causes the communication device to indicate when the predetermined time occurs.

Yet other embodiments include a medication system for performing at least one health safety function related to a medication, the system including at least one container for holding doses of a medication, the container having a specifying device containing specifying information related to the medication to be held in the container, the specifying information includes information that can be used by the processor to identify a consumption regimen for the user for which the medication was prescribed, a sensor defining a sensing area, the sensor for receiving specifying information from the specifying device when the specifying device is within the sensing area, a processor linked to the sensor, a timing device linked to the processor and a consumption indicator linked to the processor, the consumption indicator activatable to indicate that the user is consuming a dose of medication from the container, wherein, when the specifying device is within the sensing area, the sensor receives the specifying information and provides the specifying information to the processor, the processor identifies the consumption regimen from the specifying information, thereafter, the processor monitoring the consumption indicator to identify activation and upon activation determining if the activation time occurs at a consumption regimen time.

Some embodiments including a warning indicator, the processor causing the warning indicator to indicate an occurrence related to the health safety function. In some of these cases the processor, warning indicator and sensor are integral. Also, in some of these cases the warning indicator is one of a visual and an audible warning indicator.

In some embodiments the consumption indicator and the sensor are integral such that placement of the specifying device within the sensing area activates the consumption indicator indicating consumption.

In some embodiments that include a warning indicator the health safety function further includes, upon determining that the activation time is inconsistent with a consumption regimen time, causing the warning indicator to indicate the inconsistency.

Another health safety function includes, upon determining that the activation time is inconsistent with a consumption regimen time, storing the inconsistency in a database. Yet another health safety function includes the processor causing the warning indicator to indicate when consumption times occur and, when the activation time is prior to a next consumption time, the processor modifying the next consumption time. In some of these cases the processor modifies the next consumption time by skipping the next consumption time.

Other embodiments include a warning indicator and a timing device linked to the processor wherein, after the processor identifies the consumption regimen, the processor tracks the time and causes the warning indicator to indicate each time the medication should be consumed. In some of these embodiments the container and medication to be stored therein are a first container and a first medication and the system further includes at least a second container for holding doses of a second medication, the second container having a second specifying device containing specifying information related to the second medication, when the second specifying device is positioned within the sensing area the processor receiving the corresponding specifying information and identifying the consumption regimen for the second medication, the health safety function further including identifying consumption times for each of the first and second medications and, when a first medication consumption time is within a threshold period of a second medication consumption time, indicating that each of the first and second medications should be consumed at essentially the same time.

Some embodiments further include a consumption indicator for indicating a remote consumption period to the processor during which a medication user intends to consume the medication, the health safety function further including the processor determining consumption requirements during the remote consumption period based on the consumption regimen and indicating the consumption requirements to the user. Even more complex systems include a warning indicator and a timing device linked to the processor wherein, after the processor identifies the consumption regimen, the health safety function further includes the processor tracking the time and causes the warning indicator to indicate each time the medication should be consumed and, when the user indicates a remote consumption period, the processor cancels the consumption indications during the remote consumption period.

In another embodiment the system includes a database accessible by the processor, the database correlating the medication to be stored in the container with a consumption regimen, the specifying information identifying the medication to be stored in the container, the processor identifying the consumption regimen by correlating the medication type to be stored in the container with the corresponding consumption regimen in the database.

Yet another embodiment of the invention includes a medication system for performing at least one health safety function related to a medication, the system including at least one container for holding doses of a medication, the container having a specifying device containing specifying information related to the medication to be held in the container, the specifying information including information that can be used by the processor to determine if the user for whom the medication has been prescribed is allergic to the medication, a sensor defining a sensing area, the sensor for receiving specifying information from the specifying device when the specifying device is within the sensing area and a processor linked to the sensor, wherein, when the specifying device is within the sensing area, the sensor receives the specifying information and provides the specifying information to the processor, the processor using the specifying information to perform at least one health safety function wherein the health safety function includes determining if the user is allergic to the medication.

In this case the system may also include any of the other features indicated above including a warning indicator for various purposes (i.e., indicating allergies), a database storing allergy information for system users and which is accessible via the processor to identify allergies or any other device described above.

In other embodiment the invention includes a medication system for performing at least one health safety function related to a medication, the system including at least one container for holding doses of a medication, the container having a specifying device containing specifying information related to the medication to be held in the container;

a sensor defining a sensing area, the sensor for receiving specifying information from the specifying device when the specifying device is within the sensing area and a processor linked to the sensor, wherein, when the specifying device is within the sensing area, the sensor receives the specifying information and provides the specifying information to the processor, the processor using the specifying information to perform at least one health safety function wherein the health safety function includes storing prescription records for medication users wherein the container and medication to be stored therein are a first container and a first medication prescribed for a first user and the system further includes at least a second container for storing at least a second medication for at least a second user, the second container including a second specifying device, the sensor receiving specifying information from the second specifying device when the second device is positioned within the sensing area, the specifying information indicating at least medication type and medication user, the health safety function including organizing at least a sub-set of the specifying information for each container according to medication user.

In some of these embodiments the specifying information includes information that can be used by the processor to identify a consumption regimen for the user for which the medication was prescribed, the health safety function including identifying the consumption regimen for each container and organizing the consumption regimens according to medication user.

Other embodiments include a warning indicator and a timing device linked to the processor wherein, after the processor identifies a consumption regimen, the processor tracks the time and causes the warning indicator to indicate each time the medication corresponding to the regimen should be consumed and to indicate for which of the first and second user's the medication to be consumed has been prescribed.

Another embodiment includes a medication system for performing at least one health safety function related to a medication, the system including at least one container for holding doses of a medication, the container having a specifying device containing specifying information related to the medication to be held in the container, a sensor defining a sensing area, the sensor for receiving specifying information from the specifying device when the specifying device is within the sensing area and a processor linked to the sensor, wherein, when the specifying device is within the sensing area, the sensor receives the specifying information and provides the specifying information to the processor, the processor using the specifying information to perform at least one health safety function, wherein the health safety function includes determining the prudence of a medication user consuming each of first and second medications, the container and medication to be stored therein including a first container and first medication, the system further including a second container for holding doses of a second medication, the second container having a specifying device containing specifying information related to the second medication, when the second container specifying device is within the sensing area, the sensor receiving specifying information from the device, a data storage device including contraindication information related to a plurality of medications, the contraindication information useable to determine the prudence of a medication user consuming both the first and second medications, wherein the processor retrieves the specifying and contraindication information from the specifying devices and the data storage device, respectively, and uses the specifying and contraindication information to determine the prudence of consuming both the first and second medications.

Some embodiments may include a warning indicator wherein, when the processor determines that the first and second medications should not be consumed by the same user, the processor causes the warning indicator to indicate that the medications should not be consumed together.

In some embodiments the specifying information in the first and second container specifying devices identifies each of the first and second medications, respectively. The specifying information may include information useable by the processor to identify the first and second medication types and to determine the consumption regimens for each of the first and second medications and, wherein the processor may use the consumption regimens, medication types and contraindication information to determine the prudence of taking the medications according to the consumption regimens.

One other embodiment of the invention includes a medication system for performing at least one health safety function related to a medication, the system comprising at least one container for holding doses of a medication, the container having a specifying device containing specifying information related to the medication to be held in the container, a sensor defining a sensing area, the sensor for receiving specifying information from the specifying device when the specifying device is within the sensing area, a processor linked to the sensor, a database accessible to the processor wherein the database includes at least one message related to the specifying information, the interface for providing messages to a system user and a user interface linked to the processor wherein, when the specifying device is within the sensing area, the sensor receives the specifying information and provides the specifying information to the processor, the processor using the specifying information to perform at least one health safety function, the health safety function including accessing the database and retrieving the at least one message related to the specifying information and presenting the message to the user via the interface. Here the database may be accessible to the processor via a computer network. In the alternative the database may be stored on the specifying device.

In some cases the message includes a questionnaire including at least one question and the health safety function further includes, after the at least one question has been presented, facilitating entry of an answer via the interface and, when an answer is entered, storing the answer.

In some cases the specifying information also includes information from which the processor can identify a medication consumption regimen, the health safety function further including the processor determining the consumption regimen and, in response to at least a subset of user answers to questionnaires, modifying the consumption regimen.

In several embodiments the system further includes a warning indicator and a timing device linked to the processor wherein, after the processor identifies the consumption regimen, the processor tracks the time and causes the warning indicator to indicate each time the medication should be consumed.

In one embodiment the invention includes a medication system for performing at least one health safety function related to a medication, the system comprising at least one container for holding doses of a medication, the container having a specifying device containing specifying information related to the medication to be held in the container, a sensor defining a sensing area, the sensor for receiving specifying information from the specifying device when the specifying device is within the sensing area, a processor linked to the sensor, a timing device linked to the processor, a database accessible to the processor and a consumption indicator linked to the processor, the indicator activatable to indicate that the user is consuming a dose of medication from the container, wherein, when the specifying device is within the sensing area, the sensor receives the specifying information and provides the specifying information to the processor, the processor using the specifying information to perform at least one health safety function, the health safety function including the processor, when the consumption indicator is activated, identifying the activation time and storing the activation time as user consumption record in the database.

The health safety function may further include the processor presenting the user consumption record to the user for review.

Another embodiment includes a medication system for performing at least one health safety function related to a medication, the system including at least one container for holding doses of a medication, the container having a specifying device containing specifying information related to the medication to be held in the container, a sensor defining a sensing area, the sensor for receiving specifying information from the specifying device when the specifying device is within the sensing area and a processor linked to the sensor, wherein, when the specifying device is within the sensing area, the sensor receives the specifying information and provides the specifying information to the processor, the processor using the specifying information to perform at least one health safety function, wherein the container and medication to be stored therein are a first container and a first medication and the system further includes at least a second container for holding doses of a second medication, the second container having a second specifying device containing specifying information related to the second medication, when the second specifying device is positioned within the sensing area the processor receiving the corresponding specifying information and identifying the consumption regimen for the second medication, the health safety function including identifying relative consumption times for each of the first and second medications as a function of both the first and second container specifying information.

The system may further include a warning indicator and a timing device linked to the processor wherein, after the processor identifies the consumption regimens, the processor tracks the time and causes the warning indicator to indicate each time either of the first or second medications should be consumed.

Yet a further embodiment includes a medication system for performing at least one health safety function related to a medication, the system comprising at least one container for holding doses of a medication, the container having a specifying device containing specifying information related to the medication to be held in the container, the specifying information including information related to the number of separate medication doses to be included in the container, a sensor defining a sensing area, the sensor for receiving specifying information from the specifying device when the specifying device is within the sensing area, a processor linked to the sensor and a consumption indicator linked to the processor wherein, the consumption indicator is activatable to indicate that the user is consuming a dose of medication from the container wherein, when the specifying device is within the sensing area, the sensor receives the specifying information and provides the specifying information to the processor, the processor using the specifying information to perform at least one health safety function, the health safety function including the processor determining, based on the number of medication doses and the number of consumption indicator activations, when a medication refill should be ordered.

Here the system may include a warning indicator linked to the processor, the health safety function further including causing the warning indicator to indicate when a medication refill should be ordered. In the alternative or in addition the processor may be linked to a medication reorder server via a computer network, the health safety function further including the processor transmitting a refill order to the server when the refill should be ordered.

In addition to the systems described above the invention also includes a plurality of methods that can be used by the systems. To this end, the invention also includes a method for performing at least one health safety function, the method for use with a system including at least one container for holding doses of medication, the container having a specifying device containing specifying information useable to determine a prescribed dosing regimen for the medication, the method comprising the steps of providing a sensor defining a sensing area that is large enough to receive at least two separate specifying devices at one time, the sensor for receiving the specifying information from the specifying devices when the specifying devices are within the sensing area, the sensor linkable to the processor, positioning at least one specifying device within the sensing area, receiving the specifying information, using the specifying information to identify prescribed dosing regimen information; and performing at least one health safety function as a function of the prescribed dosing regimen information.

Here, the health safety function may include indicating when to consume each medication for which a specifying device is within the sensing area, the method further including the steps of providing a communication device that is linkable to the processor, receiving the specifying information for each specifying device in the sensing area, using the specifying information to identify a predetermined time to take each of the medications, determining when the predetermined time occurs for each of the medications, and causing the communication device to indicate the medications to be consumed at the predetermined times.

The step of providing a sensor may include providing a sensor that defines at least two separate sensing areas for receiving specifying information from separate containers, the step of providing a communication device may include providing a separate visual warning indicator adjacent each of the sensing areas and, wherein, the step of indicating may include causing the communication device corresponding to a specific medication to indicate by activating the visual warning indicator adjacent medication to be consumed.

The specifying information in some embodiments includes a serial number and the processor is linkable to a memory device that correlates serial numbers with prescribed dosing regimens and wherein the step of identifying includes identifying the dosing regimen by correlating the serial number and the regimen.

The health safety function in several embodiments includes recording consumption times, the method further for use with a readable and writable memory device and a consumption indicator that are linkable to the processor, the consumption indicator operable to obtain consumption time information which the processor records in the memory device, the method further including the step of monitoring the indicator to identify consumption time.

The method may also be for use in recording consumption times. In these cases, in some embodiments, the system further includes a readable and writable memory device and a consumption indicator that are linkable to the processor, the consumption indicator operable to obtain consumption time information which the processor records in the memory device, the method further including the step of monitoring the indicator to identify consumption time. The health safety function may include determining when determining when a medication is consumed too early.

Yet another method is for recording medication consumption times, the method to be used with a system including at least one container for holding doses of medication, the container having a specifying device containing specifying information useable to determine the type of medication in the container, a readable and writable memory device, an indication device, a sensor defining a sensing area, the sensor for receiving the specifying information when the specifying device is within the sensing area and a processor in communication with a timing device and also linkable to the consumption indicator, the memory device and the sensor, the method comprising the steps of:

positioning the memory device within the sensing area, the processor: receiving the specifying information, using the specifying information to identify the medication type, monitoring the indicator for operation, when the consumption indicator is operated, determining the consumption time and storing the consumption time and medication type in the memory device. Here, the specifying information may include a serial number and the processor may be linkable to a memory device that correlates serial numbers with medication types and the step of identifying medication type may include the step of correlating the serial number and the medication type.

In some embodiments the at least one container includes several containers, each container includes a specifying device, the sensing area can receive more than one specifying device at a time and, wherein, when more than one specifying device is within the sensing area, the step of receiving includes receiving the specifying information from each of the specifying devices.

One other inventive method is for indicating times when medication should be consumed, the method to be used with at least one container for holding doses of medication, the container having a specifying device containing specifying information useable to determine a prescribed dosing regimen for the medication, a communication device, a sensor defining a sensing area, the sensor for receiving the specifying information when the specifying device is within the sensing area and a processor in communication with a timing device and also linkable to the communication device and the sensor, the method comprising the steps of the processor: receiving the specifying information, using the specifying information to identify prescribed dosing regimen information and a predetermined time to take the medication, determining when the predetermined time occurs and causing the communication device to indicate when the predetermined time occurs.

Another method is for performing at least one health safety function related to a medication, the method for use with a system including at least one container for holding doses of a medication, the container having a specifying device containing specifying information related to the medication to be held in the container, the specifying information includes information that can be used by the processor to identify a consumption regimen for the user for which the medication was prescribed, a sensor defining a sensing area, the sensor for receiving specifying information from the specifying device when the specifying device is within the sensing area, a processor linked to the sensor, a timing device linked to the processor wherein and a consumption indicator linked to the processor, the consumption indicator activatable to indicate that the user is consuming a dose of medication from the container, the method comprising the steps of positioning the specifying device is within the sensing area, the processor: receiving the specifying information, using the specifying information to identify the consumption regimen;

Monitoring the consumption indicator to identify activation and upon activation determining if the activation time occurs at a consumption regimen time. This method may further be used with a warning indicator and the method may further cause the warning indicator to indicate an occurrence related to the health safety function. In the alternative the method may further include, upon determining that the activation time is inconsistent with a consumption regimen time, causing the warning indicator to indicate the inconsistency. As another alternative the method may, upon determining that the activation time is inconsistent with a consumption regimen time, store the inconsistency in a database. In yet another alternative the method may further includes causing the warning indicator to indicate when consumption times occur and, when the activation time is prior to a next consumption time, modifying the next consumption time. The modifying step may include skipping the next consumption time.

Some systems may include a warning indicator and a timing device linked to the processor and the method may further include, after the step of identifying the consumption regimen, tracking the time and causing the warning indicator to indicate each time the medication should be consumed.

The system may further include a consumption indicator for indicating a remote consumption period to the processor during which a medication user intends to consume the medication, the health safety function further including determining consumption requirements during the remote consumption period based on the consumption regimen and indicating the consumption requirements to the user. Here, the system may further include a warning indicator and a timing device linked to the processor wherein, after the processor identifies the consumption regimen, the method further includes tracking the time and causes the warning indicator to indicate each time the medication should be consumed and, when the user indicates a remote consumption period, canceling the consumption indications during the remote consumption period.

The system may further include a database accessible by the processor, the database correlating the medication to be stored in the container with a consumption regimen, the specifying information identifying the medication to be stored in the container, the step of identifying the consumption regimen including correlating the medication type to be stored in the container with the corresponding consumption regimen in the database.

Another method is for performing at least one health safety function related to a medication, the method for use with a system including at least one container for holding doses of a medication, the container having a specifying device containing specifying information related to the medication to be held in the container, the specifying information including information that can be used by the processor to determine if the user for whom the medication has been prescribed is allergic to the medication, a sensor defining a sensing area, the sensor for receiving specifying information from the specifying device when the specifying device is within the sensing area and a processor linked to the sensor, the method comprising the steps of positioning the specifying device within the sensing area and the processor: receiving the specifying information, using the specifying information to perform at least one health safety function wherein the health safety function includes determining if the user is allergic to the medication.

The system may further include a warning indicator and the method may further include the step of, if the processor determines that the user is allergic to the medication, causing the warning indicator to indicate that the user is allergic to the medication.

The system may further include a database accessible by the processor, the database including allergy information related to the medication user's allergies, the specifying information including at least medication type, the step of determining if the user is allergic including comparing the medication type to the allergy information.

Yet another method is for performing at least one health safety function related to a medication, the method for use with a system including at least one container for holding doses of a medication, the container having a specifying device containing specifying information related to the medication to be held in the container, a sensor defining a sensing area, the sensor for receiving specifying information from the specifying device when the specifying device is within the sensing area and a processor linked to the sensor, wherein the container and medication to be stored therein are a first container and a first medication prescribed for a first user and the method further includes at least a second container for storing at least a second medication for at least a second user, the second container including a second specifying device, the sensor receiving specifying information from the second specifying device when the second device is positioned within the sensing area, the specifying information indicating at least medication type and medication user, the method comprising the steps of positioning the specifying device within the sensing area, the processor: receiving the specifying information and organizing at least a sub-set of the specifying information for each container according to medication user.

In one embodiment the specifying information includes information that can be used by the processor to identify a consumption regimen for the user for which the medication was prescribed, the step of organizing including identifying the consumption regimen for each container and organizing the consumption regimens according to medication user.

In another embodiment the system further includes a warning indicator and a timing device linked to the processor wherein, after the step of identifying a consumption regimen, the method further includes the steps of tracking the time and causes the warning indicator to indicate each time the medication corresponding to the regimen should be consumed and to indicate for which of the first and second user's the medication to be consumed has been prescribed.

Another method is for performing at least one health safety function related to a medication, the method to be used with a system including at least one container for holding doses of a medication, the container having a specifying device containing specifying information related to the medication to be held in the container, a sensor defining a sensing area, the sensor for receiving specifying information from the specifying device when the specifying device is within the sensing area, a processor linked to the sensor, a second container for holding doses of a second medication, the second container having a specifying device containing specifying information related to the second medication, when the second container specifying device is within the sensing area, the sensor receiving specifying information from the device, and a data storage device including contraindication information related to a plurality of medications, the contraindication information useable to determine the prudence of a medication user consuming both the first and second medications, the method comprising the steps of:

Positioning each the specifying devices within the sensing area and the processor: receiving the specifying information from each of the devices, retrieving the contraindication information from the storage device and using the specifying information and the contraindication information to determine the prudence of a medication user consuming each of first and second medications.

In another embodiment the system further includes a warning indicator, the method further including, when it is determined that the first and second medications should not be consumed by the same user, the causing the warning indicator to indicate that the medications should not be consumed together. In other embodiments the specifying information includes information useable by the processor to identify the first and second medication types and to determine the consumption regimens for each of the first and second medications and, wherein the step of using further includes using the consumption regimens, medication types and contraindication information to determine the prudence of taking the medications according to the consumption regimens.

One other method is for performing at least one health safety function related to a medication, the method for use with a system including at least one container for holding doses of a medication, the container having a specifying device containing specifying information related to the medication to be held in the container, a sensor defining a sensing area, the sensor for receiving specifying information from the specifying device when the specifying device is within the sensing area, a processor linked to the sensor, a database accessible to the processor wherein the database includes at least one message related to the specifying information, the interface for providing messages to a method user and a user interface linked to the processor, the method comprising the steps of providing the specifying device within the sensing area, the processor: receiving the specifying information, using the specifying information to access the database and retrieve the at least one message related to the specifying information and presenting the message to the user via the interface.

In some embodiments the message includes a questionnaire including at least one question and the method further includes, after the at least one question has been presented, facilitating entry of an answer via the interface and, when an answer is entered, storing the answer.

According to another method for performing at least one health safety function related to a medication, the method for use with a system including at least one container for holding doses of a medication, the container having a specifying device containing specifying information related to the medication to be held in the container, a sensor defining a sensing area, the sensor for receiving specifying information from the specifying device when the specifying device is within the sensing area, a processor linked to the sensor, a timing device linked to the processor, a database accessible to the processor and a consumption indicator linked to the processor, the indicator activatable to indicate that the user is consuming a dose of medication from the container, the method comprising the steps of providing the specifying device within the sensing area and the processor: receiving the specifying information, monitoring indicator activation and when the consumption indicator is activated, identifying the activation time and the medication and storing the activation time and medication type as a user consumption record in the database.

Another method is for performing at least one health safety function related to a medication, the method for use with a system including at least one container for holding doses of a medication, the container having a specifying device containing specifying information related to the medication to be held in the container, a sensor defining a sensing area, the sensor for receiving specifying information from the specifying device when the specifying device is within the sensing area and a processor linked to the sensor, wherein the container and medication to be stored therein are a first container and a first medication and the method further includes at least a second container for holding doses of a second medication, the second container having a second specifying device containing specifying information related to the second medication, when the second specifying device is positioned within the sensing area the processor receiving the corresponding specifying information and identifying the consumption regimen for the second medication, the method including the steps of providing each of the specifying devices within the sensing area and the processor: receiving the specifying information from each of the devices, using the specifying information to identify relative consumption times for each of the first and second medications as a function of both the first and second container specifying information.

One other method is for performing at least one health safety function related to a medication, the method for use with a system including at least one container for holding doses of a medication, the container having a specifying device containing specifying information related to the medication to be held in the container, the specifying information including information related to the number of separate medication doses to be included in the container, a sensor defining a sensing area, the sensor for receiving specifying information from the specifying device when the specifying device is within the sensing area, a processor linked to the sensor and a consumption indicator linked to the processor wherein, the consumption indicator is activatable to indicate that the user is consuming a dose of medication from the container, the method comprising the steps of providing each of the specifying devices within the sensing area and the processor: receiving the specifying information from each of the devices, using the specifying information to perform at least one health safety function, the health safety function including the processor determining, based on the number of medication doses and the number of consumption indicator activations, when a medication refill should be ordered. Here the system may further include a warning indicator linked to the processor, the method further including causing the warning indicator to indicate when a medication refill should be ordered. Also the processor may be linked to a medication reorder server via a computer network, the method further including the processor transmitting a refill order to the server when the refill should be ordered.

Yet one other method is for performing at least one health safety function, the system comprising at least one container for holding doses of medication, the container having a specifying device containing specifying information useable to identify information related to the medication, a sensor defining a sensing area, the sensor for receiving the specifying information when the specifying device is within the sensing area and a processor linked to a memory device, wherein the processor receives and uses the specifying information to identify information related to the medication and the processor performs at least one health safety function as a function of the information related to the container, the health safety function being one of identifying allergies, comparing the medication information to other information to identify contraindication conditions, tracking medication consumption, after an indication is received that a medication is going to be consumed, determining if the consumption time is consistent with a regimen for the medication, scheduling medication consumption as a function of the medication information and other information stored in the memory device, determining when to reorder medication, reordering medication, modifying medication consumption regimen, creating a record of medication consumption and providing other information from the memory device that is related to the specifying information.

Another inventive method is for indicating times when medication should be consumed, the method to be used with at least one container for holding doses of medication, the container having a specifying device containing specifying information useable to determine a prescribed dosing regimen for the medication, a communication device, a sensor defining a sensing area, the sensor for receiving the specifying information when the specifying device is within the sensing area and a processor in communication with a timing device and also linkable to the communication device and the sensor, the method comprising the steps of at a first time, positioning the specifying device within the sensing area, receiving the specifying information from the specifying device in the sensing area, using the specifying information to identify a predetermined time to take the medication, determining when the predetermined time occurs at a second time subsequent to the first time, indicating via the communication device that the medication container including the medication to be consumed at the predetermined time should be positioned such that the sensor is within the sensing area, retrieving a container, positioning the retrieved container such that the specifying device on the retrieved container is within the sensing area, receiving at least a sub-set of information from the specifying device on the retrieved container that is useable to identify the container, comparing the sub-set of information to the specifying information received at the first time to determine if the retrieved container is the container storing the medication to be consumed at the predetermined time and indicating via the communication device whether or not a dose of medication from the retrieved container should be consumed.

Here the communication device in some embodiments includes a visual device and the step of indicating includes modifying the information communicated via the display. The communication device may include a light and wherein the step of indicating that a container including the medication should be positioned such that the specifying device is within the sensing area includes illuminating the light. The step of indicating whether or not a dose of medication should be consumed may include the step of modifying the illumination of the light.

One more method includes modifying consumption times of medications, the method for use with a processor linkable to a memory device where consumption regimens corresponding to at least first and second medications to be consumed by a patient are stored in the memory device, the method comprising the steps of identifying the first and second medication consumption times and when the first medication consumption time is within a threshold period of the second medication consumption time, indicating that each of the first and second medications should be consumed at essentially the same time.

Another embodiment includes a method for providing a medication regimen to a remote device for remote support of at least one health safety function, the method for use with a processor linkable to a memory device, the memory device including regimen information for at least one medication to be consumed by a patient, the method also for use with a remote device for indicating medication consumption times, the processor capable of providing information to the remote device, the method comprising the steps of indicating to the processor a remote consumption period during which medications are to be consumed remotely, identifying the medications regimens for the patient that require medication consumption during the remote consumption period, placing the remote device proximate the processor so that the processor can provide information to the remote device, providing the portions of the medication regimens that correspond to the remote consumption period to the remote device, storing the medication regimens on the remote device and indicating, via the remote device, the times prescribed by the stored medication regimen during the remote use.

Other advantages and aspects of the invention will become apparent upon review of the specification, claims and drawings.

BRIEF DESCRIPTION OF THE DRAWINGS

FIG. 14 is a front perspective view showing a sensing device used to convey information in the memory strip of the medication container to a separate computer;

FIG. 15 is a rear perspective view of the sensing device showing the sensors that engage the electrical contacts of the memory strip;

FIG. 16 is a perspective view of a third embodiment of the present medication container invention including a container in the form of a cylindrical vial with an interactive label having a number of conductive or reflective surfaces, and an automated cap that seals the open end of the vial;

FIG. 17 is an elevation view of the automated cap for the third embodiment of the invention showing a plurality of sensors on the inside of the cap that sense the conductive or reflective surfaces of the interactive label;

DETAILED DESCRIPTION

Figure 1:
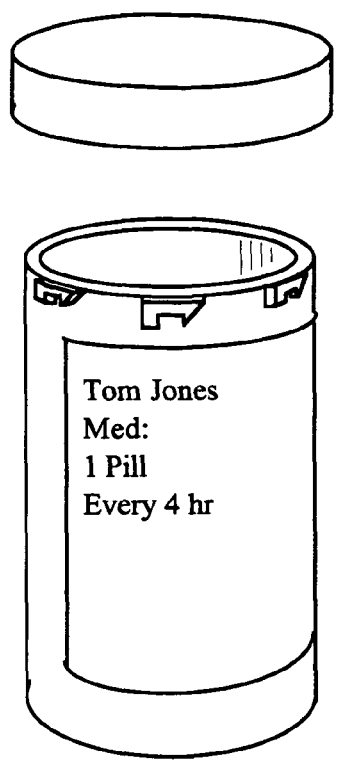
FIG. 1 is a perspective view of a conventional, childproof, medication container consisting of a cylindrical vial and a removable cap.

The present invention relates to an interactive medication container. While the invention is susceptible of embodiments in many different forms, there are shown in the drawings and will herein be described, several forms of the invention with the understanding that the present disclosure is to be considered as an exemplification of the principles of the invention, and is not intended to limit the broad aspects of the invention to the several embodiments illustrated.

First Embodiment

Figure 2:
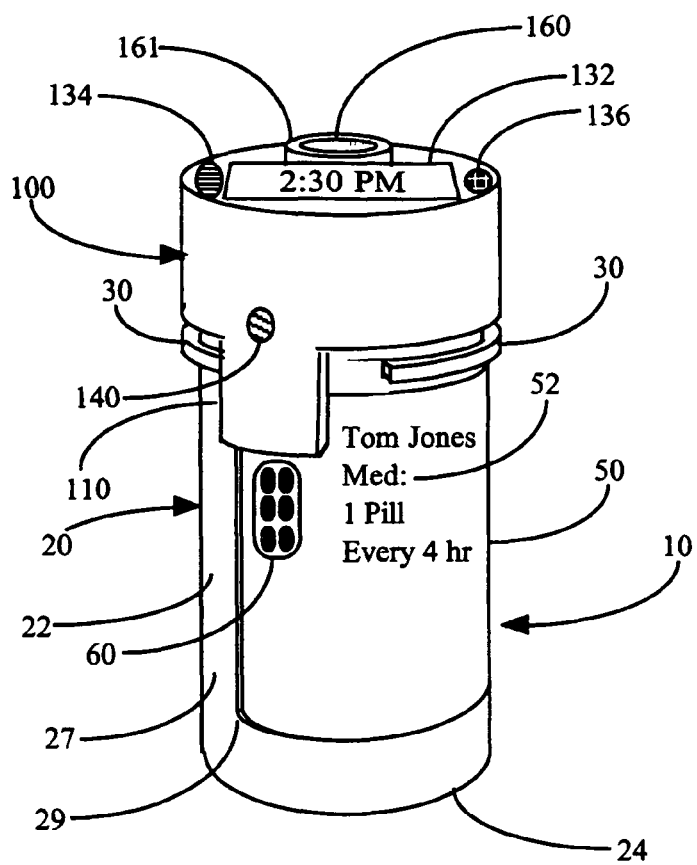
FIG. 2 is a perspective view of a first embodiment of the present medication container invention including a container in the form of a cylindrical vial with an interactive label having an electronic memory strip, and an automated cap that seals the open end of the vial.
Figure 3:
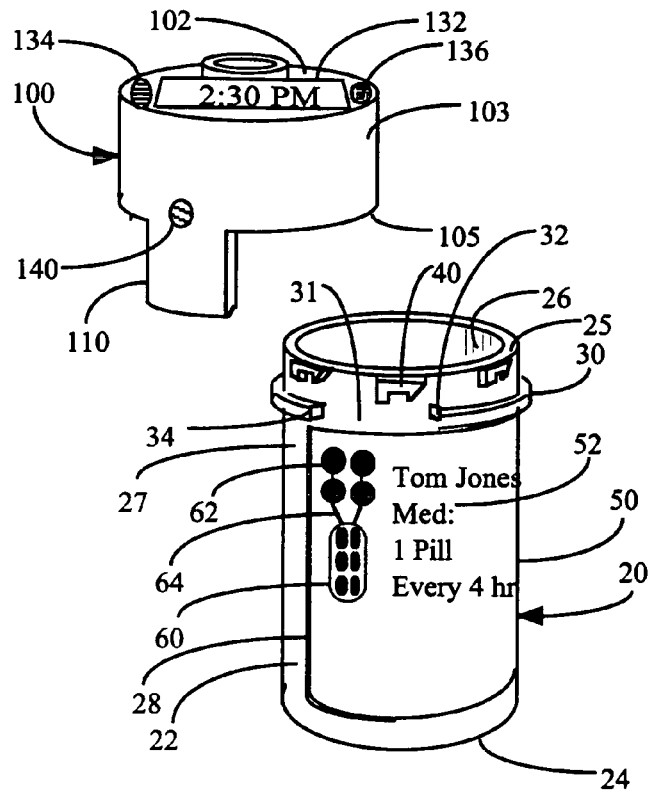
FIG. 3 is a perspective view of the first embodiment of the invention showing the automated cap removed from the vial to reveal the electrical contacts of the memory strip.
Figure 4:
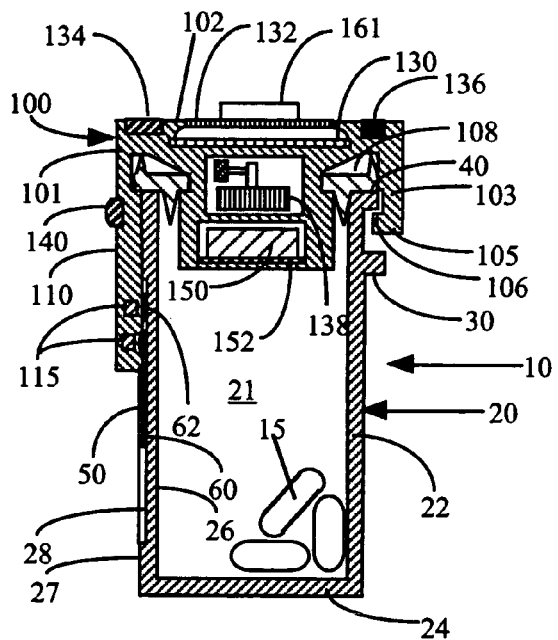
FIG. 4 is a cross sectional, side plan view of the first embodiment of the invention showing the electronic memory strip and its electrical contacts on the wall of the vial, and an automated cap with a resilient sealing disc, battery, audio, illuminating and vibrational alarms.

FIGS. 2-11 show a first embodiment of the invention where the container 10 includes a vial 20 with an interactive label or specifying device 50 (for storing specifying information useable to determine a prescribed dosing regimen or to support some other health safety function as described in more detail below) and an automated cap 100 with a sensing tab 110 for reading the electronically stored information 80 on the label and a computer processor 120 for controlling a visual display and a variety of alarms. As best shown in FIGS. 2-4, the vial 20 includes a compartment 21 defined by a cylindrical wall 22, a closed bottom end 24 and an open top end 25. Medication 15 is inserted into and removed from the compartment 21 via the open end 25 of the vial 20. The cylinder has an inner surface 26 and an outer surface 27. The vial 20 is made of a unitary piece of relatively rigid plastic similar to other conventional vial-type medication containers.

The vial 20 includes a first means for aligning the interactive label 50 with a predetermined location of the wall 22. This alignment means is accomplished by forming a recess 28 in the outer surface 27 of the wall 22. The recess 28 is defined by an inwardly projecting ridge 29 that extends around the perimeter of the recess. While this first alignment means is shown as recess 28, it should be understood that it could take on a variety of forms. For example, an outwardly projecting ridge (not shown) protruding from the wall 22 of the vial 20 or a raised substantially flat platform (not shown) protruding from the wall could be used. It should also be understood that the label 50 could be located on the inside surface 26 of the vial 20 without departing from the broad aspects of the invention.

The vial 20 includes a second means for aligning the automated cap 100 with the vial 20 so that the sensing tab 110 of the cap is properly aligned with the interactive label 50 as discussed below. The second alignment means is accomplished by a guide ring 30 protruding from the outer surface 27 of the vial 20. The guide ring 30 is located at a substantially uniform, predetermined distance from the open end 25 of the vial. The guide ring surrounds most of the wall 22 of the vial. The guide ring has an opening 31 defined by its two ends 32 and 34. The ends 32 and 34 of the guide ring 30 are spaced apart a predetermined distance so that opening 31 has a predetermined size for accommodating sensing tab 110 as discussed below. While the second alignment means is shown and described as being guide ring 30, it should be understood that the second alignment means could take on other forms without departing from the broad aspects of the invention.

The vial 20 has several securement ratchets 40 for securing and sealing the cap 100 against the open end 25 of the vial. The ratchets 40 are evenly spaced around the open end 25, and protrude from the outer surface 27 of the vial 20. The ratchets are similar to those found on conventional childproof medication containers as in FIG. 1. Each ratchet includes a cup portion 42, a top surface 44, a wedge 45 and a side surface 46. Although the ratchets 40 are shown and described as being evenly spaced from each other as in a conventional vial, it should be understood that one or more of the ratchets could be offset. Such an offset arrangement could be used to accomplish the second alignment means in lieu of guide ring 30.

Figure 5:
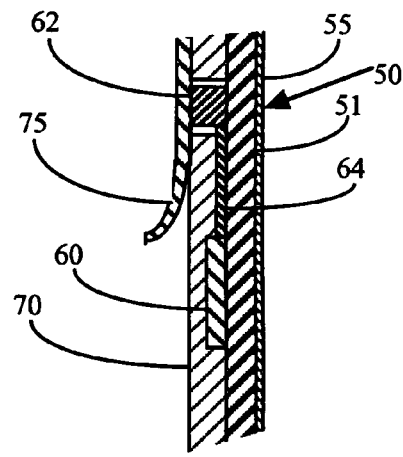
FIG. 5 is an enlarged, cross-sectional, side plan view of the interactive label showing the memory strip, electrical contacts, adhesive coating, protective coating and removable insulating layer.

As best shown in FIGS. 3-5, medication container 10 includes interactive label 50. The label 50 is affixed in the recess 28 in the wall 22 of the vial 20 so that the left edge of the label abuts and is aligned with the ridge 29 forming the left side of the recess. The upper edge of the label 50 abuts the ridge forming the upper side of the recess 28. This alignment positions the label 50 into its desired location on the wall 22 of the vial 20.

The interactive label 50 includes a paper backing 51 sized to fit in recess 28. The front surface of the paper backing 51 has a textual portion 52. The textual portion 52 includes textual information such as the patient's name, the medication name, the dosing regimen (e.g., daily, four times a day, etc.), the number of pills or capsules to consume during each dose, and any special instructions regarding the proper consumption of the medication (e.g., take an hour before meals). The rear surface of the backing paper 51 includes an adhesive coating 55 for affixing the label in the recess 28 of the wall 22 of the vial 20.

The interactive label 50 includes an electronic, machine readable and writable memory strip 60. The memory strip 60 is similar to those used in commercially available smart cards. The memory strip 50 includes contacts 62 that are in electrical communication with the information 80 in the memory strip 60 via links or electrical connections such as wires 64 as discussed below. A protective coating 70 is applied over the memory strip 60. The protective coating 70 has holes aligned over each electrical contact 62. A removable insulating layer 75 is used to prevent premature communication with the memory strip 60 before the patient begins taking the medication 15. Although the memory strip 60 is shown and described as being secured to a paper backing 51, it should be understood that the memory strip 60 could be affixed directly to the inner or outer surface 26 or 27 of the vial 20 or even imbedded in the vial. While the memory device 60 is described and shown as having the shape of a strip, it should be understood that differently shaped memory devices could be used without departing from the invention.

Figure 8:
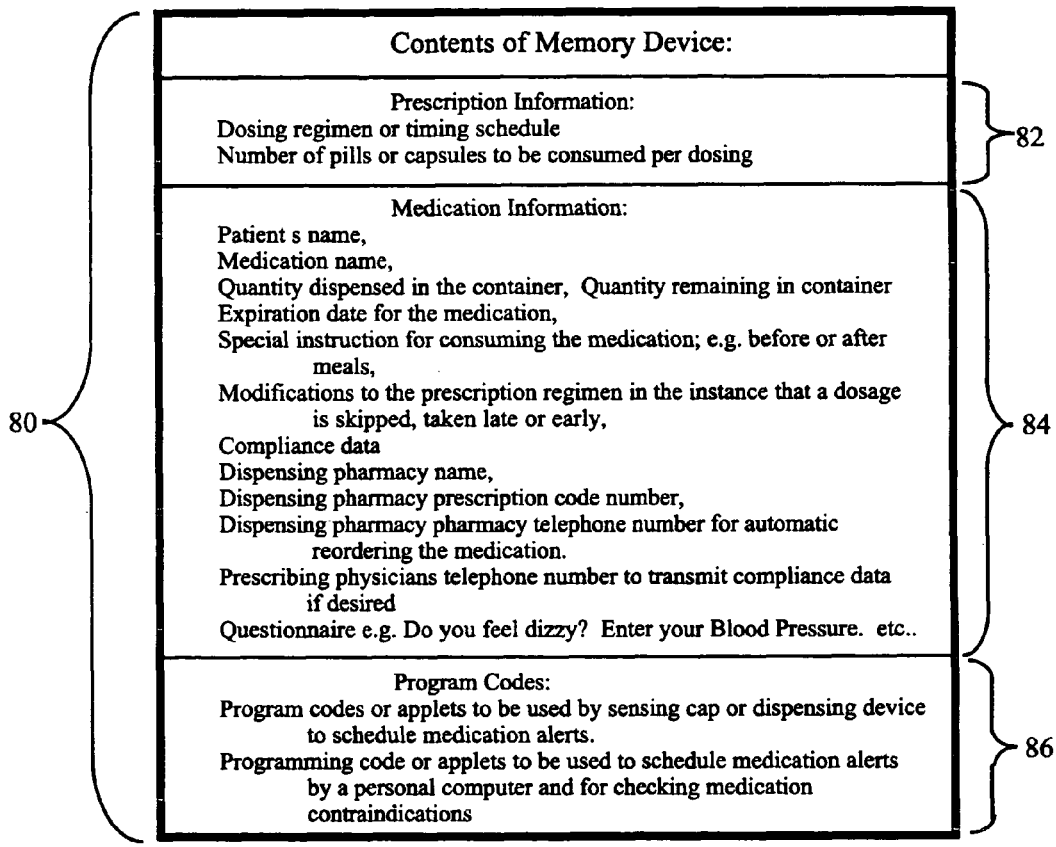
FIG. 8 is a chart listing a variety of prescription information and program codes that can be contained in the memory strip of the interactive label.

As shown in FIG. 8, the memory strip 60 contains a variety of information 80. The contents of the information 80 includes prescription information 82 such as information defining the dosing regimen and the number of pills or capsules to be consumed per dosing. The memory strip 60 also contains medication information 84 and program codes 86 for downloading into or otherwise being sensed or read by the computer processor 120 of the automated cap 100. The electrical contacts 62 and wires 64 communicate with the memory strip 60 so as to access the information 80 in or write additional information to the memory strip. As discussed below, the memory strip 60 can be electronically altered or written to via the processor 120 to store information designating when the cap 100 is removed and reattached to the vial 20, such as removal information 84 indicating that a dose of medication 15 was removed from the vial, quantity information 84 regarding the original or remaining number of doses in the container, or removal time, disruption or compliance information 84 indicating actual compliance to the prescribed dosing regimen 82. It should be understood that any combination of predetermined information taken from the contents 80 of the memory strip 60 could be communicated to the computer processor 120. The computer processor 120 could use the predetermined information to select or develop desired information for communicating to the patient or care giver.

Figure 7:
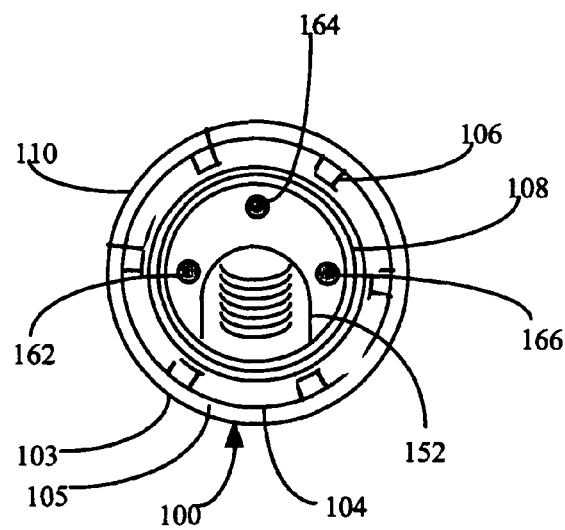
FIG. 7 is a plan view showing the underside of the automated cap used in the first vial-type embodiment of the invention.

As best shown in FIGS. 4, 5 and 7, the cap 100 includes a main body 101 with a top portion 102 and a cylindrical rim 103 having an inside surface 104 and a lower edge 105. The cap 100 includes several hold down lugs 106 and a resilient disc much like those in conventional caps of the type shown in FIG. 1. The hold down lugs 106 are located around the inside surface 104 of the rim 103 near its lower edge 105. The number of hold down lugs 106 coincides with the number of ratchets 40, and the lugs are evenly spaced to align with the ratchets. The resilient disc 108 is attached to the inside surface of the cap 100.

The ratchets 40 interact with the hold down lugs 106 to form a relatively tight, child resistant or childproof seal between the cap 100 and the vial 20. This is accomplished by placing the cap 100 over the open end 25 of the vial 20 so the lugs 106 are aligned directly between the securement ratchets 40. (See FIG. 10). The cap seals the open end 25 of the vial 20 when in this removably aligned position, but the cap is not secured to the vial. The cap 100 is then depressed and rotated clockwise so that each lug slides up the wedge 45 of its corresponding ratchet located to its left, and into a secure position where each lug rests inside the cup 42 of its corresponding ratchet 40. (See FIG. 11). When in this secured position, the resilient disc 108 biases the lugs to remain inside the cups 42 of their corresponding ratchets 40 due to a spring-like force exerted by the resilient disc 108 against the open end 25 of the vial 20. The hold down lugs 106 and ratchets 40 prevent the simple counterclockwise rotation of the cap, and thus its removal. Instead, the cap 100 must be pushed down to compress the flexible membrane 108, releasing the contact between the lugs 106 and the ratchets 40, before the cap can be rotated counterclockwise.

Figure 6:
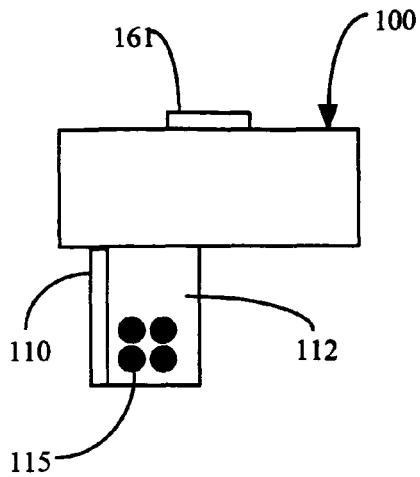
FIG. 6 is an elevation view of the automated cap showing the sensors that engage the electrical contacts of the memory strip.

The automated cap 100 includes a sensing device or sensing tab 110 for sensing the contacts 62 of the memory strip 60. The sensing tab 110 projects down from the edge 105 of the rim 103 of the cap 100. As shown in FIG. 6, the sensing tab 110 has an inside surface 112 with sensors 115. The sensors 115 are positioned to align with the contacts 62 of the memory strip 60 when the cap 100 is in the secured position on the open end 25 of the vial 20. The sensors 115 electrically engage the contacts 62. Predetermined information 80 in the memory strip 60 is electronically transmitted to or otherwise communicated or read by the computer processor 120 via the contacts 62, links 64, sensors 115 and, as discussed below, a circuit board 130.

The sensing tab 110 extends through the opening 31 in the guide ring 30. The opening 31 is sized so that the cap 100 can only be attached to the vial 20 in the one position which aligns the sensors 115 of the sensing tab 110 into electrical engagement with the contacts 62 of the memory strip 60. Specifically, the cap 100 can only be placed on the open end 25 of the vial 20 with the sensing tab 110 abutting or nearly abutting the right end 32 of the guide ring 30. The cap 100 is then rotated in a clockwise direction until the sensing tab 110 abuts or nearly abuts the left end 34 of the guide ring 30 and the hold down lugs 106 have come to rest in the cups 42 of the securement ratchets 40 so that the cap 100 is in its secured position on the vial 20.

Figure 9:
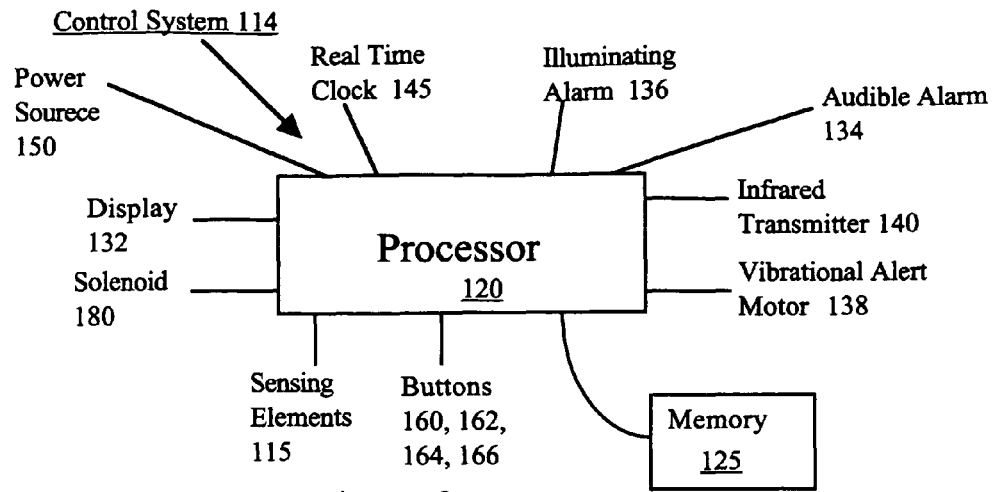
FIG. 9 is a schematic diagram showing the circuitry in the automated cap.

As shown in FIG. 9, the automated cap 100 has a control system 114 that includes a computer processor 120 with its own memory 125. The processor 120 and memory 125 are located on and in electrical communication with a circuit board 130 located inside the cap 100 for protection. (See FIG. 4). The circuit board 130 electrically connects the processor 120 to a visual communication device such as an LCD display 132. The LCD display 132 visually displays desired information to the patient, such as the date and time the next dose of medication is to be taken and the number of pills to be taken. The display 132 can also indicate an access alert or warning to the patient, such as the fact that the patient is so overdue in taking a dose of medication that that dose should no longer be taken. The circuit board 130 also electrically connects the processor 120 to a variety of alarming devices or warning indicators such as audible, visual and vibrational communication devices or alarms 134, 136 and 138, respectively. These alarms 134, 136 and 138 indicate a variety of warnings to a patient, such as when it is time to take a dose of medication. The circuit board 130 also electrically connects the processor 120 to a communication device such as an infrared transmitter 140 that transmits information to or receives information from a separate personal or business computer 270 as discussed below.

As shown in FIGS. 4 and 9, the circuit board 130 is in electrical communication with a battery 150 that powers the processor 120, the display 132, alarms 134, 136, and 138, transmitter 140 and a timing device such as a real time clock 145. An access panel 152 is provided to allow periodic replacement of the battery 150. The access panel 152 is prevented from accidental opening by friction between it and cap 100. In addition, when the cap 100 is secured to the vial 20, the battery access panel 152 cannot slide out due to interference between the wall 22 of the vial 20 and the access panel. Accordingly, the battery 150 should not fall into the medication 15 and accidentally consumed.

The circuit board 130 is in electrical communication with a button 160 for electro-mechanically communicating information to the processor 120. (See FIG. 2). By pressing button 160, the patient is able to send an electrical signal to the processor 120 in response to a question shown on the display 132 or to indicate an action to be taken, such as turn off an alert or alarm. Button 160 is surrounded by a raised ring 161 to protect it from inadvertent contact as it is located on the outside surface of the cap 100. Additional buttons 162, 164 and 166 (See FIG. 7) are located on the inside surface 104 of the cap 100 to enable the patient to set the correct date, hour and minute of the real time clock 145 that is in electrical communication with the processor 120 via the circuit board 130. The computer processor 120 uses the prescribed dosing regimen information 82 and the timing device 145 to calculate or otherwise develop the prescribed times for taking the medication 15. The timing device 145 informs the computer processor 120 when the predetermined times to take the medication occur. The computer processor then informs the patient or individual that it is time to take a dose of medication 15 via the display 132 or an alarm 134, 136 or 138. The buttons 160, 162, 164 and 166 perform a variety of functions. As discussed below, they can be used as an access indicator to indicate that the patient is accessing the medication inside the container, as a consumption indicator to indicate that the patient is consuming the medication, a removal indicator to indicate that the patient is removing medication form the container, or as an override button to indicate that the patient is removing one or more doses of medication prior to a scheduled time to take the dose of medication. While buttons 162, 164 and 166 are located on the inside surface 104 of the cap 100, it should be understood that the buttons could be located on the outside surface of the cap as well.

Figure 10:
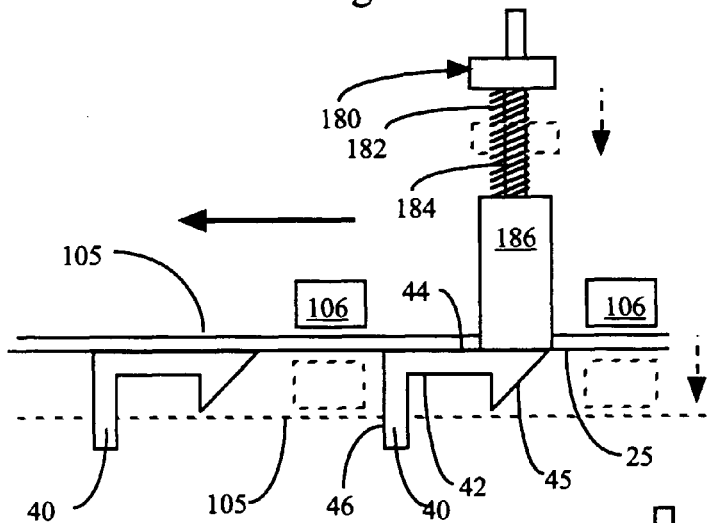
FIG. 10 is an enlarged, diagrammatic view of a portion of the automated cap positioned over the vial, the armature of the locking mechanism of the cap engaging the top of one securement ratchet of the vial, and a pair of hold down lugs of the cap aligned between the securement ratchets of the vial.
Figure 11:
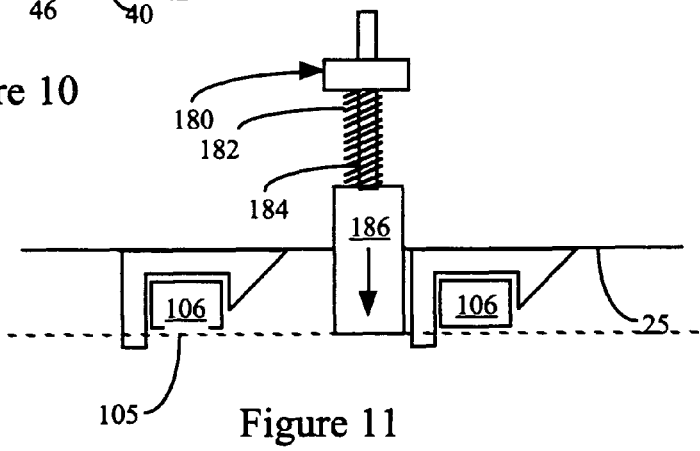
FIG. 11 is an enlarged, diagrammatic view of a portion of the automated cap in a locked position on the vial, the armature of the locking mechanism of the cap received between the securement ratchets of the vial, and the hold down lugs being received in the cup of its respective securement ratchet.
Figure 12:
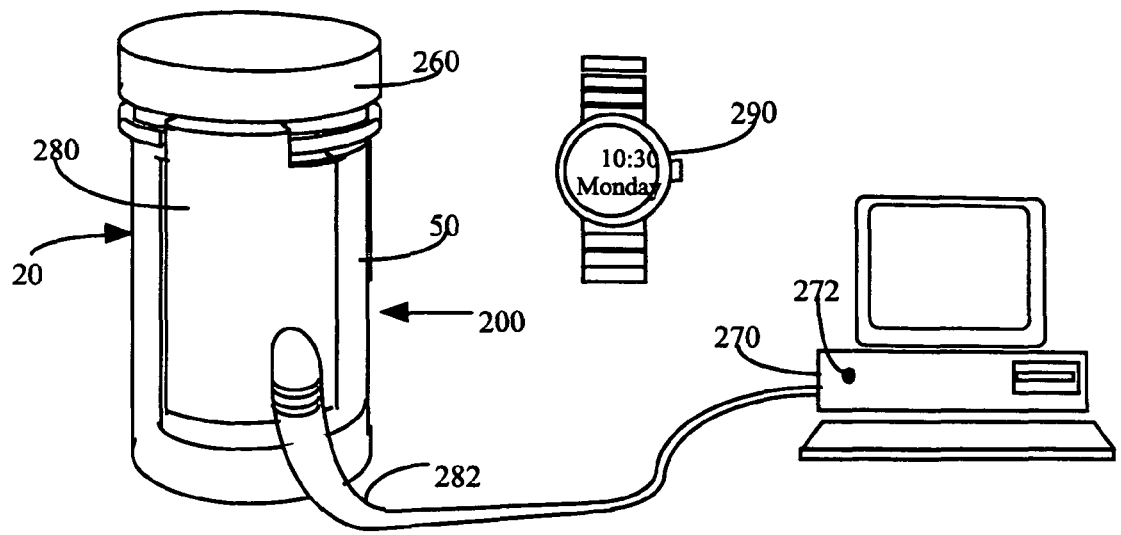
FIG. 12 is a perspective view of a second embodiment of the medication container invention including a conventional, non-automated cap that seals a vial with an interactive label, and a sensing element and cable that conveys information to a separate computer or personal alerting device.
Figure 13:
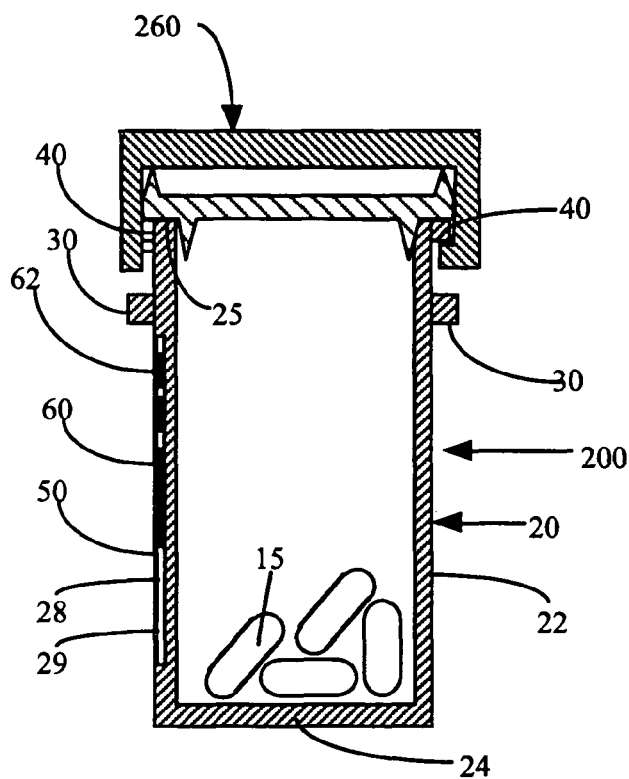
FIG. 13 is a cross-sectional view of a second embodiment of the invention where the medication container includes a cylindrical vial with an interactive label having an electronic memory strip, and a conventional cap.

As shown in FIGS. 9-11, automated cap 100 further includes an access control device formed by the computer processor 120 and a device such as solenoid locking mechanism or assembly 180 that is in electrical communication with the processor via the circuit board 130. The locking assembly 180 controls the patient's ability to access and remove the medication 15 from the vial 20 until the time the next dose of medication is due according to the prescribed dosing regimen. The assembly 180 includes an armature 182 and a spring 184 for biasing a plunger 186 into a normal, extended position as shown in solid lines in FIGS. 10 and 11. As explained above, to seal the vial 20, the cap 100 is first aligned with open end 25 of the vial so that the hold down lugs 106 are positioned above and in between the ratchets 40 of the vial. (See FIG. 10). The cap 100 is then depressed into a removably aligned position over the open end 25 so that the lugs 106 move directly between the ratchets 40. The plunger 186 contacts the upper surface 44 of the ratchet 40 which causes spring 182 to compress. This is shown in FIG. 10 in phantom lines. The cap 100 is then rotated clockwise into its secured position where each hold down lug 106 rests in the cup 42 of its respective ratchet 40. When in this secured position, plunger 186 clears the side 46 of the ratchet 40 so that spring 184 biases the plunger into its normal, extended position. Attempts to remove the cap 100 by rotating it counterclockwise are resisted by plunger 186, which abuts the side 46 of the ratchet 40. The cap 100 is now locked into its secured position. The processor 120 is programmed to activate the solenoid locking assembly 180 to draw up the armature 182 and plunger 186 when the next medication dosage is due to be taken. Only then can the cap 100 be rotated counterclockwise and removed.

The access control device can also take the form of and access indicator. The access indicator is a button such as 160 that is pressed or otherwise triggered prior to opening the container, or a sensor such as 115 that is disrupted or otherwise triggered by an attempt to remove the cap 100 from the vial 20. The sensor 115 is triggered by pressing down on the cap 100 and compressing resilient member 108, or by attempting to rotate the cap out of its locked position. Pressing button 160 or attempting to open the container 10 triggers the access indicator, which communicates this attempted access information to the processor 120. The computer processor then uses the actual time information of the clock 145 corresponding to the actual time the access indicator is triggered and compares it with the next scheduled predetermined time to take a dose of medication. If the actual time information does not correspond to the next scheduled predetermined time to take a dose of medication 15, the processor 120 causes a warning message to be shown on the display 132, or an access alert to be initiated by one of the alarm devices 134, 136 or 138. This warning or access alert informs the patient that the present or actual time is not within a scheduled or predetermined time range to take the medication 15.

Second Embodiment of Circuitry

The control system 114 shown in FIG. 9 has the processor 120 located in the cap 100. This arrangement is based on the advantage of being able to dispose of the vial 20 when the medication 10 is used up, and the information in the memory strip 60 has been transferred to another data base, such as the memory of a patient's home computer or a pharmacy, hospital or prescribing physician computer. The more expensive cap 100 is retained by the patient for further use. However, ongoing manufacturing developments continue to reduce the costs of producing memory devices with their own processors. As a result, the cost of producing the memory strip 60 is not significantly different than the cost of producing the memory strip together with its own processor.

Figure 25:
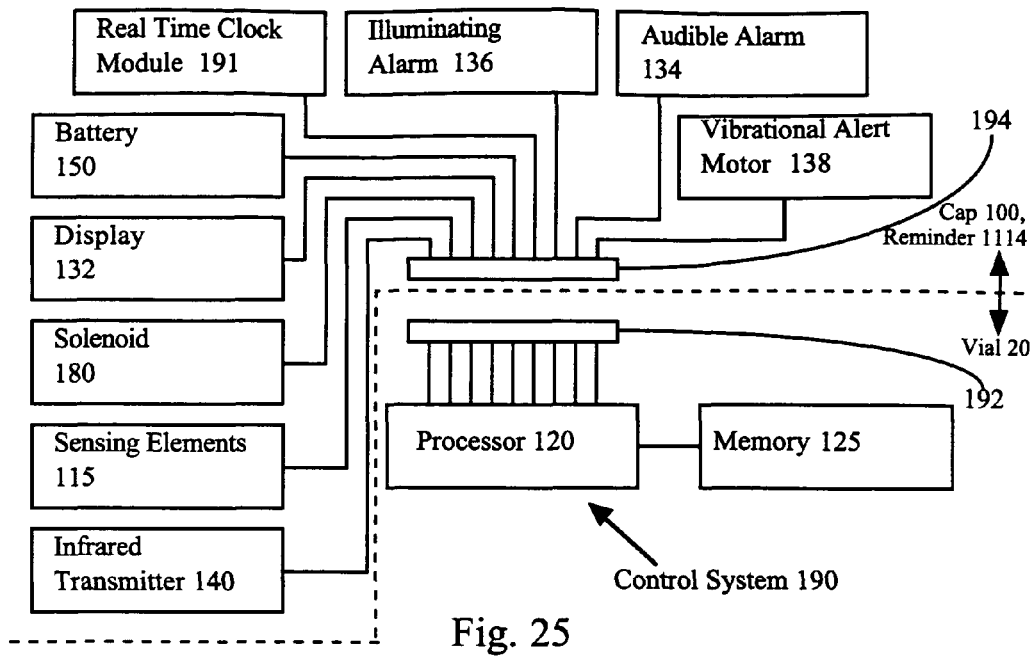
FIG. 25 is a schematic drawing of an alternate circuitry to FIG. 9 where both the computer processor and memory strip are affixed to the vial or blister pack, and the other hardware components are contained in the cap or lid.

FIG. 25 shows an alternate control system 190 where the memory strip 60 has its own processor 120. Both the memory strip 60 and processor are secured to the wall 22 of the vial 20. The memory strip 60 is directly wired to the processor 120 and serves as the memory of the processor. The memory device 125 in the cap 100 is eliminated. This saves the costs associated with producing two separate memory devices, without compromising the disposability of the vial 20. Hardware components such as the circuit board 130, display 132, alarms 134, 136 and 138, transmitter 140, battery 150 and solenoid 180 remain in the reusable cap 100. The real time clock 145 is replaced by a real time clock module 191 that is capable of maintaining time without being connected to the processor 120. The components in the cap 100 are electrically connected to the processor 120 via multiple contacts 192 and 194. Multiple contact 192 is wired to the processor 120 and replaces contacts 62. Multiple contact 194 is wired to the circuit board 130 and secured to the inside surface 112 of sensing tab 110 and replaces sensor 115. The alignment of the multiple contacts 192 and 194 is achieved in the same manner as the alignment of the contacts 62 and sensor 115.

Operation of First Embodiment

When the automated cap 100 is secured to the medication vial 20, the control system 114 is complete. The sensors 115 on the tab 110 of the cap are in electrical contact with the contacts 62 of the memory strip 60, and the information 80 in the memory strip is in electrical communication with or can otherwise be read by the processor 120 in the cap. Predetermined portions of information 80 from the memory strip 60 are compared with the information that had previously been read and stored in the memory 125 of the cap 100. If the predetermined information 80 is the same as before, the processor 120 will compute the next prescribed time for taking a dosage of medication 15 and activate an alarm or otherwise communicate that information to the patient when that time occurs. If the cap 100 is not returned to seal the vial 20 to which it was previously attached, the computer 120 will activate the audible alarm 134. The patient or caregiver can disable or deactivate the alarm 134 by securing the cap 100 back on the correct vial 20. If the cap 100 is not returned to the correct vial 20 and the alarm 134 is ignored for a period of time or the user presses button 160, the alarm is disabled, and the new information 80 in the new memory strip 60 is stored in the memory 125 of the cap 100 and used to compute the next dosage time for the new medication. The automated cap 100 is provided with a mechanism such as an access or consumption indicator that will keep an accurate count of the number of times the medication container is opened each day and advise the patient against consuming too many pills in too short a time. This is particularly useful for medications 15 that are prescribed to be used on an as needed basis (e.g. pain medication), but not to be consumed more than a certain amount in any given day.

Similar to the access control device, the consumption indicator can take a variety of forms. In one embodiment, the cap 100 is provided with a button 160 that is pressed to indicate to the processor 120 that a consumption event has occurred. In another embodiment, the consumption indicator uses the alignment of the sensors 115 of the cap 100 with the contacts 62 of the information device 60 of the vial 20 to trigger a consumption event. When the automated cap 100 is removed, the sensors 115 are no longer aligned with the contacts 62 of the information device 60. A misalignment of the sensors and contacts, such as that caused by the removal of the cap 100, results in a disruption of communication of information to the processor 120, so that it can no longer read the memory strip 60. This triggers an event that can be used to store the current date and time in memory 125 of the cap 100. The computer processor 120 uses the clock 145 and the triggered disruption to determine the time of this event. When the cap 100 is resecured to the vial 20, the date and time are then written to memory 125 or to the memory strip 60 indicating that the patient took a dose of medication 15 and the actual consumption time. The times and dates stored reflect consumption compliance information or compliance data in adhering to the prescription regimen. Other embodiments of the consumption indicator are noted below, such as the sensing of movement of an access door, lid, selector or cartridge by a corresponding removal indicator or sensor. An input device such as a keyboard could also be used.

The actual time information obtained from the clock 145 and the type and amount of medication information for this consumption event are then stored as actual compliance data 84 in the memory device 125 of the cap 100 or the memory device 60 of the vial 20. The actual compliance data 84 can be conveyed to a separate personal or business computer 270 via an interface in the computer (not shown) that can sense a controlled flashing of the illuminating alarm 136. By pressing button 160 for a period of several seconds the automated cap 100 will transmit the compliance data 84. The compliance data 84 may also be conveyed via the infrared transmitter 140 in the automated cap 100 to an infrared receiver 272 in the computer 270. The compliance data 84 is used by the physician to determine if the patient is taking too much or not enough medication 15, or is not adhering to the regular timing specified by the prescription.

By comparing the quantity of medication 15 in the container 10, as stored as medication information 84 in the memory strip 60, against the number of times the automated cap 100 was removed and the number of pills to be consumed in each dosage, the automated cap 100 can compute the inventory or remaining quantity information corresponding to the amount or number of doses of medication in the container 10, when the prescription should be refilled and alert the patient. The number of times the container 10 is opened and the numbers of doses consumed is written to the memory 125 of the cap 100 or the memory strip 60 of the interactive label 50.

As stated above, the information 80 contained in the memory strip 60 can be transmitted to a separate personal or business computer 270 or personal alerting device 290, such as a digital watch or appointment book, by equipping automated cap 100 with an infrared transmitter 140. The transmission is started by pressing button 160 for several seconds. The transferred information is used to establish a consumption alert timing schedule 82 to remind the patient when to take the medication 15. This is accomplished by having the computer 270 activate a variety of its alarms, or by having the computer page the patient with a message to consume a specific medication, or by calling the patient using a telephone to convey a verbal message to consume a specific medication. In this manner, the patient can extend the alarm and alerting devices beyond what is available in the cap 100, or to have alerts be issued even if a conventional cap is used.

If a patient is taking several medications 15 and the information 80 contained in the memory strip 60 for each container 10 is transferred to a separate personal or business computer 270, the computer can reference and compare the lists of contraindicated medications which are part of the medication information 84. Should two or more medications 15 be contraindicated for use together, the patient will be alerted to this fact. Every time a medication 15 is issued to a patient, the most recent list of contraindications is included in the memory strip 60 of the container 10. If the patient does not have a software program capable of performing this function, the program codes 86 will contain a program that is transferred from the memory strip 60 to the computer 270 to perform this check. This program may use a Java programming language so that it can be used in a wide variety of computer processors 270. Other program codes 86 can be sent to the automated cap 100 or computer 270 to perform various alerting functions.

Second Embodiment

FIGS. 12-15 show a second embodiment of the invention where the container 200 includes a conventional, childproof cap 260 as shown in FIG. 1, in place of the automated cap 100. The vial and interactive label that are interchangeable with the vial 20 and label 50 of the first embodiment. The interactive label 50 is electrically linked to the separate personal or business computer 270 via a sensing element 280. The conventional cap 260 is secured to the vial 20 via securement ratchets 40 as in the first embodiment. The guide ring 30 is located a predetermined distance from the top end 25 of the vial 20 so that the ring does not interfere with securing the conventional cap 260 to the vial 20.

The information 80 contained in the memory strip 60 is electronically conveyed to computer 270 by sensing element 280. Sensing element 280 has sensors 281 located on its inside surface in a pattern and position similar to the contacts 62 of the memory strip 60. The sensing element 280 has an arcuate shape to matingly engage the cylindrical wall 22 of the vial 20 so that when the sensing element is aligned with and placed over the interactive label 50 its sensors 281 are in electrical contact with the contacts 62 of the memory strip 60. The sensing element 280 includes a connecting cable 282 with an electronic connector 284 adapted to be plugged into or otherwise electrically communicate with the computer 270. Sensing element 280 has an upper tab sized to fit snugly into the opening 31 between the ends 32 and 34 of the guide ring 30. This can be accomplished when the conventional cap 260 is in place as shown in FIG. 11. It should also be understood that the sensing element 280 can be used to transfer predetermined information 80 to or from the memory strip 60 of either the first or second embodiment of the container 10 or 200 to the computer 270. When the sensing element 280 is used with the first embodiment, the automated cap 100 must be removed.

Third Embodiment

FIGS. 16 and 17 show a third embodiment of the invention where the container 300 includes a modified interactive label 350 and an automated cap 370 with a modified sensing tab 372. Cap 370 is otherwise interchangeable with cap 100. The container 300 includes a vial that is interchangeable with the vial 20 in the first embodiment. The label 350 includes two rows of conductive or non-conductive contacts 352 and 354. These contacts 352 and 354 can also take the form of reflective or non-reflective surfaces. These contacts or surfaces 352 and 354 represent 1s and 0s. The contacts or surfaces 352 and 354 combine to form a code representing the prescription regimen.

The inside surface of downwardly projecting sensing tab 372 includes sensors 374 that detect the presence or absence of a conductive or reflective surface 352. When the surfaces are conductive, one of the conductive surfaces 352 acts as a ground surface 356 for the remaining surfaces 352. By detecting a voltage or current between the ground 356 and any of the other conductive surfaces 352 a bit of information may be read as a 1 or a 0. By combining the bits of information together, a binary number may be created that can represent a prescription information 202.

In FIG. 16, there are a total of ten contacts or surfaces 352 and 354. One contact or surface is the ground 356. Another second contact or surface 358 is used to sense when the cap 370 is removed. Of the eight remaining contacts or surfaces 352 and 354, two are used to indicate the dosage, for example a 0 may represent one pill, a 1 to indicate two pills and a 2 to represent three pills, and a 3 to indicate four pills are to be taken as each dosage. The remaining six contacts or surfaces are combined to represent a number between 0 and 63. These surfaces 352 and 354 are used to represent the timing of the prescription regimen, 0 to represent a dosage every 2 hours, a 1 to indicate a dosage every 3 hours, a 2 to indicate a dosage every 4 hours and so on. While ten surfaces are shown and described, it should be understood that more or fewer may be used.

The conductive or reflective surfaces 352 may be part of a larger conductive or reflective surface (not shown). A non-conductive or non-reflective surface (not shown) may be created by punching a hole in or printing over a portion of the larger conductive or reflective surface. This process may be done as the label 350 is printed with the readable text 44.

The automated cap 370 is secured to the vial 20 the same way as in the first embodiment. The cap 370 includes the same processor 120, memory 125, circuit board 130, display 132, alarms 134-138, transmitter 140, clock 145, battery 150 and buttons 160-166 as automated cap 100. When the cap 370 is removed from the vial 20, the conductive path between ground surface 356 and second surfaces 358 is broken indicating to the cap 370 that a dosage of the medication is being taken. The braking of this conductive path is also used to set the alarms to indicate when the next dosage should be taken.

Fourth Embodiment

FIGS. 18-24 show a fourth embodiment of the invention where the container 400 is a single dosage, disk shaped, blister pack and an interactive label 450 with a memory strip 460. The blister pack 400 is placed in a dispenser 500 having a computer processor 530 that controls a display and a variety of alarms. Memory strip 460 is functionally and structurally substantially interchangeable with memory strip 60. It should be understood that in this embodiment of the invention, the dispenser 500 forms a part or piece of the container 400.

Figure 18:
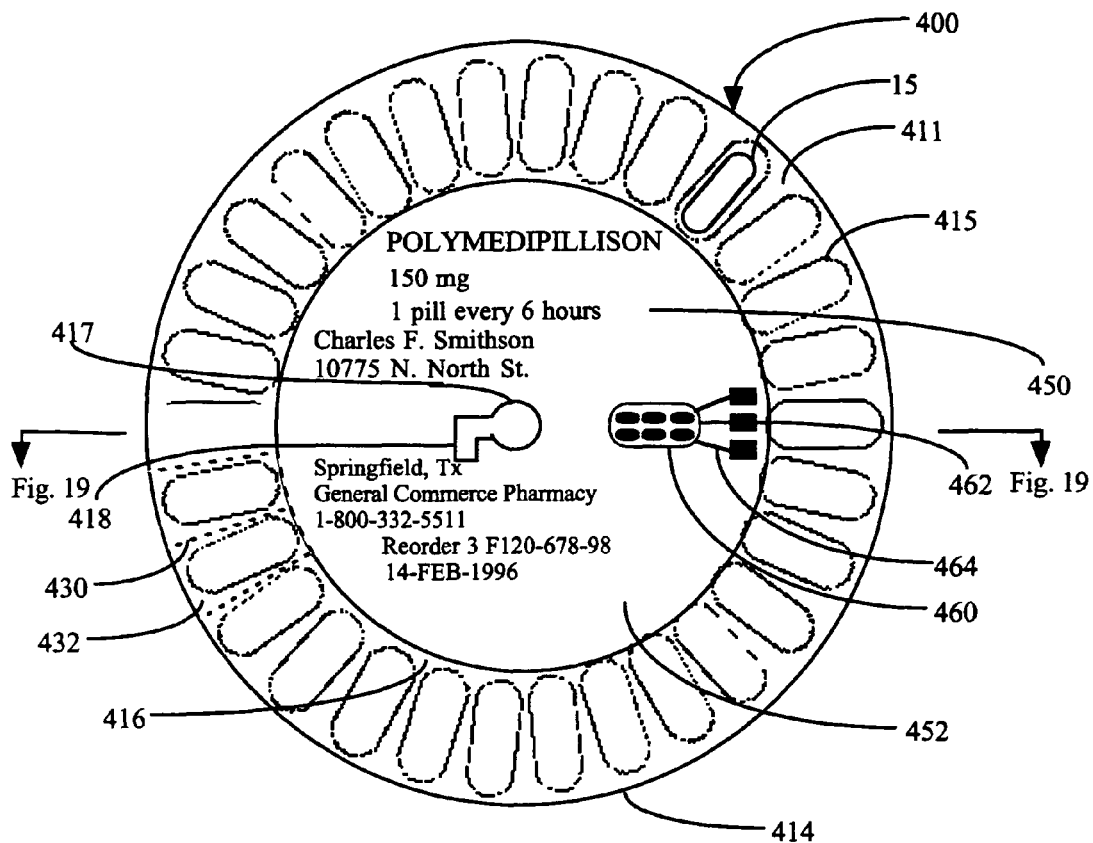
FIG. 18 is a top, plan view of a fourth embodiment of the present medication container invention including a container in the form of a disc shaped blister pack with an interactive label having an electronic memory strip affixed to a central surface of the blister pack.
Figure 19:
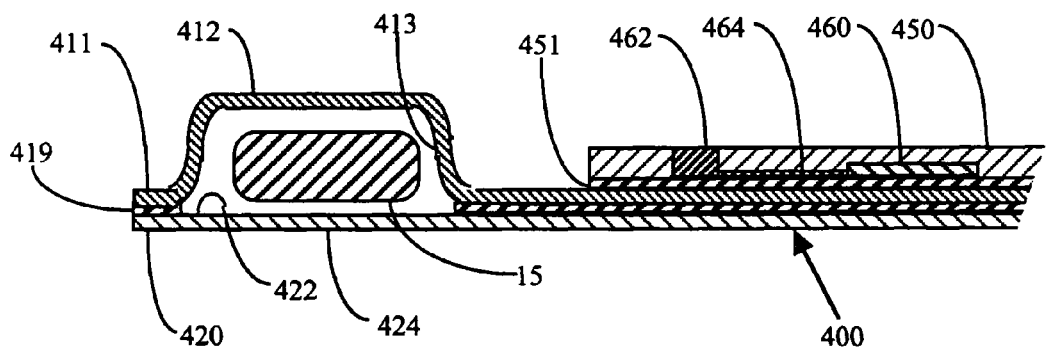
FIG. 19 is a side, cross sectional view of FIG. 18 taken along line 19-19 showing a dose of medication in a pocket of the blister back and the interactive label affixed to the tear resistant sheet.
Figure 20:
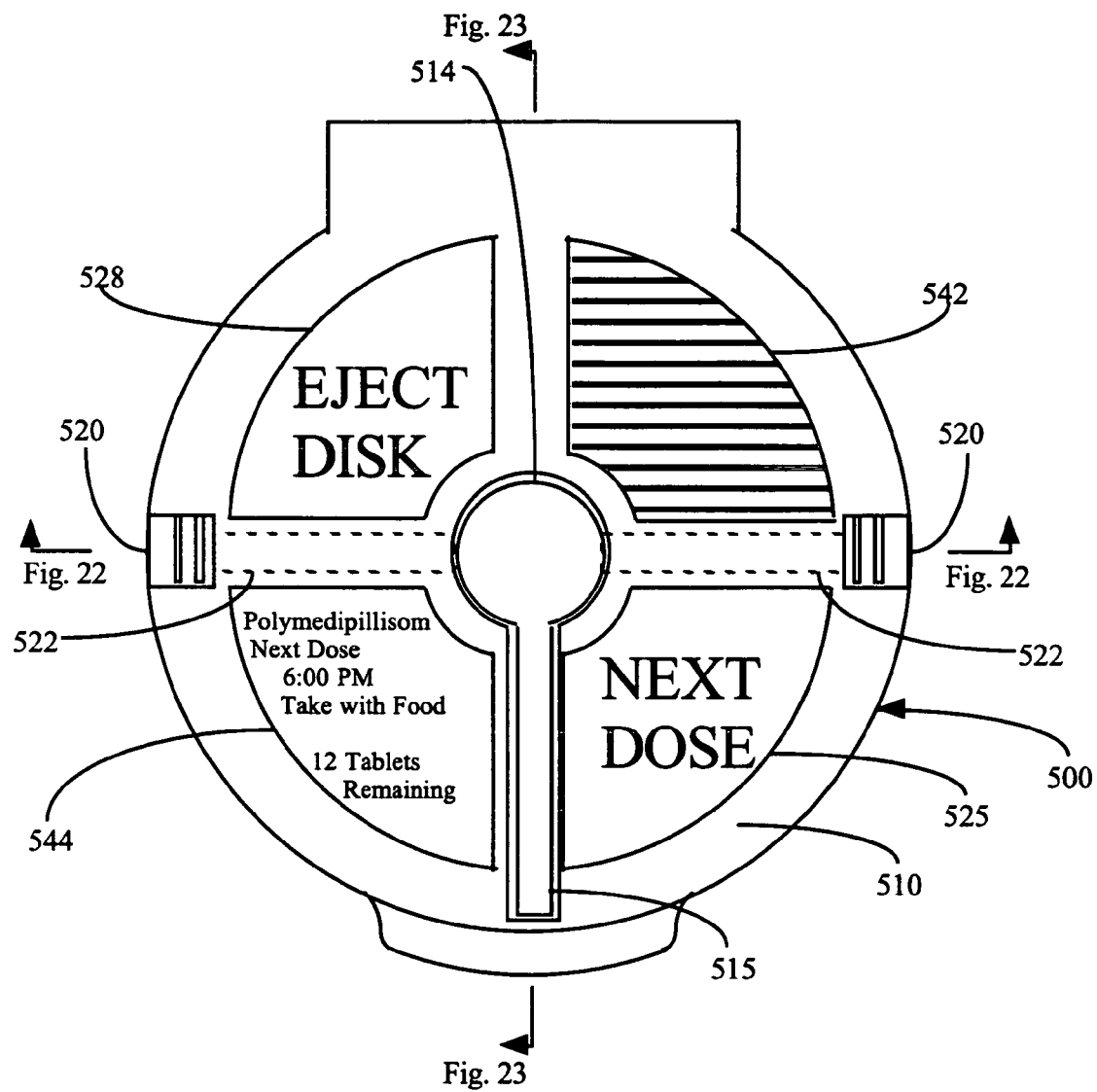
FIG. 20 is a top, plan view showing the lid of a semi-automated dispenser equipped with a dispensing lever, finger latches, a display, an audible alert, "Eject" and "Next Dose" buttons.
Figure 21:
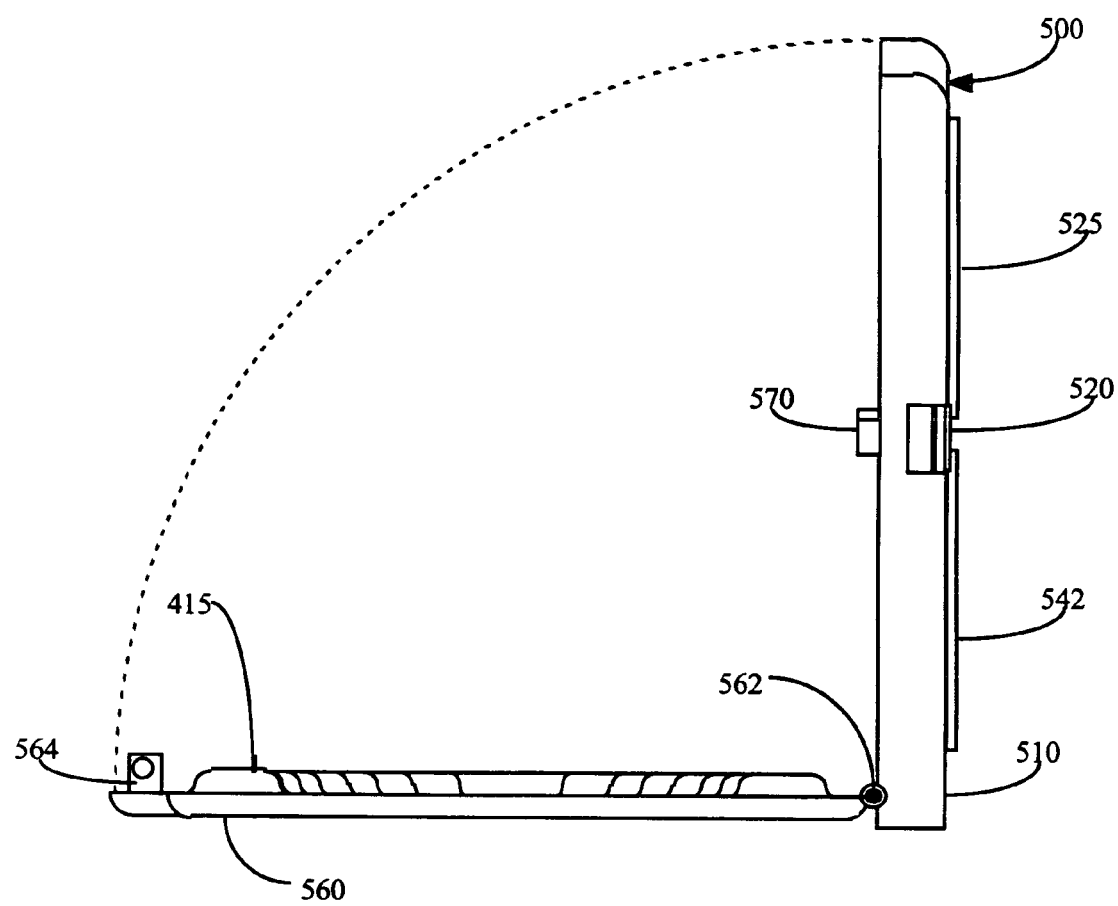
FIG. 21 is a side, plan view showing the disc shaped blister pack inside a semi-automated dispenser in an opened position.
Figure 22:
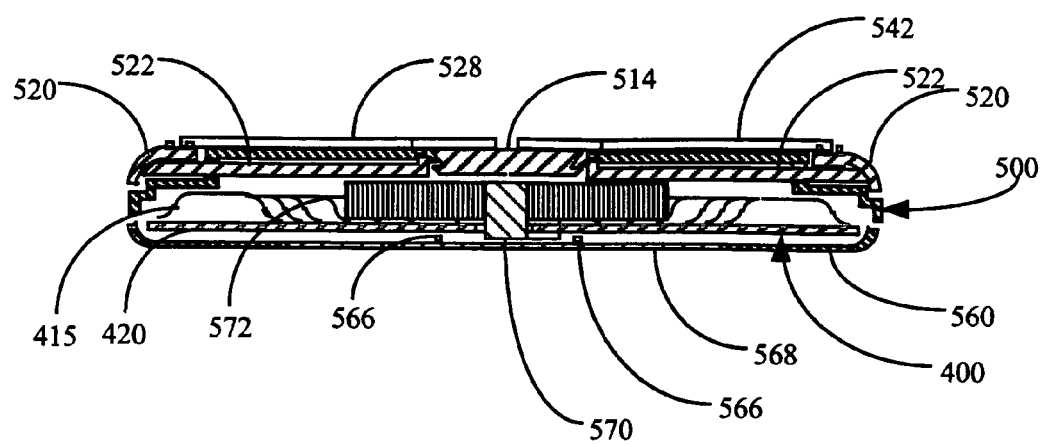
FIG. 22 is a side, cross-sectional view of FIG. 20 taken along lines 22-22 and showing the semi-automated dispenser with its plunger in a locked position.

FIGS. 18 and 19 show a blister pack 400 formed by a tear resistant sheet 411 having front and rear surfaces 412 and 413 and a perimeter 414. The tear resistant sheet 411 is formed into multiple pockets 415 located around its perimeter 414. Each pocket 415 holds a single dose of medication 15. The tear resistant sheet 411 has a substantially flat central area 416 with a central opening 417 and offset notch 418 formed through the sheet 411. The rear surface 413 of the tear resistant sheet 411 has an adhesive coating 419 applied to it, except in pockets 415. The blister pack also includes a backing sheet 420 having front and rear surfaces 422 and 424. The front surface 422 is secured to the rear surface 413 of the tear resistant sheet 411 via the adhesive coating 419. The backing sheet 420 extends over the pockets 415 so that each dose of medication 15 is sealed into its respective pocket. The tear resistant sheet 411 has perforations 430 that separate each pocket 415 into a discrete portion 432 that is separable from the remainder of the container.

An interactive label 450 is attached to the flat, central area 416 of the front surface 412 of the tear resistant sheet 411 via an adhesive layer 451. The label 450 has a textual portion 452 with prescription information printed on its front surface. The label 450 includes a memory strip 460 similar to that used in the first and second embodiments. The information in the memory strip 460 is the same as the information 80 in the first and second embodiments. The electronic memory strip 460 is sensed through its contacts 462 via an electrical connection or wire 464. The opening 417 and notch 418 in blister pack 400 are used to mount the single dosage container 400 into a predetermined position in the dispensing device 500. The opening 417 and notch 418 ensure that the blister pack 400 is placed in a secure position in said dispenser 500, and that the sensing contacts 462 are aligned with sensors for electrically communicating with the memory strip 460.

Figure 23:
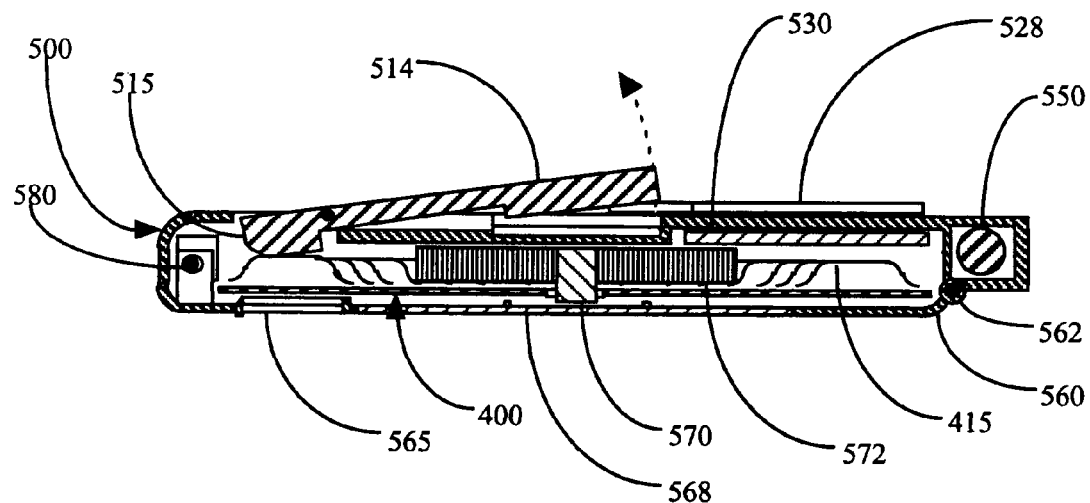
FIG. 23 is a side, cross-sectional view of FIG. 20 taken along lines 23-23 and showing the semi-automated dispenser with its plunger being raised into a dispensing position.

FIGS. 20-23 show the semi-automated, clam shell medication dispenser 500 for housing and dispensing medication 15 from the blister pack container 400. The dispenser 500 has a lid 510 with a dispensing lever 514 and a plunger 515 that combine to form a dispensing mechanism for dislodging a dose of medication 15 from its pocket 415 in the blister pack 400. Finger latches 520 are arranged on both sides of the dispensing lever 514 and plunger 515. The latches 520 are integrally connected to locking struts 522, which engage the dispensing lever 514. (See FIG. 20). To dispense a dose of medication 15, the patient pushes each finger latch 520 out and away from the body of the lid 510 so that struts 522 release the dispensing lever 514. When released, dispensing lever 514 is biased by a spring (not shown) to a raised position above the struts 522 as seen in FIG. 23. When the finger latches 520 are released, the latches and struts 522 are biased by a second spring (not shown) into their original position. The struts 522 are now located beneath the dispensing lever 514. This structure is intended to provide a relatively child-proof or resistant method for releasing dispenser lever 514.

The dispenser 500 is now ready to dispense medication 15. The lever 514 is pulled up, which causes dispensing plunger 515 to rotate down and press against the top of the blister pack pocket 415 positioned below the plunger. As the plunger continues to rotate down, the medication 15 is forced through backing sheet 420 of the single dose container 400 and through a dispenser opening 565 for the patient to consume. The predetermined information 80 in the memory strip 460 is downloaded to or sensed by the processor 530 of the dispenser 500 via a sensing mechanism (not shown) attached to the lid 510. The sensing mechanism has sensors similar to those in sensing tab 110. These sensors engage the contacts 462 of the memory strip 460. The computer processor 530 has circuitry similar to that shown in FIG. 9 and includes a memory and a real time clock that are electrically connected via a circuit board. Information 80 in the memory strip 460 is electronically transmitted to or otherwise communicated or read by the computer processor 530 via the contacts 462, links 464, sensors and the circuit board. The lid 510 also includes a "Next Dose" button 525 for advancing the single dosage container 400 to the next dosage position, and an "Eject" button 528 for ejecting the container 400. Communication devices such as audible alerting device 542 and display 544 are used to present messages and visual alerts. These buttons 525 and 528 and communication devices 542 and 544 are in electrical communication with the computer processor 530 via the circuit board.

Figure 24:
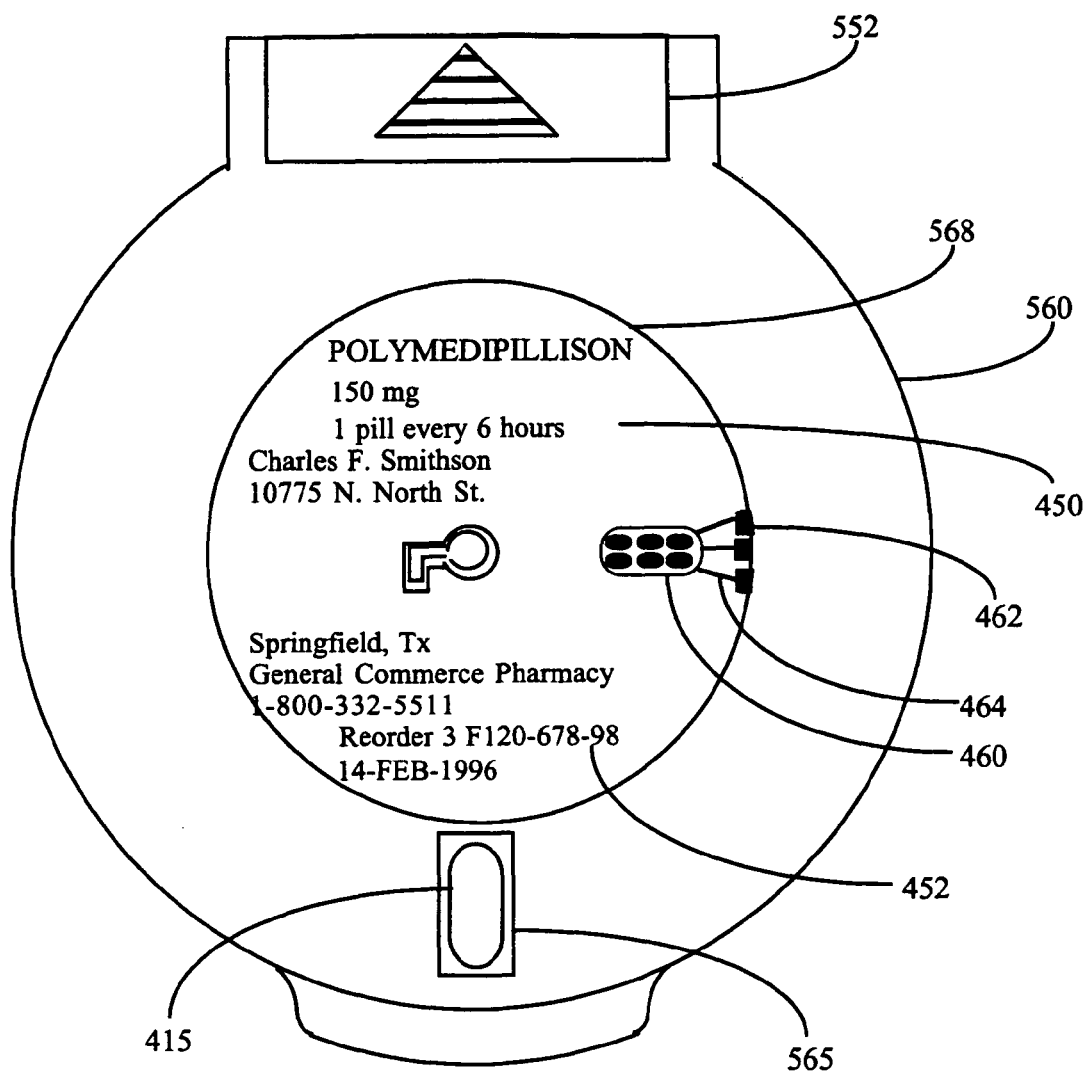
FIG. 24 is a bottom, plan view of the dispenser showing an alternate embodiment of the blister pack container where the interactive label is secured to the backing sheet of the blister pack so that the textual portion of the label is visible through a window in the base of the dispenser.

The dispenser 500 has a base 560 that is hingebly attached to the lid 510 by hinge 562. The base 560 includes a battery 550 for powering the electrical components in the dispenser, and a battery access door 552 to permit periodic replacement of the battery. The base 560 has a dispenser opening 565 through which the backing sheet 420 of one of the discrete portions 432 of the blister pack 400 can be seen, and through which individual doses of medication 15 are dispensed. To assist in breaking or tearing the backing sheet 420, a portion of the dispenser opening 565 has a sharp interior edge that cuts into the surface of the backing sheet 420 as the sheet is pressed against the edge. The base 560 of the dispenser 500 also includes a flange 564 that secures the lid 510 to the base 560 when in the closed position. Alignment ribs 566 project upwardly from the inside surface of the base 560 to keep single dosage container 400 adequately raised so a drive spindle 570 passes through the central opening 417 in the tear resistant sheet 411 when the dispenser 500 is closed. The alignment ribs 566 and the shape of the spindle 570, which matingly engages the central opening 417 and offset notch 418 of the blister pack 400, combine to form a mechanism for selectively aligning one of the pockets 415 with the plunger 515 of the dispenser. FIG. 24 shows an alternate embodiment of the blister pack container 400. In this embodiment, the interactive label 450 is affixed to the surface of the backing sheet 420. A window 568 made of clear plastic is provided in the base 560 of the dispenser 500. The window 568 allows the patient to read the contents of the prescription text 452 when the dispenser is closed.

The dispenser 500 is equipped with a drive spindle 570 and a motor 572 for automatically dispensing the medication 15. The motor 572 is relatively flat in design similar to those used in portable CD players. The computer processor 530, motor 572 and spindle 570 combine to form an access control device or advancing mechanism for rotating the single dosage container 400 when a dose is to be dispensed. The computer processor 530 controls the activation of the motor 572 and spindle 570 to prevent the patient or care giver from removing medication 15 from the blister pack 400 until the time the next dose of medication is due. The motor 572 also controls a locking solenoid 580 that prevents inappropriate access to the medication container 400 by the patient or care giver. The solenoid 580 controls a rod aligned to selectively engage or enter an opening in flange 564. When the solenoid 580 is activated to force the rod into the latch opening, the dispenser 500 is locked shut. When the solenoid 580 is activated to pull the rod out of the latch opening the dispenser 500 can be opened. The access control device can also take the form of an access indicator as noted above.

Operation of Fourth Embodiment and Dispenser

To use the personal semi-automated medication dispenser 500, the patient can press the "Eject" button 528 and insert a full blister pack container 400. Processor 530 causes the single dosage container 400 to rotate via motor 572 such that the contacts 462 of the memory strip 460 are below the sensors of the dispenser 500 (not shown) which are in electrical communication with the computer processor 530 via the circuit board. When properly positioned the processor 530 may write to the memory strip 460 to update it with the number of doses that have been dispensed, so the quantity of medication 15 stored in memory strip 460 is accurate. When all the medication 15 is dispensed, the computer processor 530 is programmed to accept input from the "Eject" button 528. The computer processor 530 then causes locking solenoid 580 to retract and allow hinged lid 510 to open under spring force. The existing single dosage container 400 is removed and a new one placed so that center opening 417 is pressed over drive spindle 570. The hinged top 510 is closed, causing the locking solenoid 580 to engage the opening in flange 564 and locking the dispenser closed.

The information 80 in the memory strip 460 is transferred to processor 530 so that the prescription regimen is shown on the display 544. When it is time to take a medication 15, the processor causes audible alarm 542 to sound an alert. The patient then presses the "Next Dose" button 525. Processor 530 causes motor 572 to rotate the spindle 570 and single dosage container 400 to the next available filled pocket 415. The patient then releases the dispensing lever 514, as previously described, and lifts the lever up to dispense a dose of medication 15. When this is done a micro switch or sensor (not shown) detects the dispensing of a dose of medication 15 and reduces the quantity of medication understood by the processor 530 to be held in container 400 by one. The dispensing lever 514 is then secured into its lowered position. It should be noted that the dispensing lever 514 could be adapted to engage the blister pack 400 near perforations 430 to separate an entire discrete portion 432 from the remainder of the blister pack while leaving the medication 15 inside its discrete portion. The discrete portion 432 of the blister pack 400 would then be discharged through opening 565 in the dispenser 500 so that the patient could remove the medication from the discrete portion themselves.

As previously described portions of the information 80 in the memory strip 460 can be transferred to the separate computer 270 or personal alerting device 290. Program codes 86 can be transferred so computer 270 is equipped with software to provide alert scheduling or to check for contra-indicated medications. Program codes 86 can be transferred to processor 530 of dispenser 500 to assist in scheduling alerts. Additional buttons (not shown) are used to enter the date and time. The dispenser can also be provided with other alarms (not shown) such as a visual or vibrational alarm, an infrared transmitter (not shown) for communicating with a separate computer, and connectors (not shown) for electrically attaching the dispenser to the separate computer 270.

Fifth Embodiment

Figure 26:
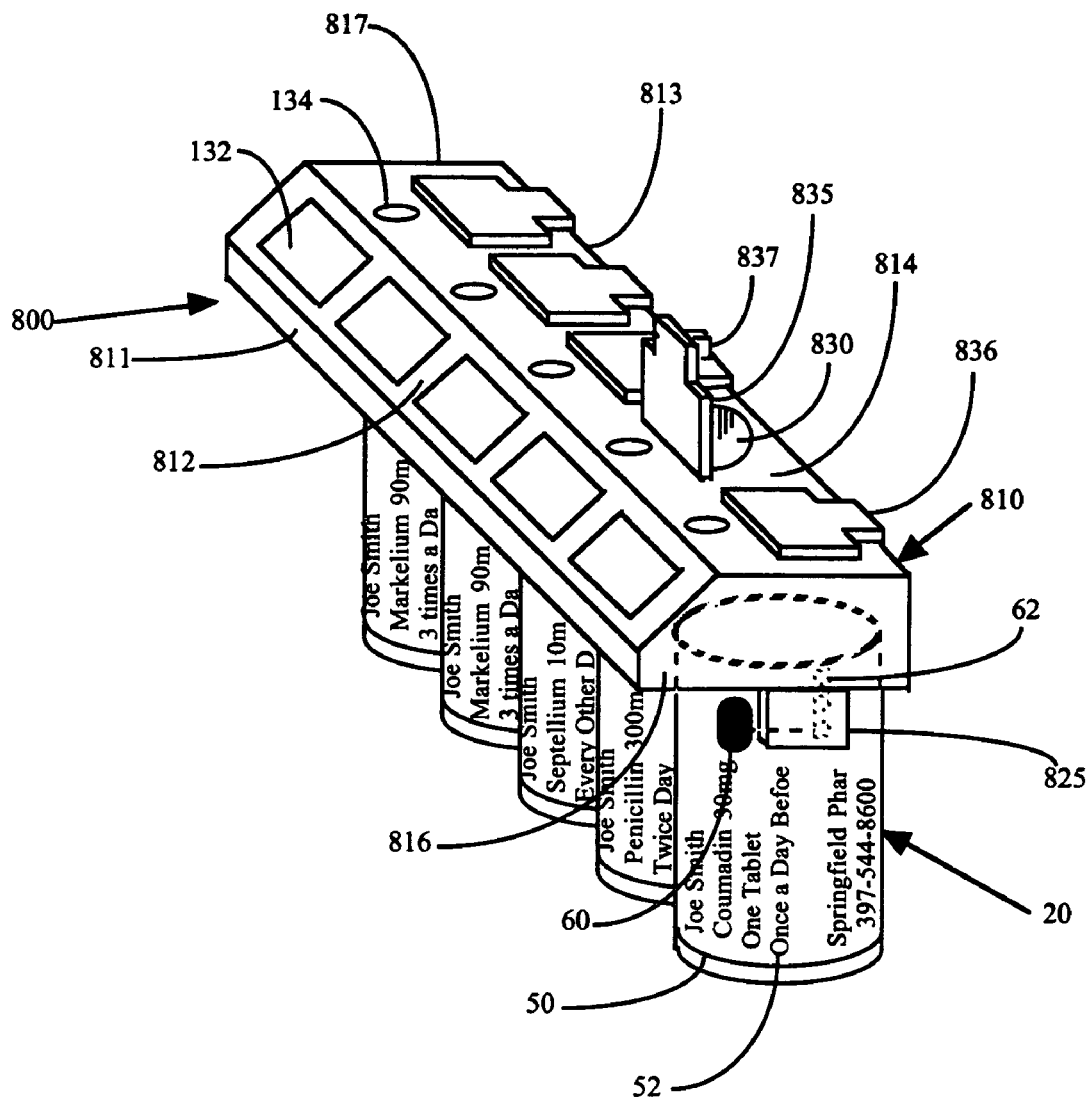
FIG. 26 is a perspective view of a fifth embodiment of the present medication container invention including several vial shaped containers of medication secured to a console or unitary lid, each vial having its own machine readable information strip, and the console having a separate indicator light, display and access door for each vial.

FIG. 26 shows a fifth embodiment of the medication container 800 for holding and organizing several different types of medication. The container 800 includes several vials that are the same as or similar to the vials 20 for containers 10, 200 and 300. Each particular vial 20 is physically separable from the other vials, but is removably secured to a unitary lid 810 as discussed below. Each particular vial 20 is equipped with its own corresponding interactive label 50 and machine readable and writable memory strip 60. However, it should be understood that in this embodiment of the invention, the label 50 need not be interactive. The machine readable and writable memory strip 60 can be replaced by a memory device that is only machine readable. For example, memory strip 60 and its contacts 62 and wires 64 can be replaced by the several conductive/non-conductive or reflective/non-reflective surfaces and ground surface 352-358 of container 300, or by a conventional bar code (not shown) applied to the surface of the label 50.

Figure 27:
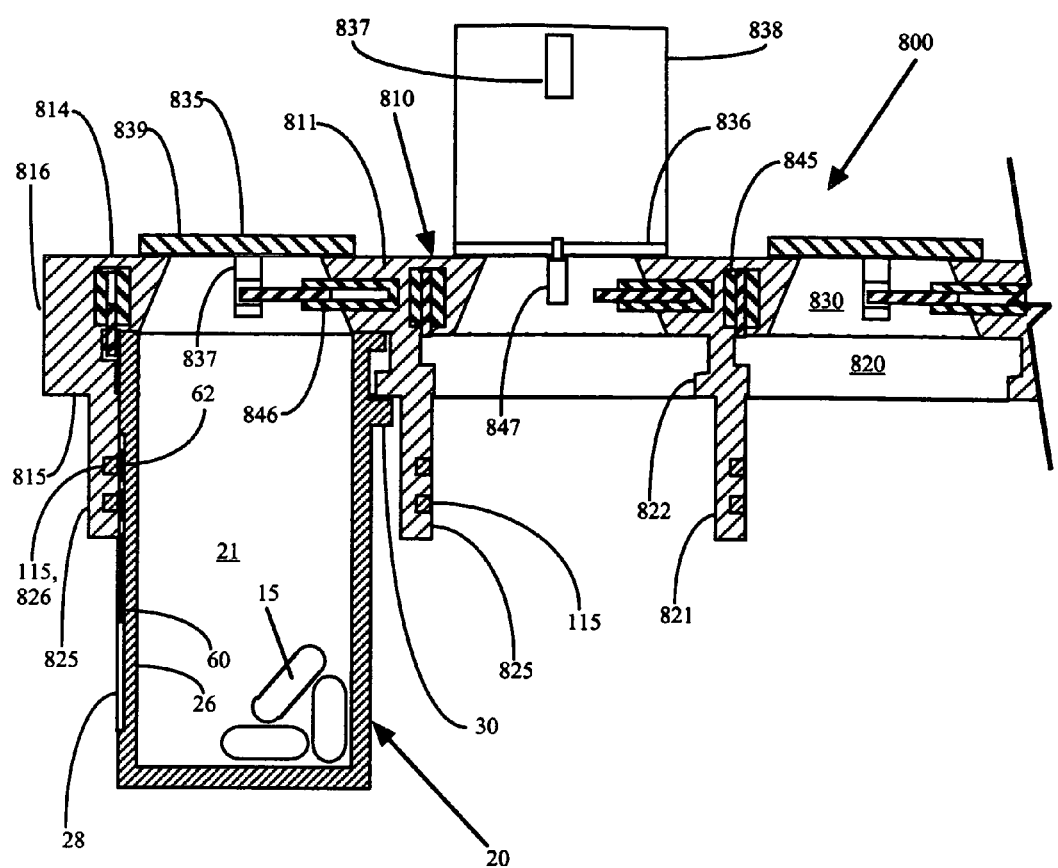
FIG. 27 is a partial, rear cross-sectional view of the multi-vial medication container of FIG. 26 with one vial secured to an associated porthole of the console or unitary lid and adjacent access doors in their open and closed positions.

The unitary lid 810 includes a housing 811 with front 812, rear 813, top 814, bottom 815, and end surfaces 816 and 817. As shown in FIG. 27, a number of ports or portholes 820 are formed along the length of the bottom surface 815. The portholes 820 are spaced equidistantly apart from one end 816 of the housing to the other 817. Each porthole 820 has an inside surface 821 that is shaped and sized to snugly receive the top end 25 and ratchets 40 of one of the vials 20. Similar to the cap 100, the inside surface 821 of each porthole 820 includes several hold down lugs 822 or threads for removably securing the vial 20 to the unitary lid 810. Each particular port 820 has a corresponding sensing tab 825 that includes sensors 115 like those in cap 100. The sensing tabs 825 projects downwardly from the bottom surface 815 of the lid 810 and have an inside surface that is substantially flush with the inside surface 821 of the porthole 820.

Each vial 20 has a guide ring (not shown) similar to guide ring 30 that receives the sensing tab 825. The label 50 is affixed in the recess 28 of the vial 20. The recess 28, guide ring 30 and sensing tab 825 combine to align the textual portion 52 facing toward the front 812 of the unitary lid 810 when the vial is secured. This ensures that each textual portion 52 is visible when several vials 20 are secured to the unitary lid 810. The guide rings 30 also ensure that sensors 115 or 826 align with and detect contacts 62 in control system 840 (FIG. 28), or that contacts 192 align with contacts 194 in control system 190 (FIG. 25).

The housing 811 of the unitary lid 810 has a number of openings 830 in its top surface 814. Each of these openings 830 is aligned directly above and forms a channel that extends through to a corresponding portholes 820. When the vial 20 is secured to the unitary lid 810, medication 15 can be removed from the vial 20 through the porthole 820 and opening 830. An access door 835 is provided to seal each opening 830. The door 835 has a hinge 836 that is secured to top surface 814 of the housing 811, and a latch 837. The door 835 pivots between open and closed positions 838 and 839. Medication 15 is sealed in the container when the vial 20 is secured to the lid 810 and the access door 835 is in its closed position 839. The latch 837 locks the door into its closed position 839. Medication 15 is removed from one of the vials 20 by releasing the appropriate latch 837, moving the corresponding door 835 to its open position 838, inverting the container 800 and pouring the medication out of the associated opening 830.

Figure 28:
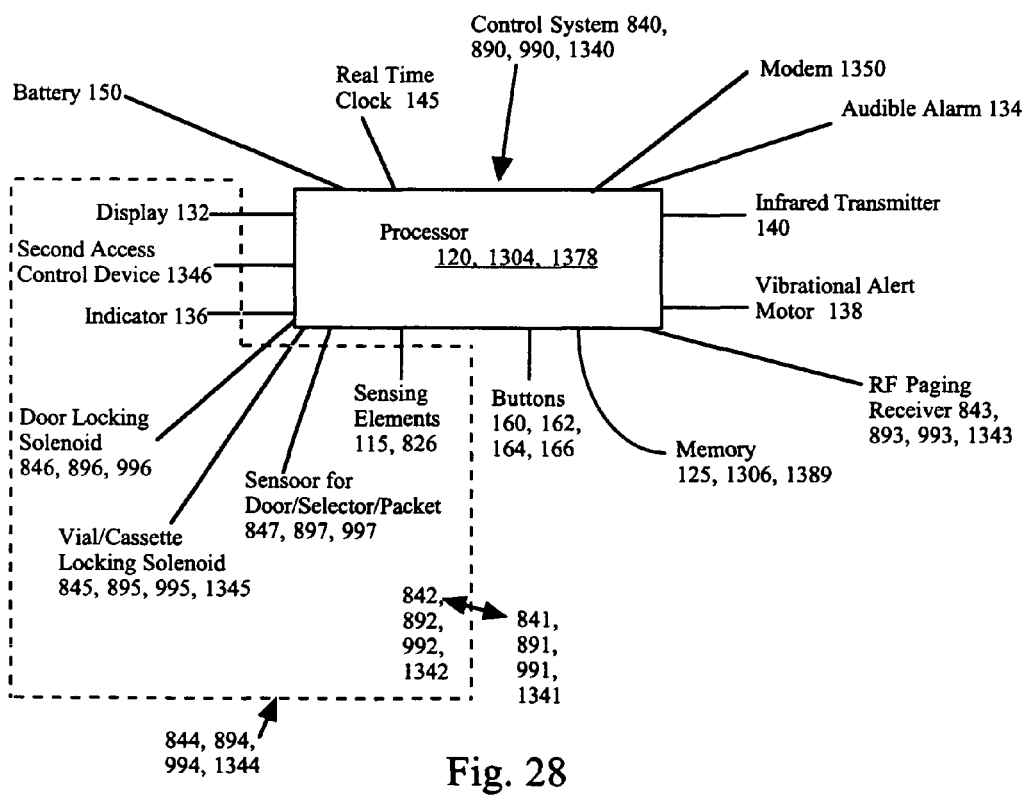
FIG. 28 is a schematic drawing of a circuitry for the multi-vial or multi-blister pack medication container with the multi-set components grouped at the lower left of the schematic.

As shown in FIG. 28, the unitary lid 810 includes a control system 840 that is similar to the control system 114 of containers 10, 300 and 400 shown in FIG. 9. The control system 840 is broken into two subsets of components 841 and 842. The components forming these two subsets 841 and 842 are the same types of components as in control system 114. The first subset 841 has a one-to-one correlation between components in system 114, and includes computer processor 120, memory 125, audible and vibratory alarms 134 and 138, real time clock 145, battery 150, and buttons 160, 162, 164 and 166. Subset 841 also includes a radio frequency (RF) receiver 843 for receiving information regarding necessary changes in the prescribed dosing regimen 82. Receiver 843 can be a transceiver for transmitting information, such as consumption information 84, back to the pharmacy or prescribing physician. The second subset 842 is broken up into multiple sets of components 844. Each set of components 844 is associated with one particular porthole. Each set of components 844 includes the sensors 115, LCD display 132 and indicator light 136 associated with that particular porthole 820. Each set 844 also includes first and second access control devices 845 and 846, and a sensor 847 for the access door 835 associated with the particular porthole 820 as discussed below. The display 132 and indicator 134 of a particular set 844 are located directly in front of the access door 835 corresponding to the particular porthole 820 and vial 20 for that set. The circuit board 130 is somewhat larger than the board in cap 100 due to the increase in number of components and the spacing apart of the various sets 844 of components along the length of the lid 810.

FIG. 27 shows the vial 20 equipped with machine readable and writable memory strip 60 and contacts 62. The sensors 115 are located on the inside surface of each sensing tab 825. When the vial 20 is secured to its particular porthole 820, the contacts 62 are in electrical communication with the sensors 115 for that porthole. As stated above, the memory strip 60 can be replaced by a memory device that is only machine readable. For example, the vial can be equipped with conductive/non-conductive or reflective/non-reflective surfaces 352-358 as in FIG. 16. Sensing tab 825 and sensors 115 are similar in construction to the sensing tab 372 and sensors 374 of container 300. When the vial 20 is equipped with the conventional bar code in lieu of memory strip 60, the sensors 115 are optical sensors that read the bar coded information when the vial 20 is slid into one of the portholes 820 or rotated into a secure position in that porthole.

As shown in FIG. 28, the control system 840 is equipped with two access control devices 845 and 846. These devices 845 and 846 are similar in design to solenoid locking mechanism or assembly 180. The first access control device or vial locking solenoid assembly 845 serves the same purpose as assembly 180. Both assemblies 180 and 845 lock the vial 20 to the cap 100 of unitary lid 810 until a predetermined time, such as when the vial is empty. The second access control device or door locking solenoid assembly 846 locks the access door 835 in its closed position 839 to prevent the removal of medication 15 until the prescribed time to take the particular medication contained in the corresponding vial 20. This second access control device 846 includes a solenoid and plunger assembly similar to assembly 180. The plunger engages the latch 837 of the access door 835 to lock the door in its closed position 839. It should be understood that the medication 15 could also be accessed by removing the desired particular vial 20 from the unitary lid 810.

When one particular vials 20 is secured to its associated porthole 820, the information 80 contained in the information strip 60 of that particular vial is received by the sensors 115 associated with that porthole and communicated to the computer processor 120 in the unitary lid 810. This communication of information 80 occurs each time one of the vials 20 is secured to one of the portholes 820 of the unitary lid 810. The processor 120 notes which medication information 80 came from which sensor 115 and corresponding porthole 820 or set 844. The processor 120 uses its clock 145 and the prescribed dosing regimen information 82 obtained from one sensor 115 and corresponding porthole 820 to compute an appropriate time or times to take the particular medication 15 held by the vial 20 secured to that porthole. The processor 120 then determines the appropriate time or times to take the particular type of medication 15 contained in each of the vials 20 held by its associated porthole 820.

When the processor 120 determines that the time to take one dose of prescribed medication in one particular vial is approaching or has arrived, the processor sends a signal to the display 132 and indicator light 136 for the set 844 associated with the porthole 820 holding that particular type of medication 15. The processor 120 also sends an electric current to the door lock solenoid 846 for that set 844 to release the plunger from engagement with the latch 837 so that the access door 835 is movable to its open position 838. As noted above, the door 835 and a corresponding sensor 847 form a consumption indicator. When the door 835 is moved toward its open position 838, the door sensor 847 sends a signal to the processor 120. The processor 120 uses this signal to indicate that the prescribed dose of medication 15 was taken from the corresponding vial 20 at the time the door 835 was opened. This consumption information is stored in the memory 125 of the unitary lid 810. The processor 120 could also send electric current to the vial lock 845 to allow access to the medication 15, and use this occurrence as the signal that medication 15 was consumed. When the memory device 60 on the vial 20 is machine readable and writable, the processor 120 alters the memory device to include this consumption information.

Sixth Embodiment

Figure 29:
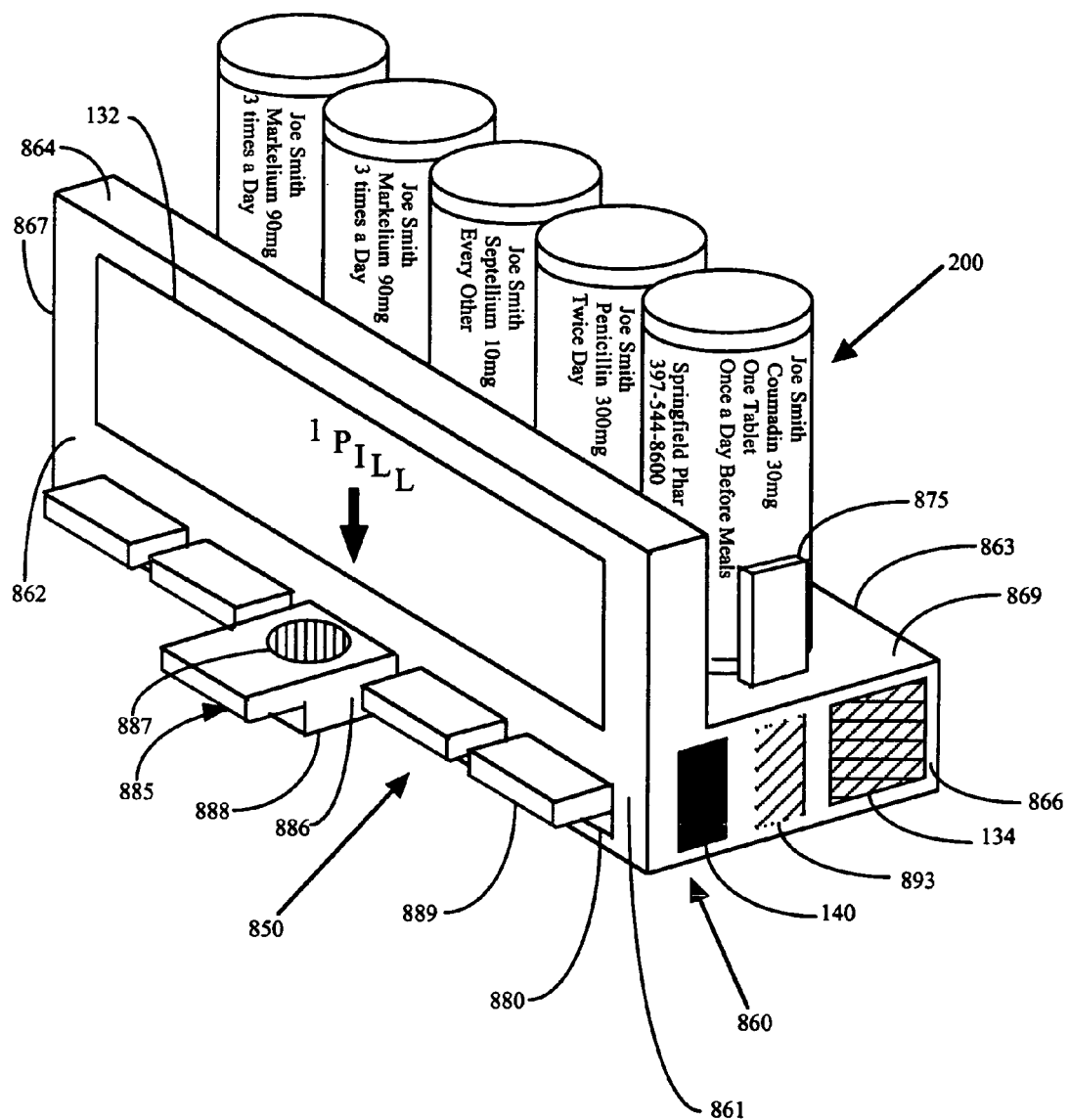
FIG. 29 is a perspective view of a sixth embodiment of the present medication container invention in the form of a multi-vial medication container with the vials secured to portholes located along a top platform of an L-shaped console or unitary lid, and the console containing a single display and several selectors for removing medication from the vials.

FIG. 29 shows a sixth embodiment of the medication container 850 for holding and organizing several different types of medication. This container 850 is similar to the container 800. Each particular vial 20 is physically separable from the other vials, but is removably secured to a unitary lid or console 860 as discussed below. Each particular vial 20 is equipped with its own corresponding interactive label 50 and machine readable and writable memory strip 60. As in the fifth embodiment, it should be understood that the label 50 of container 850 need not be interactive. One of ordinary skill in the art should understand that the terms console and unitary lid are interchangeable. Finally, one or ordinary skill in the art should understand that the machine readable and writable memory strip 60 can be replaced by a memory device that is only machine readable. For example, memory strip 60 and its contacts 62 and wires 64 can be replaced by the several conductive/non-conductive or reflective/non-reflective surfaces and ground surface 352-358 as in container 300, or by a conventional bar code (not shown) applied to the surface of the label 50.

Figure 30:
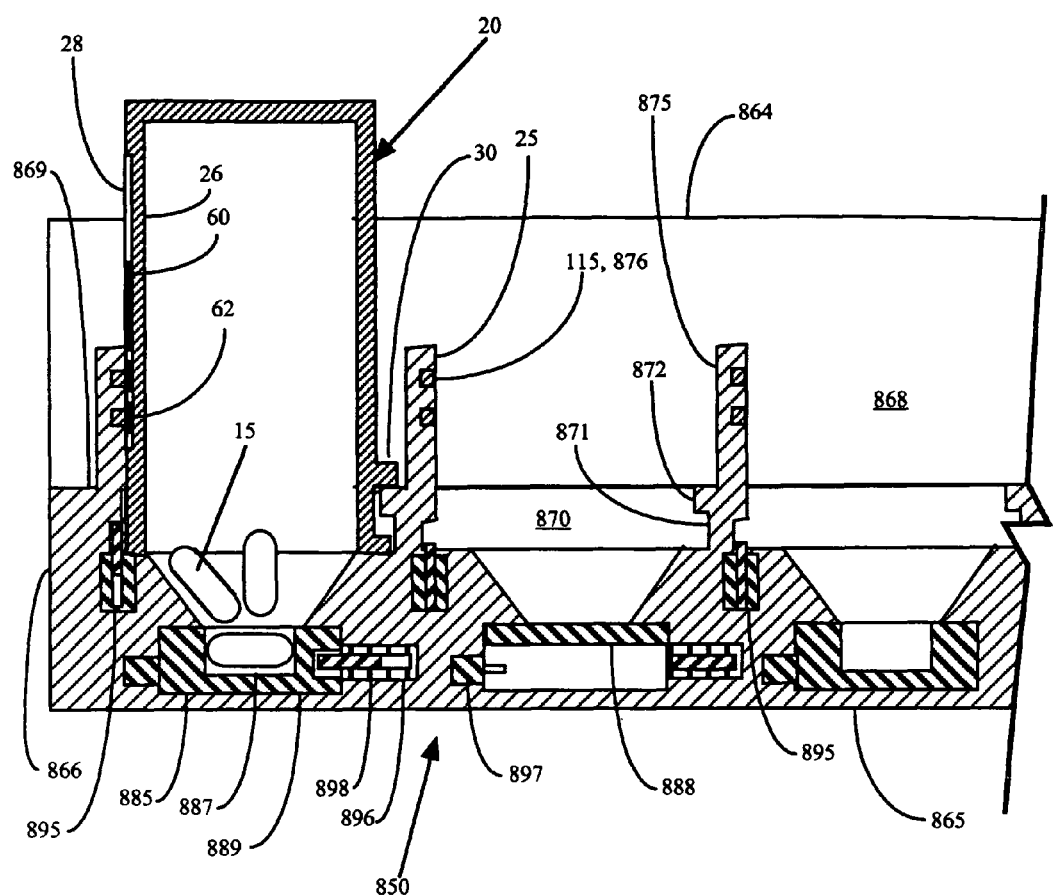
FIG. 30 is a partial, rear cross-sectional view of the multi-vial medication container of FIG. 29 showing one inverted vial secured in an associated porthole with its selector in its closed position, and an adjacent selector in its open position.

The unitary lid 860 includes an L-shaped housing 861 with a front 862, rear 863, top 864, bottom 865, and end surfaces 866 and 867. As best shown in FIG. 30, the housing 861 has an intermediate wall 868 that extends from the top 864 of the housing down to a platform 869 for holding the vials 20. The portholes 870 are similar in construction to the portholes 820 of container 800, and are spaced equidistantly apart from one end 866 of the housing to the other end 867. Each porthole 870 has an inside surface 871 shaped and sized to snugly receive the top end 25 and ratchets 40 of one vial 20. Similar to container 800, the inside surface of each porthole 870 includes several hold down lugs 872 or threads for removably securing the vial 20 to the unitary lid 860. Each particular porthole 870 has a corresponding sensing tab 875 with sensors 115 like those of cap 100. The sensing tabs 875 project upwardly from the top surface 814 of the lid 860, and have an inside surface that is substantially flush with the inside surface 871 of the porthole 870.

Each vial 20 has a guide ring (not shown) similar to guide ring 30 that receives the sensing tab 875. The label 50 is affixed in the recess 28 of the vial 20. The recess 28, guide ring 30 and sensing tab 875 combine to align the textual portion 52 facing toward the front 862 of the unitary lid 860 when the vial 20 is secured. This ensures that each textual portion 52 is visible when several vials 20 are secured to the unitary lid 860. The guide rings 30 also ensure that sensors 115 or 876 align with contacts 62 in control system 890 (FIG. 28), or that contacts 192 align with contacts 194 in control system 190 (FIG. 25).

The housing 861 has a number of openings 880 along the length of its front surface 812. Each opening 880 is aligned directly in front of and forms a corresponding channel that extends through to a corresponding porthole 870. When the vial 20 is secured to one of the portholes 870, medication 15 is removed via a medication selector 885. The selector 885 has a shaft 886 that is sized to fit snugly in the opening 880 and its corresponding channel. The shaft 886 has a medication singulating compartment 887 sized to hold a standard dose of medication 15. The selector 885 slides in the channel of the opening 880 to and from open and closed positions 888 and 889. In the closed position 889, the singulating compartment 887 is located inside its corresponding porthole 870 so that one of the doses of medication 15 falls into the compartment. The selector 885 is then pulled partially out of the opening 880 so that the compartment 887 extends beyond the front 862 of the lid so that the medication 15 in the compartment can be removed. Medication 15 is sealed in the container 850 when the vials 20 are secured to the unitary lid 860 and the selector 885 is in its closed position 889.

The unitary lid 860 includes a control system 890 that is similar to control system 840 shown in FIG. 28. The components making up the control systems 840 and 890 are similar. System 890 is broken into two subsets of components 891 and 892. The first subset 891 includes one computer processor 120, memory 125, display 132, audible and vibratory alarms 134 and 138, real time clock 145, battery 150, and buttons 160, 162, 164 and 166. The subset 891 also includes a RF receiver 893 for receiving information regarding necessary changes in the prescribed dosing regimen 82. Receiver 893 can be a transceiver for transmitting information, such as consumption information 84, back to the pharmacy or prescribing physician. The second subset 892 includes multiple sets of components 894. Each set of components 894 is associated with one particular porthole. Each set 894 includes the sensors 115 associated with that particular porthole 870. Each set 894 also includes first and second access control devices 895 and 896, and a sensor 897 for the access door 885 associated with the particular porthole 870 as discussed below. The single LCD display 132 spans the length of the front 862 of the unitary lid 860. The display visually identifies the appropriate selector 885 to pull to obtain the appropriate, prescribed medication 15. The computer processor 120 instructs the display 132 to show an arrow pointing at the appropriate selector 885. Again, the circuit board (not shown) is somewhat larger than circuit board 130 due to the increase in number of components and the spacing apart of the various sets 892 of components along the length of the lid 860.

FIG. 29 shows the vial 20 equipped with machine readable and writable memory strip 60 and contacts 62. The sensors 115 are located on the inside surface of each sensing tab 875. When one of the vials 20 is secured to a particular porthole 870, the contacts 62 of the memory strip 60 are in electrical communication with the sensors 115 for that porthole, thus allowing each sensor 115 to detect the presence of its respective contacts 62 and communicate information from the memory strip 60 to the processor 120. As stated above, the memory strip 60 can be replaced by a memory device that is only machine readable. For example, the vial 20 is equipped with conductive/non-conductive or reflective/non-reflective surfaces 352-358 as in FIG. 16. Sensing tab 875 and sensors 115 are similar in construction to the sensing tab 372 and sensors 374 of container 300. When the vial 20 is equipped with the conventional bar code in lieu of memory strip 60, the sensors 115 are optical sensors that read the bar coded information when the vial 20 is slid into one of the portholes 870 or rotated into a secure position in that porthole.

As shown in FIG. 28, the unitary lid 860 is equipped with two access control devices that are similar in design to solenoid locking assembly 180. The first access control device or vial locking solenoid assembly 895 serves the same purpose as assembly 180. Both assemblies 180 and 895 lock the vial 20 to the unitary lid 860 until a predetermined time, such as when the vial is empty. The second access control device or selector locking solenoid assembly 896 locks the selector 885 in its closed position 889 until the prescribed time to take the particular medication in the corresponding vial 20. This second access control device 896 includes a solenoid and plunger assembly 898 similar to assembly 180. The plunger engages the shaft 886 of the selector 885 and locks it in its closed position 889. It should be understood that the medication 15 could also be accessed by removing the desired particular vial 20 from the unitary lid 860.

When one particular vial 20 is secured to its associated porthole 870, the information 80 contained in the information strip 60 of that particular vial is received by the sensors 115 associated with that porthole and communicated to the computer processor 120 in the unitary lid 860. This communication of information 80 occurs each time one of the vials 20 is secured to one of the portholes 870 of the unitary lid 860. The processor 120 notes which medication information 80 came from which sensor 115 and corresponding porthole 870. This particular porthole identification information is obtained by the processor 120 via the hardwiring of the system (each porthole sensor 115 having a separate lead to the processor) or by assigning an identification tag to each porthole or one of its corresponding components such as its sensor. The processor 120 uses the its clock 145 and the prescribed dosing regimen information 82 obtained from the vial 20 in one particular porthole 870 to compute an appropriate time or times to take the particular medication 15 held by the vial 20 secured to that porthole. The processor 120 then determines the appropriate time or times to take the particular type of medication 15 contained in each of the vials 20 held by their associated portholes 870.

When the processor 120 determines that the time to take one doses of prescribed medication in one particular vial is approaching or has arrived, the processor sends a signal to the display 132 to show an arrow pointing to the associate porthole 870 holding that particular type of medication 15. The processor also sends an electric current to the selector lock solenoid 896 of the appropriate set 894 to release the plunger from engagement with the selector shaft 886 so that the selector 885 for that particular vial 20 is movable to its open position 888. As noted above, the consumption indicator is formed by the selector 885 and its corresponding sensor 897. When the selector 885 is moved toward its open position 888, the selector sensor 897 sends a signal to the processor 120. The processor 120 uses this signal to indicate that the prescribed dose of medication 15 was taken from the corresponding vial 20 at the time the selector 885 was moved to its open position 888. This removal or consumption information includes removed quantity or consumption quantity information (e.g., one dose of medication), and this information is stored in the memory 125 of the unitary lid 860. The processor 120 could also send electric current to the vial lock 895 to allow access to the medication 15, and use this occurrence as the signal that medication 15 was consumed. When the memory device 60 on the vial 20 is machine readable and writable, the processor 120 can alter the memory device to include this consumption information.

Seventh Embodiment

Figure 31:
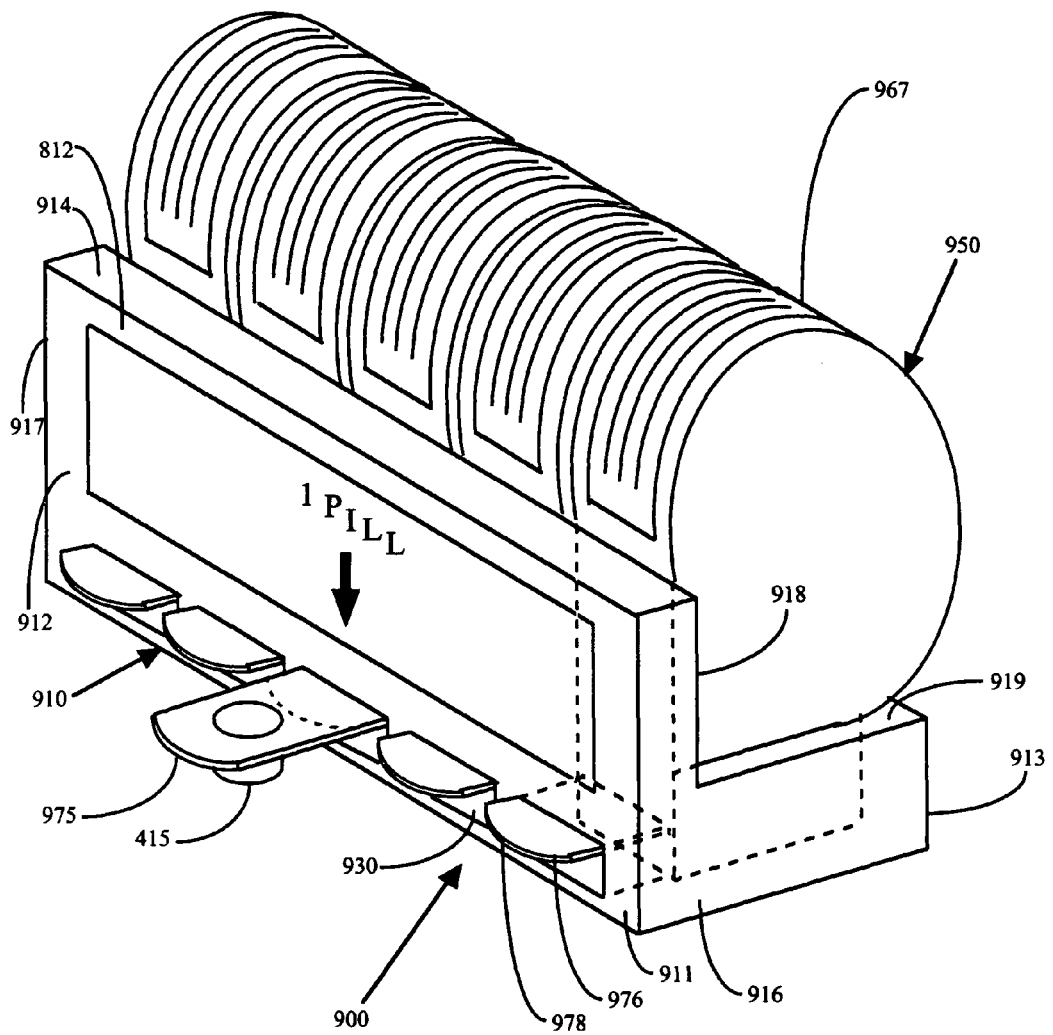
FIG. 31 is a perspective view of a seventh embodiment of the present invention in the form of a multi-blister cassette medication container, where each cassette is secured to a slot in the top of the platform of the L-shaped console or unitary lid, and each cassette holds a free end of the blister strip extending through an associated opening in the console.

FIG. 31 shows a seventh embodiment of the medication container 900 for holding and organizing several different types of medication. This container 900 has an automated, unitary lid or console 910 that is similar to the unitary lid 860 of container 850. The vials 20 are replaced by blister cassettes 950. Each particular cassette 950 is physically distinct and separable from the other cassettes, but is removably secured to a unitary lid 910 as discussed below. Each particular cassette 950 is equipped with its own corresponding machine readable memory device or bar code 960. However, it should be understood that the cassette 950 could contain an interactive label 50. A machine readable and writable memory strip 60 can be substituted for the memory device 960. In addition, several conductive/non-conductive or reflective/non-reflective surfaces and ground surface 352-358 may be substituted as in container 300.

Figure 32:
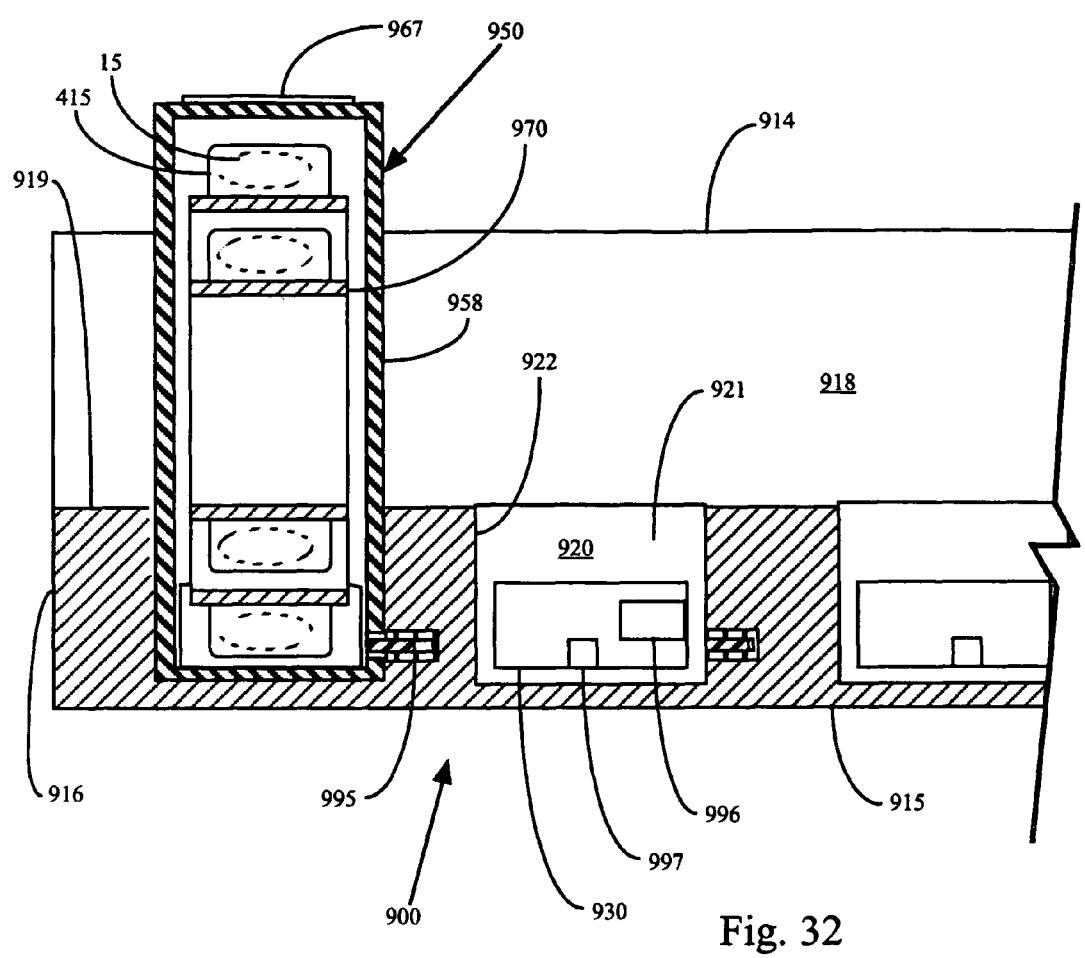
FIG. 32 is a partial, rear sectional view of the container of FIG. 31 showing one blister cassette secured in its associated slot.

The unitary lid 910 includes an L-shaped housing 911 with a front 912, rear 913, top 914, bottom 915, and end surfaces 916 and 917. As best shown in FIG. 32, the housing 911 has an intermediate wall 918 that extends from the top 914 of the housing down to a platform 919 for holding the blister cassettes 950. The platform 919 has a number of ports or slots 920 formed along the length of its surface. The slots 920 are spaced equidistantly apart from one end 916 of the housing to the other 917. Each slot 920 is formed by a forward wall 921, two lateral walls 922 and a rear wall 923 that are shaped and sized to snugly receive the sides of the cassette 950. The forward wall 921 is flush with the surface of the intermediate wall 918. The housing 911 also has a number of openings 930 formed along the length of its front surface 912. Each opening 930 is aligned directly in front of one of the slots 920. The opening 930 forms a channel extending from the front surface 912, through the lid 910 to the surface of the intermediate wall 918, and into a corresponding slot 920. An optical sensor 940 is secured in the intermediate wall 918 above the opening 930.

Figure 33:
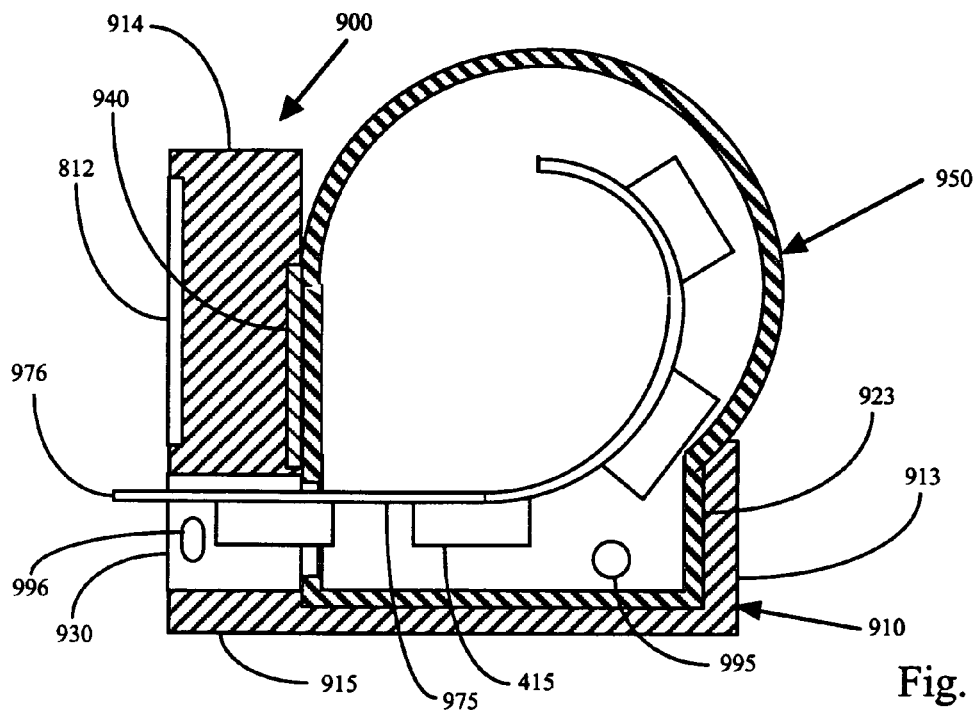
FIG. 33 is a side sectional view of the container of FIG. 31 showing its blister strip coiled inside the cassette with the blister pack at the free end in a reserve position.
Figure 34:
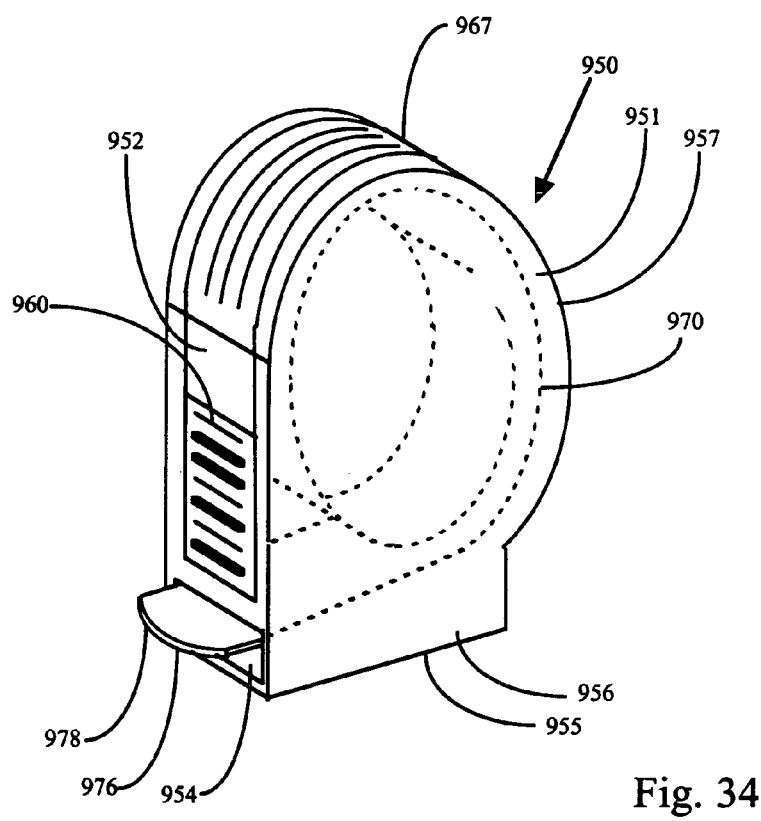
FIG. 34 is a perspective view of the blister cassette used with the medication container of FIG. 31, the cassette being equipped with a bar code memory device.

As best shown in FIG. 33, the blister cassette 950 is formed by a rigid housing 951. The front of the housing 951 is formed by a flat wall 952 with an opening 954 towards its bottom edge. The bottom is formed by a U-shaped channel 955 with lateral rims 956. The top and rear portions of the housing 951 are formed by a circular loop 957. The housing is completed by a pair of flat side walls 958. A machine readable memory device such as bar code 960 is affixed to the front wall 952 above opening 954. The bar code 960 contains a variety of information 80 about the medication 15 in the blister cassette 950. A textual label 967 is affixed to the top or loop portion 957 of the housing 951 so that each label is visible when several cassettes 950 are secured to the unitary lid 910.

The housing 951 holds a conventional blister strip 970 formed by a series of connected blister packets 975 that are separable along a perforation or score line between each adjacent packet. Each blister packet 975 holds a dose of medication 15. The strip 970 is coiled up inside the housing 951 with the outer coil laying against the U-shaped channel 955 between rims 956. A free end 976 of the outer coil passes through the opening 954 in the front wall 952 of the cassette 950.

As shown in FIG. 31, when the blister cassette 950 is secured to the unitary lid 910, the free end 976 of the blister strip 970 extends through opening 930. This places the end packet 975 in a reserve position 978. Medication 15 is obtained by pulling the end packet 975 completely through the opening 930, and tearing off the end packet 975 along the perforated line connecting it to its adjacent packet. The adjacent packet is now in the reserve position 978 with its free end 976 partially extending through opening 930, and is accessible when the next dose of medication is due to be taken.

The unitary lid 910 includes a control system 990 that is similar to control system 890 shown in FIG. 28. The components making up control systems 890 and 990 are similar. System 990 is broken into two subsets of components 991 and 992. The first subset 991 includes one computer processor 120, memory 125, display 132, audible and vibratory alarms 134 and 138, real time clock 145, battery 150, and buttons 160, 162, 164 and 166. The first subset 991 also includes a RF receiver 993 for receiving information regarding necessary changes in the prescribed dosing regimen 82. Receiver 993 can be a transceiver for transmitting information, such as consumption information 84, back to the pharmacy or prescribing physician. The second subset 992 includes multiple sets 994. Each set of components 994 is associated with one particular slot 920. Each set of components 994 includes the sensors 115 associated with that particular slot 920. Each set 994 also includes first and second access control devices 995 and 996, and a sensor 997 for the opening 930 associated with the particular slot 920 as discussed below. The single LCD display 132 spans the length of the front 912 of the unitary lid 910. The display visually identifies the appropriate blister packet 975 to pull to obtain the appropriate, prescribed medication 15. The computer processor 120 instructs the display to point an arrow at the appropriate packet 975. Again, the circuit board (not shown) is somewhat larger than circuit board 130 due to the increase in number of components and the spacing apart of the various sets 992 of components along the length of the lid 910.

Optical sensors 940 are located on the surface of the intermediate wall 918. When one of the blister cassettes 950 is slid into place in a particular slot 920, the optical sensor 940 corresponding to that slot reads the information 80 contained in the memory device or bar code 960. When the cassette 950 is equipped with machine readable and writable memory strip 60 in lieu of bar code 960, the optical sensors 940 are replaced with sensors 115. When the cassette 950 is equipped with conductive/non-conductive or reflective/non-reflective surfaces 352-358, the sensors 115 are similar in construction to sensors 374 of container 300.

As shown in FIG. 28, the control system 990 is equipped with two access control devices that are similar in design to solenoid locking assembly 180. The first access control device or cassette locking assembly 995 prevents the removal of the cassette 950 from the unitary lid 910 until a predetermined time, such as when the cassette is empty. The second access control device or solenoid locking assembly 996 prevents the extension of free end 976 of the blister strip 975 through opening 930 until the prescribed time to take the particular medication in the corresponding cassette 950. This second access control device 996 includes a solenoid and plunger assembly. The plunger engages the blister strip 975 and locks it in place so that it cannot be pulled out of the opening 930. It should be understood that the medication 15 could also be accessed by removing the desired particular vial 20 from the unitary lid 910.

When one particular cassette 950 is secured to its associated slot 920, the information 80 contained in the information strip 60 of that particular cassette is received by the sensors 115 associated with that slot and communicated to the computer processor 120 in the unitary lid 910. This communication of information 80 occurs each time one of the cassettes 950 is secured to one of the slots 920 of the unitary lid 910. The processor 120 notes which medication information 80 came from which associated sensor 115 for the particular slot 920. The processor 120 uses its clock 145 and the prescribed dosing regimen information 82 obtained from the particular cassette 950 secured to its associate slot 920 to compute an appropriate time or times to take the particular medication 15 held by that cassette. The processor 120 then determines the appropriate time or times to take the particular type of medication 15 contained in each of the cassette 950 held by the slots 920.

When the processor 120 determines that it is time to take one dos of prescribed medication in one particular cassette 950, the processor sends a signal to the display 132 to show an arrow pointing to the associate slot 920 and cassette 950 holding that particular type of medication 15. The processor also sends an electric current to the blister strip locking solenoid 996 of the appropriate set 994 associated with slot 920 to withdraw the plunger from in front of the leading blister packet 975 so that this packet can be removed from its associated opening 930. As noted above, the consumption indicator is formed by a selector sensor 997 that detects the movement of the blister strip 970 or the removal of the blister packet 975 through the discharge opening 930 of the cassette 950. When the blister packet 975 is removed and another blister packet is advanced to the reserve position 978, the selector sensor 997 sends a signal to the processor 120. The processor 120 uses this signal to indicate that the prescribed dose of medication 15 was taken from the corresponding cassette 950 at the time the blister packet 975 was removed. This consumption information is stored in the memory 125 of the unitary lid 910. The processor 120 could also send electric current to the vial lock 995 to allow access to the medication 15, and use this occurrence as the signal that medication 15 was consumed. When the memory device 60 on the cassette 950 is machine readable and writable, the processor 120 can alter the memory device to include this consumption information.

Operation of Fifth, Sixth and Seventh Embodiments

The following is provided to assist the reader in understanding the operation of the preceding embodiments of the invention. When a physician prescribes one or more medications to a particular patient, the prescription is forwarded to a pharmacy. The pharmacist or his or her staff uses the prescription to fill one or more vials 20 or cassettes 950 with the prescribed medications 15. For each vial 20 or cassette 950, the pharmacy creates prescription information 80 corresponding to the type of medication 15 placed in that vial or cassette. This information 80 is written or otherwise applied to the memory device 60, 352-358 or 960 that is secured or otherwise applied to the appropriate vial 20 or cassette 950. This information 80 includes dosage and time frequency information for the particular medication 15 in that vial 20 or cassette 950. The pharmacy staff, a healthcare worker or patient then secures the separate and distinct vials 20 or cassettes 950 to the unitary lid 810, 860 or 910 assigned to or owned by that particular patient.

The medication containers 800, 850 and 900 hold and organize several vials 20 or cassettes 950. Each unitary lid 810, 860 or 910 has several ports 820, 870 or 920 for receiving the vials 20 or cassettes 950. Each port 820, 870 or 920 has one corresponding pair of sensors 115 or 374 for reading the information 80 contained in the memory device 60, 352-358 or 960 of the vial 20 or cassette 950. Each port 820, 870 or 920 also has one corresponding opening 830, 880 or 930 through which the medication 15 in corresponding vial 20 or cassette 950 is dispensed. Each container 800, 850 or 900 includes a control system 840, 890 or 990, respectively, that includes a processor 120 for controlling the operations of the container.

The processor 120 organizes the activation of the display(s) 132 and alarm(s) 134, 136 and 138 for instructing and alerting the patient when it is time to consume one of the prescribed medications 15 held by the container. When the vials 20 or cassettes 950 are secured to the unitary lid 810, 860 or 910, the processor 120 reads the prescription information 80 from the memory device 60, 352-358 or 960, and calculates the appropriate time to take each of the medications 15 contained in the several vials 20 or cassettes 950.

The computer processor 120 uses the prescribed dosing regimen information 82 and the timing device 145 to calculate or otherwise develop the prescribed times for taking each of the different medications 15 held in the container 800, 850 or 900. The processor 120 uses its timing device 145 to determine when the predetermined time or times to take one of the particular types of medication occur. The computer processor then informs the patient that it is time to take a dose of medication 15 via the display 132, indicator 136, or other various alarms 134 and 138. Information 80 is also communicated to the processor 120 and memory 60, 125 via electrical contacts or via an RF or magnetically coupled link.

When the processor 120 determines that at least one medication 15 is due, the processor issues an audible consumption alert using speaker 134. This alert can be in the form of a voice synthesized message that indicates the correct vial 20 or cassette 950 to access and amount of medication to consume. The processor 120 also instructs the LCD display 132 to show a message or the indicator light 136 to flash directly in front of the appropriate vial 20 or cassette 950 containing the prescribed medication 15 to be taken at this time, and the amount of that medication to take.

The control systems 840, 890 or 990 operate in much the same way as control system 114 to obtain consumption information. The vials 20 and cassettes 950 are secured and locked to the ports 820, 870 or 920 of the container 800, 850 or 900 by first access control mechanism 845, 895 or 995. Each vial 20 or cassette 950 has an opening 830, 880 or 930 for removing medication 15. The vial openings 830 or 880 are closed by door 835 or selector shaft 885. The door 835 or shaft 885 is locked closed 839 or 889 by a second access control mechanism 846 or 896. The blister cassette 900 prevents individual blister packs 975 from being pulled from opening 930 by second access control mechanism 996. At the appropriate prescribed time, the processor 120 sends electrical current to the second access control mechanism 846, 896 or 996 to unlock the door 835, selector 885 or blister packet 975.

Container 800 requires the appropriate access door 835 corresponding to the particular vial 20 containing the prescribed medication 15 to be moved to its open position 838 from its corresponding porthole 820 to remove medication. When the door 835 or selector shaft 885 is moved to its open position 838 or 888, the sensor 847 or 897 sends a signal to processor 120 indicating that the appropriate dose or doses of medication 15 has been removed and consumed. When the machine readable and writable memory device 60 is used, the processor 120 writes to or otherwise alters the memory strip 60 to note this consumption information 80.

The medication containers 800, 850 and 900 compare the several medications 15 contained in their vials 20 or cassettes 950 by comparing the information 80 in each of their corresponding memory strips 60. For example, the processor 120 references and compares the lists of contraindicated medications that are part of the medication information 84. Should the processor 120 determine that two or more types of medications 15 secured to the unitary lid 810, 860 or 960 are contraindicated, the processor will display an appropriate message on the display 132 or activate one of the alarms 134, 136 or 138 to communicate this to the patient. Every time a medication 15 is issued to a patient, the most recent list of contraindications is included in the memory strip 60 or 960 of the vials 20 or cassettes 950. A list of contraindicated medications can also be maintained in the memory 125 of the lid 810, 860 or 910.

The memory 125 of each organizer 800, 850 or 900 is loaded with information containing a list of medications for whom the particular patient is known to be allergic. The organizer 800, 850 or 900 will alert the patient or care giver if one of the vials 20 or cassettes 950 secured to the unitary lid 810, 860 or 910 contains medication identified as being one of the medications in the list of allergic medications. The list of allergic medications can be downloaded from a pharmacy workstation to the memory 125 prior to giving the unitary lid to the particular patient or their care giver. The list of allergic medications can also be downloaded from the memory device 60 or 960 of one of the vials 20 or cassettes 950 and secured to the unitary lid 810, 860 or 960. The processor 120 then compares each type of medication contained by the vials 20 or cassettes 950 secured to the unitary lid to the list of allergic medications to determine if one of the vials or cassettes contains an allergic medication. If an allergic medication is identified, the processor 120 indicates an appropriate message on the display 132 or activates one of the alarms 134, 136 or 138 to warn the patient or care giver that the particular patient is allergic to one of the types of medications contained in one of the vials 20 or cassettes 950.

When medications are prescribed for consumption in paired dosing regimens, this information is noted by the pharmacy on the memory strip 60 or 960, and communicated to the processor 120 when the vial 20 or cassette 950 is secured to the unitary lid 810, 860 or 960. The memory strip 60 or 960 contains information identifying that this type of medication 15 is prescribed for use with an other type of medication. The memory strip 60 or 960 also contains information identifying this other type of medication. The processor 120 uses the prescription information 80 of both memory strips 60 or 960 to determine an appropriate medication schedule such as drug A on Monday, drug B on Tuesday, drug A on Wednesday, etc. The organizer 800, 850 or 900 alerts the patient via the display 132 or audible alarm 134 if one paired medication is attached to the organizer, but the other is not. The processor 120 checks the information received from the various memory devices 60 or 960 of the vials 20 or cassettes 950 secured to the unitary lid 810, 860 or 969 to ensure that vials or cassettes containing both types of paired medications 15. The processor 120 displays an appropriate message on the display 132 or activates an alarm 134, 136 or 138 if information identifying both types of paired medications 15 have not been received.

Each organizer 800, 850 or 900 contains medication prescribed or otherwise intended for a particular individual. The organizer 800, 850 or 900 will alert that individual if one of the vials 20 or cassettes 950 secured to the unitary lid 810, 860 or 910 contains medication intended for an individual other than this particular individual. For example, if one family member inadvertently secures the vial 20 or cassette 950 containing one type or strength of medication prescribed for another family member to their unitary lid 810, 860 or 910, the container 800, 850 or 900 will alert the individual of this fact. The memory device 60 or 960 of each vial 20 or cassette 950 contains information that identifies the particular person for whom the medication is prescribed or prescribed person information. The memory 125 of the unitary lid 810, 860 or 960 is provided with particular patient information that identifies the person that should be using the unitary lid. The particular patient information can be downloaded from a pharmacy workstation to the memory 125 prior to giving the unitary lid to the particular patient or their care giver. The particular patient information can also be downloaded from the memory device 60 or 960 of a first vial 20 or cassette 950 secured to the unitary lid 810, 860 or 960. In this case, the particular patient information is the same as the prescribed information contained in the memory device 60 or 960 of that first vial 20 or cassette 960 secured to the unitary lid 810, 860 or 960. The computer 120 then compares the particular patient information to the prescribed patient information to determine if they identify the same patient. If the two sets of patient information do not identify the same patient, the processor 120 indicates an appropriate message on the display 132 or activate one of the alarms 134, 136 or 138 to warn the patient or care giver that the particular type of medication in the vial 20 or cassette 950 is not intended for this particular patient.

When the processor 120 determines that two different medications 15 are to be taken at the same time, the organizer 800, 850 or 900 signals the indicator 136 to flash or the display 132 to indicate a message instructing the patient to consume the proper amount of each medication. The processor 120 instructs the patient to take one type of medication 15 at a time. The patient is alerted to each appropriate prescribed medication in sequence. This sequencing avoids telling the patient to simultaneously obtain two pills from a first vial 20 or cassette 950 and one pill from a second vial or cassette. Many patients may get confused and dispense them in the opposite quantities. With respect to container 800, since in the patient is removing the medication via the access doors 835, they may accidentally remove too many pills from each door, and return them to the wrong vial 20.

As in container 10, the containers 800, 850 and 900 include buttons 160, 162, 164 and 166 that electro-mechanically communicate information to the processor 120. By pressing one of the buttons, the patient is able to send an electrical signal to the processor 120 in response to a question shown on the display 132 or to indicate an action to be taken, such as turn off or deactivate an alert or alarm 134 or 136. Other buttons are located on the bottom surface 815, 875 or 915 of the lid 810, 860 or 910 to enable the patient to set the correct date, hour and minute of the real time clock 145 that is in electrical communication with the processor 120 via the circuit board 130.

Eighth Embodiment

Figures 35, 36, 36A:
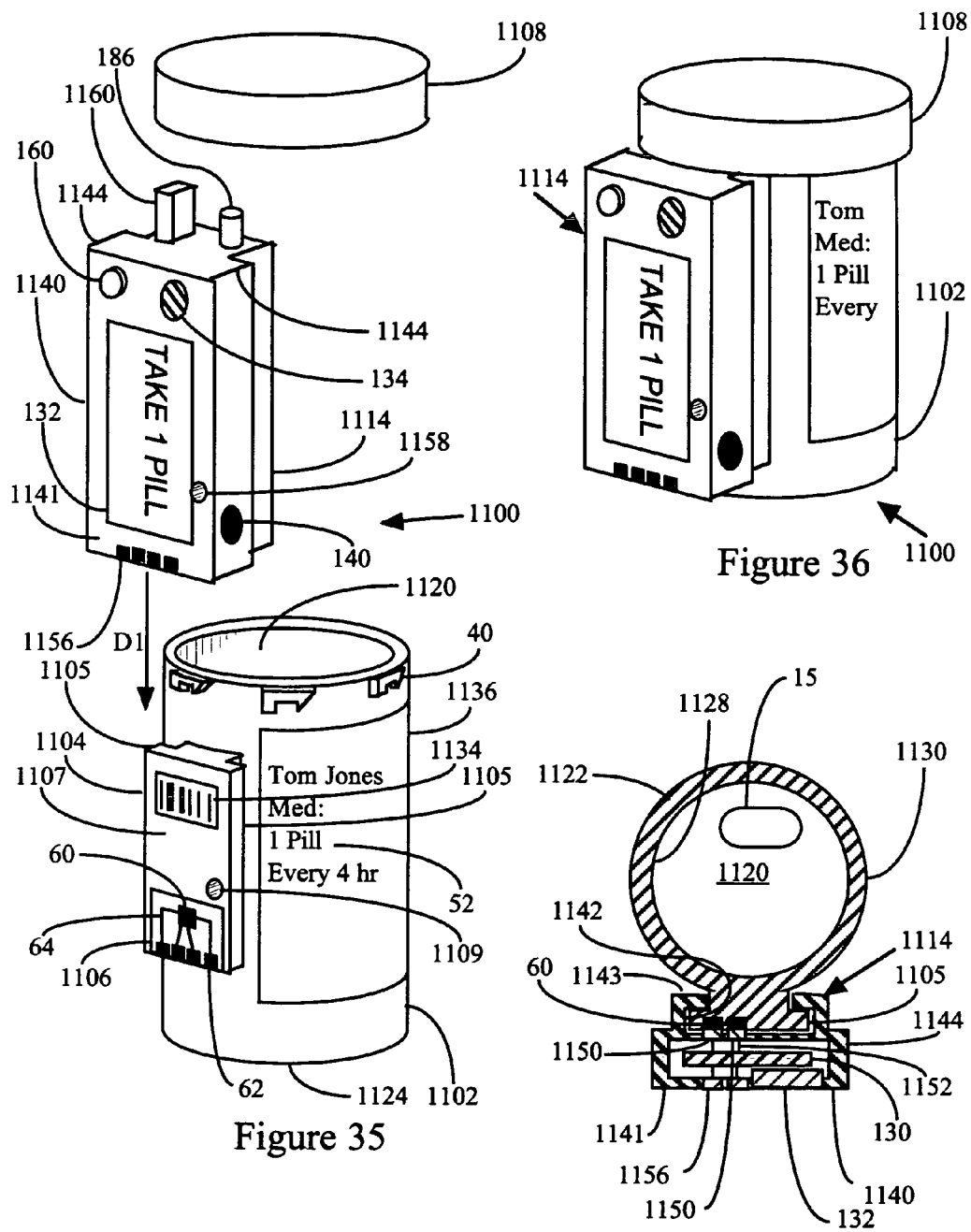
FIG. 35 is a perspective view of an eighth embodiment of the present medication container invention consisting of a cylindrical vial with an interactive label having an electronic memory strip, a removable cap that seals the open end of the vial and an automated reminder unit that mates to the vial.
FIG. 36 is a perspective view of the eighth embodiment of the present invention where vial, reminder, and cap of the medication container are secured together.
FIG. 36a is a cross sectional, plan view of the eighth embodiment of the invention showing the vial mated to the reminder unit, so that the electrical contacts of the reminder unit are in physical contact with the electrical contacts of the memory strip of the interactive label.
Figure 37:
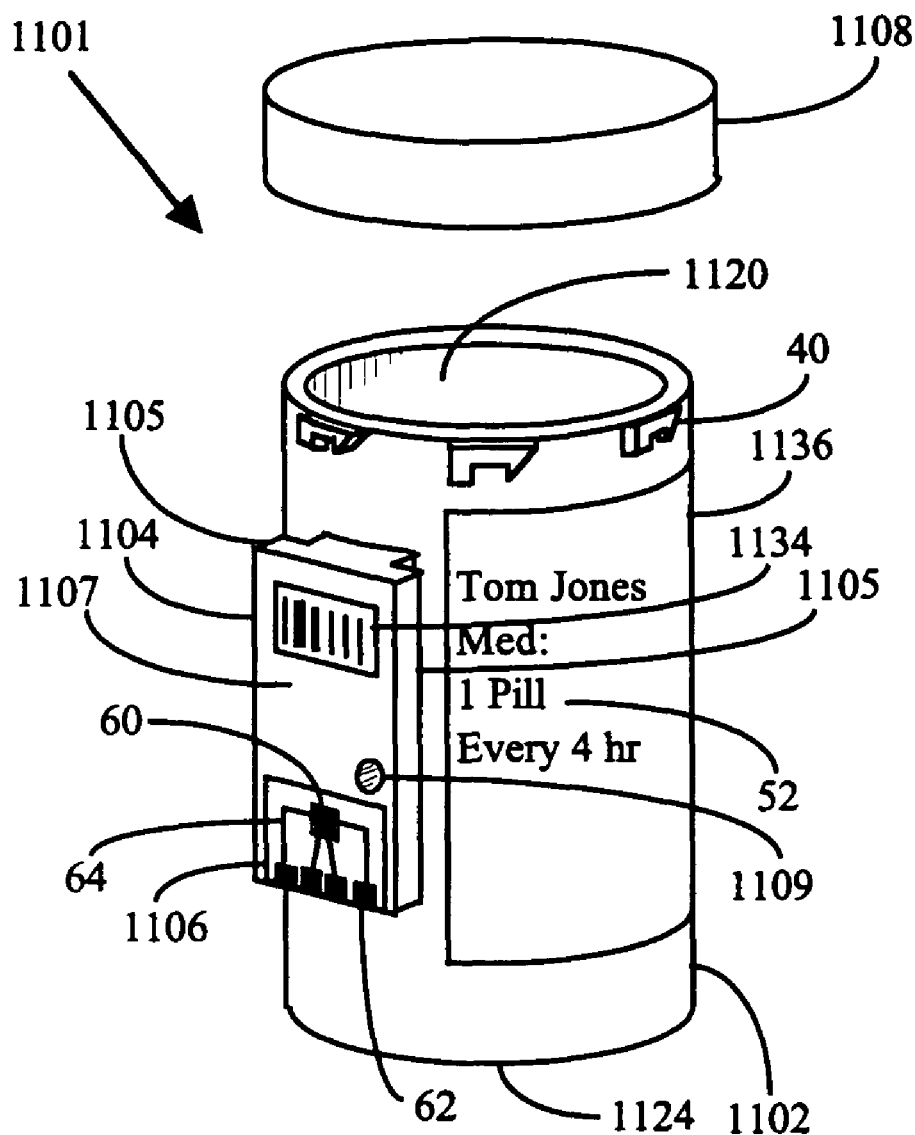
FIG. 37 is a perspective view of the eighth embodiment of the invention without a reminder unit.
Figure 38:
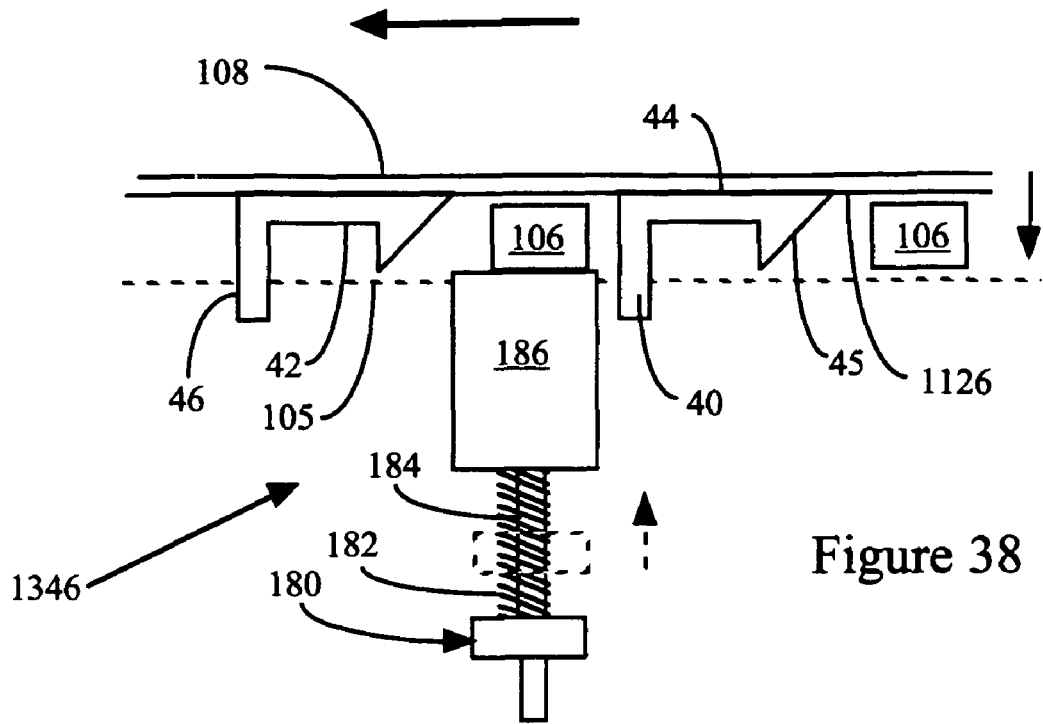
FIG. 38 is an enlarged, diagrammatic view of a portion of the reminder unit when mated to the vial so that it is positioned under the cap, the armature of the locking mechanism of the reminder engaging the bottom of one hold down lug of the cap and aligned between the securement ratchets of the vial.
Figure 39:
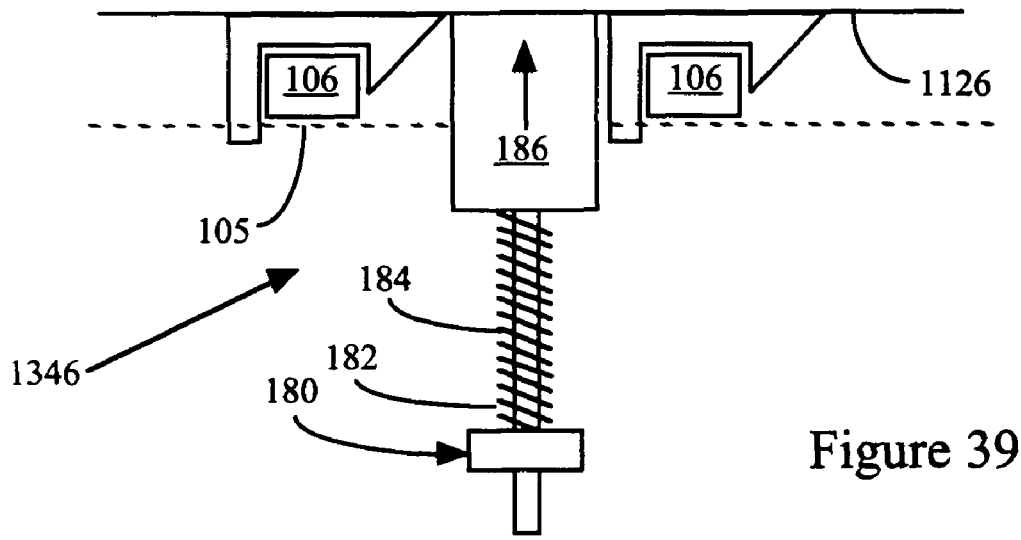
FIG. 39 is an enlarged, diagrammatic view of a portion of the reminder unit in a locked position on the vial, the armature of the locking mechanism of the reminder unit received between the securement ratchets of the vial, and the hold down lugs being received in the cup of its respective securement ratchet.

Much of the construction and operation of the eighth embodiment is similar or identical to the first and other above embodiments in construction and operation. For this reason only the distinctions between the eighth embodiment and the previous embodiments will be described here in detail. Some of the operational aspects of the eighth embodiment also apply to the earlier embodiments. In FIGS. 35-39 elements that are similar to elements described in the previous embodiments use similar numbers. For example a processor identified by the numeral 120 is identified by the same numeral in the eighth embodiment FIGS. 35-37 show an eighth embodiment of the invention where container 1100 includes a vial 1102 with an alignment plate 1104 with an exposed front surface 1107 supporting an interactive label 1106 and a cap 1108 that releasably mates to vial 1102. Plate 1104 is designed to include two side rails 1105 which project laterally from plate and are shaped so plate 1104 can be releasably mated with sensing or reminder unit 1114 comprised of computer processor 120 which when mated to plate 1104 is able to read stored information 80 on label 1106 to control a variety of alarms and visual display. Plate 1104 further includes locking aperture 1109 discussed below. When reminder unit 1114 is mated to container 1100, it forms a completed assembly. When the reminder unit 1114 is left off, the container is referred to as container 1101.

Vial 1102 includes compartment 1120 defined by cylindrical wall 1122, a closed bottom end 1124, and an open top end 1126. Medication 15 is inserted into and removed from compartment 1120 via the open end 1126 of the vial 1102. The cylinder has an inner surface 1128 and an outer surface 1130. The vial 1102 is made of a unitary plastic similar to other conventional vial-type containers. Plate 1104 can be part of vial 1102 or a separate piece attached or adhered to outer surface 1130 or vial 1102.

Vial 1102 has several securement ratchets 40 for securing and sealing the cap 1108 against the open end 1126 of the vial. The ratchets 40 are evenly spaced around the open end 1126, and protrude from the outer surface 1130 of the vial 1102. The ratchets are similar to those found on conventional childproof medication containers as in FIG. 1. The ratchets are more fully described in the first embodiment. Other methods of closing vial 1102 are contemplated, for example a lid attached to vial 1102 by a living hinge.

Vial 1102 includes interactive label 1106. The label is affixed to plate 1104 and may be constructed similar to interactive label 50 described above however it no longer has textual portion 52. Interactive label 1106 includes an electronic machine readable memory 60. Memory 60 is linked to external electrical contacts 62 via links or electrical wires 64. Memory 60 contains information 80. It is contemplated that memory 60 can include writable segments. In some applications interactive label 1106 can be replaced or augmented with a machine readable bar code 1134. When plate 1104 is adhered to vial 1102 it is placed so as not to obscure textual portion 52 of label 1136. Similarly, when plate 1104 is an integral part of vial 1102 and memory contacts 62 require physical contact in order to allow memory 60 to be read, label 1136 is positioned so as not to cover contacts 62.

Reminder unit 1114 includes housing 1140 with a front 1141 and rear 1143. The rear 1143 shaped to include blind rear slot 1142 and housing side rails 1144. The rear surface of the reminder unit has exposed sensors or electrical contacts 1150. Reminder unit 1114 is attached to plate 1104 by positioning the unit above the top surface of the plate and aligning the opening of slot 1142 with rails 1105 and sliding the unit down in direction D1 until the unit is completely down so that the top of plate is resting against the upper surface of blind slot 1142. When so positioned electrical contacts 1150 of the unit are in contact with electrical contacts 62 of interactive label 1106 allowing processor 120 to read the contents of memory strip 60. While vial 1102 is attached to reminder unit 1114 by mating plate 1104 to slot 1142, other methods of attaching vial to reminder unit are contemplated so that sensors 1150 are aligned with contacts 62.

Other features of reminder unit 1114 are exposed electrical contacts 1156 and locking aperture 1158 on the front 1141 of housing 1140 whose use is discussed below.

As shown in FIG. 9, the reminder unit 1114 has a control system including computer processor 120 with its own memory 125. Processor 120 and memory 125 are located on and in electrical communication with a circuit board 130 located in reminder unit 1114 for protection, see FIG. 36. The processor 120 of circuit board 130 is electrically connected via conductors 1152 to exposed electrical contacts 1150 on the rear surface of housing 1140. The circuit board 130 electrically connects the processor 120 to a visual communication device such as an LCD display 132. The LCD display 132 visually displays desired information to the patient, such as the date and time the next dose of medication is to be taken and the number of pills to be taken. The display 132 can also indicate an access alert or warning to the patient, such as the fact that the patient is so overdue in taking a dose of medication that that dose should no longer be taken. The circuit board 130 also electrically connects the processor 120 to a variety of alarming devices such as audible, visual and vibrational communication devices or alarms 134, 136 and 138, respectively. These alarms 134, 136 and 138 indicate a variety of warnings to a patient, such as when it is time to take a dose of medication. The circuit board 130 also electrically connects the processor 120 to a communication device such as an infrared transmitter 140 that transmits information to or receives information from a separate personal or business computer 270 as discussed above. Circuit board 130 also electrically connects processor 120 to a cap sensor 1160, such as a switch, to detect when cap 1108 is removed and replaced on vial 1102. Other sensors are contemplated such as magnetic detectors, photo detectors, and electrical contacts.

As shown in FIGS. 36 and 9, the circuit board 130 is in electrical communication with a power source 150, such as a battery or solar cell, that powers the processor 120, the display 132, alarms 134, 136, and 138, transmitter 140 and a timing device such as a real time clock 145.

The circuit board 130 is in electrical communication with a button 160 for electro-mechanically communicating information to the processor 120. (See FIG. 35). By pressing button 160, the patient is able to send an electrical signal to the processor 120 in response to a question shown on the display 132 or to indicate an action to be taken, such as turn off an alert or alarm. Additional buttons (not shown) or a touch screen membrane (not shown) for display 132 can be provided to enable the patient to set the correct date, hour and minute of the real time clock 145 that is in electrical communication with the processor 120 via the circuit board 130. The computer processor 120 uses the prescribed dosing regimen information 82 and the timing device 145 to calculate or otherwise develop the prescribed times for taking the medication 15. Computer processor 120 monitors timing device 145 to determine when the predetermined times to take the medication occur. The computer processor then informs the patient or individual that it is time to take a dose of medication 15 via the display 132 or an alarm 134, 136 or 138.

As shown in FIG. 35, reminder unit 1114 further includes an access control device formed by the computer processor 120 and a device such as solenoid locking mechanism or assembly 180 that is in electrical communication with the processor via the circuit board 130. The locking assembly 180 controls the patient's ability to access and remove the medication 15 from the vial 20 until the time the next dose of medication is due according to the prescribed dosing regimen. The assembly 180 includes an armature 182 and a spring 184 for biasing a plunger 186 into a normal, extended position as shown in solid lines in FIGS. 38 and 39. As explained above, to seal the vial 1102, the cap 1108 is first aligned with open end 1126 of the vial so that the hold down lugs 106 are positioned above and in between the ratchets 40 of the container. (See FIG. 38). The cap 1108 is then depressed into a removably aligned position over the open end 1126 so that the lugs 106 move directly between the ratchets 40. The plunger 186 contacts the lower surface of a hold down lug 106 which causes spring 182 to compress. The cap 1108 is then rotated clockwise into its secured position where each hold down lug 106 rests in the cup 42 of its respective ratchet 40. When in this secured position, plunger 186 clears the side 46 of the ratchet 40 so that spring 184 biases the plunger into its normal, extended position. Attempts to remove the cap 1108 by rotating it counterclockwise are resisted by plunger 186, which abuts the side 46 of the ratchet 40. The cap 1108 is now locked into its secured position. The processor 120 is programmed to activate the solenoid locking assembly 180 to draw down the armature 182 and plunger 186 when the next medication dosage is due to be taken. Only then can the cap 1108 be rotated counterclockwise and removed.

As previously described memory strip 60 can have its own processor 120. The memory strip 60 is directly wired to processor 120 and serves as the memory of the processor. The memory 125 in the reminder unit 1114 is eliminated. This saves the costs associated with producing two memory devices, without compromising the disposability of vial 1102. It is contemplated that as other components of reminder unit 1114 are reduced in cost that they can be mounted on plate 1104 or interactive label 1106. Similarly the components of cap 100 can be placed on interactive label 50 or vial 20 as they become affordable to dispose of.

Operation of Eighth Embodiment

When the reminder unit 1114 is mated to the container 1100, the control system is complete. The contacts 1150 of the rear 1141 wall of housing 1140 are in electrical contact with the contacts 62 of the memory strip 60, and the information 80 in the memory strip is in electrical communication with or can otherwise be read by the processor 120 in the reminder unit. Predetermined portions of information 80 from the memory strip 60 are used to compute the next prescribed time for taking a dosage of medication 15 and activate an alarm or otherwise communicate that information to the patient when that time occurs. The reminder unit 1114 will keep an accurate count of the number of times the medication container is opened each day and advise the patient against consuming too many pills in too short a time. This is particularly useful for medications 15 that are prescribed to be used on an as needed basis (e.g. pain medication), but not to be consumed more than a certain amount in any given day.

Reminder unit 1114 activates an alarm to indicate that some of the medication in container 1100 is to be consumed. The patient can remove cap 1108 from vial 1102 in response to the alarm. By momentarily pressing button 160 the patient can disable the alarm. Based on this user action, the time from clock 145 and information 80, processor 120 computes the next prescribed time for taking a dosage of medication 15 and activating an alarm at that time. To track patient compliance with the dosing regimen, the processor 120 can obtain the time the user pressed button 160 from clock 145 and record it in memory 60 or 125.

As a convenience to the patient they may press button 160 for a longer period of time to temporarily cancel the current alarm for a period of time, for example 15 minutes, when it is more convenient for the patient to consume the medication. The patient by pressing button 160 twice or by pressing a separate button (not shown) can cancel the alarm indicating to the processor that the current dose is going to be skipped. Processor 120 then computes the time of the next dose of medication 15 is to be consumed and activating an alarm then. Processor can record the time of the canceled alarm in memory 60 or 125 for compliance tracking purposes.

When button 160 is pressed to indicate a dose of medication has been consumed processor 120 uses information 80 to subtract the prescribed amount of medication to be consumed from the quantity of medication remaining in container 1100 to keep an accurate track of the current supply of medication. The user may be prompted using display 132 to use button 160 or other buttons (not shown) to indicate how many pills were actually consumed should it differ from prescription information 82. The user provided number is then used to maintain the quantity of medication remaining in container 1100.

Alternately processor 120 can use sensor 1160 to sense when the patient removes or replaces cap 1108 from vial 1102 and use the input from sensor 1160 to disable the alarm. Based on this user action, the time from clock 145 and information 80, processor 120 computes the next prescribed time for taking a dosage of medication 15 and activating an alarm at that time. To track patient compliance with the dosing regimen, the processor 120

Can obtain the time sensor 1160 indicated cap 1108 was removed or replaced, from clock 145 and record it in memory 60 or 125. Button 160 can still be used to temporarily disable or to cancel the alarm as mentioned above.

It should be noted that when the time of dosing is written to memory 125 and not to memory 60, then memory 60 can be read only or can be replaced by bar code 1134 holding information 80 and contacts 1150 can be replaced by a bar code reader (not shown).

In some cases it is desirable that medication 15 be consumed proximal but before a consumption alert is presented. In this case, button 160 can be pressed three times or another button (not shown) can be depressed to indicate to processor 120 that a dose of medication has been consumed. When sensor 1160 is used, processor 120 can use a signal from sensor 1160 and the clock 145 to indicate that medication is being consumed early. Dosing regimen 82 or program codes 86 can be used to determine that medication 15 can be consumed up to specific amount of time (e.g. 2 hours) prior when an alert is to be presented. In this case, reminder 1114 can acknowledge that medication 15 is being consumed and processor 120 can cancel the next alert that was to be presented and computing the second next consumption time to be used for presenting a consumption alert. In this case, the processor can record the consumption time in memory 60 or 125. However, if processor 120 determines that the medication is being consumed too early (e.g. 3 hours before an alert), processor can use devices 132, 134, 136, 138 to indicate that the medication is being consumed too early. It should be noted that when sensor 1160 indicates cap 1108 is removed and replaced in a short period of time (for example less than 5 seconds), processor 120 can interpret this as an attempt to visually inspect the quantity of medication in vial 1102 as opposed to a consumption event.

Ninth Embodiment

Figures 40, 41:
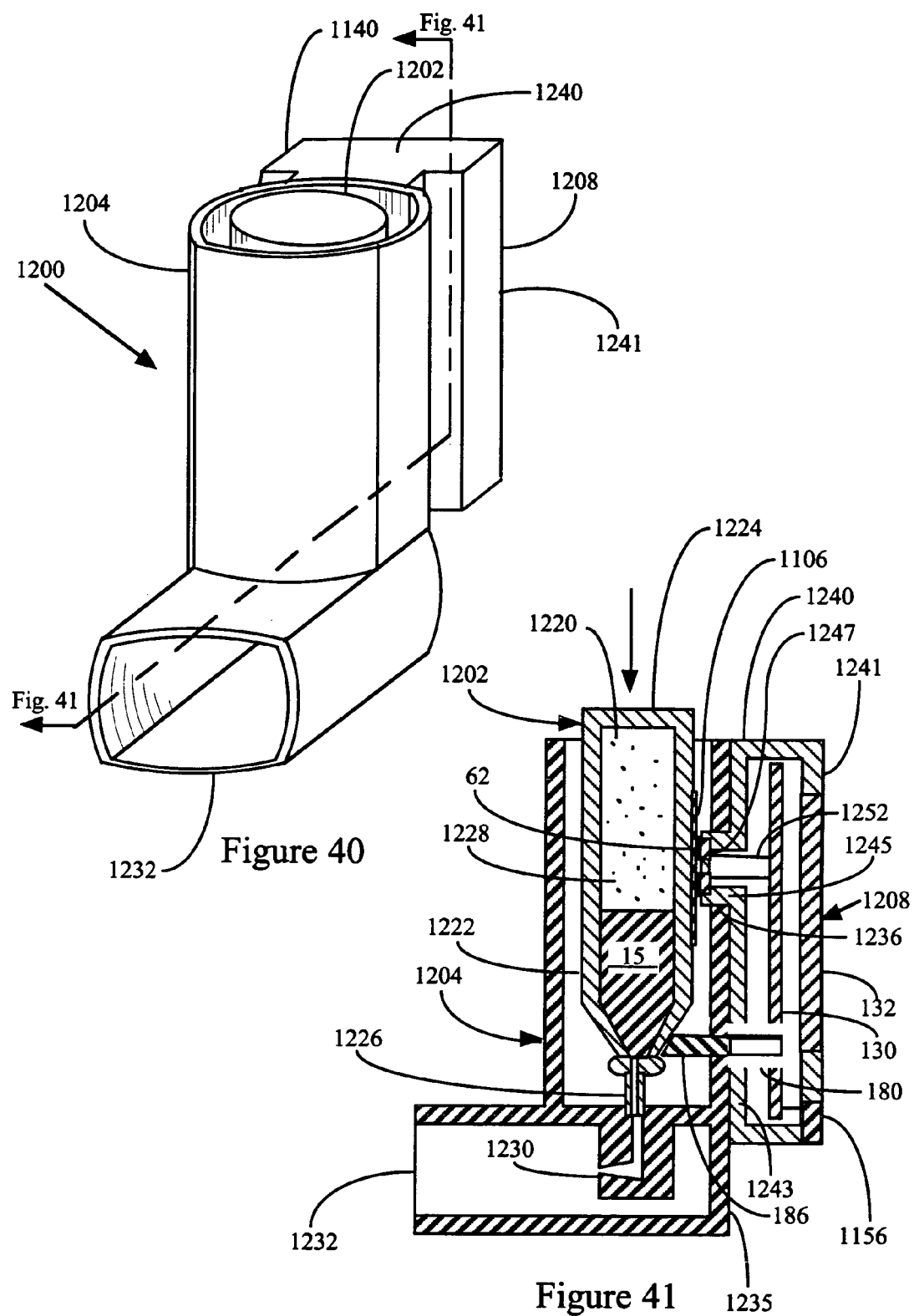
FIG. 40 is an perspective view of a ninth embodiment of the present medication container invention having of a pressurized cylindrical medication cartridge with an interactive label having an electronic memory strip, an aerosol inhaler dispenser, and an automated reminder unit that mates to the dispenser.
FIG. 41 is a cross-sectional view of the ninth embodiment of the invention showing the cartridge in the aerosol dispenser and the reminder unit mated to the dispenser, so that the electrical contacts of the reminder unit are in physical contact with the electrical contacts of the memory strip of the interactive label.

Much of the construction and operation of the ninth embodiment is similar or identical to the eighth and other above embodiments in construction and operation. For this reason only the distinctions between the ninth embodiment and the previous embodiments will be described here in detail. Some of the operational aspects of the eighth embodiment also apply to the earlier embodiments. In FIGS. 40 and 41 elements that are similar to elements described in the previous embodiments use similar numbers. For example a processor identified by the numeral 120 is identified by the same numeral in the eighth embodiment.

FIGS. 40-41 show a ninth embodiment of the invention where container 1200 is in the form of a medication inhaler, which includes an aerosol cartridge 1202 with an interactive label 1106, and an aerosol dispenser 1204. Dispenser 1204 can be releasably mated to sensing or reminder unit 1208 comprised of computer processor 120. When mated to dispenser 1204, reminder unit 1208 is able to read stored information 80 on label 1106 to control a variety of alarms and visual displays.

Cartridge 1202 is of a conventional design and includes a compartment 1220 defined by a generally cylindrical wall 1222, a closed bottom end 1224, and a valve top end 1226. Compartment 1220 holds medication 15 under pressure by a propellant 1228. Cartridge is placed in dispenser 1204 so that valve end 1226 mates with atomizer 1230. Medication is dispensed by exerting a downward force on cartridge 1202 causing the valve (not shown) of valve end 1226 to open momentarily. Propellant 1228 propels a dose of medication 15 through atomizer 1230. The patient inhales the atomized medication through delivery opening 1232.

As shown in FIG. 41 cartridge 1202 includes interactive label 1106. Interactive label 1106 is similar or identical to interactive label 50, and includes an electronic machine readable memory 60. Memory 60 is linked to external electrical contacts 62 via links or electrical wires 64. Memory 60 contains information 80. Contacts 62 may be constructed so as to extend around the cylindrical wall 1222, so cartridge 1202 can be placed in dispenser 1204 without concern about the orientation of contacts 62. It is contemplated that memory 60 can include writable segments. In some applications, interactive label 1106 is replaced or augmented with a machine readable bar code 1134. Bar code 1134 is printed as a series of horizontal stripes around cylindrical wall 1222, so cartridge 1202 can be inserted into dispenser 1204 in any orientation and bar code will still be read by a bar code reader (not shown) sensing the vertical changes in stripes (bars) as the cartridge is inserted.

Dispenser 1204 has a rear wall 1235 with opening 1236, exposing electrical contacts 62 of interactive label 50. Reminder unit 1208 includes housing 1240 with a front 1241 and rear 1243. The rear 1243 of reminder unity 1208 is contoured to fit the rear wall 1235. The rear 1243 also including a sensing projection 1245 with exposed sensors or electrical contacts 1247. Reminder unit 1208 is attached to dispenser 1204 by aligning projection 1245 with opening 1236 and pressing them together. A variety of methods can be used to secure reminder unit 1208 to dispenser 1204, such as a pressure fit between projection 1245 and opening 1236. When secured in place, electrical contacts 1247 of the unit are in contact with electrical contacts 62 of interactive label 1106 allowing processor 120 to read the contents of memory strip 60.

Other features of reminder unit 1208 are exposed electrical contacts 1156 and locking aperture 1158 on the front of housing 1240 as discussed below. This lock aperture 1158 is located in the same place as the aperture 1158 of housing 1140.

As shown in FIG. 9, the reminder unit 1208 has a control system including computer processor 120 with its own memory 125. Processor 120 and memory 125 are located on and in electrical communication with a circuit board 130 located in reminder unit 1208 for protection. (See FIG. 41). The processor 120 of circuit board 130 is electrically connected via conductors 1252 to exposed electrical contacts 1247 on the rear surface 1243 of housing 1240. Other electrical components of reminder unit 1208 are similar to those described in the seventh embodiment. The front 1241 of housing 1240 can be configured identically to front 1141 of housing 1140.

An access control device such as solenoid 180 can be implemented between reminder unit 1208 and aerosol dispenser 1204 to prevent access to medication 15 in cartridge 1202. For example, the dispenser 1204 includes ratchets 40 for securing a cap or cover 1108 to prevent access to cartridge 1202. While the form of such an access control device will differ in structure, the fundamentals of access control are well know to those knowledgeable in the art and will not be discussed further here.

Operation of Ninth Embodiment

When the reminder unit 1208 is mated to the dispenser 1204, the control system is complete. The contacts 1247 of the rear wall 1243 of housing 1240 are in electrical contact with the contacts 62 of the memory strip 60, and the information 80 in the memory strip is in electrical communication with or can otherwise be read by the processor 120 in the reminder unit 1208. Predetermined portions of information 80 from the memory strip 60 are used to compute the next prescribed time for taking a dosage of medication 15 and activate an alarm or otherwise communicate that information to the patient when that time occurs. The reminder unit 1208 will keep an accurate count of the number of times the medication container is opened each day and advise the patient against consuming too many aerosol doses in too short a time. This is particularly useful for medications 15 that are prescribed to be used on an as needed basis (e.g. pain or asthma medication), but not to be consumed more than a certain amount in any given day.

Reminder unit 1208 activates an alarm to indicate to that some of the medication in container 1200 is to be consumed. The patient presses cartridge 1202 down into dispenser 1204 to deliver a dose of medication 15 in response to the alarm. By momentarily pressing button 160 the patient can disable the alarm. The consumption indicator is triggered by either pressing the button 160 or cartridge 1202. Based on this user action, the time from clock 145 and information 80, processor 120 computes the next prescribed time for taking a dosage of medication 15, another alarm is activated at that time. To track patient compliance with the dosing regimen, processor 120 obtains the times the user depressed cartridge 1202 from clock 145 and records this actual consumption time information or compliance data in memory 60 or 125.

Alternately, processor 120 uses electrical contacts 1247 to sense when the patient administers a dose of medication 15 from container 1200. Processor 120 is normally in communication with memory 60. When the patient presses cartridge 1202 down in aerosol dispenser 1204 to dispense a dose, communication is interrupted by the movement of contacts 60 causing electrical contacts 1247 to no longer be in electrical contact with contacts 60. A separate sensor such as a switch or other contacts arranged to detect this motion (not shown) can be used to detect or sense the depression of the cartridge 1202. When the processor 120 is no longer in communication with memory 60, it disables the alarm. Based on this user action, the time from clock 145 and information 80, processor 120 computes the next prescribed time for taking a dosage of medication 15. Another alarm is activated at that time. To track patient compliance with the dosing regimen, processor 120 obtains the times the user depressed cartridge 1202 from clock 145 and records this actual consumption time information in memory 60 or 125. Button 160 can still be used to temporarily disable or to cancel the alarm as mentioned above.

It should be noted that when the time of dosing is written to memory 125 and not to memory 60, then memory 60 can be read only or can be replaced by bar code 1134 holding information 80 and contacts 1150 can be replaced by a bar code reader (not shown).

Tenth Embodiment

Figure 42:
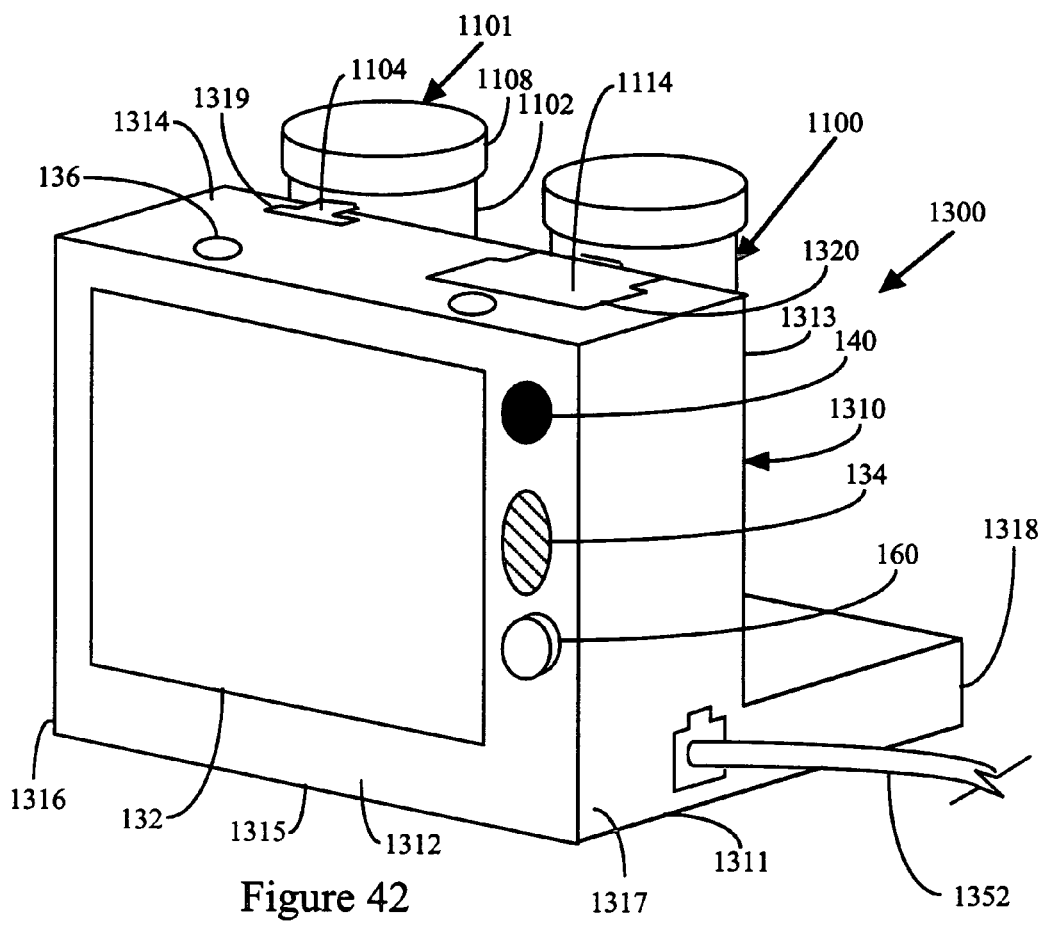
FIG. 42 is a perspective view of a tenth embodiment of the present medication container invention including several vials of medication secured to a unitary console or dispenser, each vial having its own machine readable information strip, and the dispenser having a separate indicator light, display and mating slot for each vial.
Figure 43:
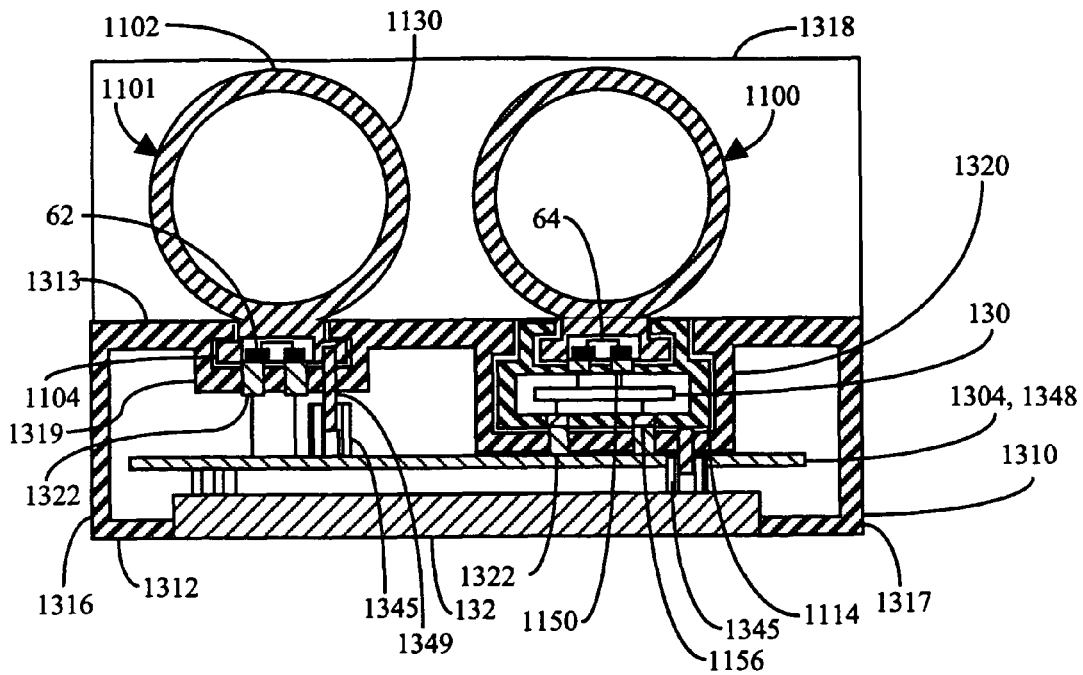
FIG. 43 is a plan cross-sectional view of the multi-vial medication container of FIG. 42 with one vial secured to an associated slot of the unitary console or dispenser and one vial with mated reminder unit secured to a separate associated slot of the of the reminder unit.
Figure 44:
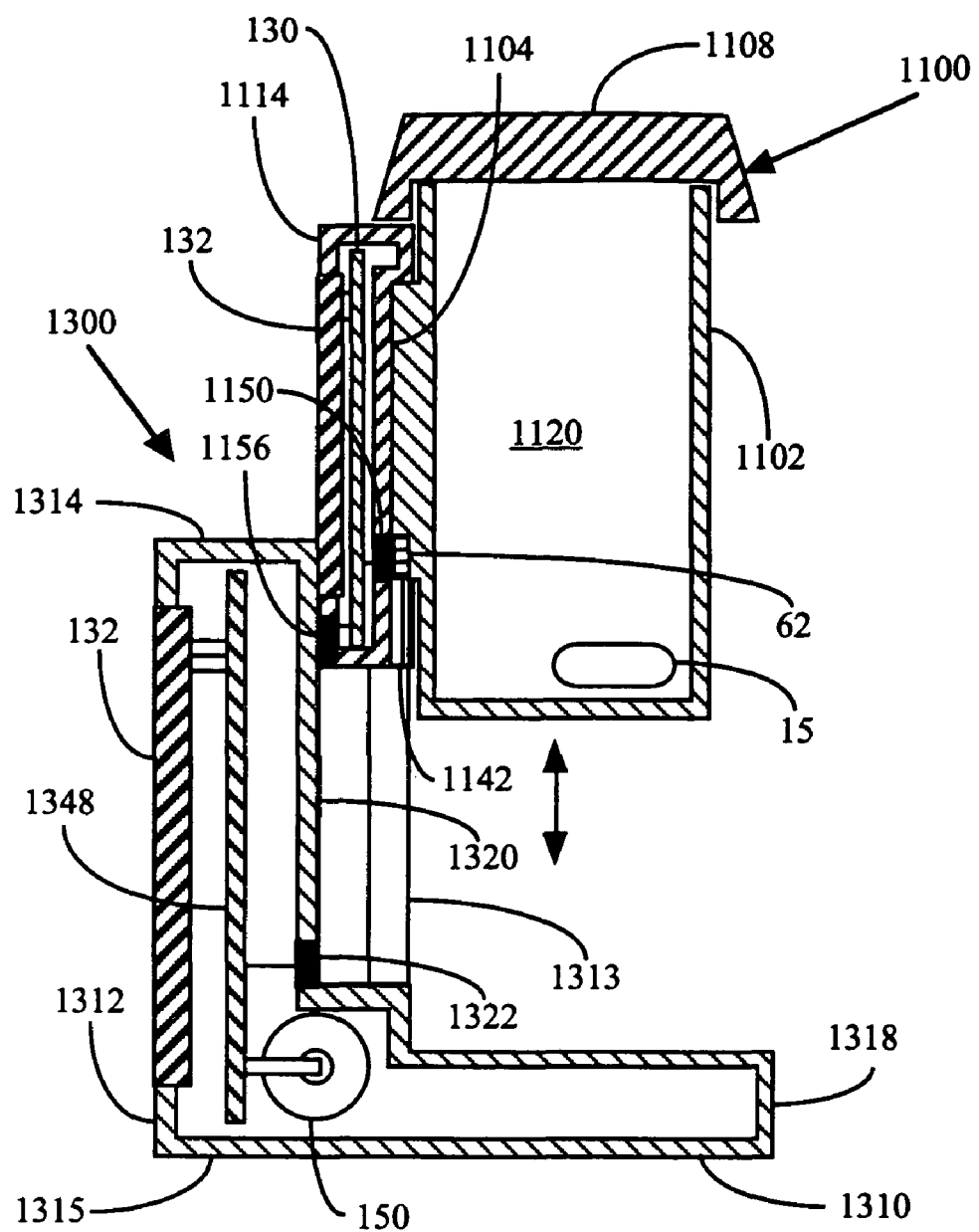
FIG. 44 is a side cross-sectional view of the multi-vial medication container of FIG. 42 with one vial and mated reminder unit secured to an associated slot of the unitary dispenser.

Much of the construction and operation of the tenth embodiment is similar or identical to the fifth, sixth, eighth and other above embodiments in construction and operation. For this reason only the distinctions between the tenth embodiment and the previous embodiments will be described here in detail. In FIGS. 42-44 elements that are similar to elements described in the previous embodiments use similar numbers. For example a processor identified by the numeral 120 is identified by the same numeral in the fifth embodiment.

This embodiment of the invention entails a medication organizing system 1300 for interacting with containers 1100 and 1101 or dispenser 1200. Other containers with either a compatible plate 1104 or reminder unit 1114 or 1208, with side rails 1144, may also be mounted to organizer 1300. For purposes of brevity, most of the description will only discuss the use of container 1100 being mated to organizing system 1300 unless a differing aspect not common to container 1100 is being described.

Physical Elements

FIG. 42 shows the medication organizing system 1300 for several different types of medication. The organizing system 1300 includes at least one container that is the same as or similar to container 1100, 1101 or dispenser 1200. Each particular container 1100, 1101 or dispenser 1200 is removably secured to a console or unitary dispenser 1310 as discussed below. Each particular container 1100 is equipped with its own corresponding interactive label 1106 and machine readable and writable memory strip 60. However, it should be understood that in this embodiment of the invention, the label 1106 need not be interactive. The machine readable and writable memory strip 60 can be replaced by a memory device that is only machine readable. For example, memory strip 60 and its contacts 62 and wires 64 can be replaced by the several conductive/non-conductive or reflective/non-reflective surfaces and ground surface 352-358 of container 300, or by a conventional bar code 1134 applied to the surface of the label 50.

Dispenser 1310 includes a housing 1311 with front 1312, rear 1313, top 1314, bottom 1315, end surfaces 1316 and 1317, and rear support foot 1318. Arranged along the rear 1313 of top 1314 are one or more ports 1319 and 1320 in the form of blind slots. Slots 1319 are designed to mate with plate 1104 of container 1101 or with any other container with a similarly designed plate 1104. Container 1101 is positioned above an empty slot 1319 of dispenser 1310, so the rails 1105 of plate 1104 can mate with the slot. The container 1101 is then slid downward so plate 1104 is fully engaged in slot 1319. When so positioned, contacts 62 are in contact with contacts 1150 of dispenser 1310 and processor 1378 can read memory 60.

Each of slots 1320 is designed to mate with the reminder units 1114 or 1208 of containers 1100 and 1200 in a manner similar to the mating of plate 1104. Slot 1320 is sized to receive and capture side rails 1144. Again when containers 1100 or 1200 are mated to dispenser 1310 medication information 80 contained in memory 60 can be accessed by processor 1378 via contacts 1322 making contact with contacts 1156. Other containers with a reminder unit with similarly designed rails 1144 can also be used. Other methods of mating containers to dispenser 1310 are contemplated. It is also envisioned that rails 1144 can be the same size as rails 1105 to allow reminder units 1114 and 1208 to mate with slot 1319 and placing contacts 1156 in electrical contact with contacts 1150.

When the container 1100 is secured to the dispenser 1310, medication 15 can be removed from the container 1100 by removing the container from the corresponding slot 1319 and removing cap 1108 in the conventional manner. When the container 1100 is secured to the dispenser 1310, medication 15 can be removed from the container by first removing the container from the corresponding slot 1119 or 1320 and removing cap 1108, or using the dispenser 1200, in the manner appropriate for the eighth and ninth embodiments.

The each slot 1319 and 1320 has a latch access control device such as solenoid 1345 with plunger 1349. Medication 15 can be sealed in the container 1100 when the container is secured to the dispenser 1310 and the plunger 1349 is in its extended position (See FIG. 43). Medication 15 is removed from one of the containers 1100 by retracting the appropriate plunger 1349.

Alternate Placement of Container 1100

While a specific alignment plate with interactive label 1106 has been shown mating container 1100 to dispenser 1310, other methods are contemplated. For example vial 1102 does not need to have plate 1104. Instead the vial 1102 can have interactive label 1106 encircle the vial, allowing contacts 62 to also encircle vial 1102. Contacts 62 are arranged as a series of stripes. Slot 1319 of dispenser 1310 is then replaced by a round hole sized to fit vial 1102. Container 1101 with vial 1102 is placed in the hole so that contacts 1150 are in electrical contact with contacts 62. Alternately, the contacts 62 can be arranged in a single vertical row, without encircling vial 1102. Contacts 1150 are arranged as circular members on the inside of the hole in dispenser 1310. When the vial is placed in the hole, contacts 1150 are in electrical contact with contacts 62. Other means of physically or logically associating container 1100, 1101 are contemplated

Control System

As shown in FIG. 28, the dispensing system 1300 includes a control system 1340 that is similar to the control system 114 of cap 100 shown in FIG. 9. The control system 1340 is broken into two subsets of components 1341 and 1342. The components forming these two subsets 1341 and 1342 are the same types of components as in control system 114. The first subset 1341 has a one-to-one correlation between components in system 114, and includes computer processor 1304, memory 1306, audible and vibratory alarms 134 and 138, real time clock 145, battery 150, a single display 132, such as an LCD, and buttons 160, 162, 164 and 166. Subset 1341 also includes a radio frequency (RF) paging receiver 1343 for receiving necessary changes in the prescribed dosing regimen. Receiver 1343 can include a transmitter for two way radio communications so patient compliance data can be transmitted to a healthcare provider and to allow the dispenser 1310 to reorder medication from a pharmacy, for example the pharmacy listed in information 80. Receiver can be replaced with telecommunications modem or Ethernet adapter 1350 and attached cable 1352 to access the conventional Internet computer network.

The second subset 1342 has at least one set 1344 of components including one sensor 1150, and one indicator light 134 for each slot 1319 and 1320 in the dispenser 1310. Each set 1344 also includes first control device 1345 and a second access control device 1346. The indicator 134 of a particular set 1344 is located directly in front of the particular slot 1320 and container 1100 for that set. The circuit board 1348 to which the components of subsets 1341 and 1342 are linked to processor 1304 is somewhat larger than the board in cap 100 or reminder unit 1114 due to the increase in number of components and the spacing apart of the various sets 1344 of components along the length of the dispenser 1310.

Reading Information 80

FIG. 43 shows slot 1319 mated to vial 1102 of container 1100, equipped with machine readable and writable memory strip 60 and contacts 62. The sensors 1150 are located on the inside surface of each slot 1319. When the container 1100 is secured to its particular slot 1320, the contacts 62 are in electrical communication with the sensors 1150 for that slot. As stated above, the memory strip 60 can be replaced by a memory device that is only machine readable. For example, the vial can be equipped with conductive/non-conductive or reflective/non-reflective surfaces 352-358 as in FIG. 16 or bar code 1134 of FIG. 32. When the vial 1102 is equipped with the conventional bar code in lieu of memory strip 60, the sensors 1150 are optical sensors that read the bar coded information when the vial 1102 is slid into one of the slot 1320.

When container 1101 is mated to dispenser 1310 contacts 1150 are in electrical contact with contacts 62, allowing processor 1304 to read the contents of memory 60. When container 1100 or 1200 is mated to dispenser 1310 contacts 1156 are in electrical contact with contacts 1322, allowing processor 1304 to read memory 60 of interactive label 1106. The processor 1304 is in communication with memory 125 of processor 120 of reminder unit 1114 or 1208.

Access Control System

As shown in FIG. 28, the control system 1340 is equipped with two access control devices 1345 and 1346. These devices 1345 and 1346 are similar in design to solenoid locking assembly 180. Control device 1345 locks the container 1101 to dispenser 1310 by extending plunger 1349 into lock aperture 1158 of plate 1104 until a predetermined time, such as when the vial is empty. The first access control device or vial locking solenoid assembly 1345 and plunger 1349 serves to retain container 1101 to dispenser 1310 until a dose of medication is to be consumed. A similar solenoid assembly (not shown) can be used to secure container 1100 or 1200 to dispenser 1310 until a dose of medication is to be consumed. The second access control device or solenoid assembly 1346 locks the cap 1108 in its closed position (See FIG. 39) to prevent the removal of medication 15 until the prescribed time to take the particular medication contained in the corresponding container 1101. This second access control device 1346 includes a solenoid and plunger assembly (not shown) similar to solenoid locking assembly 180. Alternately, the access control device 1346 can be a fixed projection that prevents cap 1108 from being removed from vial 1102 when the container 1100 is attached to dispenser 1310. When the processor 1304 uses information 80 contained in the information strip 60 of plate 1104 and the clock 145 to indicate that the prescribed dose of medication in a particular vial or container is due, the processor 1304 sends electric current to the solenoid of assembly 1345 to withdraw plunger 1349 from engagement with the locking aperture 1109 so that containers 1100 or 1101 or dispenser 1200 can be removed from unitary dispenser 1310.

When container 1101 is removed from dispenser 1310, contacts 1150 are no longer in contact with contacts 62 of interactive label 1106. Processor 1304 can no longer read memory 60 and thereby determine that vial has been removed from dispenser 1310. Other methods can be used to determine that a vial has been removed, such as a switch, photo detector, or magnetic sensor. The processor 1304 uses this to indicate that the prescribed dose of medication 15 is being taken from the corresponding container 110.

A similar process is used to unlock container 1100 or dispenser 1200 from organizer 1310 and determine that it has been removed. Processor 1304 can no longer detect the presence of the reminder unit 1114 via contacts 1322, which are not in electrical contact with contacts 1156.

Operation of Tenth Embodiment

The following is provided to assist the reader in understanding the operation of the preceding embodiment of the invention. Some of the operation of the tenth embodiment can also be applied to the previous embodiments.

Presenting Medication Consumption Alerts

When a medication is dispensed by the pharmacy, a pharmacy staff worker, a healthcare worker or a patient mates plate 1104 of container 1101 to one of the slots 1319 of dispenser 1310. Alternately, container 1100 can be mated to reminder unit 1114, or cartridge 1202 can be mated to aerosol dispenser 1204, and then either the reminder unit or aerosol dispenser is mated to a slot 1320 of dispenser 1310. It is further contemplated that other types and shapes of containers with plate 1104 or a reminder unit can be similarly attached to dispenser 1310, allowing it to be used with any form of medication the patient is to consume.

The dispenser 1310 holds and organizes at least one container 1100, 1101, or dispenser 1200. Each dispenser 1310 has at least one slot 1319 or 1320 for receiving the vials 1102 or reminder units 1114 or 1208. Each slot 1319 has one corresponding pair of sensors 1150 or 374 for reading information 80 contained in the memory device 60, 352-358, or 1134, any of which can be applied to vial 1102. Each slot 1320 has one corresponding pair of contacts or sensors 1322 for reading information 80 from reminder 1114 or 1208. Information 80 in turn having been read from memory device 60 by processor 120 of reminder 1114 or 1208 or directly by processor 1304 through linking contacts 1156 and 1150.

Processor 1304 organizes the activation of the display 132 and alarm 134, 136 and 138 for instructing and alerting the patient when it is time to consume one of the prescribed medications 15 held by the dispenser 1310. When container 1100, 1101 or dispenser 1200 is secured to the dispenser 1310, the processor 1304 reads the prescription information 80 from the memory device 60 or from processor 120 or memory 125 of reminder 1114 or 1208 and calculates the appropriate time to take each of the medications 15 contained that container 1100, 1101 or dispenser 1200.

The computer processor 1304 uses the prescribed dosing regimen information 82 and the timing device 145 to calculate or otherwise develop the prescribed times for taking each of the different medications 15 in container 1100, 1101, or dispenser 1200 mated to dispenser 1310. The computer processor 1304 monitors timing device 145 to determine when the predetermined times to take the medication occur. The computer processor 1304 then informs the patient that it is time to take a dose of medication 15 via one of the appropriate display 132, indicator 136, or other various alarms 134 and 138.

Information 80 can also be communicated to the processor 1304 from memory 60 via electrical contacts 1150 or via an RF or magnetically coupled link.

When the processor 1304 determines that at least one medication 15 is due, the processor issues an audible consumption alert using speaker 134. This alert can be in the form of a voice synthesized message that indicates the correct vial 1202, or reminder 1114 and vial 1102, or reminder 1208 and cartridge 1202 to access and the amount of medication to consume. The processor 1304 also instructs the LED display 132 to show a message or the indicator light 136 to flash directly in front of the appropriate slot 1319 or 1320 and container 1100, 1101 or dispenser 1200 with prescribed medication 15 to be taken at this time, and the amount of that medication to take.

The dispenser 1310 control system 1340 operates in much the same way as control system 114 to obtain consumption information. The container 1100, 1101 or 1200 can be secured and locked to slot 1319 or 1320 of the dispenser 1310 by first access control mechanism 1345 when processor 1304 extends plunger 1349 into locking aperture 1109 or 1158. When a medication is to be consumed the appropriate access control mechanism 1345 is activated by processor 1304 to withdraw plunger 1349 from locking aperture 1109 or 1158, allowing container 1100, 1101 or 1200 to be removed from dispenser 1310.

Medication's can be consumed before a consumption alert is presented. The consumption indicator (e.g., button 160), or other user input device, can be used to indicate that medication is to be consumed early. Dosing regimen 82 or program codes 86 can be used to determine for each medication 15 that it can be consumed up to specific amount of time (e.g. 2 hours) prior when an alert is to be presented. Dispenser 1310 acknowledges which medication 15 is to be consumed and processor 1304 will cancel the next alert that was to be presented, and computes the second next consumption time for presenting a consumption alert. In this case the processor can record the consumption time in memory 60, 125, 1306. However, if processor 1304 determines that the medication is being consumed too early (e.g. 3 hours before an alert), the processor uses devices 132, 134, 136, 138 to indicate that the medication is being consumed too early.

When container 1101 is removed from slot 1319 of dispenser 1310, the alert presented to the patient is canceled, the display still indicates the amount of medication the patient should consume. The processor 1304 detects the removal via sensors 1322. When the machine readable and writable memory device 60 is used the processor 1304 writes or otherwise alters the memory strip 60 to note this consumption information 80. Alternately, the consumption information can be written to memory 1306. As medication is consumed, the quantity of medication remaining in container 1100, 1101, or dispenser 1200 is updated by processor 1304 in memory 60, 125, or 1306. Alternately, the consumption information 80 can be written to memory 60 or 1306, when the container 1101 is reinserted into slot 1319.

The same process is performed when container 1100 or 1200 is used. When the container is removed, the alert presented by dispenser 1310 is canceled, allowing reminder unit 1114 or 1208 to present an alert. The user consumes the medication in container 1100 or 1200 in the previously described manner. The time the medication 15 is consumed is recorded in memory 60 or 125 as consumption information 80 by processor 120, or by monitoring button 160 of reminder unit 1114 or 1208, or by monitoring sensor 1160, or by noting that contacts 1247 no longer make contact with contacts 62. When container 1100 or 1200 is reinserted in slot 1320, the consumption information is transferred to processor 1304 and recorded in memory 1306. The consumption information can also be determined by processor 1304 as container 1100 or 1200 is removed from or reinserted into slot 1320 and written to memory 60, 125, or 1306.

Modifying Dosing Times

While prescription information 82 includes a dosing regimen or a timing schedule as written to memory 60 by the dispensing pharmacy, there are circumstances when the patient is allowed to modify it. For example the timing schedule can indicate that medication 15 should be consumed at 8:00 am, 4:00 p.m., and 10:00 p.m. If the patient switches from a first shift job, when they would typically be awake to consume each dose of medication 15, to a third shift job, when they would not be awake for each scheduled dose, the patient is allowed to move the scheduled dosing times to meet his work schedule. Using button 160 or others and display 132 the patient can identify each medication, review the timing schedule and adjust the timing schedule forward or backward. This can be done by advancing all the scheduled consumption times by the same amount of time. Using program codes 86, individual consumption times can be changed but only so they are not scheduled too close to a previous or following dosing time.

Determining Contraindicated Medication

The medication dispenser 1310 compares the several medications 15 contained in containers 1100, 1101 or 1200 by comparing the information 80 in each of their corresponding memory strips 60. The computer processor 1304 references and compares the lists of contraindicated medications, which are part of the medication information 84. Should two or more medications 15 be contraindicated, the patient will be alerted to this fact. Every time a medication 15 is issued to a patient, the most recent list of contraindications is included in the memory strip 60 or 960 of the vials 20 or cassettes 950. A list of contraindicated medications can also be maintained in the memory 125 of dispenser 1310.

Dosing Regimens

Dispenser 1310 can use paired and other complicated dosing regimens as described in the operation of the fifth, sixth, and seventh embodiments. Similarly dispenser 1310 can ensure that only medications for a single individual are managed by the dispenser.

Sequencing Medication

When the processor 1304 determines that two different medications 15 are to be taken at the same time, the dispenser 1310 signals the indicator 136 to flash or the display 132 to indicate a message instructing the patient to consume the proper amount of each medication. The processor 1304 instructs the patient to take one type of medication 15 at a time. The patient is alerted to each appropriate prescribed medication in sequence. This sequencing avoids telling the patient to simultaneously obtain medication from a first container 1100, 1101 or dispenser 1200 and medication from a second container. Many patients may get confused and dispense them in the opposite quantities. With respect to dispenser 1310, since medication is consumed by first removing container 1100 and then removing cap 1108 to access the medication, they may accidentally remove too many pills from the wrong vial if they remove two containers 1100 at the same time.

As in container 10, the dispenser 1310 includes buttons 160, 162, 164 and 166 that communicate information to the processor 1304. By pressing one of the buttons, the patient is able to send an electrical signal to the processor 1304 in response to a question shown on the display 132 or to indicate an action to be taken, such as cancel an alert or alarm 134 or 136.

Portable Medication Container

Figure 45:
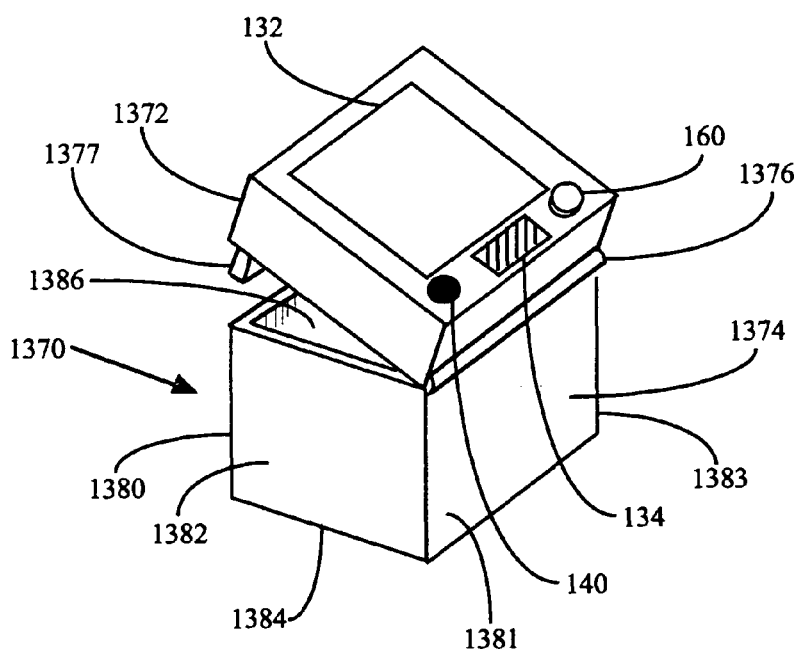
FIG. 45 is a perspective view of a portable medication container consisting of a body defining a compartment and a lid to close the compartment, the lid including a reminder unit.

The following is a description of a portable container 1370 (See FIG. 45) used in conjunction with container 1300. However, it should be noted that portable container 1370 can be used with any of the previous embodiments.

Figure 49:
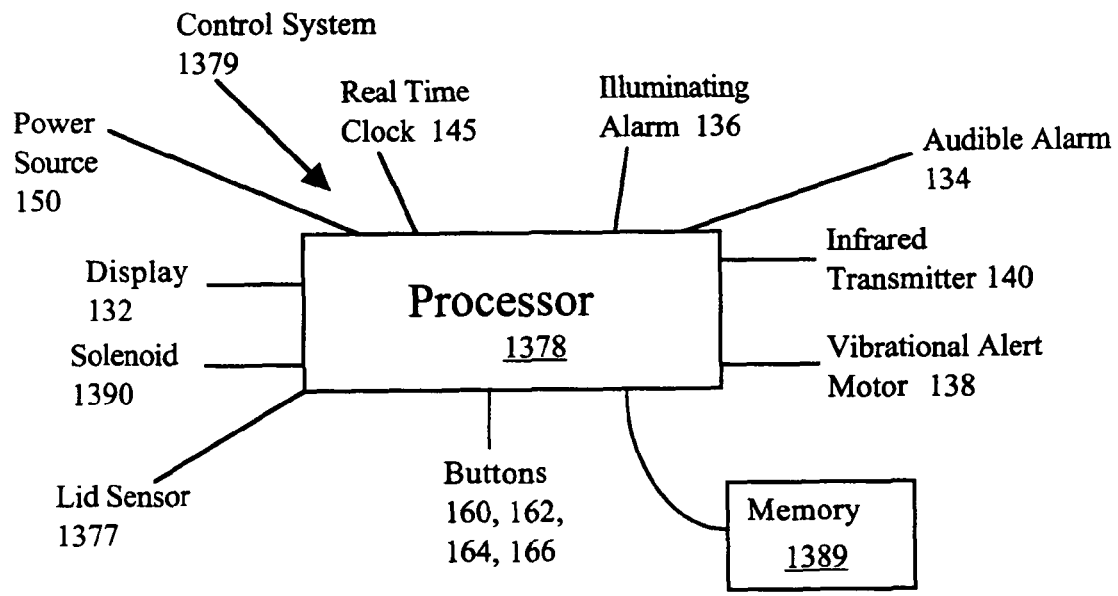
FIG. 49 is a schematic diagram showing the circuitry in the reminder unit of the portable container of FIG. 45.

Portable container 1370 is comprised of a hinged lid 1372 attached to body 1374 by living hinge 1376. Lid 1372 is shown in a partially raised position. Lid includes a control system 1379 (See FIG. 49), similar to control system 114 used by reminder 1114 and 1208. Also visible is display 132, audible alert 134, button 160, infrared transmitter 140, and lid sensor 1377; each with similar purposes to those previously described, and all in communication with processor 1378 (See FIG. 49) as is memory 1389. Body 1374 has front wall 1380, rear wall 1381, and two side walls 1382, and 1383, and a closed bottom 1384 defining compartment 1386.

When lid 1372 is closed sensor 1377 is compressed indicting to processor that container 1370 is sealed and when the lid is opened the sensor is in an extended position indicating to the processor the container has been opened. Lid 1372 can have a locking assembly 1390, such as a solenoid, that can engage body 1372 to lock container 1370 closed.

Operation of the Tenth Embodiment with Portable Container Accessory Loading Portable Container A patient's prescription regimen may call for them to consume one of more medication 15 in the middle of the day, yet dispenser 1310 may to viewed as too large to be carried during the day. Portable container 1370 is sized to be carried conveniently by and can be used to augment dispenser 1310. In this case dispenser 1310 is used to determine which medications 15 are to be consumed at the next consumption time. Button 160 or others are used to indicate to dispenser 1310 that medication 15 for consumption at the next dosing time will be removed early. Dispenser 1310 then determines which medication 15 is to be consumed next and at what time, for example 1:00 p.m. Dispenser 1300 then indicates to the patient, as described above, the amount of medication 15 to be removed from a container 1100, 1101 attached to dispenser 1310 and the time the medication 15 is to be consumed. Medication 15 is removed as though it is to be consumed immediately, but instead it is placed in medication compartment 1386 of portable container 1370.

When all the medications 15 that are to be consumed at the next consumption time have been placed in portable container 1370, lid 1372 can be closed. Processor 1378 now detecting via lid sensor 1377 that lid 1372 has been closed. To further secure medication 15 in portable container 1370 solenoid 1390 can be extended so as to lock lid 1372 to body 1374. Finally, dispenser 1310 can transfer, using IR transmitter 140, the time (e.g. 1:00 p.m.) medication 15 is to be consumed to compatible IR receiver 140 of portable container 1370. Processor 1378 receives the time and other pertinent information about the medications 15 that have been removed from dispenser 1310.

Consumption Time Alerts

The dispenser 1310 marks the medication as consumed and when the next dose of medication 15 that was just removed is due (1:00 p.m.), dispenser 1310 will skip or forego presenting an alert at that time. If an alert was presented, it would be interpreted as an alert to take another dose of the medication on top of the dose that had earlier been removed and placed in container 1370.

Processor 1378 activates alert device 134, 136, or 138 of portable container 1370 when the transferred consumption time matches the current time from clock 145. When equipped with solenoid 1390, processor 1378 can activate solenoid 1390 to retract it and unlock portable container 1370. Other pertinent information about the medication can be presented using display 132 or audible alert 134. Lid 1372 of portable container 1370 is opened and medication 15 is removed for consumption. When lid 1372 is opened, the consumption indicator is triggered via lid sensor 1377, which is communicated to processor 1378. Processor 1378 now detects that the lid is open, and deactivates the alert device 134, 136, or 138. Processor 1378 records the current time from clock 145 as the consumption time in memory 125. When solenoid is not used and it is not yet time to consume the medication, an access alert can be presented by device 132, 134, 136, 138. It is also contemplated that sensor 1377 need not be used. When a consumption alert is present to consume medication, button 160 of container 1370 can be pressed to cancel the alert and indicate to processor that medication 15 has been consumed. As before, button 160 can be pressed more than once to indicate to processor 1378 that the alert should only be temporarily canceled.

Recording Consumption Information

Prior to the next time portable container 1370 is loaded with medication 15 or any time portable container is placed close to dispenser 1310, processor 1378 can transfer the recorded consumption time using IR receiver 140, now including a transmitter. Dispenser 1310 receives the transferred consumption time and recording it in memory 60 of the appropriate vial 1102, memory 125 of the appropriate reminder unit 1114, or in memory 1306. The transferred consumption time can also be used to modify the appropriate next consumption time for the consumed medication, in the case the medication in container 1370 was consumed substantially before or after the originally transferred consumption time.

Using Alternate Containers

Instead of using portable container 1370, medication 15 removed from dispenser 1310 can be placed in any container, pocket or purse. The patient is expected to remind himself of the time to consume the medication 15. When desired, the next consumption time (1:00 p.m.) can be transferred to reminder device 290 to present an alert when it is time to consume the medication. The dispenser marks the medication as consumed and when the next dose of medication 15 that was just removed is due (1:00 p.m.), dispenser 1310 will not present an alert. If an alert was presented, it would be interpreted as an alert to take another dose of the medication on top of the dose that had earlier been removed and placed in container 1370.

As a convenience, at the next sequential medication 15 consumption time (the next dose after 1:00, for example 6:00 p.m.) dispenser 1310 presents a question to the patient asking them if they consumed the previously removed medication and at what time. This information is recorded in memory 60, 125, or 1306 as previously described.

Using Reminder Unit As A Portable Container

Finally, when the medication 15 to be consumed next is in container 1100 or dispenser 1200, container 1100 or dispenser 1200 can be removed from dispenser 1310. Reminder unit 1114 or 1208 will present an alert at the next consumption time (1:00 p.m.). When container 1100 or dispenser 1200 is used to remove medication 15 the consumption information is recorded in memory 60 or 125.

The dispenser 1310 will not present a consumption alert at the next consumption time (1:00 p.m.). If an alert was presented, it would be interpreted as an alert to take another dose of the medication on top of the dose that had earlier been removed and placed in container 1370. When container 1100 or dispenser 1200 is mated with dispenser 1310, consumption information is transferred from memory 60, 125 to memory 1306.

RFID Tag Use

It is also contemplated that interactive label 60 or 1106 can be in the form of a radio frequency identification (RFID) tag where contacts 62 are replaced by an antenna. Sensors 1150, 1322 are now in the form of at least one RF antenna. With an adequate power source and suitable antenna, dispenser 1300 can read the interactive label 50 of vials 1100 within a distance of up to 10 feet. The vials are now associated with dispenser 1300. In this case, visual indicators 136 may no longer be appropriate, as they may not be able to indicate the position of a specific vial 1100. Many aspects of the operation of dispenser below are retained, however to indicate that a specific medication has or has not been consumed button 160 or another consumption indicator is pressed in response to an alert presented using devices 132 or 134. Using display 132, the dispenser can indicate which of several patients is being alerted to consume medication.

Figure 51:
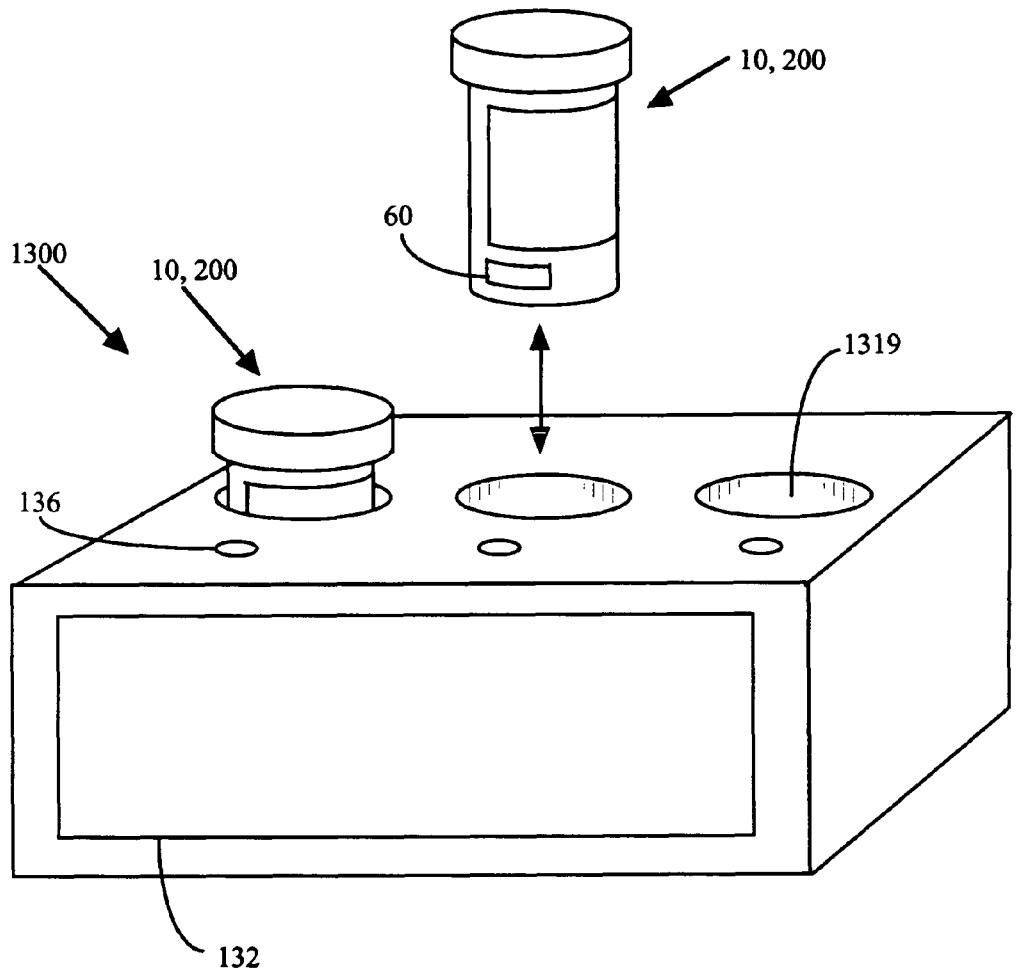
FIG. 51 is a perspective view of an alternate structure of the tenth embodiment of the present invention where the medication container includes several vials of medication that use a radio frequency identification (RFID) tag as the interactive label with electronic memory strip.
Figure 52:
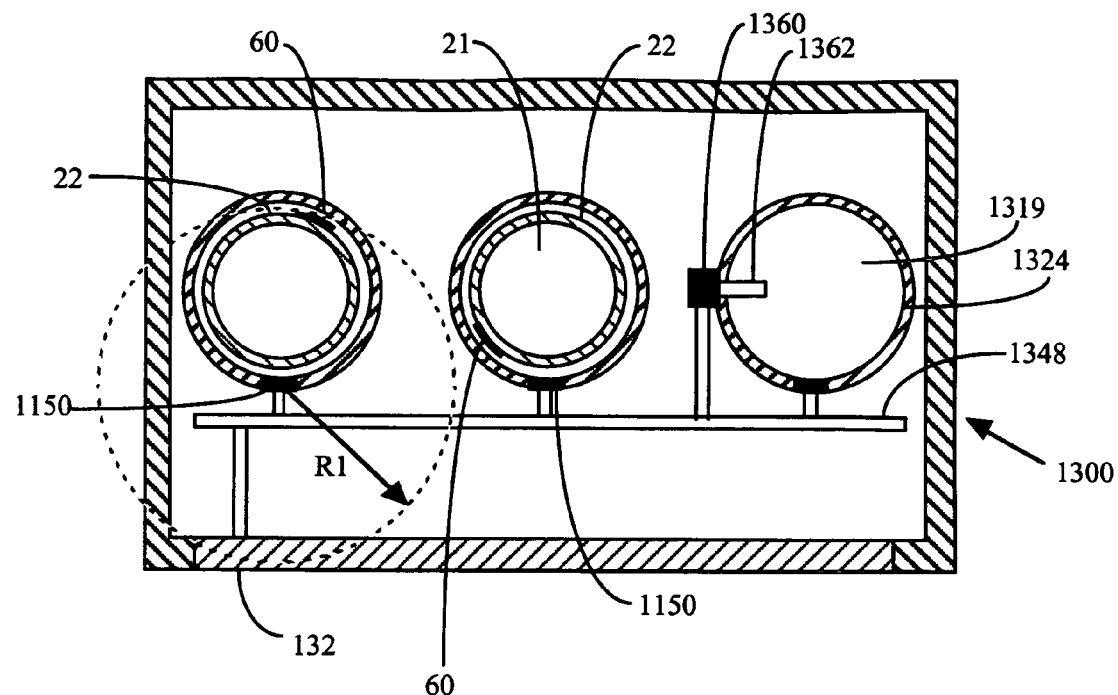
FIG. 52 is a plan cross-sectional view of the multi-vial medication container of FIG. 51 with two vials placed in adjoining slots of the multi-vial medication container.

FIG. 51 shows dispenser configured to use a medication container 10 with an interactive strip 60 or 1106 in the form of a RFID tag. In this configuration, each container 10 is placed in a slot 1319 shown in the form of a blind well. FIG. 52 is a cross sectional view of dispenser 1300. FIG. 52 shows a separate sensor 1150 positioned in the cylindrical wall 1324 for each slot 1319 and proximate to any container placed in slot 1319. Antenna 1150 is designed so that it can only read RFID tags within radius R1. This prevents one of the antennas 1150 from reading memory strip 60 of an adjacent container 10 placed in the next slot 1319 no matter the orientation of its RFID tag memory strip 60 or 1106. Now dispenser 1300 can read information 80 for each container and associate that information with a specific slot 1319 for alerting the patient which medication to consume. Although the containers 10 are shown placed in a slot 1319 of the console 1310, it should be understood that the containers and console could be brought together in any number of ways, such as simply placing the container in the near vicinity of the antenna 1150.

A suitable radius R1 can be achieved by limiting the power to antenna 1150 or by placing appropriate ground planes or other RF absorbing material between the antenna 1150 of one slot 1319 and the next slot 1319.

When separate antenna 1150 are not used, dispenser 1300 can be configured to use a single antenna 1150. When a medication container 10 with an interactive strip 60 or 1106 in the form of a RFID tag is brought near dispenser 1300, information 80 can be read by antenna 1150. By comparing information 80 such as the patient's name 84 with a patient name associated with dispenser 1300, it can be determined if dispenser is to use prescription information 82 to determine dosing times. This can be done without container 10 being attached or affixed to dispenser 1300. However, to more specifically associate medication containers 10 with dispenser 1300 each slot 1319 can be configured with micro-switch 1360 and distal micro-switch arm 1362 (see FIG. 52). As medication container 10 is brought near dispenser 1300 the single antenna 1150 reads information 80 and as the container is placed in slot 1319 and microswitch arm 1362 is depressed closing microswitch 1360 indicating to processor 1304 into which slot the container has been placed. When dispenser 1300 determines that a medication is to consumed it can indicate the specific slot 1319 the corresponding medication container has been placed.

Figure 53:
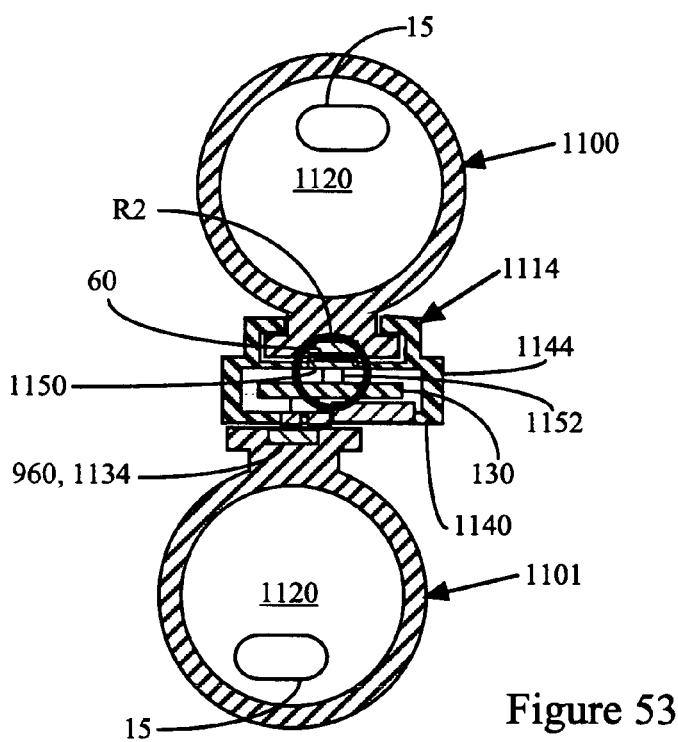
FIG. 53 is a cross sectional, plan view of the eighth embodiment of the invention showing the vial mated to the reminder unit, the reminder unit now using a radio frequency (RF) antenna to read the RFID tag of an interactive label attached to a vial, but not the interactive label of an adjoining second vial.

FIG. 53 shows container 1100 where sensor 1150 is now configured as a RFID tag reader and memory strip 60 is a RFID tag. The sensor is designed to limit its ability to read RFID tags beyond radius R2. This prevents reminder unit 1114 from accidentally reading information 80 of an adjacent container 1101 and using that information to determine the dosing regimen for the medication to which the reminder 1114 is attached.

Medication Consumption and Time Recording

Figure 54:
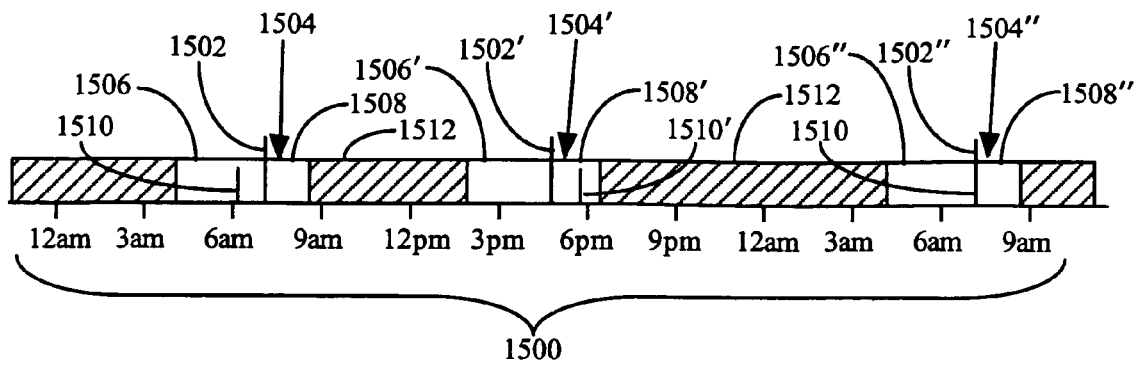
FIG. 54 is a representation of a time line showing predetermined times to consume a medication.
Figure 55:
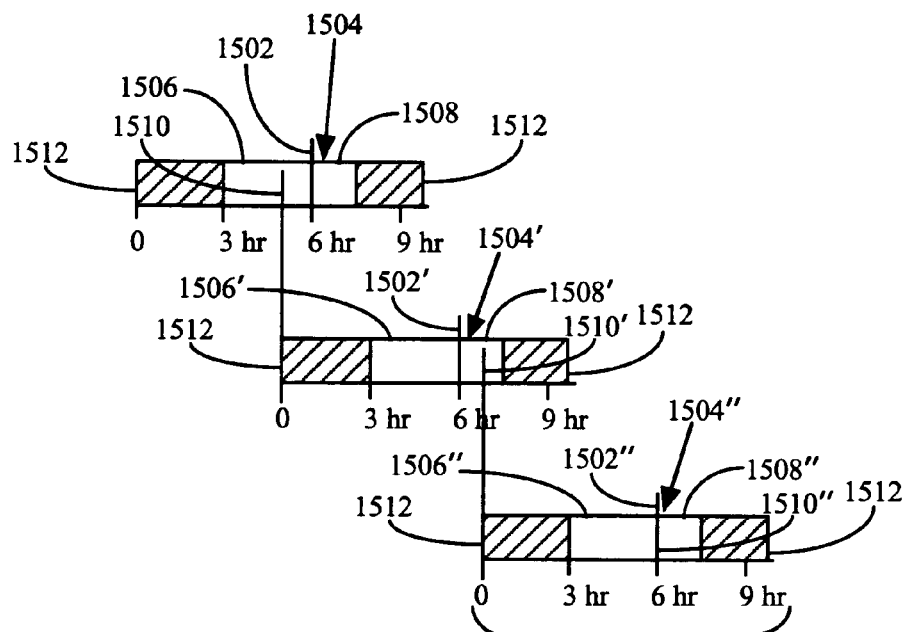
FIG. 55 is an alternate representation of a time line showing predetermined times to take a medication.
Figures 56, 57:
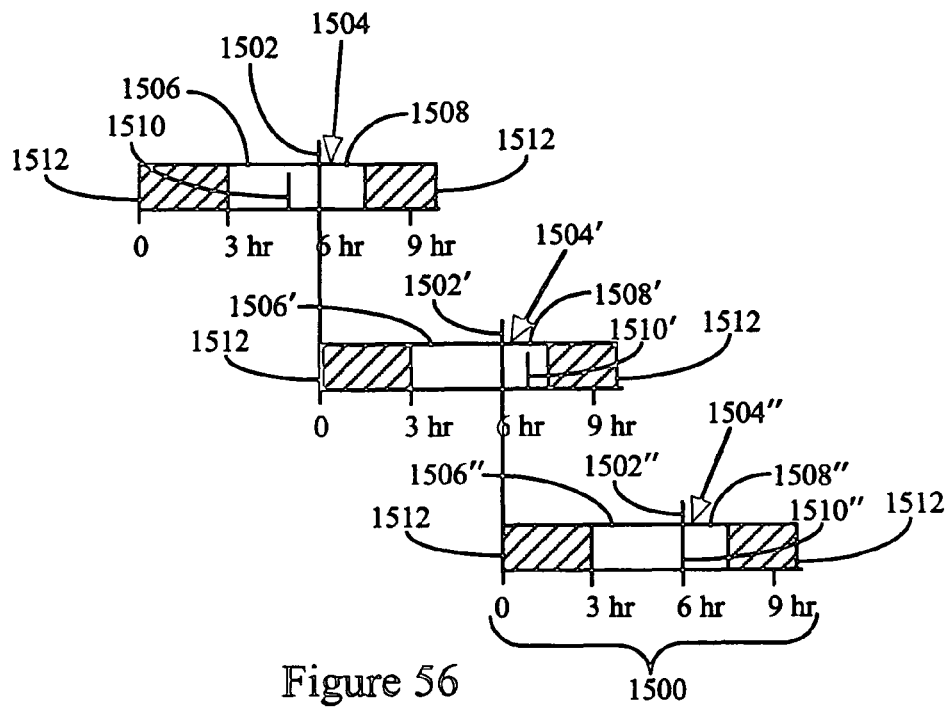
FIG. 56 is another alternate representation of a time line showing predetermined times to take a medication.
FIG. 57 is a representation of a medication consumption table showing specific medication consumption times for specific medications.

FIGS. 54, 55, and 56 show several time lines that can be used to determine when a patient is to consume a medication. Time line 1500 of FIG. 54 shows hours of the day over a couple of days. A series of predetermined times 1502, 1502' and 1502" are the times of the day when one or more of the communication devices 132-138 or 542-544 are to be activated to notify the patient to consume a medication. Although the predetermined times 1502, 1502' and 1502" are shown to be at evenly spaced intervals of time apart from each other, it should be understood that the dosing regimen could specify increasing, decreasing or fluctuating time intervals. Associated with each predetermined time 1502 is a window of time or total time range 1504. This window of time 1504 includes a time range 1506 before predetermined time 1502 and a time range 1508 after predetermined time 1502, during which the medication can be safely consumed. When the patient consumes the medication within time range 1506 the consumption alert that normally would be presented to the patient at predetermined time 1502 will not be presented as the patient has consumed this dose of medication. When the patient consumes the medication within time range 1508, the consumption alert that has been presented by communication device 132-138 or 542-544 at predetermined time 1502 will be canceled. Likewise, when the actual time information obtained from the clock 145 passes time range 1508, the consumption alert presented by the communication device 132-138 or 542-544 will be canceled, indicating the medication is no longer to be consumed until the time range 1504 of the next predetermined time 1502'.

The patient consumes several doses of medication in a series of actual consumption times 1510, 1510' and 1510", which are recorded in memory 60, 1384, or 1408. Time range 1512, shown as a shaded block, represents the times of the day when the patient is not to consume the medication either because it is too close to the last time the medication was consumed or because it is too close to the next predetermined time 1502' or 1502". Any attempt to consume medication during time range 1512 will cause the communication device 132-138 or 542-544 to indicate that it is not appropriate to consume medication at this time. Medication information 84 or 1430 can include dosing regimen information with variables that will modify the predetermined times 1502, 1502', 1502" when a dose is skipped, taken early or late. These variables will also modify the predetermined times 1502, 1502', 1502" based upon meal schedules.

FIG. 55 shows an alternate method of determining the time schedule for consuming medication. Instead of being based on a set predetermined time of day, the time schedule is based on elapsed time. In this method, the next scheduled time 1502' to take a dose of medication is coupled to the actual consumption time of the previous dose 1502 of medication. Similarly, each subsequent scheduled time 1502" to take a dose of medication is coupled to the actual consumption times of the previous doses 1502 and 1502'.

FIG. 56 shows yet another alternate method of determining the time schedule to consume doses of medication. This alternate method again uses elapsed time instead of a set time of day. In this method, the subsequent predetermined time to consume medication 1502' and 1502" is in a fixed interval of time relative to the immediately preceding predetermined time 1502 or 1502'.

When medication is consumed, an actual consumption time entry can be written to Medication Consumption Table 1520 in memory 60, 1384, or 1408. The actual consumption time entry can be in the form of a time of day or elapsed time since the previous actual consumption time entry. When container 1300 or medication system 1400 (see below) is used, the actual consumption time is written in a portion of table 1520 reserved for the specific medication 1424 that was consumed.

Medication System

Figure 46:
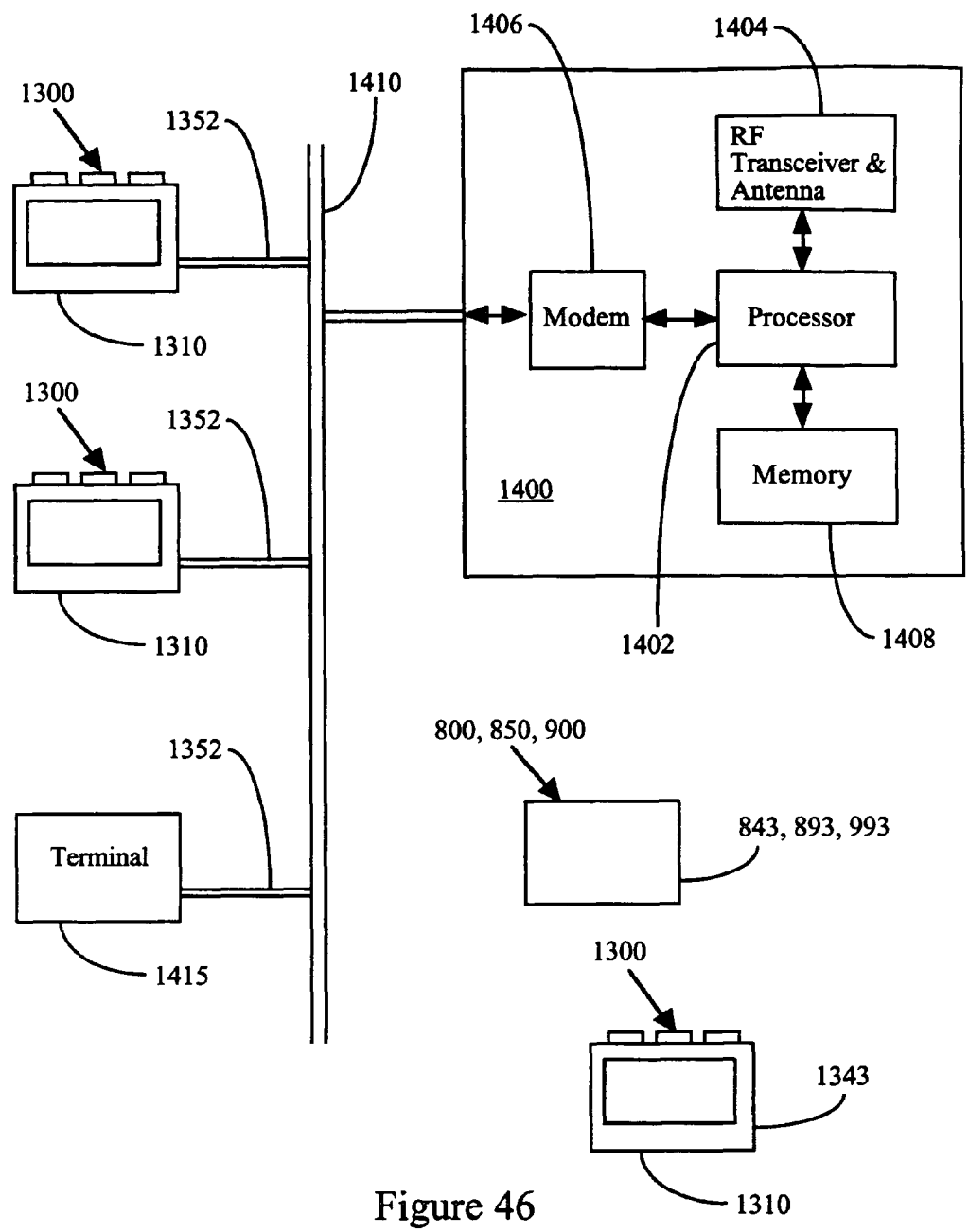
FIG. 46 is a schematic of a comprehensive medication management system consisting of medication dispensers and a remote medication system that communicate with each other using a communication network.

The following is a description of a medication system 1400 (See FIG. 46) used in conjunction with container 1300. However, it should be noted that medication system can be used with any of the previous embodiments.

Medication system 1400 consists of a processor 1402 in communication with a database or memory 1404, and communications equipment such as modem or Ethernet transceiver 1406 or a radio frequency (RF) transceiver and antenna 1404. Modem 1406 is used to receive and send information via network 1410, such as a telephone system or the conventional Internet communications system, to dispensers 1310 when equipped with modem 1350 and cable 1352. RF transceiver 1408 is used to send and receive information from dispenser 1310 when it is equipped with RF paging receiver 1343. Medication system 1400 is associated with a pharmacy or a healthcare giver.

Medication system 1400 also communicates with containers 800, 860, 900 when equipped with a compatible RF paging receiver 843, 893, 993 including a transmitter. Dispensers 800, 860, and 900 are also equipped with modem 1350 to communicate with medication system 1400.

Figure 50:
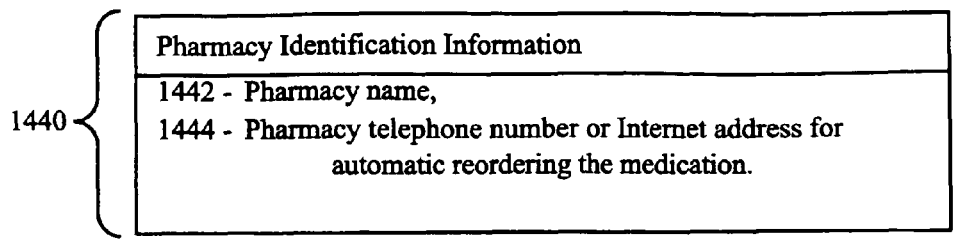
FIG. 50 is a chart listing pharmacy identification information used by a dispenser to identify an associated pharmacy from which to reorder medication.

Container 1300 can have pharmacy identification information 1440 (See FIG. 50) stored in memory 1306. Information 1440 can include pharmacy name 1442 and pharmacy telephone number of Internet address 1444 used to contact a specific pharmacy medication system 1400 using network 1410 to transfer consumption information, requests to refill specific a medication 15 in a container 1100 or 1200, and to allow other information to either be sent to or received from medication system 1400. Alternately, the pharmacy telephone or Internet address part of medication information 84 in memory strip 60 of container 1100, 1101 or dispenser 1200 can be used by dispenser 1310 to contact medication system 1400.

Transferring Information

Figure 47:
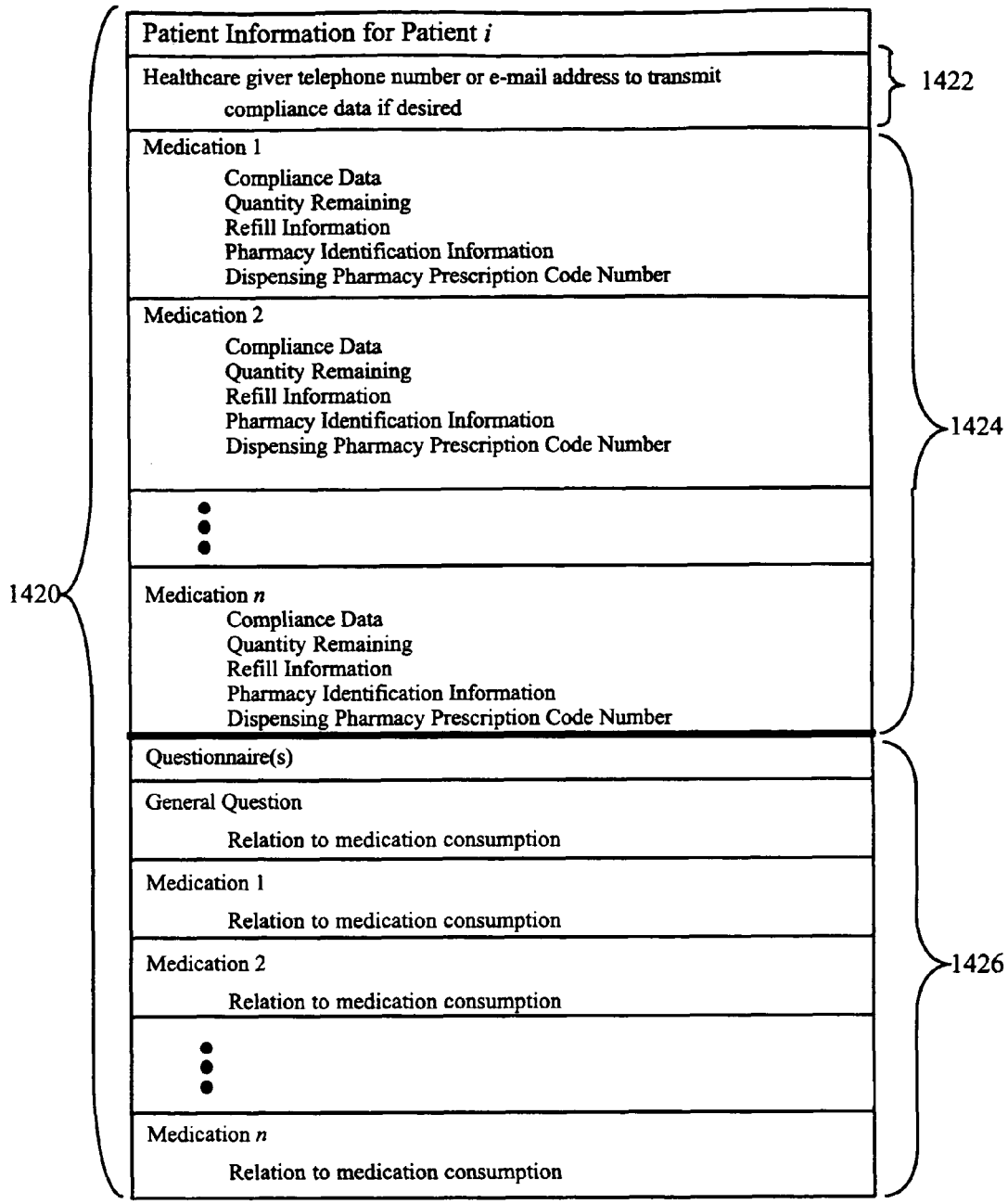
FIG. 47 is a chart listing a variety of information for a patient, including information about each medication they have been prescribed to consume, and questionnaires that are presented to the patient, and stored in the memory of the medication system, and transferred to the memory of dispensers or interactive labels.

FIG. 47 is the patient information 1420 contents of a section of memory 1404. This section includes many of the fields previously seen in medication information 86, but now the fields have been collected for all the medications a single patient has been prescribed to consume. The telephone number or the e-mail address 1422 of a healthcare giver responsible for the patient is used to contact the healthcare giver in case the patient misses one or more doses of a medication so that the care giver can be warned to take an appropriate action. Medication information section 1424 includes compliance data and quantity remaining fields are used to replace or eliminate the same fields in medication information 84. As medication is consumed using dispenser 1310 consumption information is communicated using modem 1350 or RF transceiver 1343 to medication system 1400 with the patient name or other patient identifier and the medication name from medication information 84 of memory 60. The consumption information is added to the medication information section 1424 for the specified patient and the medication.

Using a similar process as medication is consumed the amount removed from dispenser 1310 is transmitted to medication system 1400 and used to adjust the quantity remaining field of medication information section 1424 for a specific patient and medication.

Medication system 1400 uses network 1410 to contact a healthcare giver by activating terminal 1415, such as a telephone via a computer generated voice or a computer terminal via an e-mail message. The healthcare giver telephone number or e-mail address 1422 that is part of patient information 1420 or medication information 80 in memory 60, can be used by medication system 1400 to transmit to the healthcare giver consumption information for a patient or the fact that a consumption time was not accompanied by medication being removed from container 1300.

Questionnaires

Questionnaire section 1426 includes questions to be posed to the patient using display 132 relative the consumption of medication. Questionnaire section 1426 can be sent to dispenser 1310 using modem after a specific patient name or other unique patient identification is sent from the dispenser or container to the medication systems 1400. The questions can be used as part of a clinical trial for new drug or other therapy. The questionnaire section 1426 can include questions that are posed to the patient in relationship to when medication is consumed. The relationship to medication consumption can be a time period after or before the medication is consumed and the question is to be asked. For example, 2 hours after a medication is consumed the patient is asked if they are dizzy. Depending on the response additional questions can be posed to the patient.

Other questions can be related to the consumption of an individual medication. It is contemplated that the questions will be modified heuristically so that a response to the question "How do you feel?" which is "I feel dizzy" can result in one of the next questions to be phrased as "Are you still dizzy?".

The contents of questionnaire section 1426 can alternately be included in medication information 86 of memory 60, but in this case limited to questions for the medication in a specific container 1100, 1101 or dispenser 1200. The responses to the questionnaire can also be recorded to dispenser 1300 or 1400.

Determining Contraindicated Medication

Figure 48:
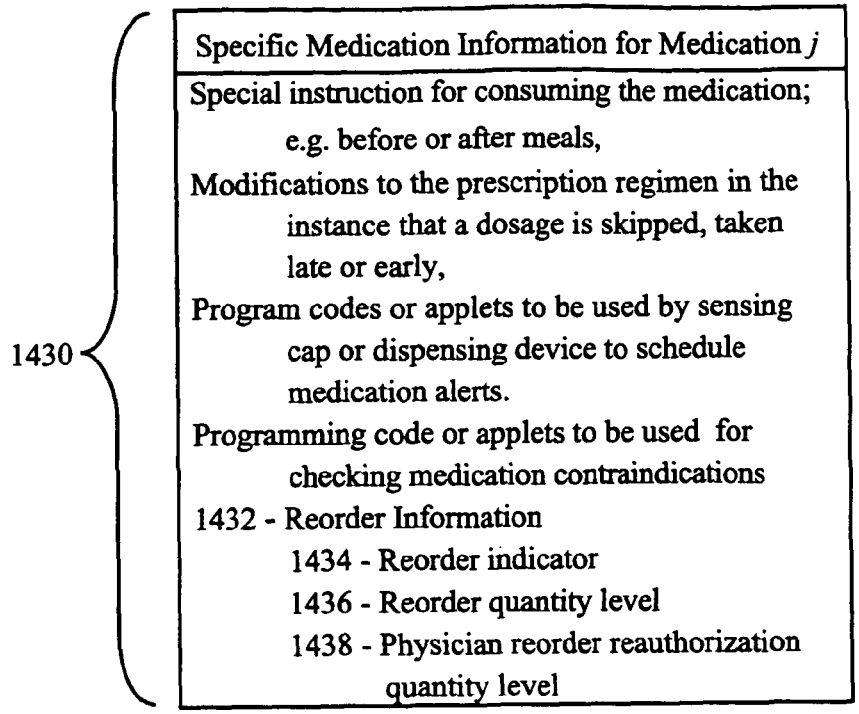
FIG. 48 is a chart listing medication information for a specific medication, the information being stored in the memory of the medication system.

FIG. 48 is the specific medication information 1430 contents of memory 1404. This section includes many of the fields previously seen in medication information 84 and program codes 86. The medication information 1430 can be sent to dispenser 1300 via network 1410 or RF transceiver 1404 in lieu of storing this information in memory 60. The medication information 1430 for a specific medication is transmitted when dispenser 1400 transmits to medication system 1400 the medication name 84 of a medication 15 used with the dispenser or container. Upon receiving the medication names for each medication, medication system 1400 can use the program codes in medication information 1430 to determine if any are contraindicated for use with another medication 15 and then medication systems 1400 can send to dispenser 1310 a message alerting the patient to this dangerous condition, protecting the from such dangerous conditions. Furthermore, an alert can be sent by an audio message via telephone or a text e-mail message via the network 1410 to a healthcare giver terminal 1415.

Alternately, the list of contraindications for each medication (part of specific medication information 1430) in a container 1100, 1101 or 1200 can be received by modem 1350 or RF receiver 1343 from memory 1408 of medication system 1400. To receive contraindications, 1430 processor 1304 sends the medication name 84 or other identifying information for each medication 15 used with dispenser 1310 to processor 1402. Processor 1402 in turn retrieves the specific medication information 1430 from memory 1408 and sends it back to processor 1304. Processor 1304 will then determine if any medication mated to dispenser 1310 is contraindicated for use with another medication mated to dispenser 1310.

Transferring Medical Measurement Data

Dispenser 1310 is used to transfer information from other medical devices to medication system 1400. Dispenser 1310 is used to request a medical device (not shown) be used to measure a medical parameter, for example blood pressure, insulin levels, or blood clotting times. This request can be related to questionnaire 1426. The medical device after making a measurement can transmit the measurement via an infrared transmitter to IR receiver 140. The dispenser 1310 is also used to send measurements that are not related to a questionnaire via dispenser 1310 to medication system 1400. Medical measurements are also entered using button 160 or others, or dispenser 1310 can include the medical device using processor 1304 to operate it.

Modifying Medication Dosing Regimen

A healthcare giver can determine that a patient's condition has changed due to a current evaluation of the patient or in response to a medical measurement transferred to medication system 1400 from dispenser 1310. The healthcare giver can use terminal 1415 to send new prescription information 82 for one or more medications 15 that is in a container 1100, 1101, or dispenser 1200 mated to dispenser 1310. The new prescription information 82 for a specific medication 15 is first transferred to medication system 1400 identifying a specific patient name 84 or other identifier. Medication system 1400 then transfers the new prescription information 82 to dispenser 1310 using network 1410. Dispenser 1410, after receiving new prescription information 82, can record it to memory 1306, or to memory 60 of the appropriate interactive label 1106, 50 related to the specific medication 15. Alternately, the healthcare giver can transfer the new prescription information 82 directly to dispenser 1310 vial network 1410.

It is contemplated that either medication system 1400 or dispenser 1310, in response to the entry of a medical measurement, uses special instructions for consuming medication 84 to alter the prescription information 82 for a specific medication 15. The altered prescription information 84 is written to memory 1306 or 60 of the container 1100, 1202 of the specific medication 15. For example, Coumadin is a pharmaceutical that increases the clotting time for blood. If a measurement of clotting time is entered or transferred to dispenser 1310 indicating that clotting time has increased beyond an acceptable level since a previous reading, the number of pills to be consumed per dosing 82 for Coumadin can be reduced.

Reordering Medication

As a convenience, dispenser 1310 automatically determines when medication 15 is to be reordered to ensure a timely resupply. To reorder a medication 15, dispenser 1310 or medication system 1400 uses specific medication information 1430 including medication type information and reorder information 1432. The reorder information 1432 is displayed via a communication device such as an LED display and includes a reorder indicator 1434 that identifies the medication vials or containers containing medication that can be reordered, how long the medication can be reordered, the reorder quantity level or amount without additional physician reauthorization 1436, and the reorder quantity level with physician reauthorization 1438. Typically, quantity level 1438 is greater than or equal to quantity level 1436, acknowledging the practice that it takes longer to reorder a medication that must first include a physician reauthorization than one that does not.

While reorder information 1432 is shown as part of memory 1408 to be downloaded to dispenser 1310 via network 1410, it should be understood that reorder information 1432 can be part of medication information 84 and stored in memory 60. In the description of reordering medication dispenser 1310 will be used to determine when a medication is to be reordered, but medication system 1400 can be used to do this.

As medication 15 is consumed, dispenser 1310 alters the quantity of medication remaining 84 in container 1100, 1202 as recorded in memory 60, 1306, and 1408 for each medication 15. As the quantity of medication 84 is altered, reorder indicator 1434 is checked to determine if this medication 15 can be reordered. If the medication cannot be reordered no additional tests need to be made. If the medication can be reordered but only with the reauthorization of a physician (typically set due by the number of refills previously authorized or by a specific date), the quantity of medication remaining 84 is compared with quantity level 1348. If the quantity remaining is less that quantity level 1438, dispenser 1310 can present a message on display 132 indicating that a medication is low and that to refill this medication requires extra time due to the need to contact the physician for reauthorization. Button 160 or others can be used to indicate that medication 15 is to be reordered. Dispenser then sends a message to medication system 1400 or to terminal 1415 indicating that a reorder of medication 15 is desired and that the physician is to be contacted to obtain a reauthorization prior to the pharmacy refilling the medication. The physician is then contacted either by dispenser 1310, medication system 1400 (for example by secure e-mail), or by staff working with medication system 1400 (for example by telephone). The pharmacy, upon receiving the physician's reauthorization the medication 15, fills a new container 1100 or cartridge 1202 with medication 15 for delivery to or pick up by the patient.

When medication 15 can be reordered without the reauthorization of a physician, the quantity of medication remaining 84 is compared with quantity level 1346. If the quantity remaining is less than quantity level 1436, dispenser 1310 can present a message on display 132 indicating that a medication is low and that that the medication can be reordered. Button 160 or others can be used to indicate that medication 15 is to be reordered. Dispenser then sends a message to medication system 1400 reorder of medication 15 is desired. The pharmacy is contacted by medication system 1400 (for example by e-mail) indicating that medication 15 is to be refilled for the patient. The pharmacy then fills a new container 1100 or cartridge 1202 with medication 15 for delivery to or pick up by the patient.

It is anticipated that dispenser 1310 uses information about weekends and holidays to anticipate when the quantity of medication remaining 84 will be less than or equal to quantity level 1436, 1438 during a weekend or holiday, when the physician may not be available or the pharmacy closed. Dispenser 1310 indicates that a refill is needed one or more days earlier than quantity of medication remaining 84 reaching quantity level 1436, 1438.

The pharmacy telephone or Internet address 84 of memory 60 attached to container 1100 or cartridge 1202 is used by dispenser 1310 to reorder medication 15. It is anticipated that the pharmacy may also operate medication system 1400. It is further anticipated that dispenser 1310 and memory 1306 may store a second pharmacy telephone number 84 or Internet address 84. The dispenser may ignore the first pharmacy telephone number 84 stored in memory 60 and use the second pharmacy telephone number stored of the in memory 1306. Any medication 15 initially filled by first pharmacy and stored in dispenser memory 1306, will only be reordered by dispenser 1310 through the second pharmacy.

It is also contemplated that when medication system 1400 maintains the quantity of medication remaining 84 in memory 1408, that medication system can determine when a medication is to be reordered using reorder information 1432.

Using a Medication Serial Number

Figure 58:
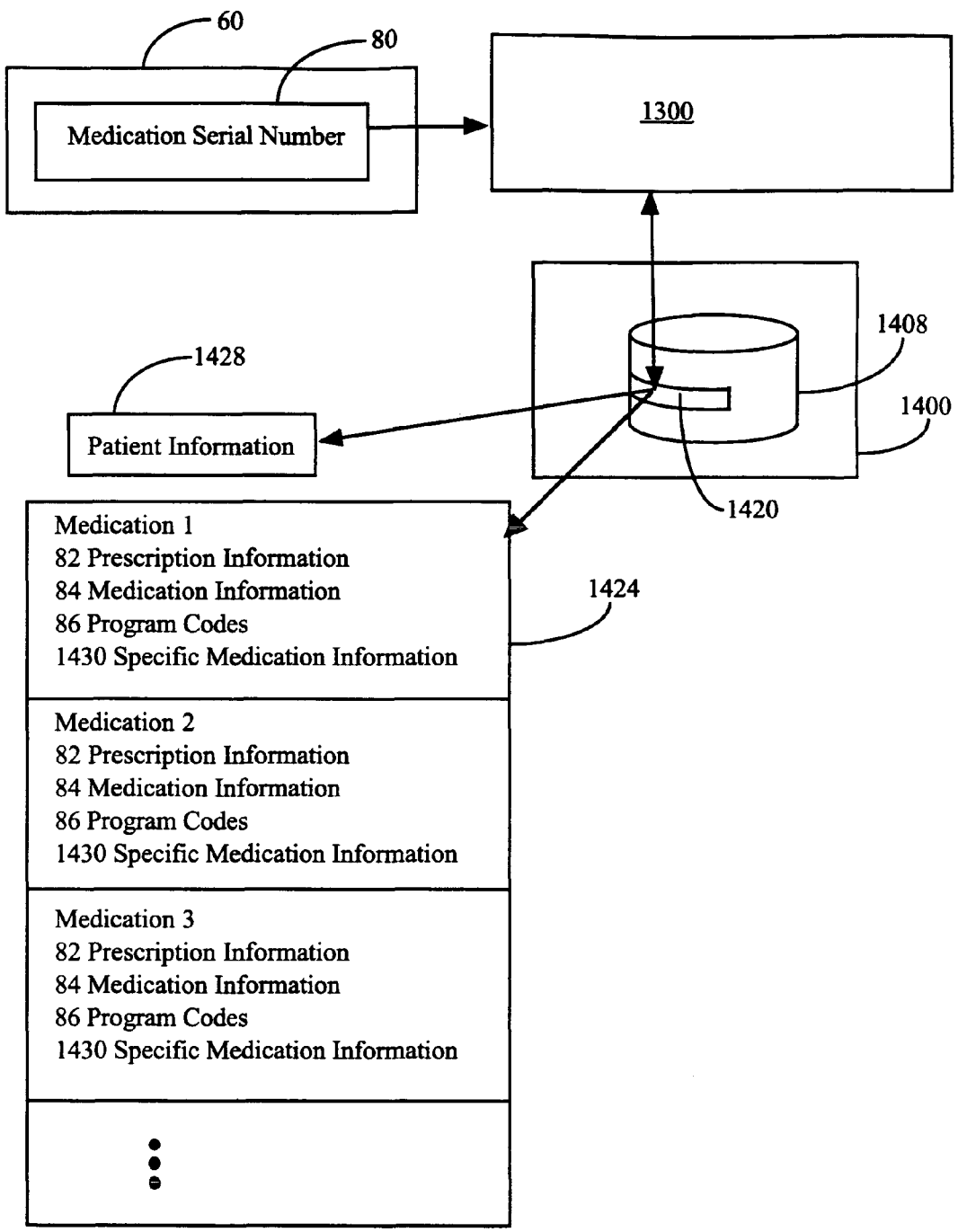
FIG. 58 is a flow chart of information between a memory strip to a multi-vial medication container to a comprehensive medication management system and then back to the multi-vial medication container.

Interactive label 60 or 1106 can be in the form of a bar code 960 or 1134. The contents 80 of the bar code can be a unique medication serial number 80 or other unique identifier describing the medication, as shown in FIG. 58, for each medication container 80 dispensed by the pharmacy. When communication is established between dispenser 1300 and medication system 1400, the medication serial number is transferred from the interactive label 60 of container 1101 by to medication system 1400. Medication system 1400 uses the serial number to access a medication data field 1420 in memory 1408. Data field 1420 can have patient identification information 1428, such as their name, phone number, age, sex, and other relevant data. Data field 1420 can also store medication information 1424, which is transmitted from medication system 1400 to dispenser 1300 and then used by dispenser 1300 to determine when the patient is to be alerted to consume the medication. As needed all of the medication information for each patient's prescriptions can be consolidated into a single data field 1420.

Using a serial number allows a simple bar code or other read only interactive label to be used with dispenser 1300 to control medication dosing alerts when a medication system 1400 is available to provide the prescription information 82 and as desired medication information 84, program codes 86, and specific medication information 1430. Medication information 1424 can be transferred when medication container 1101 is first attached to dispenser 1300 or each time container 1101 is attached to dispenser.

It should also be understood that the invention as a whole may be embodied in other specific forms without departing from the spirit or central characteristics thereof. The present examples and embodiments thereof are to be considered in all aspects as illustrative and not restrictive, and the invention is not to be limited to the details given herein. It will be understood by those of skill in the art that various changes may be made and equivalents may be substituted without departing from the broader aspects of the invention. Specifically, while the invention has been shown and described as including a vial, blister pack or cassette container or aerosol dispenser, it should be understood that other forms of containers could be used with equal effectiveness. For example, the container could be a tray or a cassette that does not include a cap, cover or lid. The memory device or memory strip could also communicate with the processor of the container via RF technology. It should therefore be understood that the container can take on a variety of shapes and forms without departing from the broad aspects of the invention.

Although the above mentioned interactive medication containers 10, 200, 300, 500, 800, 850, 900, 1100, 1101, 1200, 1300 and 1370 have been generally shown and described as having computer processors 120, 530, 1304 and 1378, memory devices 125, 1306, and 1389, sensors 115, 826, 847, 876, 897, 940, 997, 1150, 1160, 1247, 1322 and 1377, communication devices 132-140, 525, 528, 542 and 544, timing device 145, access, removal and consumption indicators (e.g., buttons 160-166), as well as other components, being in electrical communication with each other and physically located on or within the housing, or otherwise integral with the container, console, unitary lid or dispenser, it should be understood that certain components could be physically separated from the container or its housing or their associated reminder unit 1114 or 1208 without departing from the broad aspect of the invention. For example, the communication device 132 could be a wall mounted display that is in infrared or radio frequency communication with the interactive medication container.

Eleventh Embodiment

Figure 59:
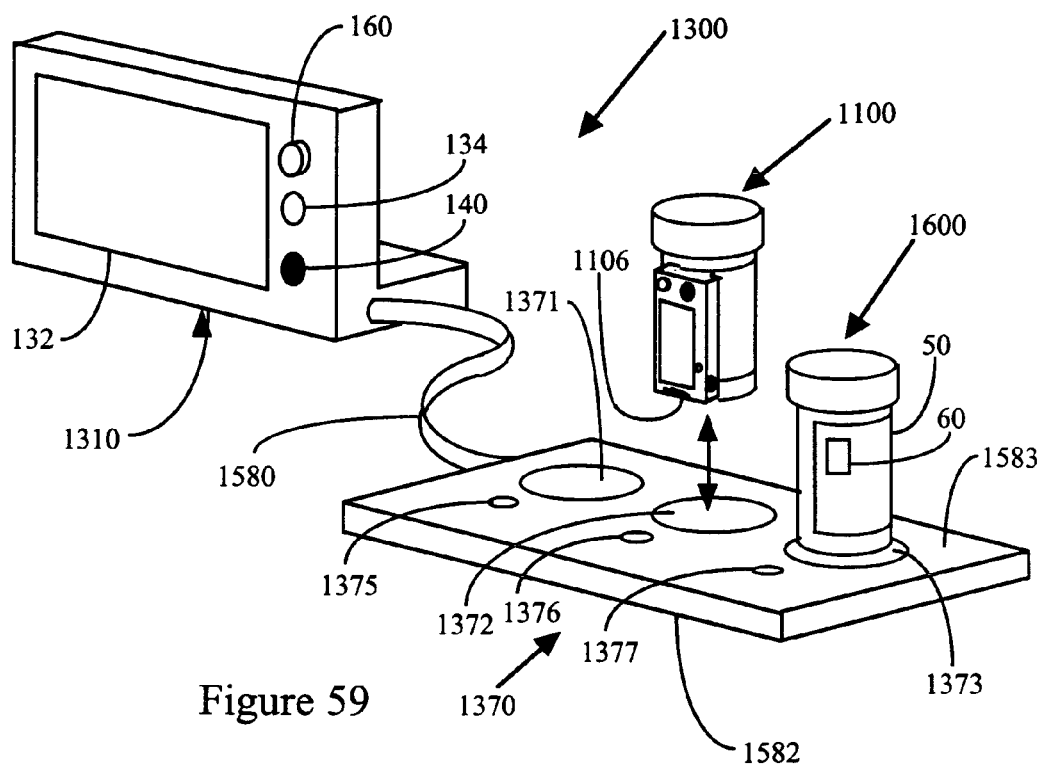
FIG. 59 is a perspective view of an eleventh embodiment of the present medication container invention including several containers of medication placed on a unitary console or dispenser, each container having its own machine readable information strip, and the dispenser having a separate indicator light, display and mating slot for each vial.
Figure 60:
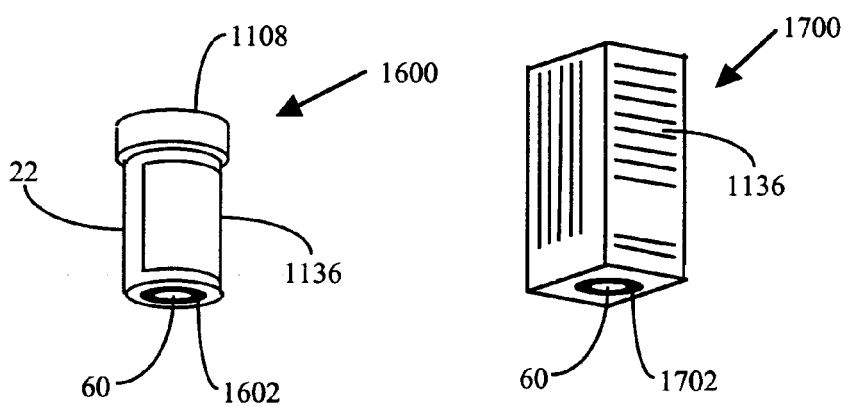
FIG. 60 is a perspective view of medication containers with machine readable labels.

Much of the construction and operation of the eleventh embodiment is similar in construction and operation to many of the embodiments described above. For this reason only the distinctions between the eleventh embodiment and the previous embodiments will be described here in detail. In addition, many of the features described below with respect to this eleventh embodiment are applicable to the previous embodiments. In FIGS. 59 and 60 elements that are similar to elements described in the previous embodiments are similarly numbered.

Referring to FIGS. 59 and 60, the eleventh embodiment includes a medication organizing system 1300 for interacting with containers such as containers 10 and 1100, one or more dispensers 1200 (see also FIGS. 40 and 41), one or more blister packs 400 (see FIG. 18) or any other suitable container having a readable identification or information tag. For instance, other containers that may be used with system 1300 that are not illustrated in the present specification include boxes, tubes, syringes, bottles, etc. For purposes of brevity, most of the following description will only describe use of container 10 with organizing system 1300 unless an aspect unrelated to container 10 is being described.

System 1300 defines an essentially flat plate 1370 for supporting containers 10 for sensing purposes. To this end, among other advantages associated with a flat sensor, it has been recognized that a flat sensor enables use of essentially any type of container without requiring a specifically configured receiving ring or other mechanical restriction for aligning memories and sensors.

Physical Elements of the Eleventh Embodiment

FIG. 59 illustrates medication-organizing system 1300 including an interface 1310, a sensor pad 1370 and variously configured containers 10 and 1100. Interface 1310 includes, among other things, a display 132, an infrared transmitter 140, an interaction button 160 and a female receiving recess (not separately numbered) for linking interface 1310 via a cable 1580 to sensor pad 1370. Referring also to FIG. 28, like the other embodiments described above, interface 1310 also includes a processor 1378, a memory 1389, a clock 145, some type of power source (e.g., a battery 150), an alarm 134 and may include other features as illustrated. In addition, although not illustrated, interface 1310 may also be linked to a computer network such as the Internet for remote communication with a server or the like.

Pad 1370, as illustrated, is an essentially flat pad including a top surface 1583, a female receiving recess (not separately numbered) for receiving cable 1580 and indicators or aligners 1375, 1376 and 1377. Surface 1583 defines a sensing area or volume adjacent thereto. In the illustrated embodiment, because surface 1583 faces upward, the sensing area is above surface 1583. Surface 1583 may also be provided with some indicia indicating where on the surface 1583 medication containers (e.g., 10) should be placed so that the container memories can be read. For example, in FIG. 59 three indicia are indicated by circular indicators 1371, 1372 and 1373. Indicia 1371, 1372 and 1373 may be either mechanical (e.g., slight indentations or recesses), visual such as sections of surface 1583 that have a different color than the other parts of surface 1583, or a mechanical and visual combination (e.g., a recess including a disparate color).

In one embodiment plate 1370 includes a separate sensor corresponding to and positioned below each of indicia 1371, 1372 and 1373, respectively, for a total of three separate sensors so that the surface of plate 1370 includes sensing sections adjacent indicia 1371, 1372 and 1373 and non-sensing sections laterally disposed from indicia 1371, 1372 and 1373. Referring also to FIG. 52, each of the plate 1370 sensors defines a limited sensing area or volume having a sensing radius (e.g., R1) so that the sensor can only sense a memory attached to a vial placed adjacent the indicia (e.g., indicia 1371). Thus, each separate sensor defines a separate sensing area above a corresponding indicator for a total of three sensing areas so that three separate memories can be read and correlated with specific locations (e.g., indicia 1371) and corresponding indicators (e.g., 1375) on plate 1370.

In one embodiment indicia 1371, 1372 and 1373 have shapes that are essentially identical to the shapes of the surfaces of the containers that are likely to be used with pad 1370. For example, as illustrated, circular indicia 1371 essentially mirrors or matches the shape and, is slightly larger in size than, the undersurface of container 10 thereby guiding a system user to place container 10 on surface 1583 for proper reading of the label.

While surface 1583 is illustrated as including placement indicia (e.g., 1371), it should be appreciated that, in at least one embodiment of the invention, such placement indicia is not required. For example, sensor pad 1370 may include a sensor that is capable of sensing information from any container placed within the sensing area defined by the pad (e.g., above pad 1370 in FIG. 59). In addition, it should be appreciated that, while the indicia 1371 may indicate a specific shape corresponding to the most likely shape (e.g., circular in the case of a vial) of a related container surface, other containers that do not have the most likely surface may still be used with pad 1370. For example, in the case of the illustrated pad having circular indicia 1371, pad 1371 may still be used with a blister pack (e.g., see FIG. 18) that is equipped with an appropriate tag (e.g., an RFID tag where an RF sensor is employed within pad 1370). In the case of a blister pack, while the entire pack likely will not fit within the indicia, an indicator may be provided on the exterior of the pack that instructs the pack user to position the tag adjacent the indicia and hence adjacent the RF sensor there below. Other embodiments of the invention where a sensor pad is capable of sensing within a large area are described in more detail below.

In one embodiment pad 1370 comprises an RFID sensor including one or more RF transmitters and receivers. In this embodiment pad 1370 it is contemplated that pad 1370 would be capable of sensing any suitably constructed memory device placed within the sensing area. For example, if the sensing area is defined as immediately adjacent surface 1583, pad 1370 is capable of sensing any device on a container surface immediately adjacent surface 1583 (e.g., likely a memory device in the form of an RFID tag on an undersurface of a container). Similarly, if pad 1370 includes a relatively more powerful transmitter and more sensitive receiver, the sensing area may extend above surface 1583 so as to define a volume (e.g., extending above surface 1583 with a radius of 2 to 4 inches—see FIG. 52 in this regard) so that even memory devices on lateral sides or top surfaces of containers could be interrogated.

Referring still to FIG. 59, indicators 1375, 1376 and 1377 are provided adjacent indicia 1371, 1372 and 1373, respectively. Each indicator (e.g., 1375) may be either audible or visual or both. For the purposes of this invention it will be assumed the indicators are visual such as LEDs or the like.

Container 1100 is similar to the container illustrated in FIG. 36 including reminder unit 1114 securable to container 1102. Unit 1114 includes interactive label 1106 near the bottom thereof such that, when container 1100 is placed on surface 1583, the transmitter within pad 1370 can interact with label 1106 and either receive information therefrom or, in some embodiments, write information thereto.

Container 10 is similar to the container illustrated in FIG. 2 including at least a readable and, perhaps a readable/writable interactive label 50 that in turn includes a memory device or strip 60. Again, the transmitter and receiver within pad 1370 are constructed such that when container 10 is placed on surface 1583, the sensing area or volume includes the space in which device 760 resides. In this manner the information stored in device 60 can be read and, in some cases, new information can be written to device 60, via pad 1370.

Referring to FIG. 60 there are illustrated two other embodiments of containers identified by numerals 1600 and 1700, respectively. Container 1600 includes a cylindrical vial 22 and a cap 1108 that securely locks thereto. In addition a print label 1136 is provided around the lateral surface of vial 22 and an RFID tag or memory device 60 is provided on an undersurface 1602 of vial 22. Referring also to FIG. 59, when container 1600 is placed so that surface 1602 rests on surface 1583, tag 60 is adjacent surface 1583 and pad 1370 may be designed such that the sensing area is proximate surface 1583.

Referring still to FIG. 60, container 1700 includes a square box 1704 with a print label 1136 on lateral surfaces and an RFID tag or memory device 60 on an undersurface 1702. Once again, with this embodiment of the container, when container 1700 is placed so that surface 1702 rests on surface 1583, tag 60 is adjacent surface 1583 and pad 1370 may be designed such that the sensing area is proximate surface 1583.

In operation, referring to FIGS. 59 and 60, assuming indicia 1371, 1372 and 1373 are provided on surface 1583, upon a system user receiving a medication in a tagged container e.g., 10, the user places the container 10 on one of the indicia 1373.

Referring also to FIG. 28, processor 1378 (not illustrated in FIG. 59) within interface 1310 is programmed to periodically pole pad 1370 to determine if any containers have been placed on surface 1583. For example, processor 1378 may pole pad 1370 every second or every half-second. Therefore, when container 10 is placed on indicia 1373, pad 1370 essentially immediately determines that a container has been placed on surface 1583. After determining that a container has been placed on surface 1583 processor 1378 interrogates the container tag (e.g., 60) to retrieve at least some information therefrom.

Next, processor 1378 may perform any of several different functions described above, depending on how processor 1378 has been programmed. For example, where the retrieved information indicates a "new" container or medication that has never been on pad 1370 before, processor 1378 may retrieve information from which a dosing regimen can be derived and thereafter may provide an alarm each time the medication should be consumed. The information to derive the consumption regimen may be either completely obtained from the vial memory or, in the alternative, may be retrieved from some other source as a function of information taken from the vial memory. For instance, specifying information read from the vial memory may include a serial number and processor 1378 may be linkable to a memory device (not illustrated) that correlates serial numbers with prescribed dosing regimens. In this case processor 1378 identifies the dosing regimen by correlating the serial number and the regimen.

The alarming may include, at a predetermined consumption time, providing a consumption indication via display 132 that prompts a system user to place container 10 back on surface 1583 to confirm that the medication within container 10 is to be consumed. In the alternative, where container 10 remains on surface 1583, the alarming may include an indication via an indicator light 1377 that the medication within the container associated with indicia 1373 should be consumed. Many other alarming routines including those described above in regard to other embodiments are contemplated.

In addition to the alarming features, system 1300 in FIG. 59 may also track medication consumption in any of several different ways such as, after an indication that medication should be consumed and after placement and removal of a container 10 on pad 1370, assuming that medication has been consumed and updating a remaining quantity counter in either a label memory device (e.g., 60), an interface memory (e.g., 1389 in FIG. 28) or some remote memory such as an Internet linked server memory. The updating process may also include noting the consumption dates and times and so on.

Moreover, other health safety functions may also be performed by processor 1378 that are based at least in part on information retrieved from the readable and/or writable container memory device 60. For instance, upon a user indicating that a medication is going to be taken by placing the medication container (e.g., 1600) on surface 1583, processor 1378 may be programmed to indicate when the user is attempting to take the medication to early according to the regimen. The early consumption indication may comprise an audible alarm with a message via display 132 including a blinking indicator (e.g., 1377) or some other suitable indication. If the user indicates consumption despite the warning, processor 1378 may record the ill-advised consumption in a memory and/or may revise the regimen going forward, based on the change in consumption pattern. For instance, if a medication prescription calls for a medication to be consumed at 2 AM followed by 5 AM and 8 AM and the medication is actually initially consumed at 10 PM, the system may revise the final two consumption times to be 12 PM and 2 AM, respectively, to maintain the temporal relationship between consumption times.

In addition, if medication is consumed to early processor 1378 may be programmed to skip indicating consumption at the regimented time. For instance, if a medication were to be consumed at 11 AM but was consumed at 10 AM, the processor would not indicate required consumption at 12 AM as such a medication schedule could result in an overdose.

Moreover, where more than one system user may use system 1300, processor 1378 may be programmed to, along with indicating that a medication is to be consumed, also indicate which of several system users is to consume the medication. For example, where a husband and wife are users A and B, respectively, and both use system 1300, processor 1378 may be programmed to indicate via display 132 which of users A and B should consume a medication at a regimented time. In this case it is contemplated that the machine-readable information on each vial memory would include some type of medication user identifier (e.g., name, unique user number, etc.) useable by processor 1378 to correlate prescription information with medication user.

Furthermore, where more than one user uses system 1300 processor 1378 may be programmed to pose a question to a user via display 132 such as "For which of users A or B would you like to see the medications to take at this time?". By selecting one of users A or B a user would then cause processor 1378 to identify the regimen for the selected user and provide indications of which medications should be consumed either at the current time or from that time forward.

In addition, processor 1378 may have access to other system user information in memory 1389 (see FIG. 28) or in some other network linked and remotely located memory (e.g., a storage area network (SAN)) which may be used to check for contraindications (i.e., indicators related to other medications that may indicate some relationship between a specific medication and some other medication the patient is currently consuming, exemplary medication relationships being that the medications should not be taken together, that the medications should be taken in some sequence or in some temporal relationship or with food, etc.) or allergies. The allergy information or contraindication information may be retrieved from the remote memory for consideration or may be remotely manipulated by a remote server. If a contraindication or allergy is identified processor 1378 may be programmed to indicate via an alarm or warning indicator.

In addition, processor 1378 may be programmed to make sure that, if medications have been paired, the paired medications are both tracked by system 1300. For example, some medications are prescribed as having to be taken together. If the information on a tag 60 indicates that first and second medications must be taken together, processor 1378 may require pairing of the medications and may alarm if such pairing is not evident. To this end processor 1378 may indicate a pairing requirement via interface 1310 and may require that each of two paired medication vials be placed on plate 1370 prior to indicating that the medications should be consumed. For instance, after a first of the paired medication vials is placed on indicia 1371 and is sensed, processor 1378 may indicate that the second of the paired medication vials should be placed on one of the other indicia 1372 or 1373. Upon placing the second of the vials on one of the other indicia and after sensing the second vial and confirming that the second vial corresponds to the paired medication an "OK to consume" or other suitable message may be provided to the user via display 132.

In addition, processor 1378 may be programmed to present messages to a system user based on the type of medication in a container. For instance, where a medication is manufactured by a specific company, the information retrieved from a tag 60 may specify a message to be displayed via display 132 related to the manufacturing company. Where interface 1310 is linked to the Internet an exemplary message may ask if the system user wants more information regarding the medication manufacturer or the medication which, when answered in the affirmative, hyperlinks to a web site providing the requested information via display 132 or some other device (e.g., a palm computer, a PC, a network device, etc.) associated with the system user.

In addition, processor 1378 may be programmed to provide specific questions regarding symptoms either before or after a medication is consumed and may track the answers. An exemplary question may inquire regarding dizziness one hour after medication consumption. Based upon questionnaire answers processor 1378 may either send information to a prescribing physician or may modify dosing regimen for the system user or both.

Figure 63:
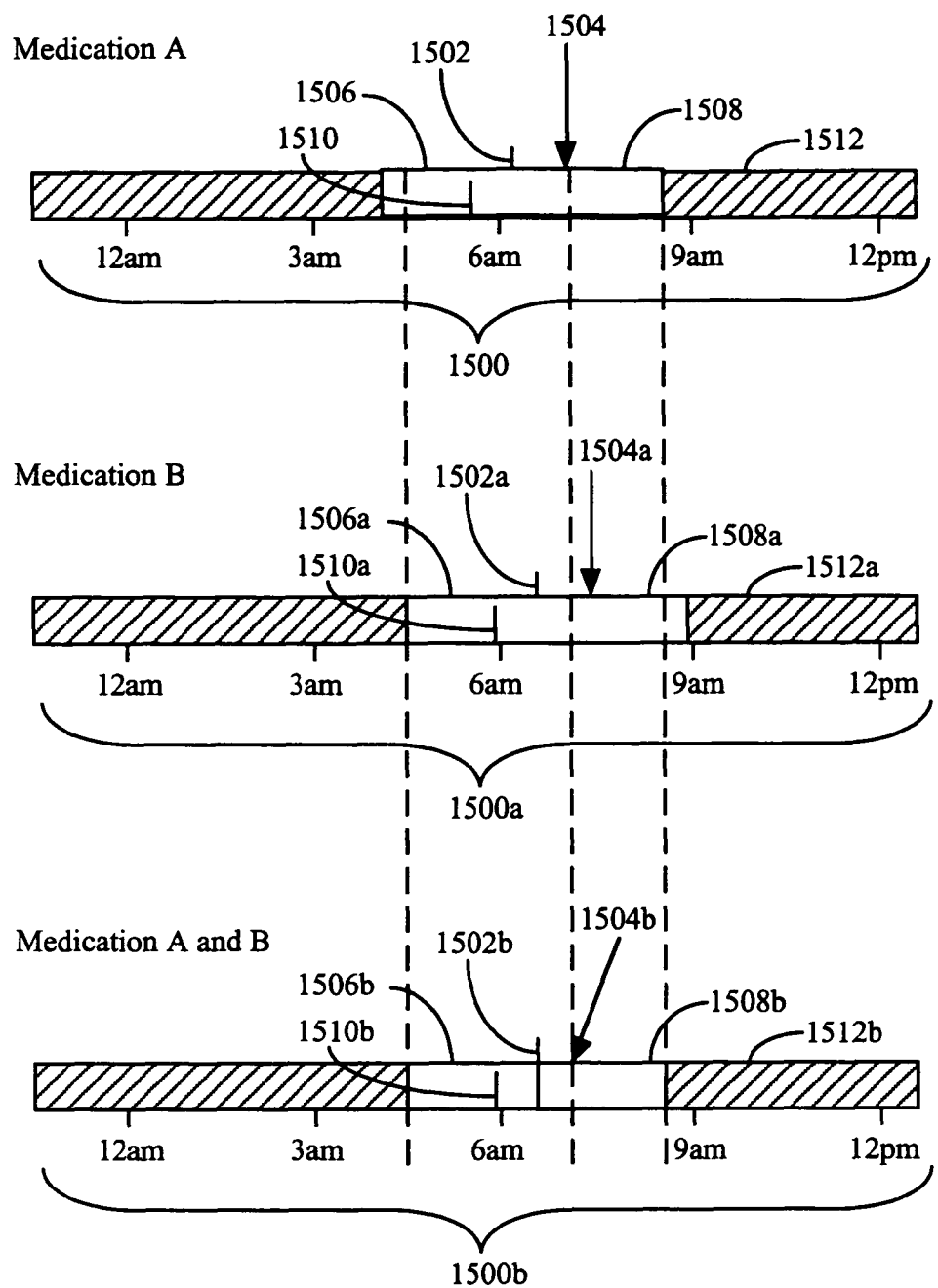
FIG. 63 is a representation of two time lines showing two proximal predetermined times to alert a patient to consume two different medications and a third time line showing a single time to alert the patient to consume both medications.

In addition, processor 1378 may be programmed to recognize when two medications are to be consumed within a relatively short period and may then provide a single alert indicating one time to consume both medications. To this end, refer now to FIG. 63, first and second time lines 1500 and 1500a schematically identify when a system user is to consume medications A and B, respectively. Medication A is to be consumed at predetermined time 1502 and medication B is to be consumed at predetermined time 1502a. Thus, times 1502 and 1502a correspond to times when one or more of the communication devices (e.g., display 132 in FIG. 59) are to be activated to notify the system user to consume medication.

Associated with predetermined time 1502 is a window of time or total time range 1504 that includes a time range 1506 before predetermined time 1502 and a time range 1508 after predetermined time 1502 during which medication A can be safely consumed. Similarly, associated with predetermined time 1502*a* is a window of time or total time range 1504*a* that includes a time range 1506*a* before predetermined time 1502*a* and a time range 1508*a* after predetermined time 1502*a*, during which medication B can be safely consumed.

When consumption times 1502 and 1502*a* are close together (e.g. 30 minutes) it may be undesirable to alert the system user once to consume medication A and then shortly thereafter alert the system user to consume medication B. Instead, medication information provided on a tag (e.g., 60) or accessible by medication organizing system 1300 can include consumption regimen information with variables that modify predetermined times 1502 and 1502*a* so that one alert is presented at a time 1502*b* when it is safe to consume both medications as shown on time line 1500*b*. Modified time ranges 1506*b* and 1508*b* can also be determined as appropriate. This process of consolidating alerts can be performed any time two or more medications are to be consumed within a short period.

In addition, processor 1378 may be programmed to automatically cause a refill order to be generated when the quantity of a refillable medication is nearly gone, may check the date on which a prescription was filled to make sure the medication is fresh or check if medication has been recalled prior to issuing a consumption alert.

Moreover, processor 1378 may be programmed to update a prescription from a physician. For example, if system 1300 is linked to a physician's computer via the Internet and a patient indicates dizziness one hour after medication consumption the physician may receive an e-mail indicating dizziness. In response to the e-mail the physician may send, via the Internet, an updated prescription to modify the dosing regimen. For instance, the physician may affirmatively reduce the consumption doses or may alter the regimen so that the periods between medication doses are longer.

In addition, processor 1378 may be programmed to develop a comprehensive medication consumption page for review by either the system user or a physician. To this end referring to FIG. 69, an exemplary simple consumption screen shot, display view or page 1800 is illustrated for three medications A, B and C. It is assumed that two tablets of medications A are to be taken every 4 hours beginning at time 10 AM, while two tablets or each of medications B and C are to be taken every 8 hours beginning at 10 AM.

The consumption page includes a graph having vertical and horizontal axes that indicate consumption quantity and time, respectively. There are three horizontal axis, a separate one of the axis corresponding to each of medications A, B and C where each of the horizontal axis have the same time divisions.

Figure 69:
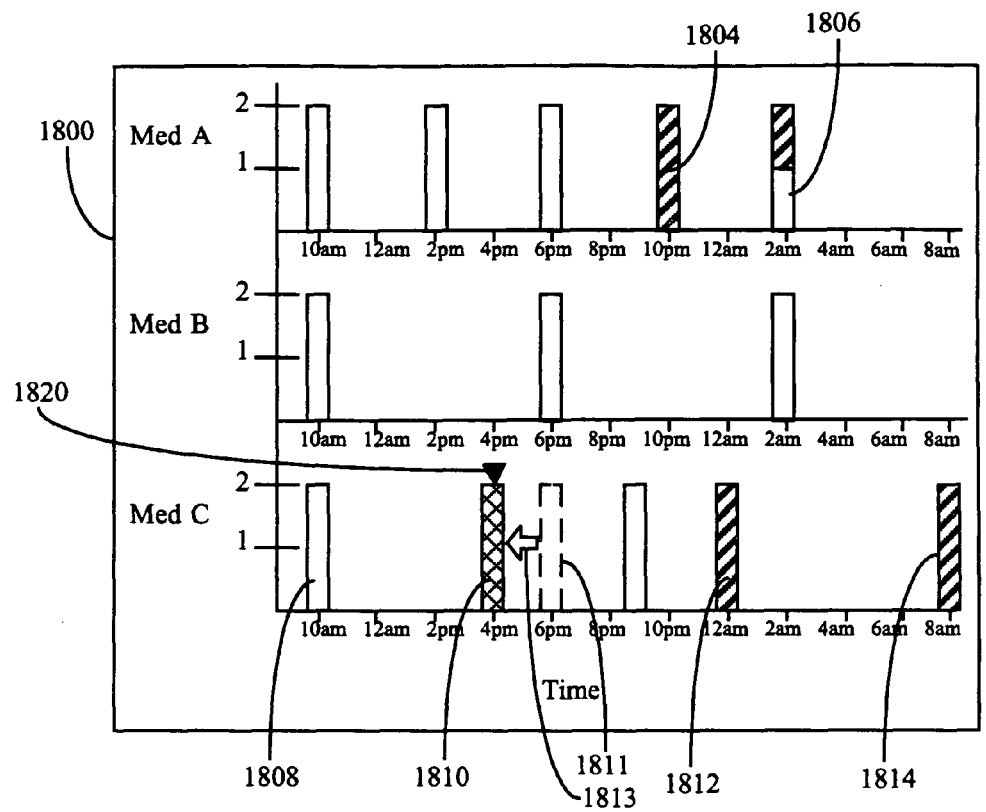
FIG. 69 is a schematic diagram of a schedule page or screen shot generated by an integrative device.

In the case of FIG. 69 it is assumed that a system user is to take each of medications A, B and C at the times specified above, that each of the medications has been provided within a unique container (e.g., 10 in FIG. 59) including an RFID tag 60 indicating the medication regimens, that each of the containers 10 has been placed on surface 1583 such that information from the tags has been read therefrom, that the regimens have been used to alert the user regarding consumption and that the user attempted to follow the regimens precisely.

On page 1800 there are several different indication types indicating how well the system user has followed the prescribed regiments as well as the occurrence of several other functions supportable by processor 1378. For example, bars collectively identified by numeral 1802 having a first appearance indicate consumption at a time specified by a regimen. Thus, at each of 10 AM, 2 PM and 6 PM on the day illustrated, two tablets of medication A were consumed as prescribed by the regimen. Similar indications are provided for various times regarding medications B and C.

Similarly, bar 1804 indicates that at 10 PM two tablets of medication A were supposed to be consumed but were not. Bar 1804 has an appearance that is different than bar 1802 so that the missed medication is clearly identified.

Bar 1806 includes a bottom portion that resembles bar 1802 and a top portion that resembles bar 1804 indicating that while two tables of medication A were to have been consumed according to the regimen, only one tablet was actually consumed at 2 AM. In this example it is assumed that there is some way to determine either manually or automatically that less than two tablets of medication were actually taken. For example, referring again to FIGS. 28 and 59, processor 1378 may be programmed to recognize activation of button 160 as an indication of tablets consumed. For instance two activations may indicate consumption of two tablets while a single activation may indicate consumption of one tablet. Other indicating mechanism methods and apparatus are contemplated.

With respect to automatically determining the number of tablets consumed the container 10 may be provided with some means of determining how many tablets remain in the container after some have been removed. In this case it would be assumed that all of the tablets removed were consumed at the time of removal.

Figure 61:
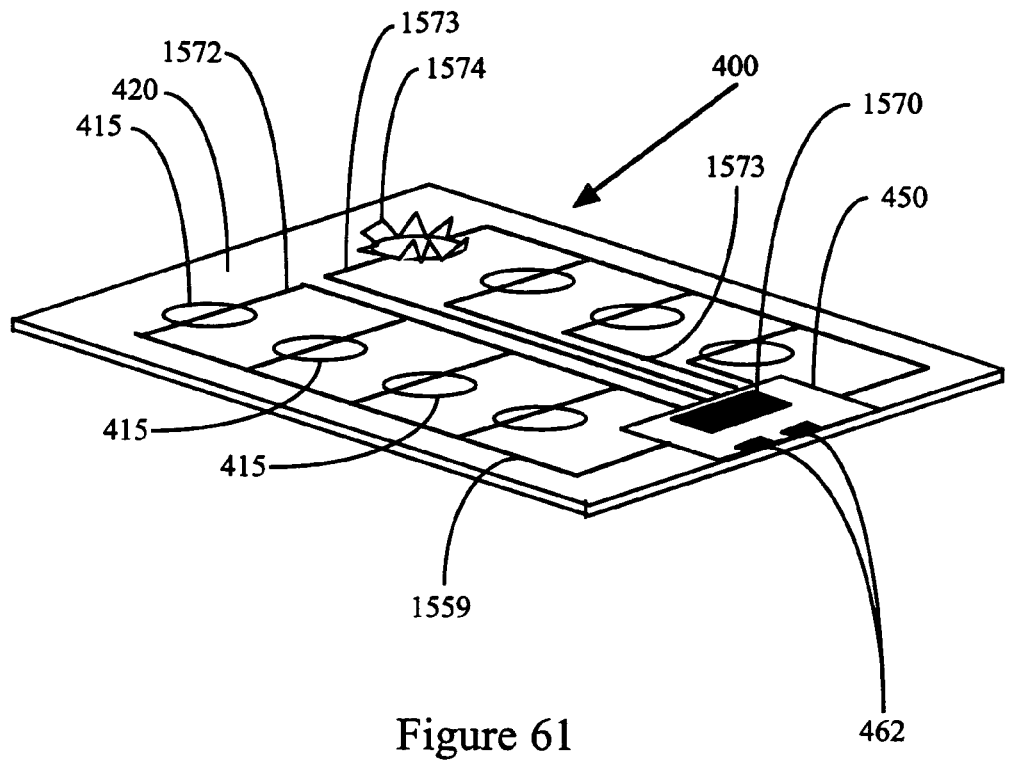
FIG. 61 is a perspective view of a blister pack medication container with a machine readable label and conductive runs that are machine readable and used to determine when medication has been removed from an individual blister.

As another example of a container that can be used to determine the number of tablets consumed refer now to FIG. 61 where a blister pack container 400 is illustrated. Pack 400 includes a back sheet 420, a label 450 having an RFID tag 1570 and electrical runs collectively identified by numerals 1572 and 1573. Sheet 420 defines a closing wall for a plurality of plastic blister compartments or pockets (not illustrated in FIG. 61 but similar to blister pockets formed from front and rear walls 412 and 413, respectively, in FIG. 19). In the illustrated embodiment of FIG. 61 sheet 420 forms a wall for each of eight separate compartments, each compartment having a wall identified by one of the circles in FIG. 61. Three of the separate compartment walls are indicated by numerals 415.

Figure 62:
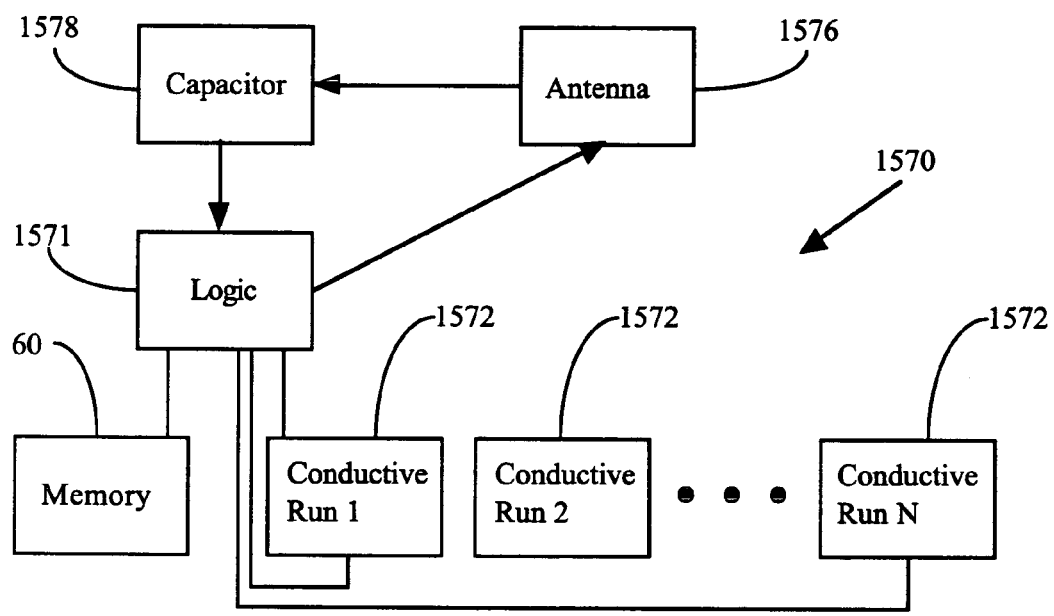
FIG. 62 is a schematic drawing of a circuitry used with the blister pack of FIG. 61, showing a RF transceiver, memory, conductive runs, and control logic circuits.

Referring also to FIG. 62, RFID tag 1570 includes a memory 60, logic 1571, a capacitor 1578 and an RF antenna 1576. In the illustrated embodiment 400 two separate conductive run configurations are shown including a first configuration having parallel arranged runs 1572 and a second configuration having a separate run for each f the blister pockets corresponding to the configuration. The parallel configuration includes four conductive runs 1572, one run for each of compartment walls 415. Each run 1572 passes across a separate one of walls 415 and all of the runs 1572 are linked at their ends in a parallel fashion to first and second return runs 1555 and 1557, respectively. Each return run 1555 and 1557 extends back to tag 1570 forming a loop therewith.

Together the four runs 1572 provide known impedance. When one of the runs 1572 is broken the impedance increases, when a second run is broken the impedance increases even further and so on. The impedances corresponding to each combination of broken runs 1572 (e.g., 1 broken, 2 broken, 3 broken, etc.) is also known. Thus, by measuring the combined impedances of the non-broken runs 1572 and comparing the measured impedance to the known impedances, the number of broken pockets (and hence consumed tablets) can be determined. This configuration is advantageous as the parallel configuration of runs reduces the overall run length required to provide the sensing function.

Referring still to FIG. 61, the second configuration of runs including runs 1573 that form separate sensing circuits or sensing loops for each of four corresponding pockets. To this end, a separate run 1573 extends from tag 1570 across each of four pockets (not separately numbered), each run linked to a common return run 1559 that returns to tag 1570. In this case logic 1571 monitors each of the runs 1573 and, when an open circuit is identified, logic 1571 concludes that the corresponding pocket has been broken.

With each of the first and second configurations described above, when a tablet is pressed through a wall 415 a break occurs in the corresponding run 1572 or 1573. An exemplary opened or broken wall is illustrated by numeral 1574. Because logic 1571 is linked to each run 1572 and 1573, logic 1571 can sense either a change in impedance (i.e., a impedance increase or an open circuit) each time a tablet compartment is opened and, upon opening a compartment, it is assumed a tablet is consumed.

Logic 1571 is also linked to antenna 1576 for sending and receiving information, is linked to capacitor 1578 for receiving power through RF excitation and is linked to memory 60 to read the memory and update the memory.

Referring to FIGS. 59, 61 and 62, any time antenna 1576 is placed within a sensing area (e.g., adjacent surface 1583), antenna 1576 is excited and charges up capacitor 1578. When capacitor 1578 discharges the capacitive power energizes logic 1571 at which point logic 1571 can perform any of several different functions. For example, logic 1571 may simply transmit medication information to sensor pad 1370 via antenna so that the system 1300 of FIG. 59 can identify a consumption regimen. In addition, logic 1571 may interrogate each run 1572 to identify any breaks in the runs 1572. When a break is identified, logic 1571 may update memory 60 to reflect the break and, may also send a message via antenna 1576 to pad 1370 indicating any new breaks which are assumed to correspond to tablet consumption. In any case the configuration of FIG. 61 clearly can be used by system 1300 to automatically identify consumption.

Referring still to FIG. 69 all of the bars related to medication B indicate that medication B was taken at each of the times specified by the regimen in the specified amounts (i.e., two tablets each time).

Regarding the portion of the graph related to medication C, bar 1808 indicates that medication C was taken as prescribed at 10 AM. However, at 4 PM medication C was taken two hours prior to the time specified by the regimen (i.e., the specified time was 8 hours after time 10 AM and therefore medication C should have been taken next at 6 PM, not 4 PM). To indicate consumption at an incorrect time bar 1810 is placed at 4 PM and has an appearance that is different than the other bars (e.g., 1802, etc.).

In addition to indicating mis-medication, when early consumption occurs, processor 1378 modifies the next consumption times for medication C in an attempt to get the system user back on the prescribed medication cycle. To indicate a medication cycle adjustment a bar 1811 and an adjustment arrow 1813 are provided to indicate the regimen adjustment. In addition, alert times following consumption bar 1810 are modified such that consumptions occur at 8 hour intervals beginning with bar 1810 and as consistent with the original prescription. Consumption bars corresponding to the modified times are identified by numerals 1812 and 1814.

In addition to the indicators identified above, a notification indicator 1820 is provided at the 4 PM time corresponding to medication C that indicates that a notification was sent to the prescribing physician that a regimen has been altered as a function of mis-medication. As described above the notice may be sent in any manner including an e-mail, page, automatic phone call, etc.

Consumption page 1800 may be displayed via display 132 in FIG. 59 or by way of some other interface such as a personal computer associated with the system user or by a personal computer associated with a physician.

While the consumption page 1800 illustrates past consumption, it should be appreciated that the consumption page may also be used to view future consumption regimens or to modify consumption regimens. To this end, although not illustrated, other mechanical or on-screen buttons and icons may be provided to enable a system user to view and edit.

Twelfth Embodiment

The twelfth embodiment is similar to the eleventh embodiment except that the twelfth embodiment includes a much smaller sensing pad and therefore represents a relatively inexpensive configuration.

Figure 64:
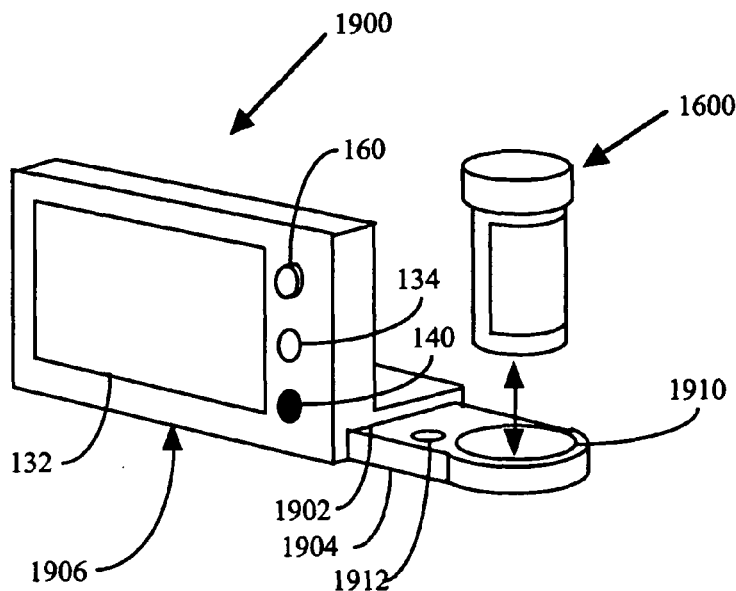
FIG. 64 is a perspective view of a twelfth embodiment of the present medication container invention using one or more containers of medication that are associated with a unitary console or dispenser, each container having its own machine readable information strip.

Much of the construction and operation of the twelfth embodiment is similar or identical to many of the above embodiments in construction and operation and therefore only the distinctions between the twelfth embodiment and the previous embodiments will be described here in detail. In FIG. 64 components that are similar to components described above are often identified by similar numbers.

Referring specifically to FIG. 64 the twelfth embodiment includes a medication organizing system 1900 for interacting with any of the containers described above (e.g., containers 10, 200, 400, 950, 1100 and 1101 or 1200) and for any other suitably labeled container type (e.g., boxes, tubes, syringes, bottles, etc.). For purposes of brevity, most of the following description only discusses the use of container 1600 with organizing system 1900 unless a feature not represented by container 1600 is being described. Once again referring to FIG. 60 container 1600 has a memory strip 60 in the form of an RFID tag placed on undersurface 1602.

Referring to FIG. 64 system 1900 includes an interface 1906 and a relatively small sensor pad 1904 that are used in conjunction with container 1600. Referring also to FIG. 59, interface 1906 is essentially identical to interface 1310 except that interface 1906 includes an enlarged port 1902 for receiving a male end of pad 1904. For this reason components and operation of interface 1906 will not be described here in detail.

Sensor pad 1904 is relatively small having a top surface 1910 that defines a sensing area just above surface 1910. In the illustrated embodiment surface 1910 is essentially the same shape as and slightly larger than the under surface of the containers (e.g., 1600) likely to be used with system 1900. In this manner surface 1910 can help a system user to place containers 1600 correctly adjacent the sensor that resides just under surface 1910.

An indicator (e.g., LED) 1912 is also provided adjacent surface 1910. A male extension (not illustrated in FIG. 64 but similar to the extension of FIG. 65) is constructed so as to be receivable within port 1902 so that the processor within interface 1906 can communicate with sensor pad 1904.

Referring to FIGS. 9, 28 and 64, in one embodiment pad 1904 includes a sensing element 115 (e.g., an RF sensor in the form of an antenna just below surface 1910). When pad 1904 is linked to interface 1906 via port 1902 the processor 1378 within interface 1906 is linked to the sensing element 115 for retrieving information from any RFID tag within the sensing area.

When a container 1600 is placed on top of slot or surface 1910 processor 120 retrieves information from memory 60 via the RF sensor 115 just below surface 1910. Processor 120 transfers retrieved information to the interface memory 1389 (see also FIG. 28) for each medication placed on surface 1910.

In operation, initially a container 1600 containing medicine provided by a pharmacy and including an RFID tag 60 is placed on surface 1910. When more than one medication in separate containers 1600 are to be organized by system 1900, processor 1378 uses the information retrieved from each medication container to determine times when the medications are to be consumed. System 1900 issues consumption alerts using display 132 and/or indicator 1912 and may also use an audible alarm (i.e., 134 in FIG. 28). The alert continues until the RFID tag 60 on the correct medication container 1600 is brought into the sensing area above surface 1910. When a RFID tag 60 is brought within the sensing area above surface 1910, processor 1378 retrieves information from the container RFID tag 60 and compares the retrieved information to previously stored information in memory 1389 to determine if the container is the container that corresponds to the alert (i.e., is the container from which medication should be consumed).

If the sensed container 1600 corresponds to the alert, processor 1378 turns off the alert. When the container 1600 is removed from the sensing area for a period having duration at least as long as the minimum time required to consume the prescribed dose, it is assumed that the prescribed consumption dose has been consumed. For example, the period duration may be 10 seconds, a minimum likely time required to uncap the container, dispense the prescribed dose, recap the container and consume the dose. After the prerequisite time required to assume consumption, processor 1378 may record the consumption information to memory 1389. When it is inconvenient to bring container 1600 in proximity to surface 1910 button 160 or a touch screen icon can be used to indicate medication consumption.

Alternately, the alert can be temporarily delayed by pressing button 160 twice or it can be canceled (the recommended consumption is skipped) by pressing button 160 three times or by selecting another button or touch screen icon. This information can be recorded in memory 1389. To cancel or delay the alert does not require that a container be positioned within the sensing area adjacent surface 1910.

The processes of modifying dosing times, determining contraindicated medications, pairing medications and sequencing medications described above with respect to other embodiments are also contemplated with respect to this twelfth embodiment.

Thirteenth Embodiment

Figure 65:
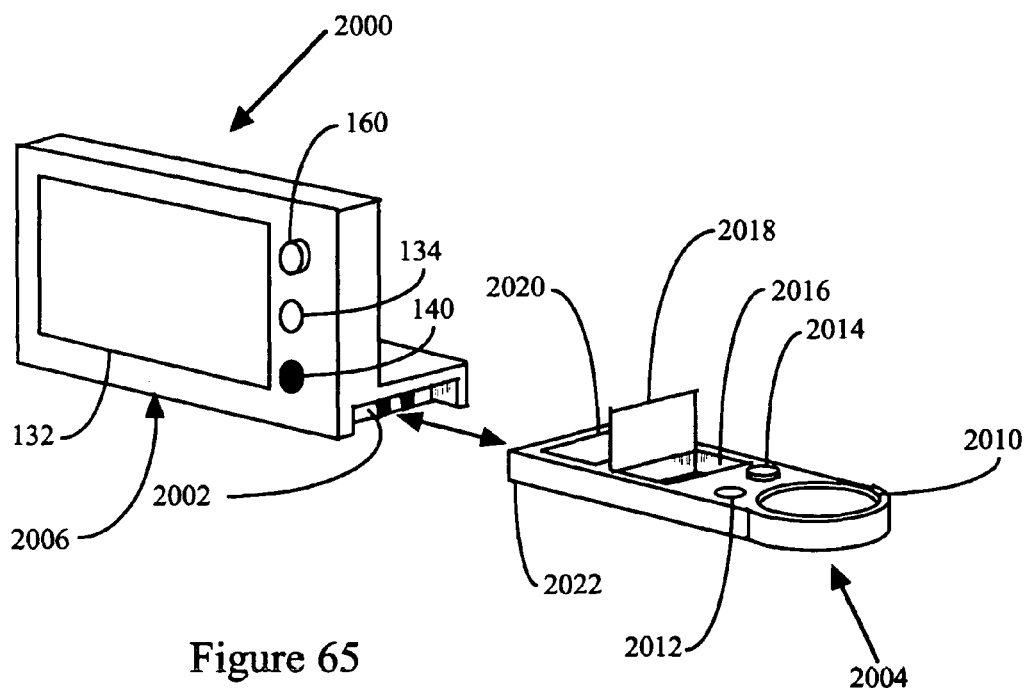
FIG. 65 is a perspective view of an alternate form of the twelfth embodiment of the present medication container invention using one or more containers of medication that are associated with a unitary console or dispenser, each container having its own machine readable information strip and the console is used with a portable container and reminder device.
Figure 66:
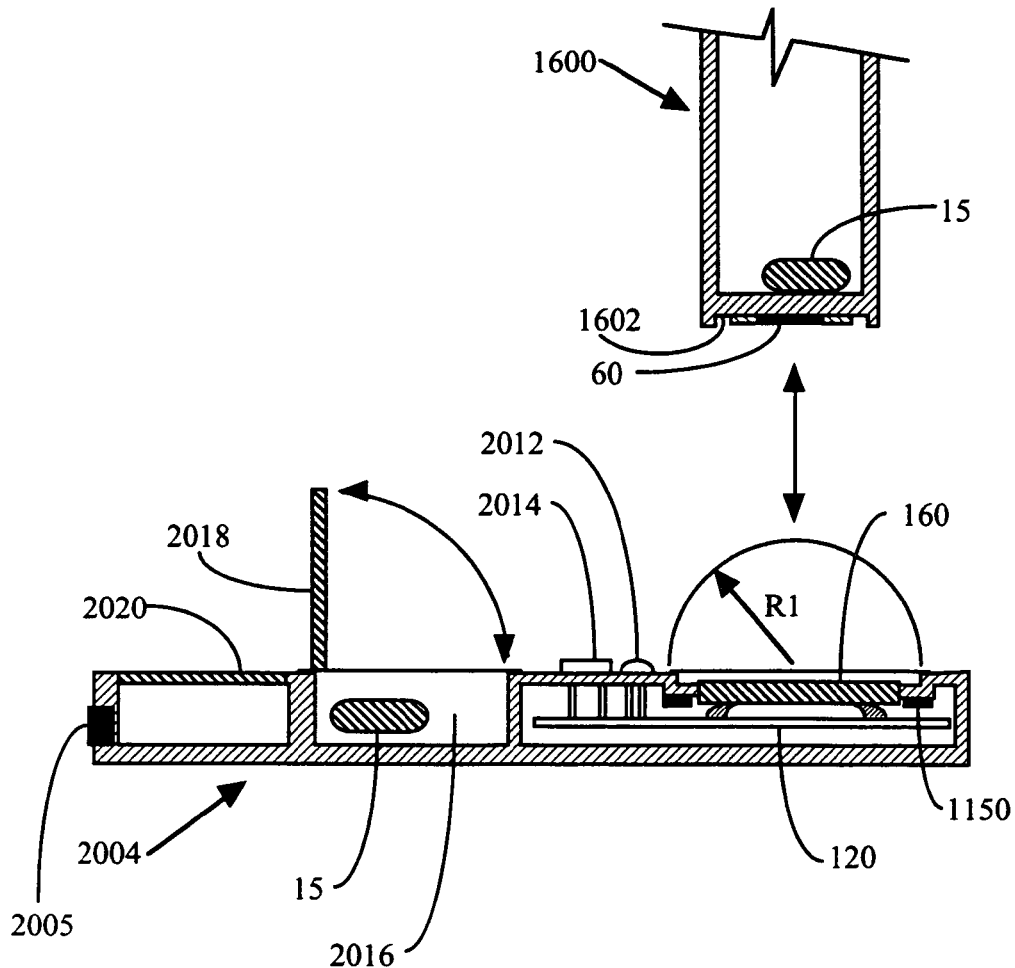
FIG. 66 is a side sectional view of the removable, portable subassembly of the twelfth embodiment of the present medication container invention showing placement of a sensor to read the memory strip of a container and a medication compartment.

Referring to FIGS. 65 and 66, yet another embodiment or system 2000 of the invention is illustrated. The thirteenth embodiment or system 2000 is similar to the embodiment of FIG. 64 in many respects and therefore, in the interest of brevity, only unique features of the thirteenth embodiment will be described here in detail.

System 2000 includes an interface 2006 and a portable or remote reminder unit 2004 that are to be used in conjunction with any container that is suitably labeled for information retrieval. Again, in the interest of brevity it will be assumed that only containers 1600 as described above with respect to FIG. 60 are used with system 2000 and any system components that are similar to components described above will not be described again here in detail.

Interface 2006 is essentially identical to interface 1906 in FIG. 64 and therefore will not be explained again in detail. Suffice it to say that interface 2006 includes at least one interface button 160, a display screen 132, an audible indicator 134 and a female port 2002 including contacts 1596 for receiving a male end of reminder unit 2004 and matching contacts 2005. In addition, referring also to FIG. 28, interface 2006 includes a processor 1378 and other components including an interface memory 1389, a clock 145 and a power source 150 (e.g., a battery). Moreover interface 2006 may also be linked to a computer network such as the Internet.

Unit 2004 is a portable pad including a sensing surface 2010, a visual/audio indicator 2012, an interface button 2014, first and second compartments 2016 and 2017 closable by first and second compartment lids 2018 and 2020, respectively, and a male extension 2022 including contacts 2005 configured to be that is receivable within female port 2002. In addition, referring also to FIG. 9, in the illustrated embodiment unit 2004, like some of the portable smart vial embodiments, also includes a processor 120 linked to a memory 125 (not illustrated in FIG. 66), a sensing element 115 (e.g., an RFID tag reader) that resides just below surface 2010, a clock 145 (not illustrated in FIG. 66) and a power source 150 (e.g., a battery not illustrated in FIG. 66). In addition, in some embodiments unit 2004 may also include some means for locking each of lids 2018 and 2020 closed until prescribed consumption times.

Operation of unit 2004 and interface 2006 together may take many different forms depending upon the functions supported by system 2000 as a whole. For example, reminder unit 2004 may be programmed to simply alert and record consumption and may not be programmed to identify a consumption regimen from RFID tag information, regimen identification reserved for interface 2006. In the alternative unit 2004 may be able to identify medication regimens from RFID tag information. According to another alternative unit 2004 may simply alert and may not be programmed to record consumption or may be programmed to record consumption without providing consumption alerts. An exemplary embodiment of how the reminder unit 2004 and interface 2006 may operate together is provided below.

Remote and portable unit 2004 is used when a system user's prescription regimen calls for the user to consume one or more medications in the middle of the day and where interface 2006 is too large to be carried during the day. Unit 2004 is sized to be carried conveniently by a system user and can be programmed with alert information regarding all medications that are to be taken remotely.

In operation, referring to FIGS. 65, 66, 9 and 28, with extension 2022 plugged into port 2002 so that processor 1378 can communicate with sensor 115 (i.e., the sensor just under surface 2010), when more than one medication in separate containers 1600 are to be organized by system 2000, processor 1378 uses the information retrieved from each medication container to determine times when the medications are to be consumed. For fixed system use, system 2000 may issue consumption alerts using display 132 and/or indicator 2012 and may also use an audible alarm. The alert continues until the RFID tag 60 on the correct medication container 1600 is brought into the sensing area above surface 2010. When a RFID tag 60 is brought within the sensing area above surface 2010, processor 1378 retrieves information from the container RFID tag 60 and compares the retrieved information to previously stored information in memory 1389 to determine if the container is the container that corresponds to the alert (i.e., is the container from which medication should be consumed).

If the sensed container 1600 corresponds to the alert, processor 1378 turns off the alert. When the container 1600 is removed from the sensing area for a period having duration at least as long as the minimum time required to consume the prescribed dose, it is assumed that the prescribed consumption dose has been consumed. After the prerequisite time required to assume consumption, processor 1378 may record the consumption information to memory 1389.

It is contemplated that a medication user's regimen may require that the user consume more than one medication at about the same time. While system 2000 may be equipped to provide a single alert for several different medications at the same time by listing medications on display 132, in some embodiments it may be advantageous to provide separate consecutive alerts to the user one at a time to avoid confusion. Thus, where medications A, B and C are to be consumed at about the same time system 2000 may provide a first alert corresponding to medication A and, after medication A has been consumed (i.e., medication A vial has been placed on pad 2010, confirmed and removed), provide a second alert for medication B and, after medication B has been consumed, provide yet a third alert for medication C.

In this case, when an alert for medication A is provided but each of medications A, B and C are to be taken at about the same time, if the medication user selects one of medications B or C and places that medication on pad 2010, system 2000 may be programmed to recognize that the vial on pad 2010 does not correspond to medication A but does correspond to medication B or C and that the medication B or C also must be consumed at the alerting time. Here, system 2000 may be programmed to halt the current alert and allow consumption and, after a short interlude to allow consumption, may provide the medication A alert a second time and so on until all of the medications to be consumed at the alerting time are consumed.

This multi-consumption feature may also be supported via other embodiments of the present invention including each of the remote devices and systems described in more detail above and in the following paragraphs.

To explain remote use via reminder unit 2004 it will be assumed that a system user expects to be remotely located for 10 hours between 8 AM and 6 PM and that during that time the user is to consume two tablets of a medication A every two hours beginning at 10 AM and one tablet of a medication B every four hours also beginning at 10 AM. Assuming the consumption schedule described above is already stored in memory 1389 a system user may use interface 2006 to indicate that the user will be remotely located for the specified period between 8 AM and 6 PM and that the user wishes to use the reminder unit 2004 remotely. Such information can be indicated in any of several ways including interface button 160 or selection of icons provided on display 132.

After indicating a desire to medicate remotely via interface 2006, interface processor 1378 identifies a remote consumption schedule corresponding to the remote use period specified (i.e., 8 AM to 6 PM). Thus, the remote schedule includes alerts to consume two tablets of medication A at each of times 10 AM, 12 AM, 2 PM, 4 PM and 6 PM as well as alerts to consume one table of medication B at each of times 10 AM, 2 PM and 6 PM. Processor 1378 then transfers the remote schedule alert regimen to reminder unit memory 125 (see FIG. 9).

In addition processor 1378 instructs (e.g., via display 132) the system user to retrieve each of medications A and B so that the medications can be transferred to compartments 2018 and 2020 for remote transport. When the container corresponding to medication A is positioned such that its RFID tags is within the sensing area above surface 2010, processor 1378 reads the RFID tag on the bottom of the container, recognizes the container as the container including medication A, instructs the system user to remove the number of tablets required for remote consumption and instructs the user to place the tablets within one of compartments 2018 or 2020. When the medication A container is removed from the sensing area it is assumed that the indicated number of tablets have been removed and placed within the compartment. Similarly processor 1378 instructs the user to remove the prescribed number of tablets for remote consumption from the medication B container for placement in one of compartments 2020 or 2018. Where two medications are to be taken remotely at about the same time, processor 1378 may instruct the medication user to place each of the two medications in a single compartment (e.g., 2016) for transport.

Once medications A and B have been stored for remote consumption processor 1378 cancels the alerts at interface 2006 so as those alerts will be handled remotely. Moreover, processor 1378 may store an indication within memory 1389 that medications A and B were dispensed for remote consumption so that, after the remote period, interface 2006 can require the user of the remote device to confirm consumption and consumption times. Furthermore, processor 1378 may update the medication quantities in container memory devices (e.g., 60) or in an interface memory 1389 either upon dispensing or upon subsequent consumption confirmation.

After medications A and B have been placed in the specified compartments the user is instructed that unit 2004 can be detached from interface 2006 for remote use. Thereafter, while the user is remotely located, processor 120 tracks the remote regimen and provides alerts to the remote device user indicating when each of medications A and B should be consumed. Consumption alerts may be provided either audibly, visually, via vibration, or any combination thereof, depending upon mechanical capabilities of remote unit 2004.

In addition to providing consumption alerts, processor 120 may be programmed to perform any of the functions described above with respect to the stationary interface processors. For example, remote unit 2004 may be equipped with a locking mechanism (e.g., a solenoid-powered latch) that locks each of the compartment lids (e.g., 2018) closed until the consumption times. In addition, after an alert and after a lid is opened processor 1378 may record the lid opening time as a consumption time for the medication stored in the corresponding compartment. Other functions are contemplated.

After a remote use period system 2000 may cause synchronization of the information stored in remote device 2004 and interface 2006 so that the consumption records may be complete. To this end, at the end of the remote period interface 2006 may prompt the system user to re-link remote device 2004 to interface 2006 so that the consumption information can be read and stored in memory 1389. In the alternative, upon the next consumption alert generated by interface 2006, interface 2006 may request that remote device 2004 be re-linked via port 2002 for two purposes. First, upon re-linking a vial can be placed on surface 2010 to confirm which of several medications should be consumed. Second, the information related to remote consumption in memory 115 can be read and synchronized at that time.

Moreover, if some of the medication was not consumed at the prescribed remote use times, processor 1378 can instruct the system user to return the un-consumed medication back to the correct vial. To this end, assume that despite effort to follow the remote regimen, a system user missed one prescribed consumption of medication A and therefore, upon returning to interface 2006, there are two tablets of medication A in one of the compartments (e.g., 2016). In this case, remote device 2004 would have recognized that, at one of the prescribed times, compartment 2016 was not opened and therefore would assume mis-medication. Thus, upon returning to interface 2006, interface processor 1378 identifies that two medication A tablets remain in compartment 2016 and request that the user place the medication A container (i.e., a vial 1600) on surface 2010. When the correct container 1600 is placed on surface 2010, processor 1378 recognizes the container and instructs the user to return the medication A tablets back to the container for future consumption.

Where more than two medications are to be consumed remotely or where the volume required to transport medications for remote consumption is greater than the volume of a compartment 2016, remote device 2004 may be equipped to operate with separate vials (e.g., 1600, see FIG. 66) when medication is to be consumed. To this end it is assumed that a medication user may transport both device 2004 and one or more vials 1600 that store medications to be remotely consumed. Then, when device 2004 generates a consumption alert, the medication user retrieves one of the vials and places the under surface of the vial adjacent sensor 160. Device 2004 then determines if the vial adjacent sensor 160 corresponds to the alert. If the vial corresponds to the alert, device 2004 indicates a match and discontinues the alert. If the vial does not correspond to the alert, device 2004 would either continues the alert or provide a different alert indicating that a match was attempted but did not occur.

The processes of modifying dosing times, determining contraindicated medications, pairing medications and sequencing medications described above with respect to other embodiments are also contemplated with respect to this thirteenth embodiment.

Fourteenth Embodiment

Figure 67:
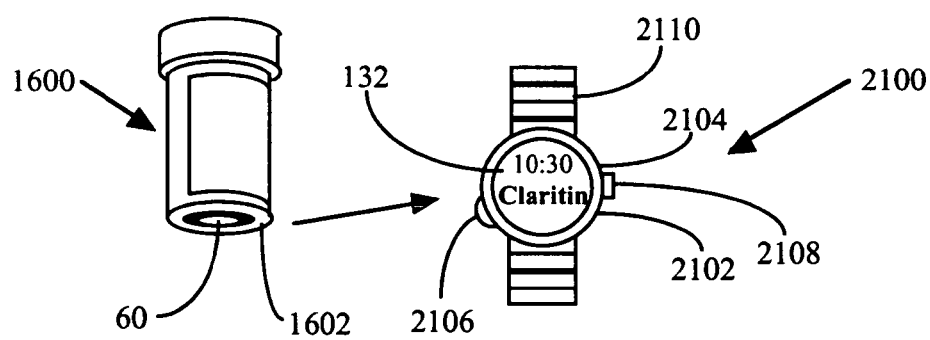
FIG. 67 is a plan view of an alternate form of the twelfth embodiment of the present medication container invention now in the form of a portable personal that can be worn.

Referring now to FIG. 67 yet another embodiment 2100 of the invention is illustrated. This fourteenth embodiment 2100 is similar to the embodiment described in conjunction with FIGS. 65 and 66 and other embodiments above and therefore will only be described in general terms to highlight the differences between this and the other embodiments. To this end, it is contemplated that a remote reminder/recording device 2102 that is relatively small and that does not include a container itself may be configured. Again, as with the embodiments described above, device 2102 may be used with any of the containers described above but, in the interest of simplifying this explanation, will only be described in the context of exemplary container 1600 including an RFID tag 60 disposed on an undersurface 1602 where the tag is either readable or readable/writable.

As illustrated device 2102 may take the form of a watch including a small display 132 that forms a sensing surface 2104 and has one or more audible or visual indicators 2106 and an interaction button 2108. Referring also to FIG. 9, as in the case of the remote device in FIGS. 65 and 66, device 2102 includes a processor 120, a memory 115 and, of course, a power source 150 and a clock 145. In this embodiment device 2102 may also be equipped with contacts (not illustrated) for linking to an interface cable like cable 1580 in FIG. 59. In the alternative, an interface (e.g., 1310 in FIG. 59) may be equipped to communicate via RF or IR transmission and reception with a proximate remote device like device 2102. To this end note that device 2102 already includes an RF antenna for reading and perhaps writing to RFID tags 60 on the undersides of containers 1600.

Device 2102 operates in a fashion similar to that described above with respect to FIGS. 65 and 66 except that, because device 2102 does not include medication compartments, in addition to a user having to travel with device 2102, the user must also take one or more containers (e.g., 1600) when travelling remotely so that medications can be transported. Thus, referring also to FIG. 65, assuming device 2102, instead of device 2004, is used with interface 2006 and assuming medication regimen information is already stored to be accessed via interface 2006, when a system user indicates via interface 2006 that the user will be travelling remotely and wants to use remote device 2102 for a specified time, interface 2006 identifies the medications to be consumed and the consumption times that will occur during the remote use. Then, interface 2006 instructs the user to select each of the medications to be remotely used and requests that each medication container be placed such that its tag (e.g., 60) is proximate surface 2104 so that tag information can be read and the interface processor (e.g., 1378) can determine if the container is the correct container.

Assuming the correct medication container is held adjacent surface 2104, interface 2006 indicates that the user should take the container along and also writes the remote regimen information for the specific medication to the remote device 2102 memory. A similar process is followed for each of the medications to be consumed during the remote use.

Once all of the remote regimen information has been written to the device 2102 memory 115, during remote use of device 2102, device 2102 alerts the user each time a medication is to be consumed. An exemplary alert may indicate that two tablets of a medication A are to be consumed and may request that the user place the medication A container such that a corresponding RFID tag 60 is adjacent surface 2104. When the medication A container is properly positioned the device 2102 processor 120 reads the container memory and confirms that the container is the correct container from which to take medication. If, for example, a medication B container is positioned with respect to surface 2104 instead of the required medication A, device 2102 may alert via indicator 2106 or some other device that the wrong container has been selected. Once the correct container has been positioned relative surface 2104, device 2102 indicates the correct container.

When the container is removed from surface 2104 device 2102 assumes that the quantity of medication prescribed for consumption and indicated via display 132 has been consumed. Assuming consumption device 2102 updates its internal memory 115 to reflect medication consumption. Thereafter, at some suitable time after the remote use that was earlier specified (e.g., upon the next interaction with interface 2006), interface 2006 may query the user or device 2102 to provide the remote use information which is then stored as part of a complete consumption record for the patient.

Embodiment 2100 may operate independently of a stationary or home interface like interface 2000 in FIG. 65 such that device 1202 would collect information from vial memories and perform all of the consumption sequencing and reporting tasks as well as any other health safety functions contemplated in this description.

The processes of modifying dosing times, determining contraindicated medications, pairing medications and sequencing medications described above with respect to other embodiments are also contemplated with respect to this fourteenth embodiment.

Fifteenth Embodiment

Figure 68:
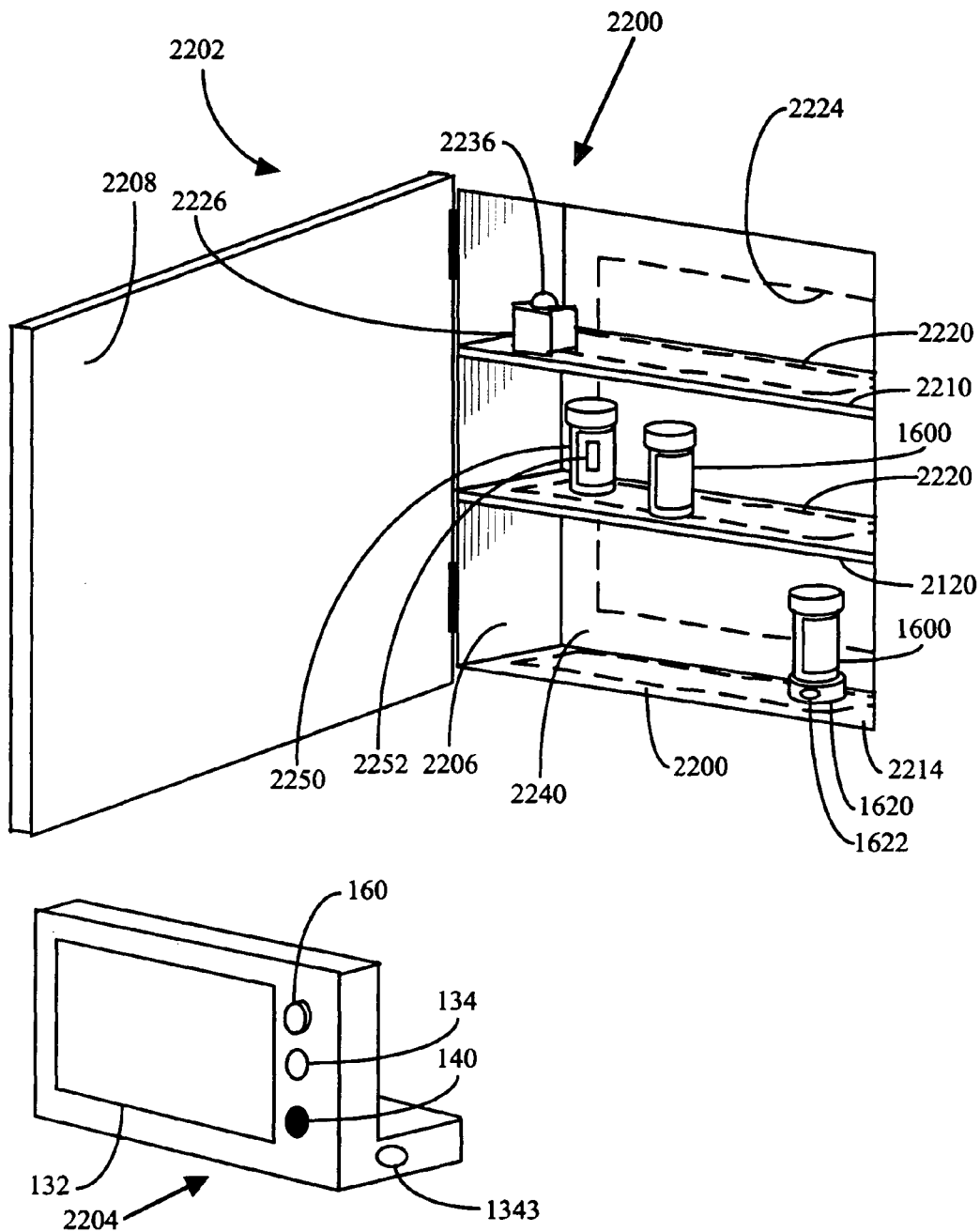
FIG. 68 is a perspective view of the thirteenth embodiment of the present medication container invention in the form of a medication cabinet for housing one for more medication containers with machine readable memory strips and a unitary console or dispenser.

Referring now to FIG. 68 therein is illustrated yet one other embodiment 2200 of the present invention. Embodiment 2200 includes an enclosure which, as illustrated, may be a medicine cabinet or, in the alternative, the enclosure may be a kitchen cabinet or the like. Enclosure 2202 includes a relatively large compartment 2206 and a door 2208 hinged adjacent compartment 2206 that can be used to close or open compartment 2206. Compartment 2206 is sized to receive, among other things, a plurality of containers (e.g., 1600) and, in the illustrated embodiment, includes several shelves 2210, 2212 and 2214 for supporting containers thereon and a back wall 2240.

Embodiment 2200 is similar to the embodiments described above and therefore only features unique to embodiment 2200 will be described here in detail. In addition, embodiment 2200 may be used with any of the container types described above but, in the interest of simplifying this explanation, embodiment 2200 will be described in relation to operation with containers 1600 like the one illustrated in FIG. 60 having an RFID tag 60 mounted to an undersurface 1602.

In addition to enclosure 2202, embodiment 2200 includes an interface device 2204, a compartment mounted device 2226, a plurality of horizontal RF sensor antennas collectively referred to by numeral 2220 and a back wall antenna 2224. Interface 2204 may be positioned either inside or outside compartment 2206 when door 2208 is closed. In the illustrated embodiment interface 2204 is positioned outside compartment 2206 and, for example, may rest upon a kitchen or bathroom countertop. Referring again to FIG. 28, interface 2204 includes a processor 1378, a memory 1389, an audible (and perhaps a visual) alarm 134, a power source 150, interface button 160 and a transceiver 1343. Processor 1378 is linked to and controls all other interface components and, in that regard, can be programmed to perform any of the functions described above.

Referring again to FIG. 28, compartment mounted device 2226 includes a processor 2230 linked to each of antennas 2220 and 2224, a memory 2248 and a transceiver 2236 for sending and receiving signals to and from transceiver 1343. Processor 2230 is capable of using antenna 2220 and 2224 to read any tags 60 within the sensing area (i.e., the area adjacent any of antenna 2220 or 2224) and may also be capable of writing to any of devices 60 to alter the information stored thereon.

Generally speaking, any time a container 1600 is placed within compartment 2206, processor 2230 in device 2226 reads the memory device 60 on the newly positioned container and transmits the information to interface 2204 via transceivers 1343 and 2236. Thereafter processor 1378 in interface 2204 performs any of the functions described (e.g., developing a regimen based on the information, sequencing, etc.) above. For example, assuming processor 1378 is programmed to alert a system user when a medication is to be taken, when the consumption time occurs, processor 1378 may provide an alerting message via display 132 indicating which medication to consume and the quantity to consume thereby prompting the user to follow the prescribed medication.

It is also contemplated that some device inside compartment 2206 may be equipped to help a system user determine which container within compartment 2206 includes the medication to be consumed when a consumption alert is generated. For example, the embodiment illustrated in FIG. 68 includes an indicator device 1620. Device 1620 includes a top surface (not numbered) configured to receive a single container 1600 and also includes one or more indicator lights 1622 that faces the open side of compartment 2206 for easy viewing when door 2208 is opened. In addition, device 1620 includes a sensor for reading a tag 60 and communicates with processor 2230 in device 2226.

In this case, when interface 2204 indicates that a medication should be consumed via display 132, interface 2204 also sends a message to processor 2230 in device 2226 via transceivers 1343 and 2236 indicating which container from which medication should be taken. Information indicating the correct container from which to take medication is stored in device 2226 memory 2248. When a system user opens door 2208 and is faced with several different medications within compartment 2206, the user can select the container that the user believes to be the container storing the medication to be taken. After selecting the container the user places the container on the top surface of device 1620 at which point the sensor in device 1620 identifies the container and provides information to processor 2230. Processor 2230 then compares the information related to the container on device 1620 to the information in memory 2248 to determine if the two sets of information match. Where the information matches, processor 2230 causes indicator light 1622 to affirmatively indicate thereby letting the user know that the container selected includes the medication to be taken.

In another embodiment an indicator may be provided on the container so that immediately upon opening door 2208 a user can identify which of several different containers includes a medication to be consumed. To this end, referring again to FIG. 68, a container 2250 is different than containers 1600 described above in that container 2250 includes an indicator 2252 in the form of an LED. In this case it is assumed that the information initially read from a container tag 60 includes information teaching processor 2230 how to uniquely communicate with the specific container such as, for example, a unique power and frequency combination or tag address. Then, when processor 2230 receives an indication from interface 2204 that a medication is to be consumed, processor 2230 sends a signal to the specifies container (e.g., container 2250) within compartment 2206 which, via the antenna in tag 60, excites the indicator 2252 positioned on top or on the side (e.g., as part of a label that is connected to tag 60) of the container 2250. Thus, upon opening door 2208 the exact container from which to consume medication is indicated.

While an LED 2252 is preferred because such an indicator would be particularly easy to see when door 2208 is opened, where only minimal power can be provided to the indicator via the antenna in tag 60, some other low energy indicating device may be used. For example, indicator 2252 may be an LCD indicator and in this regard may be provided on a lateral edge of a container cap instead of on the top so that the indicator 2252 can easily be seen from the side when the door 2208 is opened. Other indicators are contemplated.

Referring still to FIG. 68, transceivers 1343 and 2236 may communicate via any type of communication protocol including RF or, where compartment 2206 is positioned relatively close to interface 2204 and a transceiver lead is on the outside of door 2208, via infra-red transmissions. In addition Bluetooth technology may be used to facilitate communication.

Moreover, interface 2204 may be linked to the Internet or some other communication network and, in that regard, interface 2208 may be a network computer or the like so that alerts and other messages can be provided via conventional browser pages, e-mail, page alerts or phone calls. In this case the hardware already provided for other purposes (e.g., network access) can be used for the additional purpose of providing medication alerts and the like.

Sixteenth Embodiment

Figure 70:
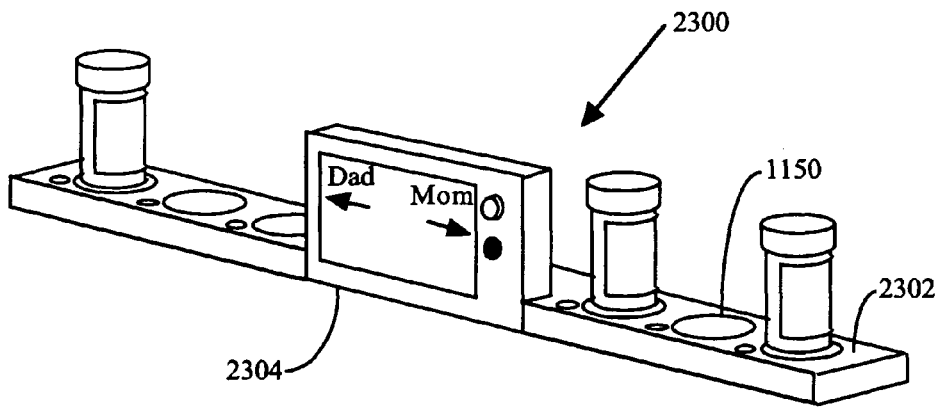
FIG. 70 is a perspective view of another embodiment of the invention particularly useful for operation by two medication users.

Referring to FIG. 70, yet one other embodiment 2300 of the invention is illustrated. Embodiment 2300 is similar to the embodiments described above in many respects and in the functions that the system can perform and therefore those function and much of the hardware used to configure embodiment 2300 are not described here in detail. In addition, while embodiment 2300 may be used with any of the containers described above, embodiment is only described in relation to how the embodiment is used in conjunction with containers like container 1600 in FIG. 60 including a tag 60 on an undersurface 1602.

Specifically, embodiment 2300 is most similar to the embodiment illustrated in FIG. 59 including a pad 2302 that extends both to the right and to the left of interface 2304. Embodiment is unique in that, when two persons use the system, the system can organize medications via physically different sides of interface 2304 for ease of use. For example, when a husband and wife each use system 2300 all of the husbands medications may be organized and alerts therefore given using the left side of pad 2302 while all of the wife's organizing and alerting is accomplished using the right side of pad 2302. Thus, when the husband is to take a medication, interface 2304 may instruct the husband to retrieve a container and place the container on one of the left side sensor indicia. When the correct container is placed on an indicia the interface may indicate so either via the interface display or via an indicator light (e.g., 136). Similar alerting and instructing is contemplated in the case of the wife. Other methods of distinguishing which medications are for which person are contemplated.

While many different embodiments of the invention have been described above and many different health safety functions have been described in conjunction with various of the embodiments it should be appreciated that almost all of the health safety functions taught could be facilitated with each of the embodiments. For instance, health safety functions including contraindication, alerting of consumption times based on questionnaires or information related to vital signs either locally or via instructions from a remote server, warnings regarding allergies, consumption outside specific time periods, etc., managing different medication users using the same systems, skipping alerts when previous events obviate the alerts, presenting messages to medication users related to the medications they are consuming, presenting questionnaires based on consumed medications, storing and displaying consumption data and remote scheduling are all functions that could be facilitated in one way or another with most all of the embodiments described above.

To apprise the public of the scope of the invention, the present inventor makes the following claims.

What is claimed is:

1. A medication system for performing at least one health safety function, the system comprising:
   at least one container for holding doses of medication, the container having a container memory device containing specifying information useable to determine a prescribed dosing regimen for the medication;
   a reminder device including:
   (i) a communication device;
   (ii) a timing device;
   (iii) a reminder device memory; and
   (iv) a processor and an associated surface, the processor for receiving the specifying information via rf communication; when the container memory device is proximate the surface, the processor linked to the timing device and the reminder device memory an linkable to the communication device;
   wherein, prior to an initial time the specifying information has not been received by the processor and the prescribed dosing regimen information is not stored in the reminder device memory, at the initial time the container memory device is disposed proximate the first surface and the processor receives the specifying information for the first time, the first time the processor receives the specifying information, the processor using the specifying information to obtain prescribed dosing regimen information from a location other than the reminder device memory and performing at least one health safety function as a function of the prescribed dosing regimen information;
   wherein, the processor further uses the at least a portion of the prescribed dosing regimen information to determine a predetermined time to take the medication, uses the timing device to identify a predetermined time, and causes the communication device to indicate when the predetermined time occurs.

2. The system of claim 1 wherein the surface includes an aligner for aligning the container with a portion of the surface.

3. The system of claim 2 wherein the aligner includes indicia on the surface.

4. The system of claim 2 wherein the facing surface has a first shape and the aligner has a second shape and the first and second shapes are essentially identical.

5. The system of claim 3 wherein the container is supportable adjacent the surface such that the memory device is adjacent to surface.

6. The system of claim 5 wherein the container includes a container surface that faces the associated surface when the container is supported adjacent the associated surface.

7. The system of claim 4 wherein the container is a vial.

8. The system of claim 1 wherein the at least one container includes several containers, each container includes a memory device, the surface can be proximate more than one memory device at a time and, wherein, when more than one memory device is proximate the surface, the processor retrieves the specifying information from each of the memory devices.

9. The system of claim 1 wherein the communication device includes a visual display.

10. The system of claim 8 further including a separate communication device for each of the several containers, the communication devices attached to the containers.

11. The system of claim 1 wherein the health safety function includes indicating when a medication is being consumed at a non-optimal time, the system further including a consumption indicator, the consumption indicator activatable to indicate when a dose of medication is to be consumed, wherein the processor receives and uses the specifying information to identify a predetermined prescribed time to take the medication, the processor monitors the consumption indicator to determine when a medication is to be consumed and, when a medication is to be consumed, the processor uses the timing device to determine if the time to consume is consistent with the predetermined time to consume.

12. The system of claim 11 further including a communication devices linkable to the processor and wherein, when the time to consume is inconsistent with the predetermined time to consume, the processor indicates that the medication should not be consumed at the time indicated by the consumption indicator.

13. The system of claim 12 wherein the indicator is activated when one of the specifying device is placed proximate the associated surface and the specifying device is removed from the associated surface.

14. The system of claim 1 wherein the at least one health safety function includes the processor using the communication device to indicate the prescribed dosing regimen information when the predetermined time occurs.

15. The system of claim 1 wherein the processor one of uses at least a portion of the specifying information as the prescribed dosing regimen information and uses the specifying information to obtain the prescribed dosing regimen information from a remote processor.

16. The system of claim 1 wherein the reminder device includes at least one container receiving space for storing the container and wherein the specifying device is disposed proximate the associated surface when the container is stored in the container receiver space.

17. The system of claim 16 wherein the processor obtains specifying information from a container memory device each time a new container is received in the container receiving space and wherein the processor associates prescribed dosing regimen information associated with the specifying information with the container receiving space.

18. The system of claim 16 wherein the remainder device includes a plurality of container receiving spaces and a separate associated surface for each of the container receiver spaces and wherein, when a container is located in one of the container receiving spaces, the container memory device is proximate an associated surface and the processor obtains the specifying information form the container memory.

19. The system of claim 1 further including a sensor defining a sensing area adjacent the associated surface.

20. The system of claim 19 wherein the timing device, processor, communication device and sensor form a portable device.

21. The system of claim 20 wherein the portable device includes a strap such that the device is wrist mountable.

22. The system of claim 19 wherein timing device, processor, communication device and sensor form a console for stationary use.

23. The system of claim 19 further including an enclosure wherein the sensor and the sensing area are concealed within the enclosure and the communication device is outside the enclosure.

24. A medication system for performing at least one health safety function, the system comprising:
 at least one container for holding doses of medication, the container having a specifying device containing specifying information useable to determine a prescribed dosing regimen for the medication;
 a reminder device including:
 (i) a sensor defining a sensing area, the sensing area capable of receiving at least two specifying devices at the same time, the sensor for receiving the specifying information from each specifying devices within the sensing area via rf communication; and
 (ii) a reminder device memory; and
 (iii) a processor linked to the remainder device memory;
 wherein, prior to an intitial time the specifying information has been received by the processor and the prescribed dosing regimen information is not stored in the reminder unit memory, at the initial time, the memory device is disposed proximate the sensor and the sensor receives the specifying information and provides the specifying information to the processor for the first time, the first time the processor receives the specifying information, the processor using the specifying information to identify prescribed dosing regimen information from a location other than the reminder device memory and performing at least one health safety function as a function of the prescribed dosing regimen information.

25. The systems of claim 24 further including a communication device linkable to the processor the communication device capable of indicating any of the containers.

26. The system of claim 25 further including a timing device linked to the processor wherein, when more than one specifying device is within the sensing area, the processor receives and uses the specifying information for each specifying device in the sensing area to identify prescribed dosing regimen information and a predetermined time to take each of the medications, the processor uses the timing device to determine when the predetermined time occurs for each of the medications to be consumed at the predetermined times.

27. The system of claim 26 wherein the sensing area includes at least first and second separate sensing areas for receiving specifying information from separate specifying devices.

28. The system of claim 27 wherein the communication device includes a separate visual warning indicator adjacent each of the sensing areas and, wherein, the communication device indicates which medication to consume by activating the visual warning indicator adjacent medication to be consumed.

29. The system of claim 26 wherein the sensor includes a sensor surface and the sensor surface includes a sensing section and a non-sensing section for each of the sensing areas, the sensing areas only adjacent the sensing sections and the sensor includes a separate aligner for each of the sensing sections distinguishing the sensing sections from the non-sensing section.

30. The system of claim 29 wherein the sensor defines a sensor surface, when containers are supported adjacent the sensing surface the containers each include at least one facing surface adjacent the sensor surface, the specifying devices attached to the facing surfaces.

31. The system of claim 30 wherein the facing surfaces each have a first shape and the aligners each have a second shape and the first and second shapes are essentially identical.

32. The system of claim 24 wherein the specifying device is a bar code.

33. The system of claim 24 wherein the specifying device is an electronic memory device.

34. The system of claim 25 wherein the communication device includes at least one communication device for each container and a separate communication device is attached to each container.

35. The system of claim 30 wherein the processor periodically causes the sensor to scan the sensing area to identify specifying devices in the sensing area.

36. The system of claim 35 wherein each container includes a separate communication device and wherein the processor is linkable to the communication devices to control each communication device.

37. The system of claim 36 wherein the processor controls the communication device via wireless communication.

38. The system of claim 25 wherein the communication device includes a visual display.

39. The system of claim 24 also for use in recording medication consumption times, the system further including a readable and writable memory device and a consumption indicator that are linkable to the processor, the consumption indicator operable to obtain consumption time information which the processor records in the memory device.

40. The system of claim 39 wherein the sensor and consumption indicator are integral such that one of placing and removing a specifying device in the sensing area comprises operation of the consumption indicator.

41. The system of claim 39 wherein the memory device and the specifying device are integral.

42. The system of claim 25 wherein the processor is a remote server processor linkable to the sensor and the communication device via a computer network.

43. A method for use with a medication system for performing at least one health safety function wherein the medication system comprises at least one container for holding doses of medication, a communication device, a timing device and a processor that includes a reminder device memory and that is associated with a surface, the container having a container memory device containing specifying information useable to determine a prescribed dosing regiment for the medication, wherein the processor is linked to the timing device and the reminder device memory and is linkable to the communication device and wherein the dosing regimen information is not stored in the reminder device memory prior to a first time, the method comprising the steps of:

using the processor to perform the steps of:
at a first time when the container memory device is disposed proximate the surface, receiving the specifying information via rf communication;
when the processor receives the specifying information for the first time, using the specifying information to identify prescribed dosing regimen information without accessing the reminder device memory and performing at least one health safety function as a function of the prescribed dosing regimen information; and
using the prescribed dosing regimen information to determine a predetermined time to take the medication;
using the timing device to identify the predetermined time; and
causing the communication device to indicate when the predetermined time occurs.

44. The method of claim 43 wherein there are at least first and second containers containing first and second medications, respectively, each container having a memory device containing specific information, the step of receiving the specifying information including receiving the specifying information from each memory device and the step of performing at least one health safety function including at least one of determining the first and second medications can be consumed together and determining the first and second medications can be consumed at a common time.

45. The method of claim 43 wherein the step of performing at least one health safety function includes at least one of determining a patient is allergic to the medication, determining a medication consumption time should be modified based on at least one vital sign measurement, determining a medication consumption time should be modified based on instructions from a remote server, providing an alert when medication is consumed outside a specific time period, and storing and displaying consumption data.

46. The method of claim 43 wherein the step of performing at least one health safety function includes at least one of determining a mediation consumption time should be modified based on a questionnaire, presenting messages based on medication consumed, and presenting questionnaires based on consumed medication.

47. A medication system for performing at least one health safety function, the system comprising:
at least one container for holding doses of mediation, the container having a memory device containing specifying information useable to determine a prescribed dosing regimen for the medication;
a reminder unit that defines a plurality of distinct locations, the reminder unit including:
(i) a separate sensor associated with each of the locations; and
(ii) a processor and an associated surface, the processor for receiving the specifying information via rf communication; when the memory device is proximate the associated surface and receiving a location indication identifying one of the plurality of distinct locations when the at least one container is position at the at least one of the plurality of distinct locations, the processor linked to the separate sensors;
wherein, prior to an initial time, the specifying information has not been received by the processor, proximate the initial time the at least one container is disposed at a first of the plurality of locations and the processor received the location indication indentifying the first of the plurality of distinct locations and, at the initial time the memory device is disposed proximate the surface and the processor receives the specifying information for the fist time, the first time the processor receives the specifying information and the temporally proximate location indication, the processor using the specifying information to identify prescribed dosing regimen information and associating the prescribed dosing regimen information with the first of the plurality of locations.

48. The system of claim 47 further including a communication device and a timing device, the processor linked to the timing device and likable to the communication device, wherein the processor further uses the prescribed dosing regimen information to determine a predetermined time to take the medication, uses the timing device to identify the predetermined time and causes the communication device to indicate when the predetermined time occurs.

49. The system of claim 47 wherein each sensor is capable of receiving specifying information from the container and wherein the associated surface includes a separate surface adjacent each of the sensors.

50. The system of claim 48 further including a separate visual indicator adjacent each of the distinct locations and wherein the processor activates the visual indicator adjacent one of the distinct locations when a time specified by the prescribed dosing regimen information associated with the location indicates that a mediation should be consumed.

51. The system of claim 48 wherein the communication device includes a separate indicator adjacent each of the distinct locations.

* * * * *

UNITED STATES PATENT AND TRADEMARK OFFICE
CERTIFICATE OF CORRECTION

| | | |
|---|---|---|
| PATENT NO. | : 7,978,564 B2 | |
| APPLICATION NO. | : 09/832770 | |
| DATED | : July 12, 2011 | |
| INVENTOR(S) | : Carlos De La Huerga | |

It is certified that error appears in the above-identified patent and that said Letters Patent is hereby corrected as shown below:

Claim 1, column 96, line 2, "an" should be --and--.

Claim 5, column 96, line 33, "to" should be --the--.

Claim 16, column 97, line 18, "receiver" should be --receiving--.

Claim 18, column 97, line 25, "remainder" should be --reminder--.

Claim 18, column 97, line 27, "receiver" should be --receiving--.

Claim 18, column 97, line 31, "form" should be --from--.

Claim 24, column 97, line 59, "remainder" should be --reminder--.

Claim 24, column 97, line 61, "has been" should be --has not been--.

Claim 26, column 98, line 17, "medication to" should be --medications and the processor causes the communication device to indicate the medications--.

Claim 43, column 99, line 7-18, "regiment" should be --regimen--.

Claim 46, column 100, line 1, "mediation" should be --medication--.

Claim 47, column 100, line 7, "mediation" should be --medication--.

Claim 47, column 100, line 20, "position" should be --positioned--.

Claim 47, column 100, line 26, "received" should be --receives--.

Signed and Sealed this
Twenty-seventh Day of September, 2011

David J. Kappos
*Director of the United States Patent and Trademark Office*

CERTIFICATE OF CORRECTION (continued)
U.S. Pat. No. 7,978,564 B2

Claim 47, column 100, line 31, "fist" should be --first--.

Claim 48, column 100, line 40, "likable" should be --linkable--.

Claim 50, column 100, line 55, "mediation" should be --medication--.